United States Patent
Rongved et al.

(10) Patent No.: US 10,961,223 B2
(45) Date of Patent: Mar. 30, 2021

(54) COMPOUNDS

(71) Applicant: UNIVERSITETET I OSLO, Oslo (NO)

(72) Inventors: Pål Rongved, Oslo (NO); Ove Alexander Høgmoen Åstrand, Haslum (NO); Ørjan Samuelsen, Tromsø (NO); Christian Schnaars, Oslo (NO); Geir Kildahl-Andersen, Oslo (NO)

(73) Assignee: UNIVERSITETET I OSLO, Oslo (NO)

( * ) Notice: Subject to any disclaimer, the term of this patent is extended or adjusted under 35 U.S.C. 154(b) by 20 days.

(21) Appl. No.: 16/325,966

(22) PCT Filed: Aug. 15, 2017

(86) PCT No.: PCT/GB2017/052401
§ 371 (c)(1),
(2) Date: Feb. 15, 2019

(87) PCT Pub. No.: WO2018/033719
PCT Pub. Date: Feb. 22, 2018

(65) Prior Publication Data
US 2019/0284167 A1  Sep. 19, 2019

(30) Foreign Application Priority Data

Aug. 15, 2016 (GB) .................. 1613946.1

(51) Int. Cl.
| | | |
|---|---|---|
| *C07D 401/14* | (2006.01) | |
| *A61P 31/04* | (2006.01) | |
| *C07H 15/26* | (2006.01) | |
| *C07H 19/056* | (2006.01) | |
| *A61K 31/44* | (2006.01) | |
| *A61K 31/4436* | (2006.01) | |
| *A61K 47/54* | (2017.01) | |
| *A61K 31/69* | (2006.01) | |
| *A61K 31/496* | (2006.01) | |
| *A61K 31/706* | (2006.01) | |
| *A61K 31/5377* | (2006.01) | |
| *A61K 47/61* | (2017.01) | |
| *A61K 31/407* | (2006.01) | |
| *A61K 31/444* | (2006.01) | |
| *A61K 45/06* | (2006.01) | |

(52) U.S. Cl.
CPC .......... *C07D 401/14* (2013.01); *A61K 31/407* (2013.01); *A61K 31/44* (2013.01); *A61K 31/444* (2013.01); *A61K 31/4436* (2013.01); *A61K 31/496* (2013.01); *A61K 31/5377* (2013.01); *A61K 31/69* (2013.01); *A61K 31/706* (2013.01); *A61K 47/54* (2017.08); *A61K 47/549* (2017.08); *A61K 47/61* (2017.08); *A61P 31/04* (2018.01); *C07H 15/26* (2013.01); *C07H 19/056* (2013.01); *A61K 45/06* (2013.01)

(58) Field of Classification Search
None
See application file for complete search history.

(56) References Cited

U.S. PATENT DOCUMENTS

| | | |
|---|---|---|
| 6,410,570 B1 | 6/2002 | Fernandez-pol |
| 2003/0039956 A1 | 2/2003 | Choi et al. |
| 2003/0225155 A1 | 12/2003 | Fernandez-pol et al. |
| 2005/0013836 A1 | 1/2005 | Raad |
| 2006/0014230 A1 | 1/2006 | Murata |

(Continued)

FOREIGN PATENT DOCUMENTS

| | | |
|---|---|---|
| EP | 1724263 A1 | 11/2006 |
| RU | 2491009 C2 | 8/2013 |

(Continued)

OTHER PUBLICATIONS

Thallaj, N. K., Mandon, D., & White, K. A. (2007). The Design of Metal Chelates with a Biologically Related Redox-Active Part: Conjugation of Riboflavin to Bis (2-pyridylmethyl) amine Ligand and Preparation of a Ferric Complex. European journal of inorganic chemistry, 2007(1), 44-47. (Year: 2007).*

Leadbetter, M. R., Adams, S. M., Bazzini, B., Fatheree, P. R., Karr, D. E., Krause, K. M., . . . & Quast, K. (2004). Hydrophobic vancomycin derivatives with improved ADME properties. The Journal of antibiotics, 57(5), 326-336. (Year: 2004).*

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

(Continued)

*Primary Examiner* — Dale R Miller
(74) *Attorney, Agent, or Firm* — Meunier Carlin & Curfman LLC

(57) ABSTRACT

The invention provides compounds for use in a method of treating and/or preventing a bacterial infection in a human or non-human mammal, said method comprising administration of said compound in combination with (either simultaneously, separately, or sequentially) a β-lactam antibiotic, wherein said compound has the general formula I: (I) (wherein: Q is a lipophilic, zinc chelating moiety which is selective for $Zn^{2+}$ ions and which comprises at least one, preferably two or more (e.g 2, 3 or 4), optionally substituted, unsaturated heterocyclic rings, e.g. 5 or 6-membered heterocyclic rings (such rings preferably include at least one heteroatom selected from N, S and O, preferably N); wherein any optional substituents may be selected from $C_{1-6}$ alkyl, $C_{1-6}$ alkoxy, halogen, nitro, cyano, amine, and substituted amine; each L, which may be the same or different, is a covalent bond or a linker; each W, which may be the same or different, is a non-peptidic hydrophilic group which comprises one or more hydroxy groups; and x is an integer from 1 to 3) or a stereoisomer, pharmaceutically acceptable salt or prodrug thereof.

20 Claims, 15 Drawing Sheets

(56) References Cited

U.S. PATENT DOCUMENTS

2009/0111737 A1 4/2009 Christensen et al.
2012/0329842 A1 12/2012 Song et al.

FOREIGN PATENT DOCUMENTS

| WO | 9710225 A1 | 3/1997 |
| WO | 9730027 A1 | 8/1997 |
| WO | 9817639 A1 | 4/1998 |
| WO | 9839311 A1 | 9/1998 |
| WO | 9840056 A2 | 9/1998 |
| WO | 0076962 A1 | 12/2000 |
| WO | 0130148 1 | 5/2001 |
| WO | 0130149 A2 | 5/2001 |
| WO | 0160349 A2 | 8/2001 |
| WO | 2004071425 A2 | 8/2004 |
| WO | 2005117997 A1 | 12/2005 |
| WO | 2006043153 A2 | 4/2006 |
| WO | 2006109069 A1 | 10/2006 |
| WO | 2006117660 A2 | 11/2006 |
| WO | 2009031041 A2 | 3/2009 |
| WO | 2009140215 A2 | 11/2009 |
| WO | 2009155088 A1 | 12/2009 |
| WO | 2011063394 A2 | 5/2011 |
| WO | 2012088283 A1 | 6/2012 |
| WO | 2015049546 A1 | 4/2015 |

OTHER PUBLICATIONS

Russian Office Action dated Jun. 22, 2018, for Russian Application No. 2016116956/04(026639), pp. 1-6.
Russian Search Report dated Jun. 22, 2018, for Russian Application No. 2016116956/04(026639), pp. 1-3.
Japanese Office Action, date unknown, for Japanese Counterpart application No. 2016-519979, pp. 1-5.
Andersen, et al., "Reconciliation of opposing views on membrane-sugar interactions", PNAS, Feb. 1, 2011, vol. 108, No. 5.
Astrand, O. et al., "Synthesis and Characterization of New Selective Zn2+ Fluorescent Probes for Functionalization: In Vitro Cell Imaging Applications", Tetrahedron, 2013, vol. 69, pp. 8645-8654, Epub Aug. 1, 2013.
Astrand, O.A. et al., "Synthesis and Initial In Vitro Biological Evaluation of Two New Zinc-Chelating Compounds: Comparison with TPEN and PAC-1", Bioorganic & Medicinal Chemistry, 2013, vol. 21 (17), p. 5175-5181, Epub Jun. 26, 2013.
Bailey, G. et al., "H₂azapa: a Versatile Acyclic Multifunctional Chelator for $^{67}$GA, $^{64}$Cu, $^{111}$In, and $^{177}$Lu", Inorg. Chem. 2012, 51, 12575-12589.
Barkalifa, Randall et al., "The Lipophilic Zinc Chelator DP-b99 Prevents Zinc Induced Neuronal Death", Eur. J. Pharmacol, Sep. 15, 2009, vol. 618(1-3), pp. 15-21, Epub Jul. 19, 2009. (Abstract only).
Benoist, et al., "A Click procedure with heterogeneous copper to tether technetium-99m chelating agents and rhenium complexes. Evaluation of the chelating properties and biodistribution of the new radiolabelled glucose conjugates", Carbohydrate Research 346 (2011) 26-34.
Bertini, I et al., "A Bioinformatics View of Zinc Enzymes", Journal of Inorganic Biochemistry, Jun. 2012, vol. 111, pp. 150-156, (Abstract only).
Bozym, R.A. et al., "Free Zinc Ions Outside a Narrow Concentration Range Are Toxic to a Variety of Cells In Vitro", Exp. Biol. Med. (Maywood), Jun. 1, 2010, vol. 235(6), pp. 741-750.
Brotherton, W.S. et al., "Apparent Copper(II)-Accelerated Azide-Alkyne Cycloaddition", Organic Letters, 2009, vol. 11(21), pp. 4954-4957, Epub Oct. 7, 2009.
Bush, K. et al., "Epidemiological Expansion, Structural Studies, and Clinical Challenges of New β-Lactamases from Gram-Negative Bacteria", Annual Review of Microbiology, Oct. 2011, vol. 65, pp. 455-478, doi.org/10.1146/annurev-micro-090110-102911. (Abstract only).
Butler, M.S. et al., "Antibiotics in the Clinical Pipeline in 2013", The Journal of Antibiotics, Sep. 4, 2013, vol. 66, pp. 571-591.

Charkoudian, L.K. et al., "A Pro-Chelator Triggered by Hydrogen Peroxide Inhibits Iron-Promoted Hydroxyl Radical Formation", J. Am. Chem. Soc., 2006, vol. 128(38), pp. 12424-12425. (Abstract only).
Conrady, D.G. et al., "A Zinc-Dependent Adhesion Module is Responsible for Intercellular Adhesion in Staphylococcal Biofilms", Proc. Natl. Acad. Sci. USA, Dec. 9, 2008, vol. 105(49), pp. 19456-19461. Epub Dec. 1, 2008.
De Kraker, M.E.A. et al., "Mortality and Hospital Stay Associated with Resistant *Staphylococcus aureus* and *Escherichia coli* Bacteremia: Estimating the Burden of Antibiotic Resistance in Europe", PLoS Med., Oct. 2011, vol. 8(10), p. e1001104, Epub Oct. 11, 2011.
Donadelli, M. et al., "Zinc Depletion Efficiently Inhibits Pancreatic Cancer Cell Growth by Increasing the Ratio of Antiproliferative/Proliferative Genes", J. Cell. Biochem., May 1, 2008, vol. 104(1), pp. 202-212. (Abstract only).
Drawz, S.M. et al., "New β-lactamase Inhibitors: A Therapeutic Renaissance in an MDR World", Antimicrob. Agents Chemother., Apr. 2014, vol. 58(4), pp. 1835-1846, Epub Dec. 30, 2013.
Drawz, S.M. et al., "Three Decades of β-Lactamase Inhibitors", Clin. Microbiol. Rev., Jan. 2010, vol. 23(1), pp. 160-201
Rongved, P. et al. "Nye antibakterielle legemiddelkandidater med effekt mot metallo-beta-laktamase (MBL)," Farmasøytisk institutt Masteroppgaver 2014/2015, Jan. 2014, 37 pages.
Ellison, M.L. et al., "The Transcriptional Regulator Np20 is the Zinc Uptake Regulator in Pseudomonas aeruginosa", PLoS One, Sep. 23, 2013, vol. 8(9), e75389, pp. 1-11, eCollection 2013.
Ferreira, et al., "Cationic technetium and rhenium complexes with pendant carbohydrates", Applied Radiation and Isotopes 68(2010)1087-1093.
Ganta, S.R. et al., "Approaches to the Simultaneous Inactivation of Metallo-and Serine-β-Lactamases", Bioorg. Med. Chem. Lett., Mar. 15, 2009, vol. 19(6), pp. 1618-1622, Epub Feb. 8, 2009.
Search Report dated Jun. 1, 2017 for Application No. GB1613946.1.
Goto, M. et al., "Inhibition of the Metallo-Beta-Lactamase Produced from Serratia Marcescens by Thiol Compounds", Biol. Pharm. Bull., Nov. 1997, vol. 20(11), pp. 1136-1140. (Abstract only).
Graham, A.I. et al., "Severe Zinc Depletion of *Escherichia coli*: Roles for High Affinity Zinc Binding by ZinT, Zinc Transport and zinc-Independent Proteins", J. Biol. Chem., Jul. 3, 2009, vol. 284(27), pp. 18377-18389, Epub Apr. 19, 2009.
Hanaoka, K. et al., "Development of a Zinc Ion-Selective Luminescent Lanthanide Chemosensor for Biological Applications", J. Am. Chem. Soc. 2004, 126, 12740-12476.
Hazell, et al., "Mononuclear non-heme iron(m) peroxide complexes: syntheses, characterisation, mass spectrometric and kinetic studies", J. Chem. Soc., Dalton Trans., 2002, 310-317.
Hsu, D.C. et al., "Parallel Synthesis and Biological Evaluation of 837 Analogues of Procaspase-Activating Compound 1 (PAC-1)", ACS Comb. Sci., Jan. 9, 2012, vol. 14(1), pp. 44-50, Epub Oct. 28, 2011.
Huang, S. et al., "Highly Sensitive Fluorescent Probes for Zinc Ion Based on Triazolyl-Containing Tetradentate Coordination Motifs", Organic Letters, 2007, vol. 9(24), pp. 4999-5002, Epub Oct. 23, 2007.
Johnson, A.P. et al., "Global Spread of Antibiotic Resistance: The Example of New Delhi Metallo-β-Lactamase (NDM)-mediated Carbapenem Resistance", J. Med. Microbiol., Apr. 2013, vol. 62(Pt 4), pp. 499-513, Epub Jan. 17, 2013. (Abstract only).
King, A.M. et al., "MA Overcomes Antibiotic Resistance by NDM and VIM Metallo-β-Lactamases", Nature, Jun. 26, 2014, vol. 510(7506), pp. 503-506.
Kobayashi, T. et al., "DNA Degradation by the Copper (II) Complex with Tripodal-Ligands Containing Peptide Group", Polyhedron, 1998, vol. 17(9), pp. 1553-1559.
Liang, X. et al., "Synthesis, Structure, and Antibiotic Activity of Aryl-Substituted LpxC Inhibitors", J. Med. Chem., Sep. 12, 2013, vol. 56(17), pp. 6954-6966, Epub Aug. 21, 2013.
Anonymous, "List of Clinically Important Bacteria", retrieved from Wikipedia on Apr. 9, 2018, 7 pages.
Liu, L. et al., "Synthesis of Novel Macrolide Derivatives with Imidazo[4,5-b]Pyridinyl Sulfur Contained Alkyl Side Chains and

(56) References Cited

OTHER PUBLICATIONS their Antibacterial Activity", Bioorganic & Medicinal Chemistry Letters, Aug. 1, 2009, vol. 19(15), pp. 4079-4083. (Abstract only).
Makhov, P. et al., "Zinc Chelation Induces Rapid Depletion of the X-Linked Inhibitor of Apoptosis (XIAP) and Sensitizes Prostate Cancer Cells to TRAIL-Mediated Apoptosis", Cell Death Differ., Nov. 2008, vol. 15(11), pp. 1745-1751, Epub Jul. 11, 2008.
Maret, W. et al., "Cellular Zinc and Redox Buffering Capacity of Metallothionein/Thionein in Health and Disease", Mol. Med., Jul.-Aug. 2007, vol. 13(7-8), pp. 371-375.
Marlin, D.S. et al., "Complexation-Induced Translational Isomerism: Shuttling through Stepwise Competitive Binding", Angrew. Che. Int. Ed., 2006, vol. 45, pp. 77-83.
Martinez, J.L. et al., "The Antibiotic Resistome: Challenge and Opportunity for Therapeutic Intervention", Future Med. Chem., Mar. 2012, vol. 4(3), pp. 347-359. (Abstract only).
Mikami, Y. et al., "Novel Microbial Inhibitors of Angiotensin-converting Enzyme, Aspergillomarasmines A and B", Agricultural and Biological Chemistry, 1983, vol. 47(11), pp. 2693-2695.
Moore, A.L. et al., ""Click" Labeling Strategy for M(CO)(3) (M = Re, (99m)Tc) Prostate Cancer Targeted Flutamide Agents", Dalton Trans., 2010, vol. 39(8), pp. 1926-1928, Epub Jan. 6, 2010.
Napolitano, M. et al., "Characterization of the Response to Zinc Deficiency in the *Cyanobacterium anabaena* sp. Strain PCC 7120", J. Bacteriol., May 2012, vol. 194(10), pp. 2426-2436, Epub Mar. 2, 2012.
Nikaido, H. et al., "Broad-Specificity Efflux Pumps and their Role in Multidrug Resistance of Gram-Negative Bacteria", FEMS Microbiology Reviews, Mar. 1, 2012, vol. 36(2), pp. 340-363.
Niklas, N. et al., "Dipicolylglycyl-Phenylalanine Zinc (II): A Metallopeptide with a Built-In Conformational Switch and it's Homochiral Helical Coordination Polymer", Chem. Comm., 2003, pp. 1586-1587.
Page, M.G.P. et al., "In Vitro and In Vivo Properties of BAL30376, a β-Lactam and Dual β-Lactamase Inhibitor Combination with Enhanced Activity Against Gram-Negative Bacilli that Express Multiple β-Lactamases", Antimicrob. Agents Chemother., Apr. 2011, vol. 55(4), pp. 1510-1519, Epub Jan. 18, 2011.
Page, M.I. et al., "The Mechanism of Catalysis and the Inhibition of β-lactamases", Chem. Commun., 1998, pp. 1609-1617. (Abstract only).
Palzkill, T., "Metallo-β-Lactamase Structure and Function", Ann. N.Y. Acad. Sci., Jan. 2013, vol. 1277, pp. 91-104. Epub Nov. 16, 2012.
Patel, G. et al., "Stormy Waters Ahead", Global Emergence of Carbapenemases, Front. Microbiol., Mar. 14, 2013, vol. 4, Article 48, pp. 1-17.
Payne, D.J. et al., "Inhibition of Metallo-Beta-Lactamases by a Series of Thiol Ester Derivatives of Mercaptophenylacetic Acid", FEMS Microbiol. Lett., Dec. 1, 1997, vol. 157(1), pp. 171-175. (Abstract only).
Payne, D.J. et al., "Inhibition of Metallo-62 -Lactamases by a Series of Mercaptoacetic Acid Thiol Ester Derivatives", Antimicrobial Agents and Chemotherapy, Jan. 1997, vol. 41(1), pp. 135-140.
International Search Report and Written Opinion for International Application No. PCT/GB2014/053009 dated Dec. 17, 2014.
International Search Report and Written Opinion dated Jan. 9, 2018 for International Application No. PCT/GB2017/052401.

Peterson, Q.P. et al., "PAC-1 Activates Procaspase-3 In Vitro Through Relief of Zinc-Mediated Inhibition", J. Mol. Biol., Apr. 24, 2009, vol. 388(1), pp. 144-158, Epub Mar. 10, 2009.
Putt, K.S. et al., "Small-Molecule Activation of Procaspase-3 to Caspase-3 as a Personalized Anticancer Strategy", Nat. Chem. Biol., Oct. 2006, vol. 2(10), pp. 543-550, Epub Aug. 27, 2006. (Abstract only).
Que, E.L. et al., "Metals in Neurobiology: Probing their Chemistry and Biology with Molecular Imaging", Chem. Rev., May 2008, vol. 108(5), pp. 1517-1549, Epub Apr. 22, 2008. (Abstract only).
Sauvage, E. et al., "The Penicillin-Binding Proteins: Structure and Role in Peptidoglycan Biosynthesis", FEMS Microbiology Reviews, Mar. 1, 2008, vol. 32(2), pp. 234-258.
Smith, R.M. et al., "NIST Critically Selected Stability Constants of Metal Complexes", Version 2.0, 1995, U.S. Department of Commerce: Gaithersburg, MD. (Abstract only).
Storr, et al., "A glucosamine-dipicolyamineconjugate of 99mTc(I) and 186 Re(I) for use in imaging and therapy", The Royal Society of Chemistry, Dalton Trans, 2005, 654-655.
Theuretzbacher, U., "Resistance Drives Antibacterial Drug Development", Curr. Opin. Pharmacol., Oct. 2011, vol. 11(5), pp. 433-438, Epub Aug. 19, 2011. (Abstract only).
Walsh, T.R. et al., "Dissemination of NDM-1 Positive Bacteria in the New Delhi Environment and its Implications for Human Health: An Environmental Point Prevalence Study", Lancet Infect. Dis., May 2011, vol. 11(5), pp. 355-362, Epub Apr. 7, 2011. (Abstract only).
Walsh, T.R., "Emerging Carbapenemases: A Global Perspective", Int. J. Antimicrob. Agents, Nov. 2010,vol. 36, Suppl 3, pp. S8-S14. (Abstract only).
Wanderlingh, et al., "Interaction of alcohol with phospholipid membrane: NMR and XRD investigations on DPPC-hexanol system", Spectroscopy 24 (2010) 375-380.
Wang, et al., "A Water-Soluble, Small Molecular Fluorescent Sensor with Femtomolar Sensitivity for Zinc Ion", Org. Lett., vol. 9, No. 24, 2007, pp. 4995-4998.
Wei, et al., "Rhenium Tricarbonyl Core Complexes of Thymidine and Uridine Derivatives", Inorganic Chemistry, vol. 44, No. 7, 2005, pp. 2198-2209.
Weide, T. et al., "NH-1,2,3-Triazole-based Inhibitors of the VIM-2 Metallo-β-Lactamase: Synthesis and Structure-Activity Studies", ACS Med. Chem. Lett., Jul. 8, 2010, vol. 1(4), pp. 150-154.
Xu, Z. et al., "Zn2+-Triggered Amide Tautomerization Produces a Highly Zn2+-Selective, Cell-Permeable, and Ratiometric Fluorescent Sensor", J. Am. Chem. Soc., Jan. 20, 2010, vol. 132(2), pp. 601-610. (Abstract only).
Ye, Z. et al., "Development of a novel terbium chelate-based luminescent chemosensor for time-resolved luminescence detection of intracellular Zn2+ ions", Biosensors and Bioelectronics 26 (2010) 1013-1018.
Zhang, L. et al., "A Selective and Sensitive Fluorescence Probe for Imaging Endogenous Zinc in Living Cells", Tetrahedron, Jan. 7, 2013, vol. 69(1), pp. 15-21 (Abstract Only).
Sutoh Y. et al., "Metal Chelates to Prevent or Clear the Deposits of Amyloid β-peptide(1-40) induced by Zinc(II) Chloride", Chemistry Letters, Feb. 2005, 34(2):140-141. (Abstract only).
XP002733343, Retrieved from the Internet: URL:http://www.uio.no/studier/program/farmasi/undervisning-eksamen/masteroppgaveheftet_valg-av-masteroppgave/masteroppgaveheftet_valg_2014.jan.pdh, [retrieved on Dec. 3, 2014].

* cited by examiner

Peptide-based examples for comparison

Figure 8
Figure 8A
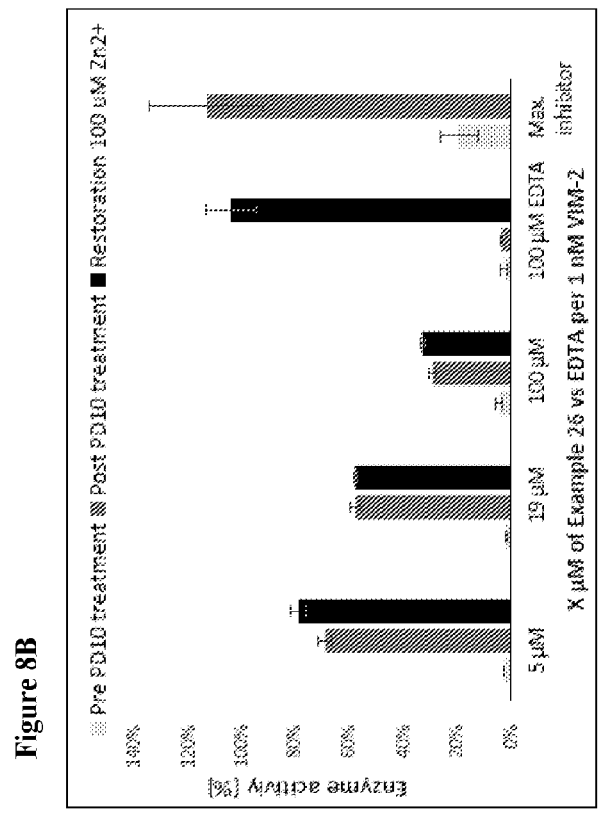
Figure 8B
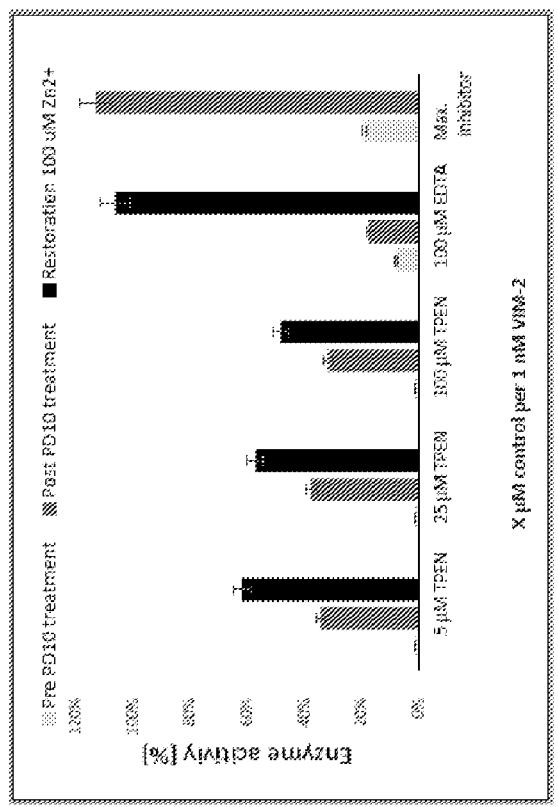

COMPOUNDS

FIELD OF THE INVENTION

The present invention relates to novel compounds which are regulators of biological zinc, to pharmaceutical compositions containing them, and to methods for their preparation. The new compounds of the invention have the ability to affect the concentration of zinc in living organisms in a controlled and safe manner. The invention thus further relates to their use in the treatment of disease states associated with abnormal zinc levels.

More specifically, the invention relates to novel compounds useful as adjuvants in antibacterial formulations and which may also be used in the treatment of diseases related to extracellular imbalance in the homeostasis of zinc. The compounds are low-toxic regulators of biological zinc. In particular, they have the ability to affect the concentration of zinc in microorganisms without generating toxic effects in the living organisms which are hosts of the microorganisms. Due to their lack of toxic effects, the compounds may also be used in the safe treatment of disease states associated with abnormal extracellular zinc levels, such as stroke, edema, epilepsy and Alzheimer's disease.

BACKGROUND OF THE INVENTION

In a number of disease states, biological zinc is present in concentrations outside the normal range for cells to have a healthy function. The disease state may be affected by biological factors such as enzymes dependent on zinc, e.g. as described in Prasad et al, *Journal of Trace Elements in Medicine and Biology* (2014), 28(4), 357-363 or in Shai et al, *ChemMedChem* (2015), 10 (3), 441-450. Herein, the group of diseases that may be affected or regulated by selectively and safely altering the zinc homeostasis is denoted the "disease".

A key element necessary for normal life of a cell is the homeostasis of zinc. Zinc is the second most abundant transition metal in the human body and is responsible for the catalytic function and structural stability of over 6000 enzymes and proteins (Bertini et al, *Journal of Inorganic Biochemistry* (2012), 111, 150-156). The biological concentration range of zinc maintaining healthy cells is narrow and is well described, e.g. by Maret in *Biometals* (2011) 24:411-418. Manipulation of the freely available zinc inside a cell has been shown to affect a great range of diseases and conditions (Que et al, *Chem. Rev.* (2008), 108, 1517-1549; Peterson, et al *Mol. Biol.* (2009), 388, 144-158; BarKalifa et al, *Eur. J. Pharmacol.* (2009), 618, 15-2; Maret et al, *Mol. Med.* (2007), 13, 371-375).

The concentration of free zinc varies in biological tissues depending on zinc buffering capacity. In PC12, HeLa, and HT-29 cell lines, as well as in primary cultures of cardiac myocytes and neurons in vitro, the concentration of free zinc has been determined to be approximately 5 nM (Bozym et al, *Exp. Biol. Med.* (2010), 235, 741-750). Zinc is a soft metal, mainly found in nature as salpherite or zinc sulfite, with an oxidation state +2 (Emsley, J. "Zinc". *Nature's Building Blocks: An A-Z Guide to the Elements*; Oxford University Press: New York, 2001). In order to chelate zinc selectively and safely and with high efficacy, the use of soft basic ligands is needed.

Non-limiting examples of disease states related to an imbalance in zinc homeostasis are cancer, Alzheimer's disease, stroke, edema, diabetes and intoxications by heavy metals like cadmium.

In Khan et al, *Journal of Diabetes and Metabolic Disorders* (2014), 13, 16/1-16/6, 6 pp., imbalance in zinc homeostasis is discussed as a factor in the development of diabetes.

In neurological disorders, it is well documented that in states of edema and stroke, there is an extraceullular zinc overload in CNS affecting the severity of the disease, e.g. as discussed by Liao et al in *Toxicology Letters* (2011), 204, 108-117. At the same time, zinc chelators may have a neuroprotective role, e.g. as discussed by Cho et al. in *Neurotox. Res.* (2010) 17:156-166. Recently, it was shown that zinc chelators may have a neuroprotective effect if they do not penetrate cell membranes in zebra fish, as described by Yu et al. in *Zebrafish* (2013), 10(1), 30-35. This is possible because both too high and too low concentrations of zinc, outside the normal concentration range, may be toxic for cells.

Alzheimer's disease is a neurodegenerative disorder characterized by extracellular deposition of b-amyloid (Ab) fibrils accompanied with progressive neurite loss. In these diseases, often a higher concentration of zinc is described, e.g. in Huang, *RSC Advances* (2014), 4(94), 52088-52099. In *Neuropharmacology* (2015), 92, 146-157, Chang et al. show how a metal chelator can reverse the development of the disease. However, the chelators used in the prior art are not zinc selective and log P (which is a measure of hydrophilicity) is high enough to provide cell penetration of the chelators in all cells. An example of a zinc chelator that has been used clinically to regulate extracellular zinc is the chelating agent DP-b99. A phase II study reported by Diener et al in Stroke (2008), 39(6), 1774-1778 reported positive results with DP-b99 on ischemic stroke. However, DP-b99 is a chelating agent with log P>5 and significant membrane penetration which would be expected to result in toxicity. Thus there is a medical need for a selective zinc chelator with negligible issues related to toxicity.

Also in a variety of cancer forms, zinc concentrations outside the normal range play a vital role. For example, in prostate cancer, zinc acetate has been used therapeutically, as described by Shah et al. in *Journal of Experimental & Clinical Cancer Research* (2009), 28:84, pp. 1-10. However, zinc acetate provides a very water-soluble formulation with low ability to transport zinc over biological membranes.

Matrix Metalloproteinases (MMPs) are a group of extracellular zinc-dependent enzymes vital to the growth of cancer cells and cancer tissue in general. General metal chelators have been shown to affect MMPs in the extracellular space, and thereby development of cancer, e.g. as discussed by Rouffet et al. in *JACS* (2010), 132, 8232-8233.

Also in hypoxic states related to cancer, zinc balance plays a role, e.g. zinc induces the accumulation of hypoxia-inducible factor (HIF)-1a, as discussed by Chun et al. in *Biochemical and Biophysical Research Communications* (2000), 268, 652-656. Zinc chelators may have a documented and significant effect on death of cancer cells as discussed by Ding et al., *Cancer Letters* (2008), 271, 251-259, by Lee et al. in *Biochemical and Biophysical Research Communications* (2007), 362, 766-772 and by Zuo in *Journal of Cellular Biochemistry* (2012), 113, 2567-2575. In the latter reference, derivatives of N,N-bis(2-pyridyl-methyl)-amine, including the well described zinc chelators TPEN (N,N,N'',N''-tetra(2-pyridyl-methyl)-ethylene diamine) strongly induce cancer cell death related to cellular zinc depletion and destabilization of the X-linked inhibitor of apoptosis protein (XIAP).

However, these chelating agents may not be used as therapeutic agents clinically because of high lipophilicity (log P) and high ability to penetrate also normal cells, inducing an unacceptable general toxicity. These agents have no structural or molecular features providing biological selectivity for the target organ or disease area.

One especially important disease area is resistant microbes. Infectious diseases are a leading cause of death worldwide and account for more than 13 million deaths annually including nearly two-thirds of all childhood mortality at less than 5 years of age. There is serious concern regarding new and re-emerging infectious diseases, in which effective therapies are lacking (*World Health Organization reports* 1999, 2012 and 2014).

Antimicrobial resistance is escalating and affects a very broad range of human diseases including tuberculosis, cholera, malaria, and AIDS. Of particular concern is the number of human pathogens developing multidrug resistance to conventional antibiotics and it is estimated that the burden of resistance will surpass that of e.g. cervical cancer (de Kraker M E A. et al, *PLoS Med*. (2011), e1001104, and cancer as a whole by 2050 (O'Neill J. Tackling drug-resistant infections. Final report and recommendations).

The introduction of new, more potent derivatives of existing antibiotics provides only temporary solutions, since existing resistance mechanisms rapidly adapt to accommodate the new derivatives (Theuretzbacher U. *Curr. Opin. Pharmacol*. (2011), 11, 433-438). Although resistant Gram-positive bacteria pose a significant threat, the emergence of multidrug resistant (MDR) strains of common Gram-negative pathogens such as *Escherichia coli* are of special concern. Pan-resistance or extreme drug resistance are now commonly used terms to describe clinically important isolates of *Pseudomonas aeruginosa, Acinetobacter baumannii* and Enterobacteriaceae that are resistant to virtually all antibiotics (Patel et al., *Front. Microbiol*. (2013), 4, 48). Unfortunately, there are few, if any, antimicrobial agents effective against Gram-negative bacteria either in or entering phase 1 clinical trials that will address this critical need (Butler M S. et al., *J. Antibiotics* (2013), 66, 571-591).

One important feature of bacteria, especially gram negative bacteria is that they have two cell membranes, one outer more permeable membrane and one inner cell membrane. One important group of enzymes involved in antimicrobial resistance is the β-lactamases (Bush K. et al., *Annu. Rev. Microbiol*. (2011), 65, 455-478). They are excreted into the volume between these membranes, the periplasmic space, thus this space is more accessible, for example for drugs.

The β-lactamases are enzymes that hydrolyse β-lactam antibiotics compromising the efficacies of β-lactams, our largest group and mainstay of antimicrobial chemotherapy for >70 years. Clearly, there is a need for inhibitors directed against these classes of enzymes that will restore the activity of their substrates—antibiotics that are cheap, non-toxic and normally effective. Serine β-lactamase inhibitors (clavulanic acid, sulbactam and tazobactam) have been a phenomenal success in extending the therapeutic life of β-lactam antibiotics and are also employed as diagnostic tools in clinical microbiological laboratories worldwide. In contrast, there is no clinical inhibitor available for metallo-β-lactamases (MBLs; Drawz et al., *Antimicrob. Agents Chemother*. (2014), 58, 1835-1846). The latter has now become one of the most clinically important families of β-lactamases showing global dissemination.

The β-lactamases are the most prevalent and clinically important resistance mechanism inactivating β-lactams by hydrolysis. They are classified according to sequence criteria (Ambler class A, B, C and D) and can be structurally grouped into two super families; the serine β-lactamases (class A, C, and D) and MBLs (class B). In contrast to the serine β-lactamases, which are characterized by a serine moiety in the active site, MBLs require divalent cations, usually zinc, as a metal co-factor of enzyme activity (Palzkill T. *Ann. N. Y. Acad. Sci*. (2013), 91-404).

MBLs belong to a large group of proteins only found in bacteria, and like penicillin-binding proteins (PBPs) have the ability to interact with β-lactams. Examples of PBPs and enzymes that bind β-lactams are MBLs, serine β-lactamase-like protein (LACTB), D,D-transferase, D-Ala(D,D)-carboxypeptidase, the D-Alanyl-D-alanine Dipeptidases VanA, VanX, VanY and others, as reviewed by Sauvage E. et al. in *FEMS Microbiol. Rev*. (2008), 32, 234-258. This class of proteins is only found in bacterial biology. Examples of compounds having affinity for PBPs are β-lactam antibiotics. β-Lactams have been the historical anchor of antibacterial chemotherapy and include penicillins, cephalosporins, monobactams and carbapenems (Bush K. et al, *Annu. Rev. Microbiol*. (2011), 65, 455-478).

MBLs are emerging as one of the most clinically important family of β-lactamases (Patel et al., *Front. Microbiol*. (2013), 4, 48, Walsh et al, *Int. J. Antimicrob. Agents* (2010), S8-S14) for the following reasons: The clinically most important MBLs, the IMP-, VIM-, GIM- and NDM-groups, are now widespread in a variety of Gram-negative species. In particular, VIM- and NDM-enzymes have emerged as the dominant MBLs. The unprecedented global dissemination of NDM highlights the enormity of the problem. Since the first report in 2008, NDM has been identified in Australia, Africa, North-America, Asia and many European countries (Johnson A P. et al, *J. Med. Microbiol*. (2013), 62, 499-513). Worryingly, NDM is found in numerous Gram-negative species and in the environment (Walsh T R. et al, *Lancet Infect. Dis*. (2011), 11, 355-362).

Successful inhibitors of class A serine β-lactamases are clinically available, but lack inhibitory activity against MBLs (Drawz S M. et al., *Clin. Microbiol. Rev*. (2010), 23, 160-201). Inspired by the commercial success of the paradigm Augmentin (clavulanic acid—a suicide substrate for serine β-lactamases—and amoxicillin) several research groups have focused on similar approaches to develop inhibitors, but as yet no molecules that combine potency with activity against multiple MBL targets have reached clinical trials (Drawz S M. et al. *Antimicrob. Agents Chemother*. 2014).

For the three clinically most threatening MBLs—the IMP, NDM and VIM groups—most inhibitors are reported for IMP-1, while few inhibitors are found for VIM-2 and NDM. For NDM, a fungal natural product, aspergillomarasmine A has been identified as an MBL inhibitor and shown in vivo activity in mouse models (King A M. et al. *Nature* (2014), 510, 503-506). However, relatively high doses of aspergillomarasmine A are required to reverse carbapenem resistance. Other therapeutic options (Martinez, *Future Med. Chem*. (2012), 4(3), 347-59) include the use of tri-β-lactam therapy incorporating a monobactam; however, the MICs are not impressive and their in vivo activity is severely compromised by the bacterial inoculum (Page et al., *Antimicrob. Agents Chemother*. (2011), 66, 867-73). Thus, there is a strong clinical need for an MBL inhibitor.

Important β-lactam antibiotics are the penicillins, cephalosporin and carbapenem classes. Many compounds have been reported as having MBL inhibiting activities. In WO 98/117639, WO 97/30027, WO 98/40056, WO 98/39311, and WO 97/110225, a class of β-thiopropionyl-amino acid derivatives has been described as the inhibitors against the MBLs.

Other compound classes that may act as MBL inhibitors are thioesters (*Biol. Pharm. Bull.* (1997), 20, 1136; *FEMS Microbiology Letters* (1997), 157, 171; *Antimicrob. Agents Chemother.* (1997), 41, 135; *Chem. Commun.* (1998), 1609; *Biochem.* (1998), 1, 331, 703; WO 00/076962) and succinic acid derivatives (WO 01/030148 and WO 01/030149).

In bacteria, zinc sensing is carried out by regulators of different families, including SmtB/ArsR, MerR, TetR, MarR, and the Fur family (Napolitano et al., *Journal of Bacteriology* (2012), 2426-2436). In some cases the MBL inhibitors contain a $Zn^{2+}$-binding group that can interact strongly with the central metal ion(s). Thus, in the prior art, compounds binding metal ions, so called metal "chelators", have been shown to affect bacterial biological mechanisms. The term "chelating" relates to the greek term "chelos" denoting a crab claw binding an object via at least two contact points. The person skilled in the art will appreciate the variety of substances described in the prior art capable of chelating metal ions, and will select an appropriate chelator for different purposes. Examples are chelators comprising variations of amino groups and hydroxyl groups, e.g. 1,10-phenanthroline, clioquinol, 1,2-dimethyl-3-hydroxy-4-pyridinone (DMHP), 1,2-diethyl-3-hydroxy-4-pyridinone (DEHP), deferasirox. In the prior art, zinc chelators have been described as inhibitors of multiple diseases simultaneously, e.g. in WO 2006/117660, WO 2001/60349, U.S. Pat. No. 6,410,570, and in WO 2009/140215.

Zinc chelators have also been suggested as inhibitors of biofilm formation, e.g. in WO 2011/63394 and WO 2009/155088, or as antiviral agents, e.g. in WO 2004/71425 and WO 2006/43153. Attractive bacterial zinc-dependent targets involved in resistance mechanisms are known in the prior art to be inhibited by zinc chelating agents. Three examples are the tightly regulated bacterial zinc uptake system Zur (Ellison et al. in *PLOS ONE* (2013), 8, e75389), biofilms (Conrady et al., *PNAS* (2008), 105 (49), 19456-19461) and the peptidase HmrA in MRSA. All these targets are inhibited by state of the art non-selective, toxic zinc chelators like TPEN, EDTA or the phenanthrolines.

Biofilm formation is an important bacterial resistance mechanism that contributes to the growing therapeutic concern globally. Biofilms consist of extracellular polymeric substances (EPS). They are natural hydrophilic carbohydrate polymers of high molecular weight secreted by microorganisms into their environment, and determine the physiochemical properties of a biofilm. Biofilm formation with the nocosomial infections produced by multidrug-resistant gram-negative species producing metallo-β-lactamases, e.g. *Acinetobacter baumannii*, *Pseudomonas aeruginosa*, *Klebsiella pneumoniae* and *E. coli* is problematic since they affect all traditional activity at hospitals, like surgery and wound healing. Of particular concern is MBL-producing *Acinetobacter baumannii*, as described by Peymani et al., *Jpn. J. Infect. Dis.* (2011), 64, 69-71. MBL-production was also found to be significantly higher in biofilm-positive isolates of *Pseudomonas aeruginosa*, as described by Heydari et al., *Jundishapur J Microbiol.* (2015), 8(3), e15514. Thus, there is a medical need for new drugs with acceptable toxicity and selectivity that are active against gram-negative bacteria harboring MBL.

Another example of vital zinc-dependent machineries is bacterial use of the efflux pumps (Nikaido, et al., *FEMS Microbiology Reviews* (2012), 36, 340-363), adapting almost all modern antibiotics as substrates, excreting them from the bacterial cell.

Yet another example is the zinc-dependent deacetylase LpxC (Liang et al., *J. Med. Chem.* (2013), 56, 6954-6966).

Another example is the highly zinc-dependent bacterial ribosomal function (Graham et al., *J. Biol. Chem.* (2009), 284, 18377-18389). The latter uses 8 zinc atoms on the 70S ribosomal unit. Administration of zinc has also been used as a therapy against bacterial infections, e.g. as different formulations of zinc oxide ZnO, often as particulate matter, e.g. as described in Shi et al., *Food Additives & Contaminants, Part A: Chemistry, Analysis, Control, Exposure & Risk Assessment* (2014), 31(2), 173-186. However, where there is a need to provide zinc to compartments protected by biological membranes, particulate ZnO has a low penetration over such membranes.

The most widely used groups of metal chelators are the so called amino-polycarboxylates, denoted hereinafter as APC chelators, comprising variations of aliphatic amino groups, hydroxyalkyl groups and carboxyalkyl groups. Common examples are ethylenediaminetetra-acetic acid (EDTA), ethylenediamine-N,N'-diacetic-N,N'-di-β-propionic acid (EDPA), diethylenetriamine pentaacetic acid (DTPA), trans-1,2-cyclohexane-diamine-N,N,N',N'-tetraacetic acid (CyDTA), carnosine, dihydroxyethylglycine (DHEG), 1,3-diamino-2-hydroxypropane-N,N,N',N'-tetraacetic (DTPA-OH), ethylenediamine-N,N'-diacetic acid (EDDA), ethylenediamine-N,N'-dipropionic acid (EDDP), N-hydroxyethylenediamine-N,N',N'-triacetic acid (EDTA-OH), N,N'-bis(2-hydroxybenzyl)ethylenediamine-N,N'-diacetic acid (HBED), hexamethylene-1,6-diaminetetraacetic acid (HDTA), hydroxyethyliminodiacetic acid (HIDA), iminodiacetic acid (IDA), methyl-EDTA, nitrilotriacetic acid (NTA), nitrilotripropionic acid (NTP), triethylenetetraaminehexaacetic acid (TTHA), ethylenediamine-di(O-hydroxyphenylacetic acid) (EDDHA), ethyleneglycol bis(2-aminoethyl ether)-N,N,N',N'-tetraacetic acid (EGTA), trans-1,2-cyclohexanediaminetetraacetic acid (CDTA), N-(2-hydroxyethyl) ethylenedinitrilotriacetic acid (HEDTA), N-(2-hydroxyethyl) iminodiacetic acid (HEIDA), citric acid, 7,19,30-trioxa-1,4,10,13,16,22,27,33-octaazabicyclo[11,11,11] pentatriacontane (O-Bistren), penicillamine, chelators also comprising sulfur or phosphorus, e.g. diethyldithiocarbamate(DEDTC), 2,3-dimercapto-1-propanesulfonic acid (DMPS), ethylmaltol (EM), 4-(6-methoxy-8-quinaldinylaminosulfonyl)benzoic acid potassium salt (TFLZn), dithiozone, N-(6-methoxy-8-quinolyl)-para-toluenesulfonamide (TSQ), ethylenediamine-N,N'-bis(methylphosphonic) acid (EDDPO), ethylenediaminetetra(methylenephosphonic) acid (EDTPO), nitrilotrimethylenphosphonic acid (NTPO), dimercaptosuccinic acid (DMSA), carboxymethyl-derivatives of 1,4,7-triaza-cyclononane or 1,4,7,10-tetra-aza-cyclododecane like DOTA, DO3A or NOTA, deferoxamine, dimercaprol, dimercaptosuccinic acid, and etidronic acid.

The APC chelators are well known in the prior art, e.g. in Smith, R. M.; Martell, A. E. *NIST Critically Selected Stability Constants of Metal Complexes, Version 2.0*; U.S. Department of Commerce: Gaithersburg, Md., 1995. They are non-selective and often strong chelating agents with no molecular targeting moieties affecting their affinity for desired biological targets relevant for the disease. Thus they usually also have antibacterial effect which is well described in the prior art, e.g. use of metal chelators against virus or bacteria in WO 2011/63394, WO 2004/71425, WO 2006/109069, WO 2001/60349, U.S. Pat. No. 6,410,570, US 2003/0225155, WO 2006/43153 and WO 2006/43153. Zinc chelators have also been suggested as antibacterial agents, e.g. in WO 2009/140215, as inhibitors of biofilm formation, e.g. in WO 2011/63394 and WO 2009/155088, or as antiviral agents, e.g. in WO 2004/71425 and WO 2006/43153, but in these cases, the claimed compounds lack biological or metal-chelating selectivity or have high solubility in fat, high log P, and are therefore often toxic to eukaryotic cells.

This lack of selectivity may lead to undesired toxicity and other biological effects when treating specific infections by a target organism in a host organism, e.g. when it is desirable to affect only specific microorganisms whilst a low toxicological effect on the host organism or other species (which are not a target for the treatment in question) is desired. One particularly serious adverse event exerted by non-selective chelating agents like the APC chelating agents is hemolytic effects even at low concentrations. A final report on the safety assessment of EDTA, calcium disodium EDTA, diammonium EDTA, dipotassium EDTA, disodium EDTA, TEA-EDTA, tetrasodium EDTA, tripotassium EDTA, trisodium EDTA, HEDTA, and trisodium HEDTA, ethylene diamine tetra acetic acid, EDTA, confirms that these have a swelling effect on erythrocytes after intravenous injections concentrations below 4 µM, eventually leading to hemolysis. This is well described in the prior art, e.g. by Witeska et al., in *Turk. J. Vet. Anim. Sci.* (2011), 35(2), 99-104, or by Igbokwe et al., *Journal of basic and clinical physiology and pharmacology* (2015), 26(2), 171-9.

EDTA is also a potent anticoagulant because of its unselective metal chelation, resulting in chelation of e.g. $Ca^{2+}$. However, this ability to bind calcium may lead to hypocalcemia, a deadly condition causing the US Food and Drug Administration (FDA) to withdraw the market approval of disodium EDTA because of the death of three patients related to hypocalcemia, as reported by P. M. Wax, J. Med. Toxicol. (2013) 9:303-307. A report by R. S. Lanigan and T. Yamarik in *International Journal of Toxicology*, (2002), 21(Suppl. 2), 95-142 concluded that EDTA, being a weaker chelating agent than other PACs, e.g. DTPA or DOTA, is a compound with biological effects incompatible with the demands for safe agents used clinically, especially for intravenous injection.

EDTA has recently been used as an adjuvant in a formulation denoted Elores or Sulbactomax comprising the β-lactam antibiotic ceftriaxone. Sulbactam and EDTA administered intravenously have a good antibacterial effect, e.g. as described by Attili et al. in *International Journal of Pharmaceutical Sciences and Research* (2015), 6(6), 2569-2578. However, no description of studies of the hemolytic or anti-coagulant effects of the formulation are mentioned.

Attractive bacterial zinc-dependent targets involved in resistance mechanisms are known in the prior art to be inhibited by zinc chelating agents. An example of vital zinc-dependent machineries is bacterial use of the efflux pumps (see Nikaido et al., *FEMS Microbiology Reviews* (2012), 36, 340-363), adapting almost all modern antibiotics as substrates, excreting them from the bacterial cell.

Ligands based on the 2-pyridyl-methyl units (see Scheme 1) demonstrate remarkably high selectivity for the group IIB elements zinc and cadmium (Xu et al., *JACS*, (2010), 132, 601), although the latter is not a natural metal ion in biological systems. Zinc chelating agents are also suggested in the prior art to act as MBL inhibitors. In WO 2012/088283 thiazolidines and analogous compounds are suggested as MBL inhibitors together with β-lactams. The use of the di-picoylamine group in zinc chelators is not mentioned herein. Also, the $IC_{50}$ values are above the micro molar range in MBL assays in WO 2012/088383.

In Ganta et al., *Bioorganic & Medicinal Chemistry Letters* (2009), 19, 1618-1622, a group of compounds have been reported having a hydroxamate group as a zinc-chelating moiety with affinity for MBLs. However, the hydroxamate group is a non-selective chelating group. In particular, its binding of $Fe^{2+}/Fe^{3+}$ and also its binding of many other metal ions makes hydroxamate ligands less specific, and more prone to interaction with human biology leading to higher human toxicity.

In the above descriptions of the prior art, there is no guidance on how to obtain selective effects of the zinc chelation therapy in the target tissue whilst the healthy part of the organism is not affected with serious adverse advents. Likewise, there is no guidance on how to avoid toxic effects like hemolysis by metal chelators whilst maintaining their desired biological effect.

Not only may a deficiency of zinc provoke the abnormal function of a cell, but also an excess of zinc may lead to abnormal cell functionality and unacceptable toxicity. Thus there is a medical and technological need within this field for new therapeutic and diagnostic agents harnessing toxicity related to uncontrolled zinc depletion in healthy tissue and cells, whilst exerting the desired therapeutic effect. Many of the disease states in mammals related to zinc imbalance are caused by enhanced zinc concentration outside the eukaryotic cells in the extracellular space. Often the disease is related to excess zinc outside the cells. Thus, there is a medical need for new zinc chelating agents that have a low ability to pass eukaryotic cell membranes, and which at the same time have a high and selective affinity for divalent zinc.

The lipophilic zinc chelators N,N,N-tris(2-pyridylmethyl) amine (TPA, structure III, Scheme 1) and N,N,N',N'-tetrakis (2-pyridylmethyl) ethylenediamine (TPEN, structure IV, Scheme 1), have been reported to display many interesting biological activities due to their zinc chelating properties as well as their lipophilic character, allowing cell-membrane penetrating abilities, e.g. as described by Huang et al., *Metalomics* (2013), 5, 648-655 and Donadelli et al. in *J. Cell. Biochem* (2008) 104, 202-212).

Scheme 1

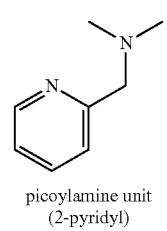

picoylamine unit
(2-pyridyl)

I

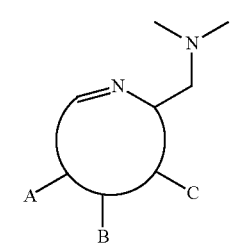

Aromatic amine unit
comprising 5- or 6-
membered rings, the A, B and
C may form larger
aromatic units

II

-continued

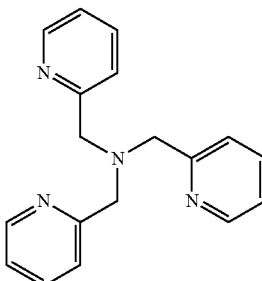

TPA
Log P: 2.7

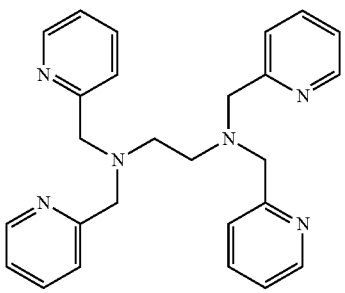

TPEN
Log P: 3.5

In TPA and TPEN, the zinc-binding ability is based on the binding of all nitrogen atoms to the metal atoms. Both TPA and TPEN have been widely reported to exert cytotoxic effects on a number of cell types because of their high lipophilicity. The main property affecting the toxicity of zinc chelating agents having a relatively high log P is the zinc-binding ability, expressed as the dissociation constant, $K_d$, or expressed as the log $K_d$ or $pK_d$. TPEN is known to have a $pK_d$ of about 16, while the $pK_d$ of TPA is about 12.

Thus, TPA and TPEN are not suitable in themselves as potential drugs since they are too toxic to normal cells, as described by Sheridan et al. in In Vitro & Molecular Toxicology (1998), 11 (2), 161-169 or by Huang et al., *Metalomics* (2013), 5, 648-655. The $EC_{50}$ values were reported by Huang et al. to be 38±1 µM for TPA and 25±1 µM mM for TPEN in an MTT assay in HeLa cells. In neurons, TPEN is known to be even more toxic, and the $EC_{50}$ for TPEN in neurons was reported by Canzoniero et al., *Neuropharmacology* (2003), 45, 420-428, to be about 5 µM.

Thus, the toxicity of zinc-selective chelating agents is a combination of their high log P value and their zinc-binding ability, $pK_d$. A high value for both evidently results in lower toxicity $EC_{50}$ values.

Toxicity issues are further demonstrated for example in Zuo in *Journal of Cellular Biochemistry*, (2012), 113, 2567-2575. The prior art is not teaching how to synthesize analogues or derivatives of, for example, TPEN with lower toxicity than TPEN itself, according to Scheme 1.

It has now surprisingly been found that in the above defined diseases, the biological zinc concentration can generally be affected safely using a novel zinc complexing moiety bound to a molecular moiety W which is a non-peptidic, hydrophilic group as defined herein.

SUMMARY OF THE INVENTION

The invention relates to compounds which comprise one or more lipophilic, zinc chelating moieties covalently bound to one or more hydrophilic moieties, wherein said zinc chelating moieties are selective for $Zn^{2+}$ ions and wherein said hydrophilic moieties are selected from non-peptidic hydrophilic monomeric, oligomeric and polymeric groups.

It further relates to the use of such compounds in therapy, in particular in the treatment or prevention of diseases or conditions associated with an imbalance in zinc homeostasis, and as adjuvants in the treatment or prevention of bacterial infections.

Embodiments of the invention include the following:

1. A compound which comprises one or more (e.g. one or two) lipophilic, zinc chelating moieties covalently bound to one or more (e.g. one, two or three) hydrophilic moieties, wherein said zinc chelating moieties are selective for $Zn^{2+}$ ions and wherein said hydrophilic moieties are selected from non-peptidic hydrophilic monomeric, oligomeric and polymeric groups.

2. A compound according to embodiment 1 having the general formula I:

$$Q\text{-}[\text{-}L\text{-}W]_x$$

(wherein Q represents a lipophilic, zinc chelating moiety which is selective for $Zn^{2+}$ ions; each L, which may be the same or different, is a covalent bond or a linker; each W, which may be the same or different, is a non-peptidic hydrophilic monomeric, oligomeric or polymeric group, preferably a non-peptidic hydrophilic group comprising hydrogen bond donor and hydrogen bond acceptor atoms selected from H, N, O, S and P, e.g. a non-peptidic hydrophilic group comprising one or more functional groups selected from —OH, —SH, —CO₂H, —SO₃H, —PO₃H₂, —B(OH)₂, and aliphatic or aromatic nitrogen-containing groups; and x is an integer from 1 to 3)

or a stereoisomer, pharmaceutically acceptable salt, or prodrug thereof.

3. A compound according to embodiment 2 which is a compound of the formula Q-L-W wherein Q, L and W are as defined in embodiment 2.

4. A compound according to embodiment 1 having the general formula II:

$$\text{Q-L-W-L-Q}$$

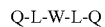

(wherein each Q, which may be the same or different, represents a lipophilic, zinc chelating moiety which is selective for $Zn^{2+}$ ions;

each L, which may be the same or different, is a covalent bond or a linker; and W is a non-peptidic hydrophilic monomeric, oligomeric or polymeric group, e.g. according to embodiment 2)

or a stereoisomer, pharmaceutically acceptable salt, or prodrug thereof.

5. A compound according to any one of the preceding embodiments having a calculated log P value, denoted c log P, which is less than 2, preferably less than 1, more preferably negative.

6. A compound according to any one of the preceding embodiments, wherein the dissociation constant, denoted $K_d$, for the zinc chelating moiety with $Zn^{2+}$ is less than or equal to $10^{-10}$ M, preferably less than or equal to $10^{-12}$ M, e.g. less than or equal to $10^{-14}$ M.

7. A compound according to any one of the preceding embodiments having a selectivity for chelating $Zn^{2+}$ over endogenous metal ions which is above 10, preferably equal to or above 11, wherein said selectivity for chelating $Zn^{2+}$ over endogenous metal ions, denoted $Zn_{sel}$, is expressed according to the following equation:

$$Zn_{sel}=\log(Kd_{Zn2+}/Kd_{Ca2+})=pK_{d\ Zn2+}-pK_{d\ Ca2+}$$

wherein $Kd_{Zn2+}$ is the dissociation constant for the compound with $Zn^{2+}$
$Kd_{Ca2+}$ is the dissociation constant for the compound with $Ca^{2+}$
$pK_{d\ Zn2+}$ is $-\log Kd_{Zn2+}$
$pK_{d\ Ca2+}$ is $-\log Kd_{Ca2+}$ 8. A compound according to any one of the preceding embodiments having an in vitro toxicity in human cells, expressed as the inhibitory concentration $IC_{50}$ for the eukaryotic cell mitochondrial function, which is higher than 8 µM, preferably higher than 10 µM, preferably higher than 20 µM, preferably higher than 50 µM, preferably higher than 100 µM, e.g. higher than 200 µM.

9. A compound according to any one of the preceding embodiments having a therapeutic score in the regulation of zinc homeostasis in a disease selected from cancer, Alzheimer's disease, stroke, edema, diabetes and intoxication by a heavy metal, which is equal to or higher than −0.8, preferably equal to or higher than 0, preferably equal to or higher than 0.5, preferably equal to or higher than 1, e.g. equal to or higher than 1.5, wherein the therapeutic score of the compound, denoted $TS_x$, is expressed according to the following equation:

$$TS_x=\log(TI\times(1+\tan h(Zn_{sel}-8))\times(1-\tan h(c\log P-2))\times(1+\tan h((pK_d-8))))$$

wherein TI is the therapeutic index ratio, which is the dividend $IC_{50}/MEC$, wherein MEC is the minimum concentration for the compound to have an effect on the disease; and $Zn_{sel}$, c log P and $pK_d$ are defined in embodiments 5 to 7.

10. A compound according to any one of the preceding embodiments having an adjuvant antibiotic activity when administered together with an antibiotic agent and which has an antibacterial score equal to or higher than −0.8, preferably equal to or higher than 0, equal to or higher than 0.5, e.g. equal to or higher than 1, or equal to or higher than 1.5, wherein the antibacterial score of the compound, denoted $AS_x$, is expressed according to the following equation:

$$AS_x=\log(TI\times(1+\tan h(Zn_{sel}-8))\times(1-\tan h(c\log P-2))\times(1+\tan h((pK_d-8))))$$

wherein TI is the therapeutic index ratio, which is the dividend $IC_{50}/MIC$, wherein MIC is the concentration of the compound giving a minimum inhibitory concentration for the antibiotic agent of 2 or less;
and $Zn_{sel}$, c log P and $pK_d$ are according to embodiments 5 to 7.

11. A compound according to any one of embodiments 1 to 10, wherein the zinc chelating moiety (e.g. Q) is a molecular moiety having the following formula:

$$(C)_m R_c (R_L)$$

where m is an integer from 2 to 10, preferably 2 to 6, e.g. 3, 4, 5 or 6;
each group C is a functional group that may be the same or different having Lewis base properties and possessing at least one heteroatom selected from N, S, O or P, preferably N, capable of donating electrons to a zinc atom;
$R_c$ is a unit linking the groups C which may contain up to 50 atoms, preferably 2 to 10 atoms, e.g. 4 to 8 atoms, and which optionally may carry one or more functional groups; and $R_L$ is a covalent bond to the remainder of the molecule, e.g. to linker, L.

12. A compound according to any one of the preceding embodiments, wherein the chelating moiety (e.g. Q) comprises at least one, preferably two or more (e.g 2, 3 or 4), optionally substituted, unsaturated heterocyclic rings, e.g. 5 or 6-membered heterocyclic rings (such rings preferably include at least one heteroatom selected from N, S and O, preferably N); wherein any optional substituents may be selected from $C_{1-6}$ alkyl, $C_{1-6}$ alkoxy, halogen, nitro, cyano, amine, and substituted amine.

13. A compound according to embodiment 12, wherein the chelating moiety comprises one or more optionally substituted heteroaryl groups, preferably two or more heteroaryl groups, e.g. such groups in which each heteroaryl ring has at least one nitrogen atom in the ring structure (e.g. pyridene, especially unsubstituted pyridine).

14. A compound according to embodiment 13, wherein the chelating moiety is derived from picolinic acid and its derivatives (e.g. from picoylamine), preferably wherein the chelating moiety comprises two or more (e.g. two, three or four) 2-pyridyl-methyl units.

15. A compound according to any one of the preceding embodiments, wherein the zinc chelating moiety comprises one or more of the following groups:

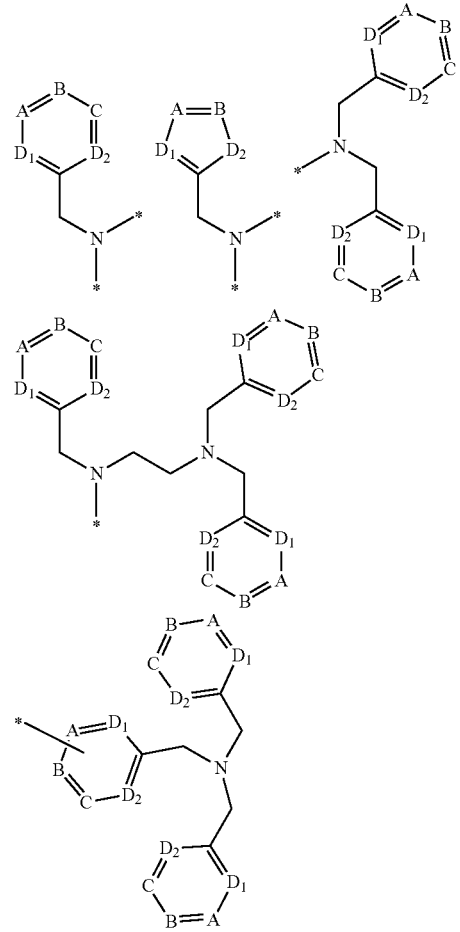

wherein in each structure:
$D_1$ and $D_2$ are independently selected from —CH— and N, provided that at least one of $D_1$ and $D_2$ is N;

A, B and C are independently —CH— or a heteroatom (e.g. N), preferably —CH—, or A, B and C may be bridgeheads participating in condensed rings thus forming polycyclic systems; and

*denotes the point (or points) of attachment of the group to the remainder of the molecule.

16. A compound according to any one of embodiments 1 to 15, wherein the percentage of aromatic nitrogen donor atoms in the compound is equal to or higher than 25%, the percentage of aliphatic nitrogen donor atoms is equal to or higher than 50% and the percentage of oxygen donor atoms is equal to or lower than 25% (based on the total number of donor atoms).

17. A compound according to any one of embodiments 1 to 15, wherein of the donor atoms which are present, the percentage of aromatic nitrogen donor atoms is equal to or higher than 50%, the percentage of aliphatic nitrogen donor atoms is equal to or higher than 25%, and the percentage of oxygen donor atoms equal to or lower than 25%.

18. A compound according to any one of embodiments 1 to 15, wherein of the donor atoms which are present, the percentage of aromatic nitrogen donor atoms is equal to or higher than 60%, the percentage of aliphatic nitrogen donor atoms is equal to or higher than 20%, and the percentage of oxygen donor atoms is equal to or lower than 20%.

19. A compound according to any one of embodiments 1 to 15, wherein of the donor atoms which are present, the percentage of aromatic nitrogen donor atoms is equal to or higher than 66%, the percentage of aliphatic nitrogen donor atoms is equal to or higher than 33%, and the percentage of oxygen donor atoms is equal to 0%.

20. A compound according to any one of embodiments 1 to 15, wherein of the donor atoms which are present, the percentage of aromatic nitrogen donor atoms is equal to or higher than 75%, the percentage of aliphatic nitrogen donor atoms is equal to or higher than 25%, and the percentage of oxygen donor atoms equal to 0%.

21. A compound according to any one of embodiments 1 to 15, wherein the zinc chelating moiety comprises one of the following groups:

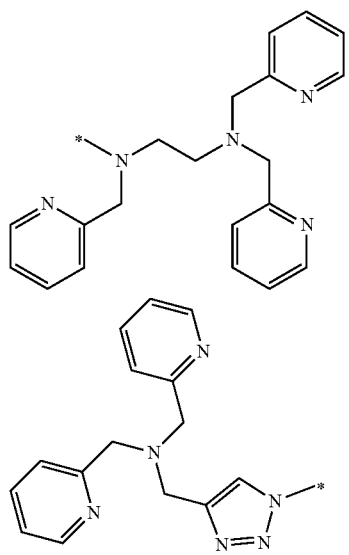

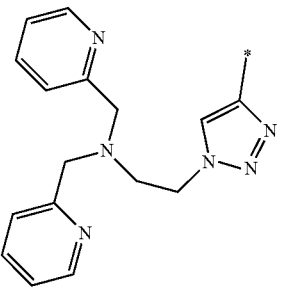

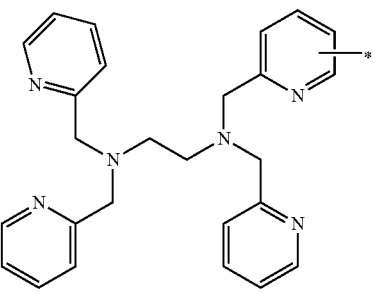

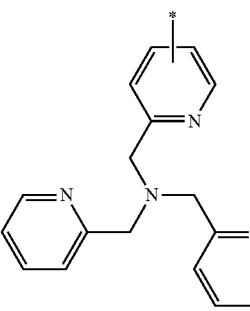

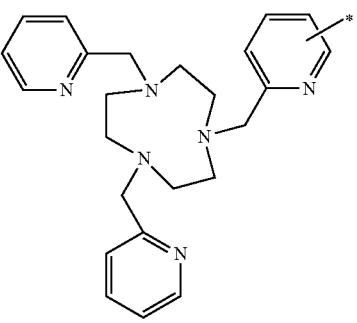

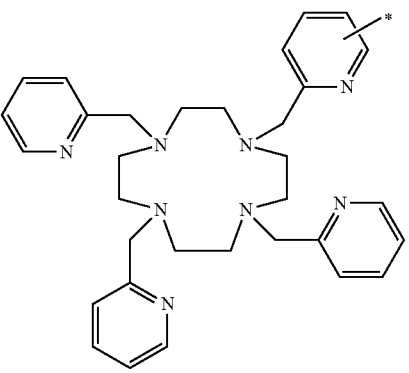

-continued

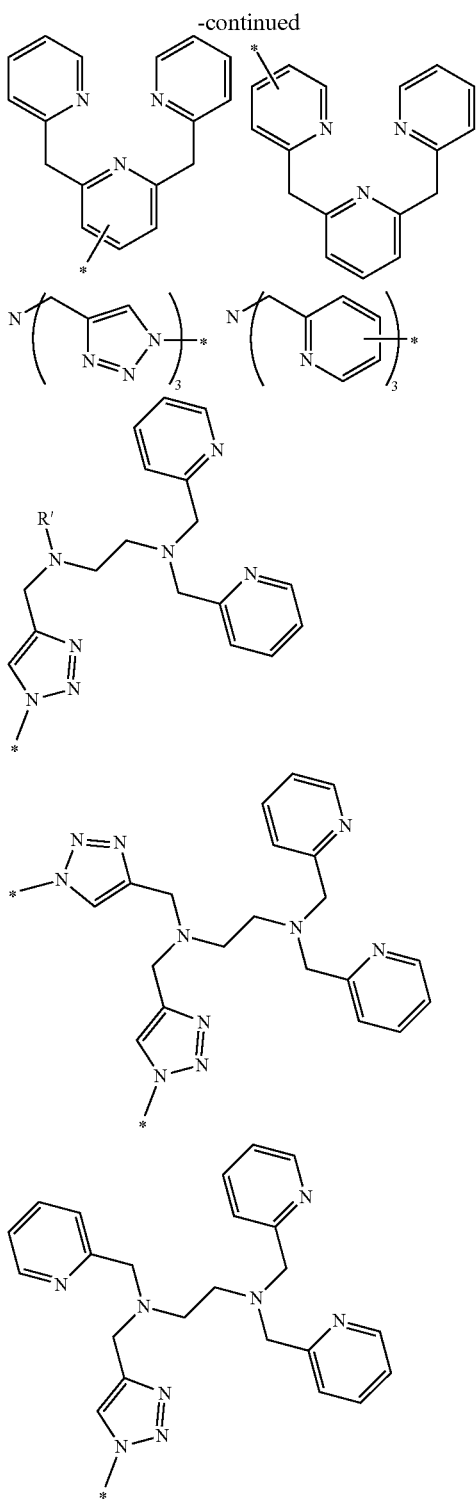

wherein * denotes the point (or points) of attachment of the chelating moiety to the remainder of the molecule, e.g. to a linker group L as herein defined; and
R', where present, is H or $C_{1-6}$ alkyl, e.g. $C_{1-3}$ alkyl, e.g methyl.

22. A compound according to any one of embodiments 2 to 21, wherein linker L comprises a bond or an alkylene chain (preferably a $C_{1-8}$ alkylene, e.g. a $C_{1-6}$ alkylene) optionally substituted by one or more groups selected from $C_{1-3}$ alkyl, —$O(C_{1-3})$alkyl, and —OR' (where R' is H or $C_{1-6}$ alkyl, preferably $C_{1-3}$ alkyl, e.g. methyl); and in which one or more —$CH_2$— groups (e.g. all —$CH_2$— groups) of the alkylene chain may be replaced by a group independently selected from —O—, —CO—, —NR"— (where each R" is independently H or $C_{1-6}$ alkyl, preferably $C_{1-3}$ alkyl, e.g. methyl), and an optionally substituted carbocyclic or heterocyclic ring (including monocyclic, bicyclic, tricyclic and fused rings; any optional substituents may be selected from $C_{1-6}$ alkyl, $C_{1-6}$ alkoxy, halogen, nitro, cyano, amine, and substituted amine).

23. A compound according to embodiment 22, wherein said linker is interrupted by an optionally substituted aryl or heteroaryl ring, preferably an optionally substituted phenyl or triazole ring, e.g. an unsubstituted phenyl ring.

24. A compound according to any one of embodiments 2 to 23 wherein the linker L comprises one or more electron donating atoms capable of chelating to a zinc atom, e.g. one or more atoms capable of supporting the metal chelating ability of group Q.

25. A compound according to embodiment 24, wherein said electron donating atoms are nitrogen atoms, e.g. wherein such atoms are provided in the backbone of the linker or within one or more substituting or interrupting ring structures.

26. A compound according to any one of embodiments 2 to 21, wherein linker L comprises a bond, or a $C_{1-8}$ alkylene chain (preferably a $C_{1-6}$ alkylene chain, e.g. a $C_{1-3}$ alkylene chain) in which one or more —$CH_2$— groups (e.g. all —$CH_2$— groups) of the alkylene chain are optionally replaced by a group independently selected from —O—, —CO—, —NR"— (where each R" is independently H or $C_{1-6}$ alkyl, preferably $C_{1-3}$ alkyl, e.g. methyl), and an unsubstituted phenyl ring.

27. A compound according to any one of the preceding embodiments, wherein each hydrophilic moiety is a non-peptidic monomeric, oligomeric or polymeric group which comprises up to 100 atoms in the form of optionally substituted, linear or branched aliphatic, alicyclic or aromatic groups comprising C, H and one or more functional groups comprising hydrogen bound to a heteroatom which is a hydrogen bond acceptor selected from the groups N, O, S and P.

28. A compound according to embodiment 27, wherein said functional groups are selected from —OH, —COOH, —SH, —$SO_3H$, —$PO_3H_2$, —$B(OH)_2$ or salts thereof, and aliphatic nitrogen-containing groups or salts thereof.

29. A compound according to embodiment 27 or embodiment 28, wherein any optional substituents which may be present are selected from $C_{1-6}$ alkyl, $C_{1-6}$ alkoxy, halogen, nitro, cyano, amine, and substituted amine.

30. A compound according to any one of the preceding embodiments, wherein each hydrophilic moiety comprises one or more of following groups: a sugar moiety, a carboxylic acid or derivative thereof (e.g. an ester), an alcohol, an amine or substituted derivative thereof, and a boronic acid.

31. A compound according to embodiment 30, wherein the sugar moiety may be a mono-, di- or polysacccharide, or an amino sugar, or a derivative thereof (e.g. an acetylated derivative).

32. A compound according to embodiment 31, wherein the sugar moiety is a cyclic or acyclic monosaccharide.

33. A compound according to embodiment 30, wherein the alcohol is a linear or branched, mono-, di- or tri-alcohol, e.g. a short-chain (e.g. $C_1$-6) linear or branched alcohol.

34. A compound according to embodiment 30, wherein the amine is linear, branched or cyclic, preferably —$NH_2$, —NHR (where R is $C_{1-6}$ alkyl, e.g. $C_{1-3}$ alkyl), optionally substituted piperazine or morpholine (any optional substituents may be selected from —OH and $C_{1-3}$ alkyl, e.g. methyl).

35. A compound according to embodiment 30, wherein the boronic acid is cyclic or acyclic.
36. A compound according to embodiment 35, wherein the boronic acid group forms part of a 6-membered ring optionally substituted by one or more functional groups, e.g. carboxyl groups or derivatives thereof.
37. A compound according to any one of the preceding embodiments, wherein the hydrophilic moiety or hydrophilic moieties (e.g. W) are selected from the following groups:

Sugars (monomeric, cyclic):

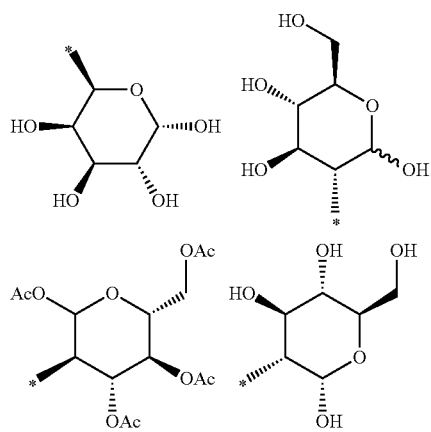

Sugars (monomeric, cyclic):

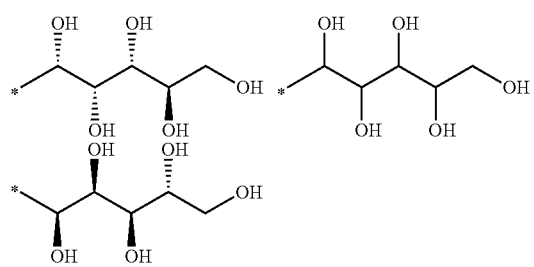

Sugars (polymeric):

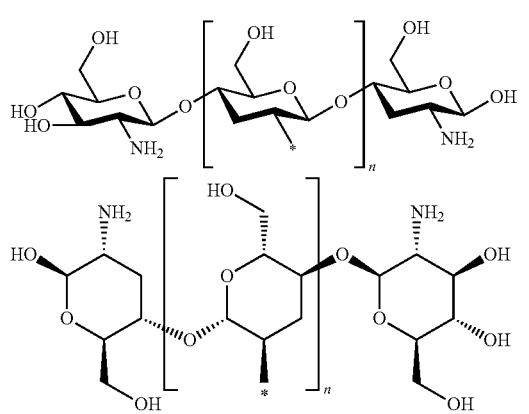

Carboxylic Acids and Derivatives:
—$CO_2H$
—$CO_2^-$
—$CO_2X$ (wherein X is a monovalent metal ion, e.g. $Li^+$, $Na^+$, $K^+$ or $C_{1-6}$ alkyl, e.g. $C_{1-3}$ alkyl)

Amines and Derivatives:
—$NH_2$
—$NH_3$
—$NH_3^+ Y^-$ (wherein Y is $Cl^-$, $Br^-$, or $I^-$)
—NHR (where R is $C_{1-6}$ alkyl, e.g. $C_{1-3}$ alkyl, e.g. methyl)

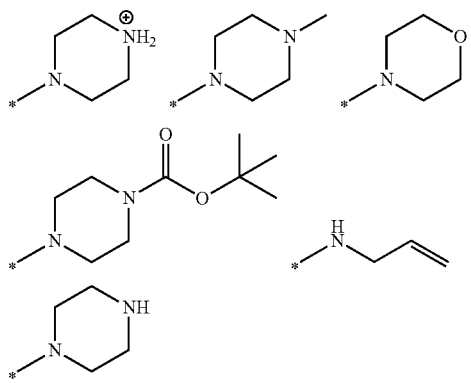

Preferred Examples of Such Amines and their Deriviatives Include:
—$NH_2$
—$NH_3$
—NHR (where R is $C_{1-6}$ alkyl, e.g. $C_{1-3}$ alkyl, e.g. methyl)

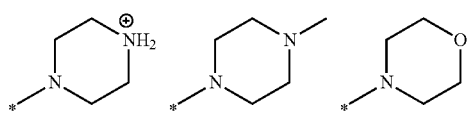

Alcohols and Derivatives:
—OH
—OX (wherein X is a monovalent metal ion, e.g. $Li^+$, $Na^+$, $K^+$ or $C_{1-6}$ alkyl, e.g. $C_{1-3}$ alkyl)
—OR (where R is $C_{1-6}$ alkyl, e.g. $C_{1-3}$ alkyl, e.g. methyl)

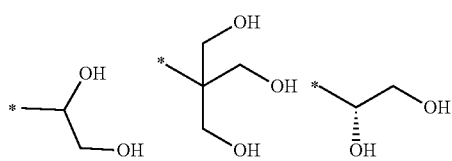

Cyclic Boronic Acids:

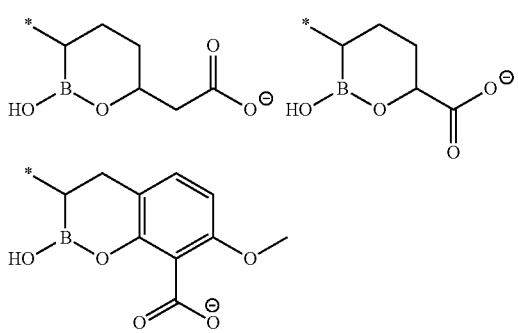

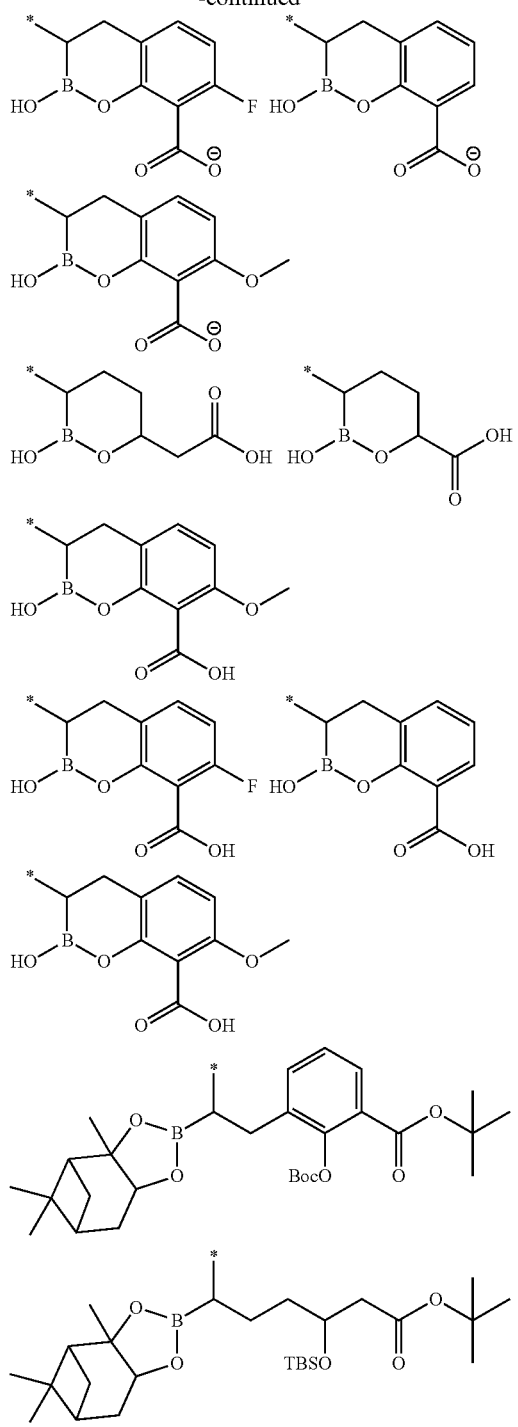
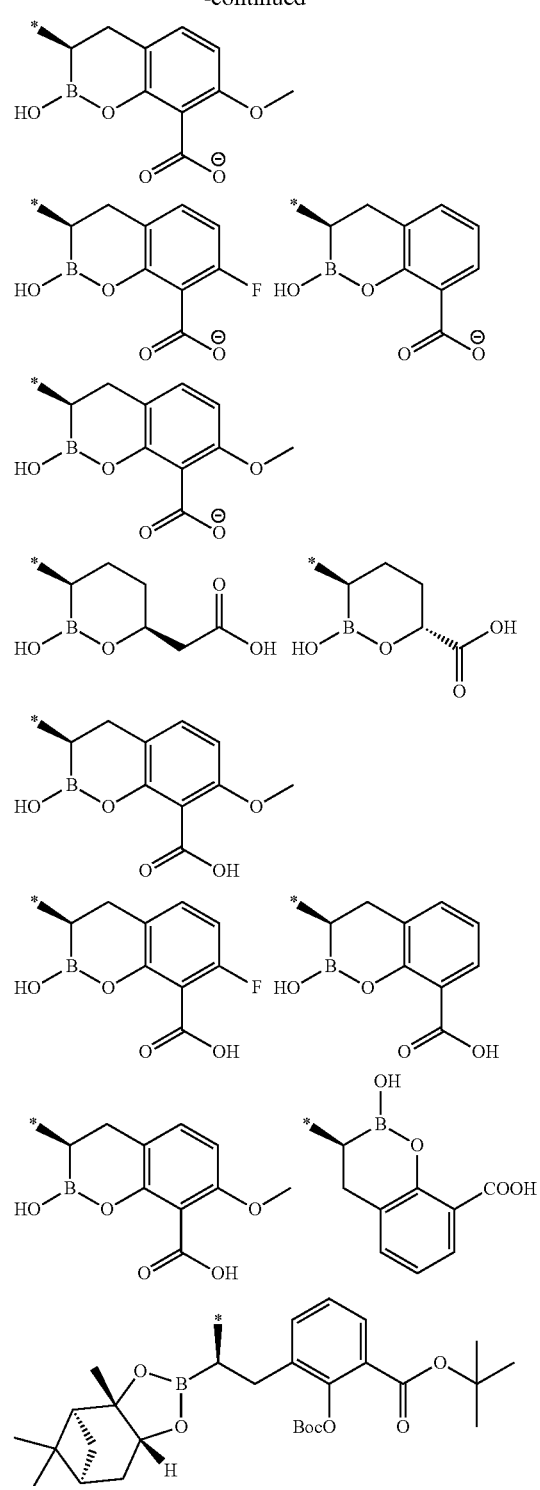
Examples of Such Cyclic Boronic Acids Include the Following:
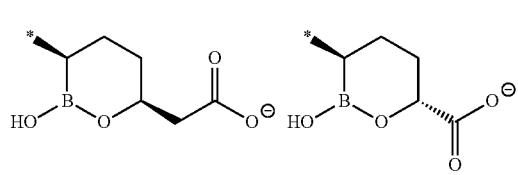
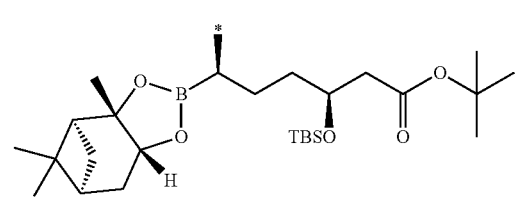

Preferred Examples of Such Cyclic Boronic Acids Include:
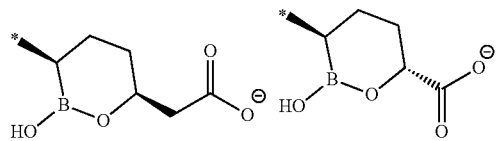
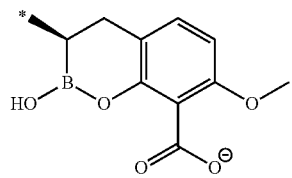
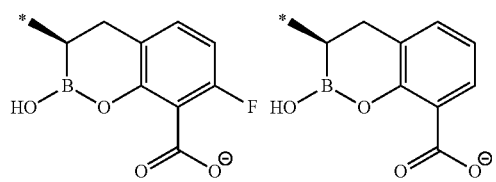
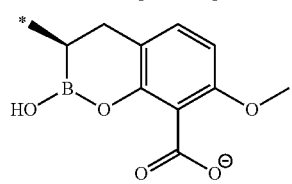
Acyclic Boronic Acids:
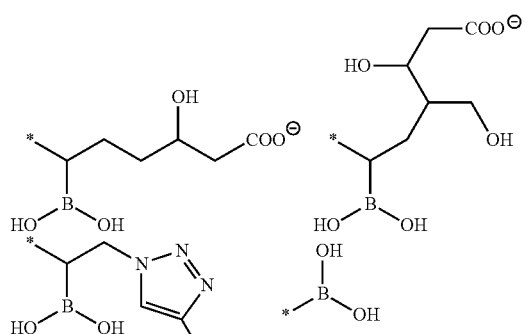
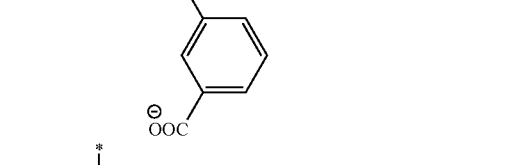
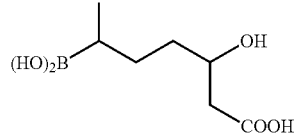
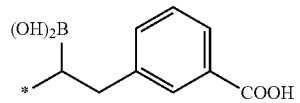
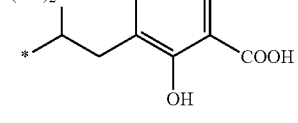
-continued
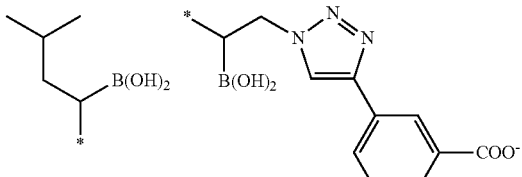
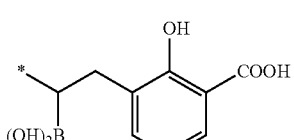
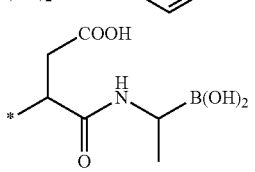
Examples of Such Acyclic Boronic Acids Include:
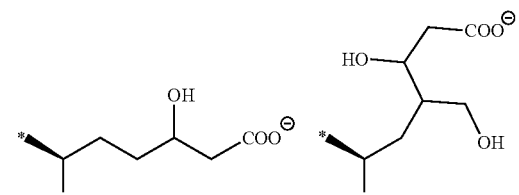
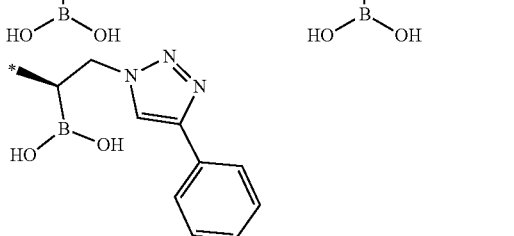
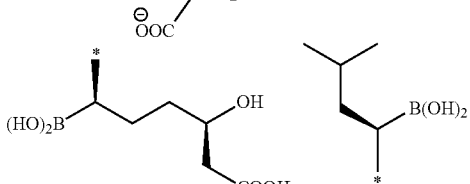
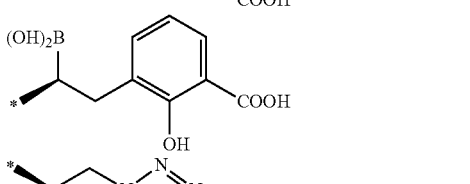
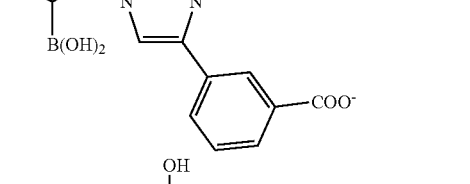
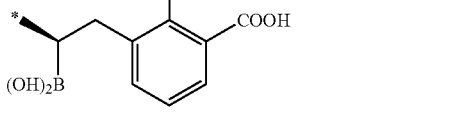

-continued

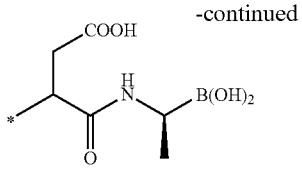

Preferred Examples of Such Acyclic Boronic Acids Include:

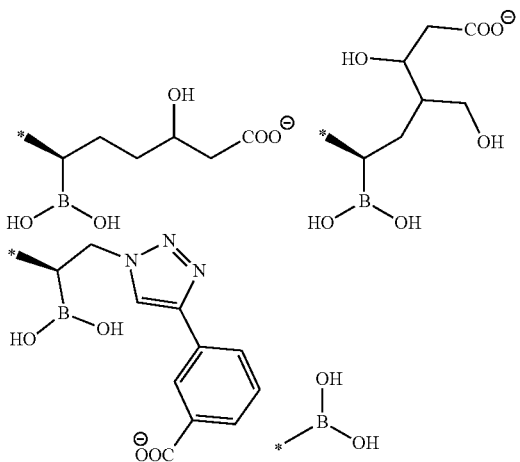

where * denotes the point of attachment of the hydrophilic group to the remainder of the molecule, e.g. to a linker group L as herein defined.

38. A compound according to any one of the examples herein, or a stereoisomer, pharmaceutically acceptable salt or prodrug thereof.

39. A pharmaceutical composition comprising a compound according to any one of embodiments 1 to 38, together with one or more pharmaceutically acceptable carriers or excipients.

40. A compound according to any of embodiments 1 to 38, or a pharmaceutical composition according to embodiment 39 for use in therapy.

41. A compound according to any one of embodiments 1 to 38 or a pharmaceutical composition according to embodiment 39 for use in a method of treatment or prevention of a disease or condition associated with an imbalance in zinc homeostasis, preferably cancer (e.g. prostate cancer), a neurological disorder (e.g. Alzheimer's disease), stroke, edema, diabetes or heavy metal intoxication.

42. A method of treating and/or preventing a disease or condition associated with an imbalance in zinc homeostasis, preferably cancer (e.g. prostate cancer), a neurological disorder (e.g. Alzheimer's disease), stroke, edema, diabetes or heavy metal intoxication in a human or non-human mammal, said method comprising the step of administering to said mammal an effective amount of a compound according to any one of embodiments 1 to 38 or a composition according to embodiment 39.

43. A compound according to any one of embodiments 1 to 38 or a pharmaceutical composition according to embodiment 39 for use in a method of treating and/or preventing a bacterial infection in a human or non-human mammal, said method comprising administration of said compound or said composition in combination with (either simultaneously, separately, or sequentially) a β-lactam antibiotic.

44. A method of treating and/or preventing a bacterial infection in a human or non-human mammal, said method comprising the step of administering to said mammal an effective amount of a compound according to any one of embodiments 1 to 38 or a composition according to embodiment 39 in combination with (either simultaneously, separately, or sequentially) a β-lactam antibiotic.

45. A compound for use, or method according to embodiment 43 or 44, wherein the infection is associated with Gram positive or Gram negative bacteria (preferably Gram negative bacteria) which are resistant to one or more antibiotics, e.g. a β-lactam antibiotic, preferably wherein said bacteria comprise metallo-β-lactamases.

46. A compound for use, or method according to any one of embodiments 43 to 45, wherein the infection is associated with gram negative multiresistant bacteria harboring extended spectrum metallo-β-lactamases (ESBL).

47. A compound for use, or method according to any one of embodiments 43 to 46, wherein the compound is administered together with a carbapenem antibiotic agent and the infection is associated with gram negative carbapenem-resistant bacteria harboring metallo-(β-lactamases, or with gram negative carbapenem-resistant bacteria harboring Klebsiella pneumoniae carbapenemases, KPC and/or metallo-β-lactamases.

48. A compound for use, or method according to any one of embodiments 43 to 47, wherein the compound and β-lactam antibiotic are provided in the same formulation.

49. A compound for use, or method according to any one of embodiments 43 to 47, wherein the compound and β-lactam antibiotic are provided in different formulations.

50. A pharmaceutical formulation comprising a compound according to any one of embodiments 1 to 38 together with a β-lactam antibiotic, and optionally one or more pharmaceutically acceptable carriers or excipients.

51. A kit comprising:
  (i) a first container containing a compound according to any one of embodiments 1 to 38 or pharmaceutical composition according to embodiment 39; and
  (ii) a second container containing a β-lactam antibiotic.

52. A compound for use, method, pharmaceutical formulation or kit according to any one of embodiments 43 to 51, wherein said β-lactam antibiotic is selected from the following: penams, cephems, monobactams, penems, carbapenems, and clavams, preferably from penams, cephams and carbapenems, e.g. a carbapenem.

53. A compound according to any one of embodiments 1 to 38 or a pharmaceutical composition according to embodiment 39 for use in a method of inhibiting biofilm formation in the treatment of a disease or condition associated with an imbalance in zinc homeostasis, preferably cancer (e.g. prostate cancer), a neurological disorder (e.g. Alzheimer's disease), stroke, edema, diabetes or heavy metal intoxication.

54. A method of inhibiting biofilm formation in the treatment of a disease or condition associated with an imbalance in zinc homeostasis, preferably cancer (e.g. prostate cancer), a neurological disorder (e.g. Alzheimer's disease), stroke, edema, diabetes or heavy metal intoxication in a human or non-human mammal, said method comprising the step of administering to said mammal an effective amount of a compound according to any one of embodiments 1 to 38 or a composition according to embodiment 39.

55. A method for determining whether a carbapenem-resistant microorganism produces a metallo-β-lactamase (MBL), a *Klebsiella pneumoniae* carbapenemase (KPC) or an OXA-48-producing bacterial strain comprising the steps of:
  (1) isolating a carbapenem-resistant bacterial strain of interest and providing it on an agar plate;
  (2) preparing the following disks: a) disk A with meropenem alone, b) disk B with meropenem added to a compound according to any one of embodiments 1 to 38, c) disk C with imipenem alone, d) disk D with imipenem added to a compound according to any one of embodiments 1 to 38, and e) disk E with temocillin;
  (3) adding the disks at five different places in the agar plate or in four different plates;
  (4) incubating the agar plate overnight at 37° C.:
  (5) reading all zone diameters of the lobes, wherein absence or minimal increase in all zone diameters indicates an OXA-48-producing strain, a significant increase with disk B and D only indicates an MBL-producing strain, and a significant increase with disk C only indicates a KPC-producing strain.

56. A kit comprising:
  (i) a compound according to any one of embodiments 1 to 38;
  (ii) meropenem
  (iii) imipenem
  (iv) temocillin
  (v) optionally, instructions for carrying out a method as defined in embodiment 55.

DETAILED DESCRIPTION OF THE INVENTION

In its broadest aspect the invention provides compounds which comprise one or more (e.g. one or two) lipophilic, zinc chelating moieties covalently bound to one or more (e.g. one, two or three) hydrophilic moieties (W), wherein said zinc chelating moieties are selective for $Zn^{2+}$ ions and wherein said hydrophilic moieties are selected from non-peptidic hydrophilic monomeric, oligomeric and polymeric groups.

In the compounds herein described the (or each) moiety W functions to lower the log P value for the whole molecule of interest, thus reducing the general passage of the zinc complexing moiety over biological membranes of eukaryotic cells. The latter is mandatory for an acceptable toxicity of the zinc complexing moiety which is used in the compounds of the invention. Procaryotic cells, especially gram negative bacterial cells, have two membranes; the outer membrane is more penetrable than the inner, which resembles a eukaryotic cell membrane. As documented by the examples in this application, the new compounds herein described are devoid of the toxicological effects, such as for example hemolysis, of the above mentioned chelating agents, e.g. the PAC chelators like EDTA or DTPA.

As evident from the experimental part in the present application, the invention also teaches how the strength of a zinc chelator can be tuned to achieve the minimum toxic or inhibiting effect on the cells or tissue in the diseased area whilst leaving healthy cells or tissue relatively unaffected, whilst at the same time maintaining a relevant medical efficacy in the desired indication.

According to the invention, tuning the strength of a zinc chelator is achieved by designing a favorable combination of number and conformation of donating atoms in the chelator and an optimal number of ring atoms between two neighboring donor atoms bound to the metal atom. This is illustrated, by way of example, in Scheme 2.

The higher the number of donating atoms in the ligand, the stronger (higher $pK_d$) the chelating agent. The higher the $pK_d$, the potentially more toxic is the ligand (when used without the hydrophilic side groups in accordance with the invention). For example, TPEN or TPA are toxic to all cells and cannot be used as a drug with acceptable toxicity. However, TPEN and TPA have no hydrophilic side chain lowering their hydrophilicity or provide any functional side chain to insert vectors for biological selectivity.

As illustrated by formulas X-XII, if some donating groups (donor atoms) in the molecule can bind to the metal atom such that 5-membered chelating rings to the zinc atom may be formed, this will contribute to a higher $pK_d$. As illustrated by structures V and VI in Scheme 2, this is possible to achieve with a variety of heterocyclic compounds, e.g. imidazole, pyrrole, isoxazole, pyridine, pyrimidine, purine, indole, quinoline or iso-quinoline. The rings may also be substituted with functional groups like keto groups or hydroxyl groups to help regulate their physiological properties.

In a metal chelate where 3 donating groups D participate in donating to the zinc atom, the ligand may be denoted a "3-pod" ligand, as illustrated in Scheme 2. The structural unit VII is denoted dipicoylamine or DPA, and defines an important synthetic building block in the compounds of the present invention.

However, 3-pod ligands may not have sufficient chelator strength to be efficient as adjuvants. EP 1724263 relates to chelating compounds. These are intended for use against HIV, rheumatism and cancer metastasis, but not as antibacterial adjuvants or in relation to any neurological disorders. The metal chelators formed by the two imidazole rings and the tertiary nitrogen only have 3 donating atoms giving insufficient metal-binding ability for relevant adjuvant capacity according to experimental data in the present application.

Another example of 3-pod chelators is described by Wei, L. et al. in Inorganic Chemistry, Vol. 44, No. 7, 2005. The document relates purely to crystallographic and analytical work on rhenium chelates. In the text, potential use against cancer is mentioned, but no data are provided. There is no suggestion for use against bacteria or infectious diseases or any other indication for which the compounds of the invention may be used. There are no larger hydrophilic side chains, but only a DNA base.

Thus, in one embodiment, the chelating moiety may preferably comprise more than three donating atoms, D. If 4 donating groups D participate in donating to the zinc atom, the ligand may be denoted a "4-pod" ligand (Scheme 2, X). If the number of donating atoms D is increased, the ligands may correspondingly be denoted "5-pod" or "6-pod" (general structures XI and XII in Scheme 2), which contribute to stronger chelating agents (unless sterical constraints contribute to less favorable ligand conformations).

Scheme 2

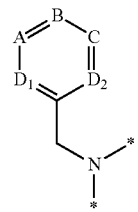

V

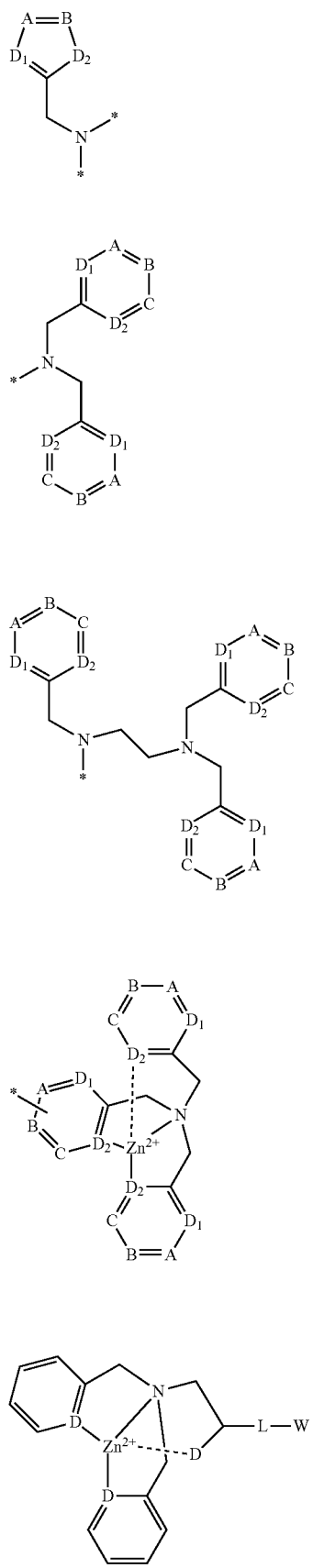
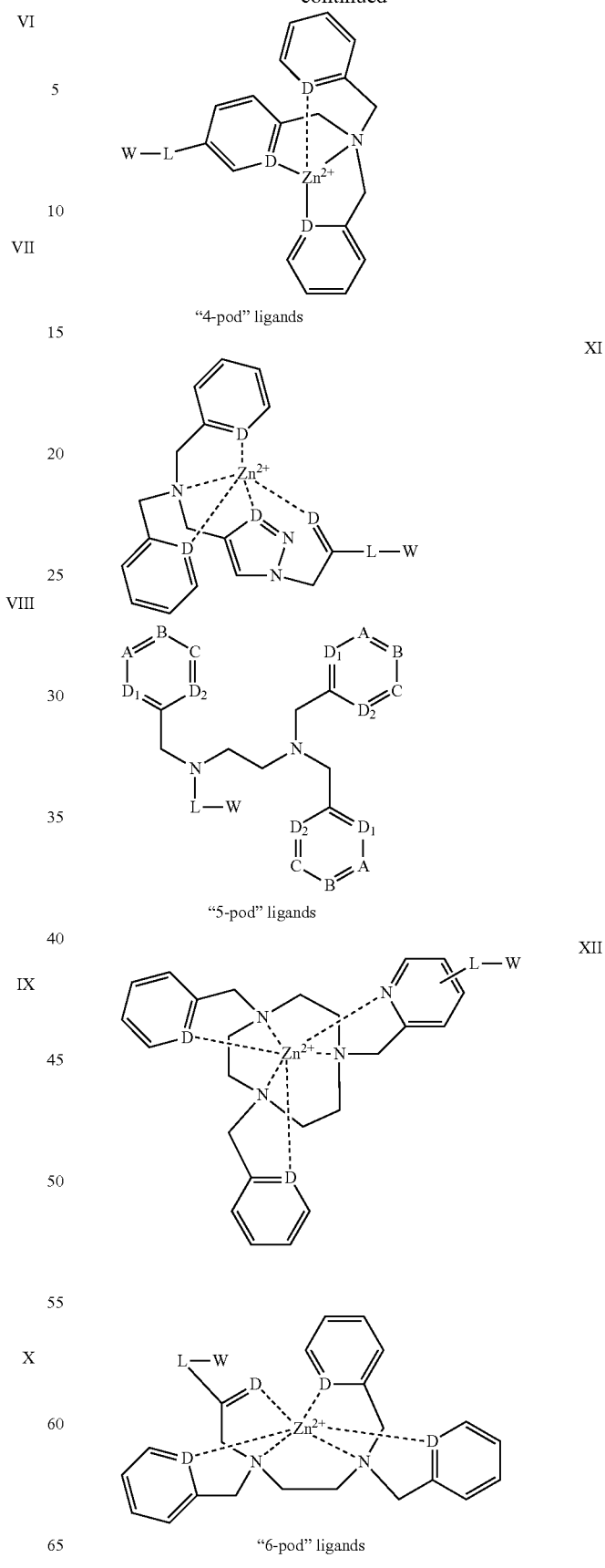
"4-pod" ligands
"5-pod" ligands
"6-pod" ligands

In Scheme 2:

D is a heteroatom, preferably nitrogen or oxygen (where present in a ring structure, D is preferably nitrogen);

$D_1$ and $D_2$ are the same or different and may be —CH— or a heteroatom, preferably nitrogen, wherein at least one of $D_1$ and $D_2$ is a heteroatom, preferably nitrogen;

A, B and C may be —CH— or a heteroatom, preferably nitrogen;

A, B and C may also be bridgeheads participating in condensed rings, i.e. forming polycyclic systems;

L is a covalent bond or a linker as herein defined;

W is a hydrophilic group as herein defined;

* denotes the point (or points) of attachment of the chelating moiety to the remainder of the molecule.

In Scheme 2, the linker L may comprise or consist of a functional group —(C=X)—Y— where X denotes O or S; and Y denotes O or NR (where R is H or $C_{1-6}$ alkyl, preferably $C_{1-3}$ alkyl, e.g. methyl).

The divalent cation $Zn^{2+}$ is normally six-coordinate, so ligands with a higher number than 6 donating groups do not increase $pK_d$ for zinc. According to this definition, TPEN is a 6-pod ligand, since TPEN has four 2-pyridyl-methyl units, rendering the zinc chelating ability stronger. TPEN, as noted above, has been widely used in many academic biological applications in the prior art.

In the invention the zinc-chelating moiety is any selective $Zn^{2+}$ chelating group which preferably comprises at least two aromatic nitrogen atoms.

In one embodiment the compounds according to the invention may be represented by the general formula I, or a pharmaceutically acceptable salt thereof:

$$Q+L-W]_x \qquad (I)$$

wherein Q represents a lipophilic, zinc chelating moiety which is selective for $Zn^{2+}$ ions;

each L, which may be the same or different, is a covalent bond or a linker;

each W, which may be the same or different, is a non-peptidic hydrophilic monomeric, oligomeric or polymeric group, preferably a non-peptidic hydrophilic group comprising hydrogen bond donor and hydrogen bond acceptor atoms selected from H, N, O, S and P, e.g. a non-peptidic hydrophilic group comprising one or more functional groups selected from —OH, —SH, —CO$_2$H, —SO$_3$H, —PO$_3$H$_2$, —B(OH)$_2$, and aliphatic or aromatic nitrogen-containing groups; and x is an integer from 1 to 3, preferably 1.

In another embodiment the compounds according to the invention may be represented by the general formula II, or a pharmaceutically acceptable salt thereof:

$$Q\text{-}L\text{-}W\text{-}L\text{-}Q \qquad (II)$$

wherein each Q, which may be the same or different, represents a lipophilic, zinc chelating moiety which is selective for $Zn^{2+}$ ions;

each L, which may be the same or different, is a covalent bond or a linker; and

W is a non-peptidic hydrophilic monomeric, oligomeric or polymeric group as herein defined, e.g. as defined above in respect of formula (I).

The compounds according to the present invention are useful as potential new drugs. Their use as drugs is related to a set of parameters that need to have a certain numerical value for the compounds to have a desired therapeutic effect without exerting unacceptable toxic signs in the mammal suffering from a disease or the host organism for an invasion of micro-organisms or parasites. Surprisingly, it has been found that these parameters can be used to calculate a certain therapeutic score, herein denoted $TS_x$, where x denotes the particular compound. The therapeutic score for the compounds of the invention differs from the therapeutic score of compounds known from the prior art. The parameter can be expressed by the following equation:

$$TS_x = f_1(MEC) + f_2(IC_{50}) + f_3(\log D) + f_4(pKd_{Zn}) + f_5(TI) + f_6(Zn_{sel}) \qquad (1)$$

wherein $f_1$-$f_6$ are functions of the relative parameter, MEC expresses the minimum effective concentration of compound X to achieve a therapeutic effect of an enzyme or an undesired physiological effect for a microorganism. $IC_{50}$ expresses the toxicity in a mammal cell, useful to indicate the general toxicity of the compound X. The log D parameter is defined as the logarithm of the partition coefficient for compound X between n-octanol and water at physiological pH, TI is the therapeutic index ratio of compound X, which is the dividend $IC_{50}/MEC$. A certain chelator strength, $pKd_{Zn}$, is one of the most important parameters for the compounds to achieve high therapeutic effects and a low level of toxic effect according to the present invention. $pKd_{Zn}$ is defined as the negative logarithm of the dissociation constant for the zinc chelate, and $Zn_{sel}$ is the selectivity for a compound X to chelate $Zn^{2+}$ in competition with other metals, especially physiologically important metal ions like $Na^+$, $K^+$, $Ca^{2+}$, $Mg^{2+}$, $Ni^{2+}$, $Fe^{2+}$, $Fe^{3+}$, $Cu^+$, $Cu^{2+}$, $Cr^{3+}$, or the heavy metals generally viewed as pollutants, e.g. $Cd^{2+}$, $Hg^{2+}$, $Co^{2+}$, $Pb^{2+}$, or even heavier elements.

Generally the most common ligands in the prior art, i.e. the PAC ligands discussed above, e.g. EDTA, DTPA and DOTA, have high affinity for metal ions having a larger ionic radius, high number of unpaired d-shell electrons and higher coordination number than zinc. Those metal ions are especially $Fe^{2+}$, $Fe^{3+}$, $Mn^{2+}$ and $Cr^{3+}$ or the heavy metals generally viewed as pollutants, e.g. $Cd^{2+}$, $Hg^{2+}$, $Co^{2+}$ and $Pb^{2+}$. These principles are well described in the prior art, e.g. by Smith, R. M.; Martell, A. E. in *NIST Critically Selected Stability Constants of Metal Complexes, Version 2.0*; U.S. Department of Commerce: Gaithersburg, Md., 1995. Thus the PAC ligands bind zinc poorly relative to the ions mentioned above. Of particular concern is that the PAC ligands also bind $Ca^{2+}$, $Mg^{2+}$, $Fe^{2+}$, $Fe^{3+}$ and to some extent they also affect $Na^+$ and $K^+$ because of their high negative charge at physiological pH. These are all vital metal ions in regulation of numerous biological processes in mammals. Thus, this lack of specificity is the main reason for the higher general toxicity seen in the prior art for the PAC ligands.

An important feature of the ligands which are used in the present invention, affecting their selectivity for binding zinc, is the theory of hard and soft acids and bases, the HSAB principle which is well described in the field of inorganic chemistry, and in numerous papers, e.g. by R. D. Hancock and A. E. Martell in *Chem. Rev.* (1989), 89, 1875-1914. In the present invention, a high content of aromatic nitrogen donor atoms, a medium content of aliphatic nitrogen donors, and a low content of oxygen donor atoms favors binding of the periodic table group IIB elements like zinc and cadmium; the typical PAC ligands DTPA, EDTA and DOTA have the opposite trend, with a high content of oxygen donors, lower content of aliphatic nitrogen and no aromatic nitrogen donors, favoring binding of larger transition elements with a high number of unpaired d-shell electrons, e.g. the VIB, VIIB and VIII elements such as $Fe^{2+}$, $Fe^{3+}$, $Mn^{2+}$ and $Cr^{3+}$, and also the group IIA elements, such as $Ca^{2+}$ and $Mg^{2+}$.

As a consequence, in the zinc chelator moiety herein described, a preferred percentage of aromatic nitrogen donor atoms is equal to or higher than 50%, while the percentage of aliphatic nitrogen donor atoms is equal to or higher than 25% while keeping the percentage of oxygen donor atoms equal to or lower than 25%. Even more preferred is a percentage of aromatic nitrogen donor atoms equal to or higher than 60%, while the percentage of aliphatic nitrogen donor atoms equal to or higher than 20% while keeping the percentage of oxygen donor atoms equal to or lower than 20%. Even more preferred is a percentage of aromatic nitrogen donor atoms equal to or higher than 66%, while the percentage of aliphatic nitrogen donor atoms is equal to or higher than 33% while keeping the percentage of oxygen donor atoms equal to zero. Especially preferred is a percentage of aromatic nitrogen donor atoms equal to or higher than 75%, while the percentage of aliphatic nitrogen donor atoms is equal to or higher than 25% while keeping the percentage of oxygen donor atoms equal to zero.

As emphasized, the parameter $Zn_{sel}$ is the most important parameter to maintain the therapeutic effect whilst keeping the level of adverse effects low towards eukaryotic cells and in living animals. Such selectivity can be demonstrated by competition studies when all the mentioned metals are present in a mixture, as described in many prior art documents, e.g. in Åstrand et al., *Tetrahedron* 69, (2013), 8645-8654. In the prior art, e.g. using formula 6 in R. D. Hancock and A. E. Martell, selectivity quotients for amine-based ligands can be calculated from dissociation constants for $Zn^{2+}$ vs. $Ca^{2+}$. Herein it is an accepted indicator for selectivity that $Zn_{sel}$ it can be expressed according to the following equation:

$$Zn_{sel} = \log(K_1(Zn^{2+})/K_1(Ca^{2+})) \quad (2)$$

Using selectivity towards chelation of calcium in the formula is necessary and relevant because of the severe consequences for toxicity in eukaryotic biological systems when chelating this group II element. As noted above, EDTA is a potent anti-coagulant because of its non-selective metal chelation, resulting in chelation of e.g. $Ca^{2+}$. As a consequence, this ability to bind calcium may lead to hypocalcemia. Since EDTA is a weaker chelating agent than the other PACs, e.g. DTPA or DOTA, the same toxicity concern holds for all PACs as a class of compounds.

The parameters in equation (1) may be weighted according to known empirical and measured data, to differentiate the importance of the different parameters, as seen in the empirical experimental data below, in a general expression for $TS_x$ in equation (1).

Other parameters characterizing the most effective compounds according to the present invention are the therapeutic index TI, and the lipophilicity, log P.

The core of the present invention and the most surprising finding documented herein is the high efficacy of the compounds in important medical indications in spite of the high water solubility and low log P values of the compounds. In the prior art, therapeutic substances are often required to have a log P value high enough to traverse eukaryotic cell membranes, normally higher than 2 to 2.5, to have a therapeutic effect. However, they then often also show toxicological signs. This will be further illustrated in the following:

As a representative example, the compounds according to the present invention have a strong suppressive effect on the MBL-mediated resistance in multi-resistant bacteria, such as *Pseudomonas aeruginosa*, *Klebsiella pneumoniae* or *Escherichia Coli*.

The optimization of the globally desired performance for the compounds according to the invention can be mathematically modeled, for example for use as a tool to identify new compounds useful in the invention. The model is based on observations from biological experimental data given in the experimental part of this application and in literature data. In the case of an antibiotic agent, a general parameter, antibacterial score (denoted $AS_x$) where X is the representative compound of the invention, can be optimized. Thus, $AS_x$ can be expressed as a function of the key parameters in equation (3):

$$AS_x = \log(TI \times (1+\tan h(Zn_{sel}-8)) \times (1-\tan h(c \log P-2)) \times (1+\tan h((pK_a-8)))) \quad (3)$$

wherein TI is the therapeutic index ratio, which is the dividend $IC_{50h}/MIC_x$, where $MIC_x$ is defined as the lowest concentration of the respective compound X of the present invention that results in a MIC value of ≤2 mg/L for carbapenem antibiotics. The $IC_{50}$ value for tolerance of compounds X in human hepG2 cells assays is a common in vitro toxicity standard comparable to other eukaryotic cell assays. This dividend defines the superiority of the compounds of the present invention as compared to those in the prior art. For example, in WO 2015/049546 by Rongved et al., zinc chelators are disclosed that improve the activity of the carbapenems against resistant gram-negative bacteria harboring metallo-β-lactamases (MBL). However, WO 2015/049546 does not teach how to tune the strength of the zinc chelator to achieve a sufficiently high efficacy, or acceptable $MIC_x$ activity at sufficiently low concentrations, whilst simultaneously securing an acceptable toxicological profile in eukaryotic cells. With respect to the adjuvant compounds described in WO 2015/049546, there is also a need to further improve MIC values for carbapenem antibiotics, e.g. to provide compounds having a MIC value ≤2 mg/L for carbapenem antibiotics at adjuvant concentrations lower than 100 μM. This results in higher dividend $IC_{50h}/MIC_x$ values and higher $AS_x$ numbers.

Surprisingly, as evidenced by the results presented herein, the compounds defined by the scope of the present invention demonstrate significantly improved $MIC_x$ performance over those which are disclosed in WO 2015/049546, with MIC ≤2 mg/L for carbapenem antibiotics at adjuvant concentrations as low as 15.6 to 31 μM while maintaining an acceptable toxicological profile in human hepG2 cells. This is described in detail below and in the experimental part of the present specification. Example 101 in the present application, for example, is based on the structural combination of a DPA unit combined with a triazole ring to form a 4-pod ligand linked to a carbohydrate linker. Example 194 is the same chelating agent linked to a peptide. This is the strongest chelator exemplified in WO 2015/049546. In the present invention, the MIC of Example 101 is investigated in Example 197, and in Table 4 it is evident that Example 101 is not as efficient at 50 μM concentration as the best examples investigated in Tables 3-5. However, Examples 101 and 194 are efficient at concentration ranges 100-150 μM, and with the favourable toxicity reported for these ligands, they are useful as adjuvants. These examples nevertheless demonstrate that, with respect to overall performance, the present invention relates to compounds which are superior to those described in WO 2015/049546.

In equation (3), the factor $1+\tan h(Zn_{sel}-8)$ expresses the experimental finding that increasing $Zn_{sel}$ increases $AS_x$ and that a $Zn_{sel}$ lower than 8 leads to low $AS_x$ values. The numerical values used in the calculations of $Zn_{sel}$, as given in Table 1 below, are based on calculations using formula 6 in R. D. Hancock and A. E. Martell in Chem. Rev. (1989), 89, 1875-1914. The $Zn_{sel}$ factor also emphasizes that low $Zn_{sel}$ values represent metal chelators with unspecific metal chelation, e.g. as described above for the APC chelators. Low $Zn_{sel}$ may lead to undesired biological effects.

In equation (3), the factor 1−tan h(c log P−2) expresses that descending c log P, meaning increased water-solubility, increases $AS_x$, and that c log P values less than 2 according to the prior art, minimizes membrane penetration in eukaryotic cells, and thereby minimizes unspecific toxicity. The c log P (i.e. calculated log P) may be calculated using Chem-Biodraw Ultra version 13.0.2.3021.

In equation (3), the factor 1+tan h($pK_d$−8) expresses that descending $pK_d$ reduces $AS_x$, in accordance with experimental data in the present application. A $pK_d$ less than 8 is not useful in the invention since it results in higher $MIC_x$ values or no $MIC_x$ value at all. The $pK_d$ values of the compounds in the present invention have been estimated using literature methods, e.g. as described by G. Anderegg et al., *Helv. Chim. Acta*, (1977), 60, 123-140, and J. T. Simmons et al, *Inorg. Chem.*, (2013), 52, 5838-5850, and the stability constant collections of A. E. Martell.

To illustrate the usefulness of equation (3) in the present invention, six prior art zinc-chelating ligands are used as examples; four of them are illustrated in Scheme 3. TPEN and EDTA are already described in the present specification. The gadobutrol ligand Butrol is the ligand binding lanthanide metals like gadolinium, which is used as a MR contrast agent, as described by Cheng, K. T. in Molecular Imaging and Contrast Agent Database (MICAD), Bethesda, National Center for Biotechnology Information (US); 2006. The parameters used in Table 1 for Butrol have been estimated in accordance with E. Toth et al, *Inorg. Chim. Acta* (1996), 249, 191-199. Ligand 1 is a highly Zn-selective lipophilic literature compound for ratiometric fluorescent measurements of zinc concentration described by Xu et al., Tetrahedron 65 (2009) 2307-2312. Captopril is a drug on the market used as an ACE inhibitor and is a zinc chelator as described by Ng K. K. F. and Vane J. R. in Nature (1967), 216, 762-766. The parameters used in Table 1 for captopril have been estimated in accordance with K. S. Siddiq et al., *Chin. J. Chem.*, (2009), 27, 1755-1761. Vancomycin is an antibiotic agent on the market, described as a copper and zinc chelator in the prior art, e.g. in Kucharczyk et al., Inorganic Biochemistry 102 (2008) 936-942. The parameters used in Table 1 for vancomycin have been estimated in accordance with A. Zarkan et al., *Sci. Rep.*, (2016), 6, 19602.

Scheme 3

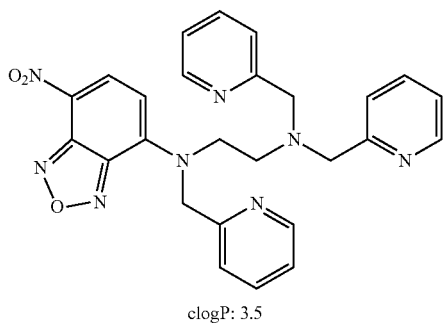

Ligand 1
clogP: 3.5

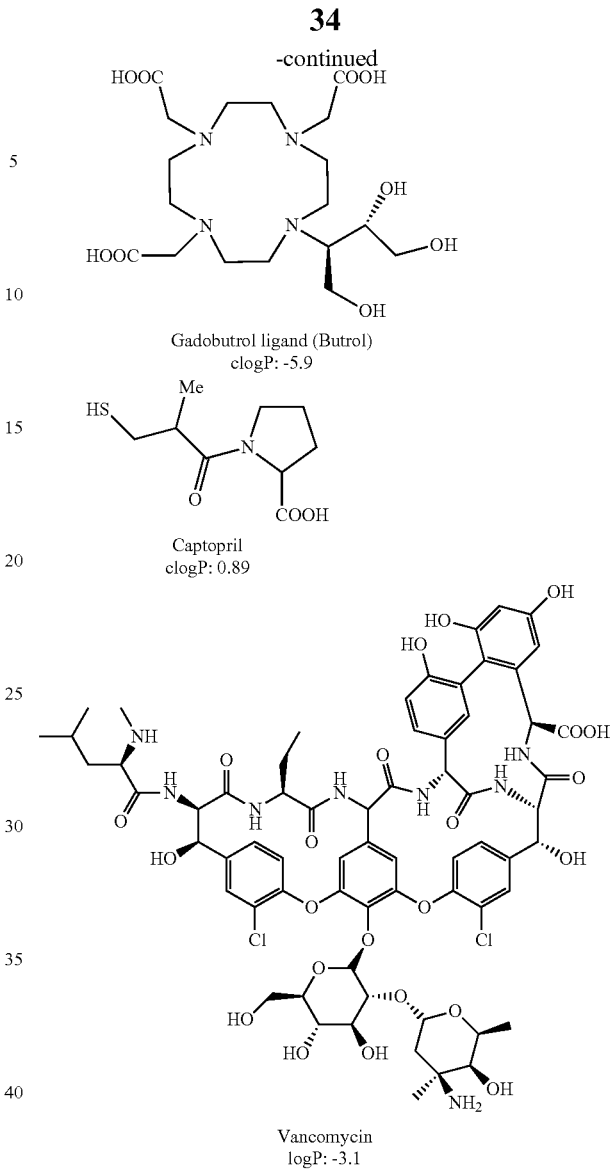

Gadobutrol ligand (Butrol)
clogP: -5.9

Captopril
clogP: 0.89

Vancomycin
logP: -3.1

Table 1 summarizes the experimental literature and estimated parameters for the ligands according to the prior art together with ligands representative for the present invention. Column 1 denotes which compounds are included, and gives example numbers for the compounds of the invention for which $AS_x$ is calculated. As evident from column 8, a negative value for the parameter $AS_x$ indicates a lack of performance in one or more of the vital parameters, i.e. $MIC_x$, $IC_{50h}$, $Zn_{sel}$, c log P, or $pK_d$ and defines which compounds may be useful in the present invention.

Furthermore, an important feature of the present invention is the method which uses the independent parameters in equation (3) in statistical modelling to optimize $AS_x$ as a principal component. This method forms part of the invention and can be used to select new compounds that will have the desired performance as potential drugs with acceptable efficacy and toxicity.

As evident from these data, it is not sufficient for a compound to have a low log P, such as for example captopril, if the $pK_d$ with zinc is too low (in this case a value of 6). Likewise, it is not sufficient to use a highly selective zinc chelator like Ligand 1, if the c log P is high enough to allow eukaryotic cell penetration. Likewise, even if EDTA has a higher binding affinity for iron and copper than zinc, and also binds calcium (i.e. EDTA has a $pK_d$ with zinc of 16), lack of selectivity renders EDTA a relatively toxic compound for intravenous injections in mammals.

2013, relates to chelating compounds comprising the well-known dipyridylamine (DPA) unit in the form of an amide derivative. No suggestion for use against bacteria or infectious diseases or other disease areas attractive in the present invention are given. The compounds do not comprise a

TABLE 1

| Ligand X | $MIC_x^a$ (μM) | $IC_{50\,h}$ (μM) | clogP | $pK_d$ | TI = $IC_{50\,h}/MIC_x$ | $Zn_{sel}$ | $AS_x$ |
|---|---|---|---|---|---|---|---|
| TPEN[b] | 15 | 7 | 3.5 | 15.6 | 0.5 | 16.5 | −0.75 |
| Butrol | 15[c] | 60[c] | −5.9 | 19 | 1.2 | 4.7 | −1.36 |
| Ligand 1[b] | 15[c] | 7[c] | 3.5 | 15 | 0.5 | 13.7 | −0.75 |
| Captopril[b] | 1000[d] | 33 | 0.9 | 6 | 0.033 | 0.22 | −9.14 |
| EDTA | 15 | 30[c] | −2 | 16 | 2 | 4 | −2.27 |
| Vancomycin[b] | 1000[d] | 20 | −3.1 | 2.9 | 0.02 | 5 | −7.83 |
| Example 12[b] | 31 | 16.45 | 1 | 11 | 0.5 | 11 | 0.57 |
| Example 14[b] | 31 | 12.4 | 0.3 | 11 | 0.4 | 11 | 0.49 |
| Example 24 | 31 | 60 | 1.6 | 15 | 1.9 | 13.7 | 1.18 |
| Example 25 | 31 | 113.3 | 0.7 | 15 | 3.7 | 13.7 | 1.43 |
| Example 26 | 31 | 116 | −0.9 | 11 | 3.7 | 11 | 1.48 |
| Example 84[b] | 125 | 116 | −2.4 | 9 | 0.5 | 11 | 0.82 |
| Example 91 | 31 | 165.2 | −1.7 | 15 | 5.3 | 16.5 | 1.63 |
| Example 96[b] | 125 | 118 | 0.13 | 9 | 0.9 | 11 | 0.81 |
| Example 98 | 125 | 259 | 1 | 9 | 2.1 | 11 | 1.11 |
| Example 99 | 31 | 217.3 | 0.34 | 11 | 7 | 11 | 1.74 |
| Example 100 | 31 | 118 | 1.2 | 11 | 3.8 | 11 | 1.44 |
| Example 103 | 31 | 67.6 | 0.3 | 11 | 2.2 | 11 | 1.23 |
| Example 105 | 31 | 100[c] | 0.25 | 11 | 3.2 | 11 | 1.40 |
| Example 163 | 31[c] | 100[c] | 1[c] | 11 | 3.2 | 11 | 1.35 |

[a]$MIC_x$ is defined as the lowest concentration of the respective compound X of the present invention that results in a MIC value of ≤2 mg/L for carbapenem antibiotics.
[b]Compounds that show an $IC_{50\,h}$ < $MIC_x$ would not be applicable as a potential clinical drug against resistant gram-negative MBL-based bacteria.
[c]Estimated values.
[d]Measured MIC values >1000 μM are set to that value.
[e]Measured $IC_{50\,h}$ values could not be determined due to minimally falling non-sigmoid curves above 50% reduction of fluorescence and are set to 116.

A requirement for compounds to be useful according to the invention is that these have no toxicity issues at the effective concentration. Thus, with the provision that TI is >1, preferred values of antibiotic score according to the invention are $AS_x$ values equal to or higher than −0.8, preferably equal to or higher than 0, equal to or higher than 0.5, e.g. equal to or higher than 1, or equal to or higher than 1.5.

The chelating agents described in EP 1724263 mentioned above would render high $MIC_x$ values due to their low chelator capacity (3-pod). This technology has another unfavourable property related to lipophilicity. Calculated log P values (ChemBiodraw 2017) from representative structures in EP 1724263 show that they are lipophilic with log P values around 3. This probably results in more toxic compounds. No toxic doses are given in the document. However, this technology would give negative $AS_x$ values because of too high $MIC_x$ values and high log P.

Another chelator technology relating to chelating compounds in the form of ester pre-chelators is described by Ye, Z. et al. in Biosensors and Bioelectronics, Vol. 26, No. 3, 2010. The technology relates to esters of chelating compounds selective for $Tb^{3+}$ for time-resolved luminescent chemosensing of intracellular $Zn^{2+}$ ions in the second chelating moiety. No suggestion for use against bacteria or infectious diseases or other disease areas attractive in the present invention are given. The agents are designed to penetrate cell membranes aided by the lipophilic ester groups, and thus probably more toxic than the compounds herein described. Further, upon ester hydrolysis, they would generate amino-polycarboxylate (APC) chelator moieties, leading to unspecific metal chelation.

Yet another chelator technology, described by Astrand, O. et al in Bioorganic & Medicinal Chemistry, Vol. 21, No. 17, hydrophilic moiety lowering log P. Thus, the agent would give negative ASx values because of low chelator strength and high log P values.

The chelating agents described by Wei, H. et al. in Organic Letters, Vol. 9, No. 24, 2007 comprise the well-known dipyridylamine (DPA) unit combined with an 8-hydroxy-quinoline unit. No suggestion for use against bacteria or infectious diseases or other disease areas attractive in the present invention are given. This technology also has an unfavourable property related to lipophilicity. Calculated log P values (ChemBiodraw 2017) from representative structures shows that they are lipophilic with log P values around 3. This likely gives rise to problems with eukaryotic toxicity. This technology would probably give negative $AS_x$ values because of high log P values.

Yet another chelator technology is described by Hanaoka, K. et al in J. Am. Chem. Soc. Vol. 126, 2004. The technology relates to chelating compounds for luminescent chemosensoring for time-resolved luminescence detection of intracellular $Zn^{2+}$ ions. The compound is a derivative of the very strong APC chelator DTPA. DTPA is a very strong and unselective chelating agent well-known in the prior art to generate severe toxicity because of chelation of $Ca^{2+}$ and $Fe^{3+}$. No suggestions for use of the agent against bacteria or infectious diseases or other disease areas attractive in the present invention are given.

Yet another chelator technology is described by Bailey, G. A. et al in Inorganic Chemistry, Vol. 51, No. 22, 2012. The intended use is in nuclear radio imaging using PET and SPECT. The chelators are unspecific, chelating Ga, Cu, In and Lu amongst others. There are no suggestions for use against bacteria or infectious diseases or other disease areas attractive in the present invention given. There are no larger hydrophilic side chains present. Calculated log P values (ChemBiodraw 2017) from representative structures in Bailey et al show that they are lipophilic with log P values above 3. This is likely to result in toxic compounds.

As described above, the most important parameter to maintain the therapeutic effect whilst keeping the level of adverse effects low towards eukaryotic cells and in living animals is the parameter $Zn_{sel}$. As described in by R. D. Hancock and A. E. Martell in Chem. Rev. (1989), 89, 1875-1914, to achieve a high $Zn_{sel}$, a high content of aromatic nitrogen donor atoms, a medium content of aliphatic nitrogen donors and a low content of oxygen donor atoms favors binding of the periodic table group IIB elements; the typical PAC ligands DTPA, EDTA and DOTA have the opposite trend, with a high content of oxygen donors, a lower content of aliphatic nitrogen and no aromatic nitrogen donors, favoring binding of larger transition elements with a high number of unpaired d-shell electrons.

As defined above, the moiety W may be a group having atoms possessing hydrogen-donating or hydrogen-accepting properties, thus having the ability to form hydrogen bonds with water or biological fluids, lowering log P and increasing the water-solubility of the whole construct. This implicates lowering of the membrane-penetrating ability of the construct, reducing the tendency to induce undesired effects in the host organism, like signs of toxicity. It is generally accepted that low molecular weight compounds with a log P above 2 to 2.6 have a good cell-penetrating ability, and if the compound in addition has undesired side effects, normal cell life may be seriously affected. Examples of functional groups W useful in the present invention are non-peptidic, aliphatic or alicyclic moieties comprising hydroxy, carboxy, or boronic acid groups.

In another embodiment, moiety W may comprise a highly hydrophilic antibacterial drug structural unit having the ability to reduce the log P of the construct. Examples of drugs useful in the invention are exemplified by, but not limited to those described in the book "Antibacterial Agents", by R. J. Anderson et al., John Wiley & Sons, U K 2012, e.g. rifamycins or aminoglycoside antibiotics, or polymyxins. These classes represent large classes of antibiotic agents on the market, and many building blocks in their synthetic process are commercially available for use in the construct of the present invention.

Another attractive class of molecules useful in the invention for lowering of log P is carbohydrate monomers, oligomers or polymers, such as oligomers of chitosan, alginate hyaluronic acid or derivatives thereof. Especially attractive are oligomers of chitosan, which are oligomers of 2-deoxy-2-amino glucose. Chitosan has antibacterial activity in itself, e.g. as described by Kim et al., in *Biotechnology and Bioprocess Engineering* (2016), 21(1), 183-189.

As depicted above, altering the zinc concentration may have a therapeutic effect. Zinc oxide particles are widely in use as antibacterial agents. The mechanism for the therapeutic effect is discussed, e.g. by Manzoor Umair, M. et al., in *PloS one* (2016), 11(5), e0154704. The compounds of the invention may also be used in formulations of ZnO nanoparticles, such as described by Pati et al. in *Nanomedicine* (2014), 10(6), 1195-1208. Further, there is a documented correlation between low zinc level and prostate cancer (PCa), e.g. as discussed by Costello et al. in *Prostate Cancer and Prostatic Diseases* (2004) 7, 111-117.

In the present invention, a variety of combinations of structures comprising the 2-methyl-pyridyl units have been synthesized possessing one or more linkers that can be linked to a functional group. A non-limiting set of preferred building blocks useful in the invention is illustrated by the general structures XIII-XXII in Scheme 4. In this scheme, the groups -L'-Y—C(=X)— and -L'-Y—C(=X)—CH$_2$— may denote the linker, L, as herein defined (where X is a donor atom, this part of the "linker" may alternatively be considered to form part of the chelating moiety); X denotes O or S, and Y denotes —O— or —NR— (where R is H or C$_{1-6}$ alkyl, e.g. C$_{1-3}$ alkyl); and W may be any of these groups as herein defined. In these structures, all zinc-chelating units have a percentage of aromatic nitrogen equal to or higher than 50%. Appropriate choice of W-L'-Y—C(=X)— and W-L'-Y—C(=X)—CH$_2$— provides desired properties, e.g. increased water-solubility, lowered toxicity, methods for attachment of targeting vectors, prodrug functionalities monoclonal antibodies or macromolecular carriers.

Each of the below schemes are provided for the purpose of illustration and description of a part of the invention only, and are not intended as a definition of the limits of the present invention. Thus, members of the library of compounds that may be used in the respective disease, are exemplified, but not limited to the general structures XIII-XXII in Scheme 4, or to any of the specific structures shown in Schemes 9-12. To the extent that any of the compounds produced in Schemes 5-9 are novel, these intermediates and the methods for their preparation also form part of the invention.

Scheme 4

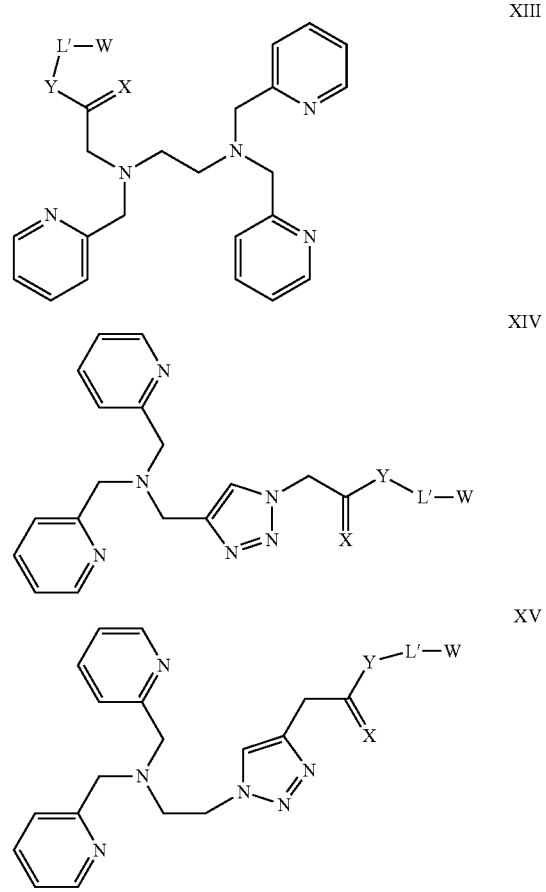

XVI 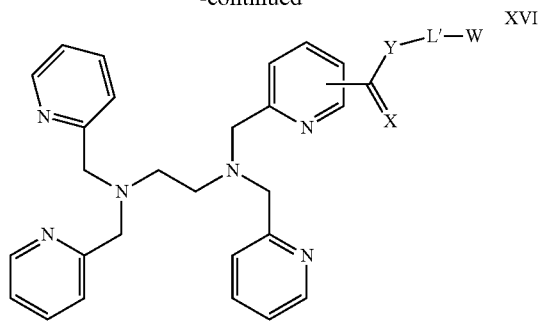

XX 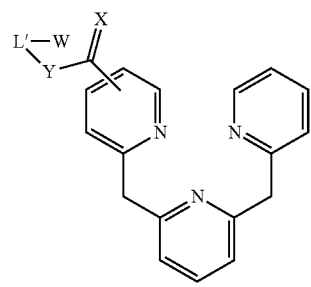

XVII 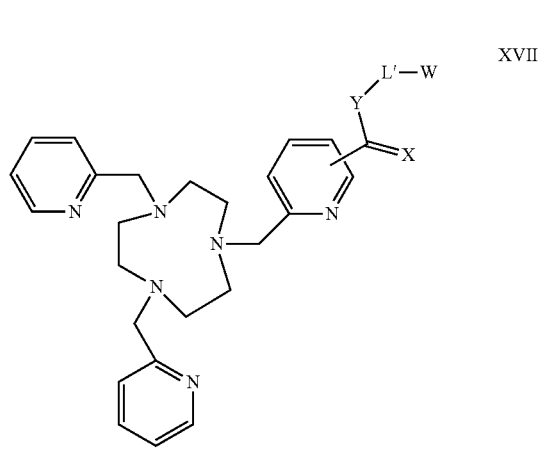

XXI 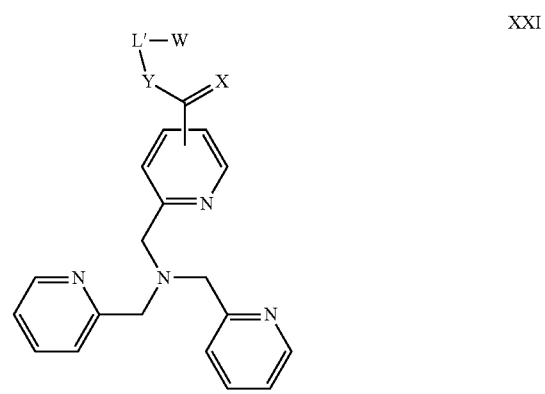

XVIII 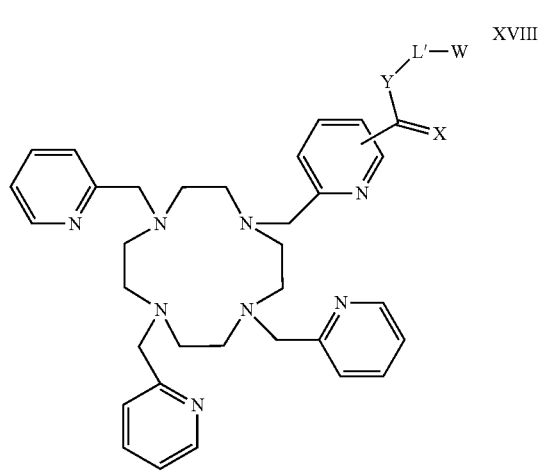

XXIIa 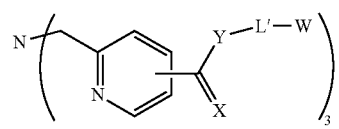

XXIIb 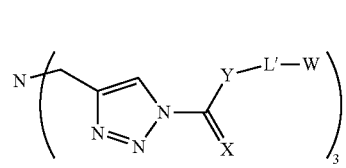

The substances according to the invention may be synthesized using well-known state of the art methods in organic chemistry. Schemes 5-9 exemplify synthetic building blocks useful in the invention and which are used in the synthesis of the structures illustrated in Schemes 10-18. The resulting compounds are preferred compounds according to the invention.

XIX 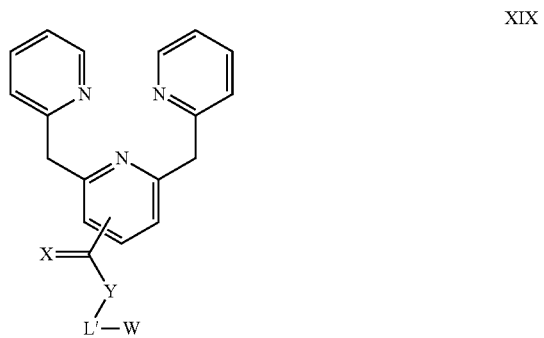

Scheme 5

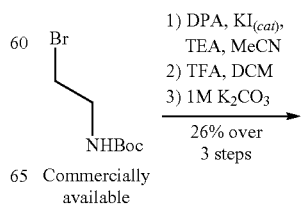

1) DPA, KI$_{(cat)}$, TEA, MeCN
2) TFA, DCM
3) 1M K$_2$CO$_3$

26% over 3 steps

Commercially available

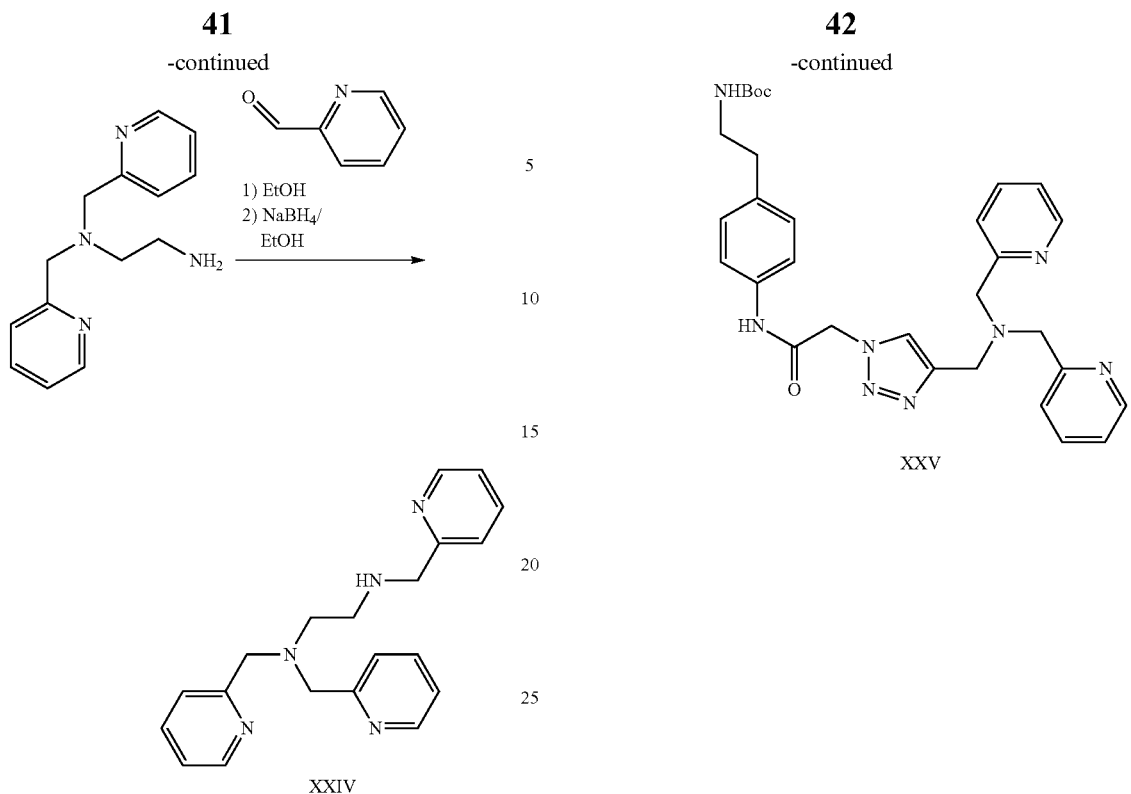
XXIV
Scheme 6
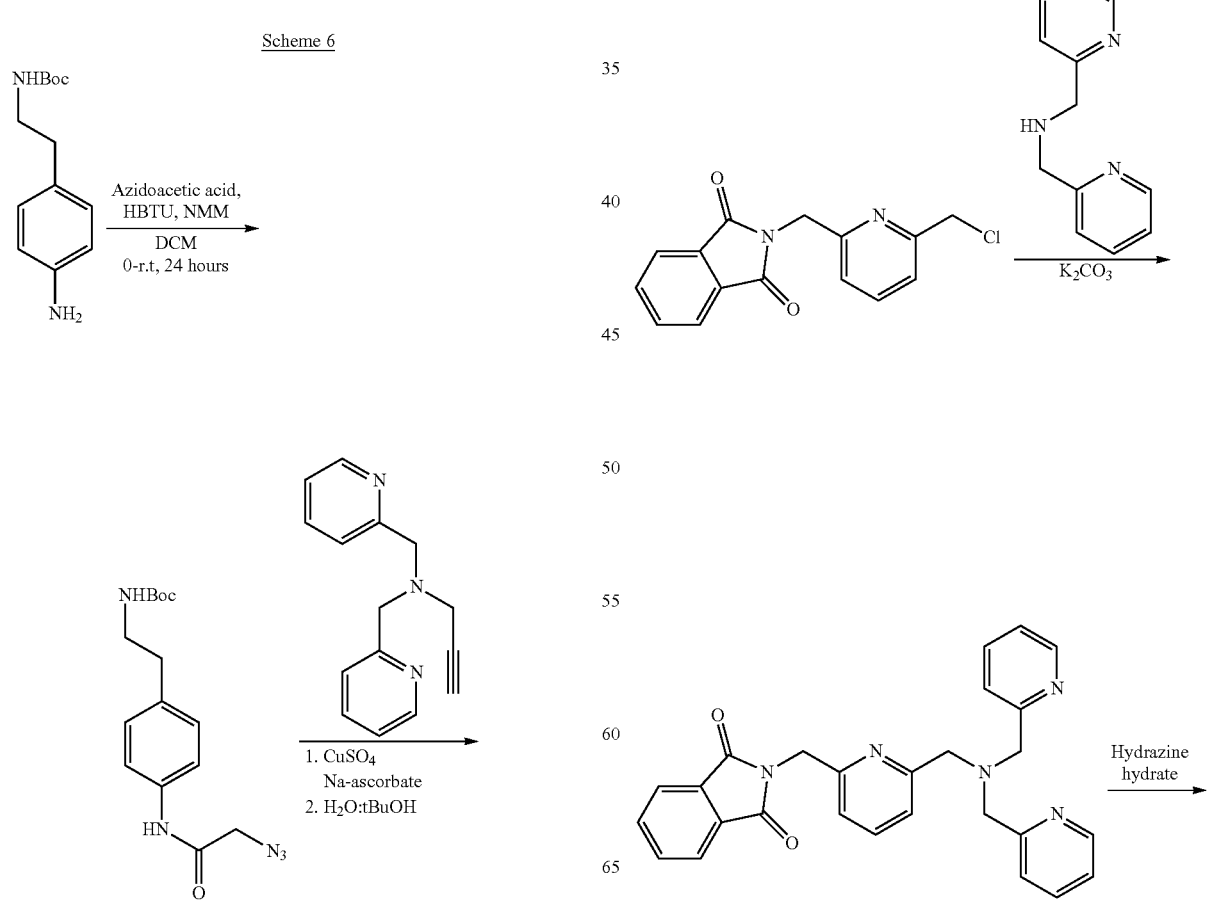
XXV
Scheme 7

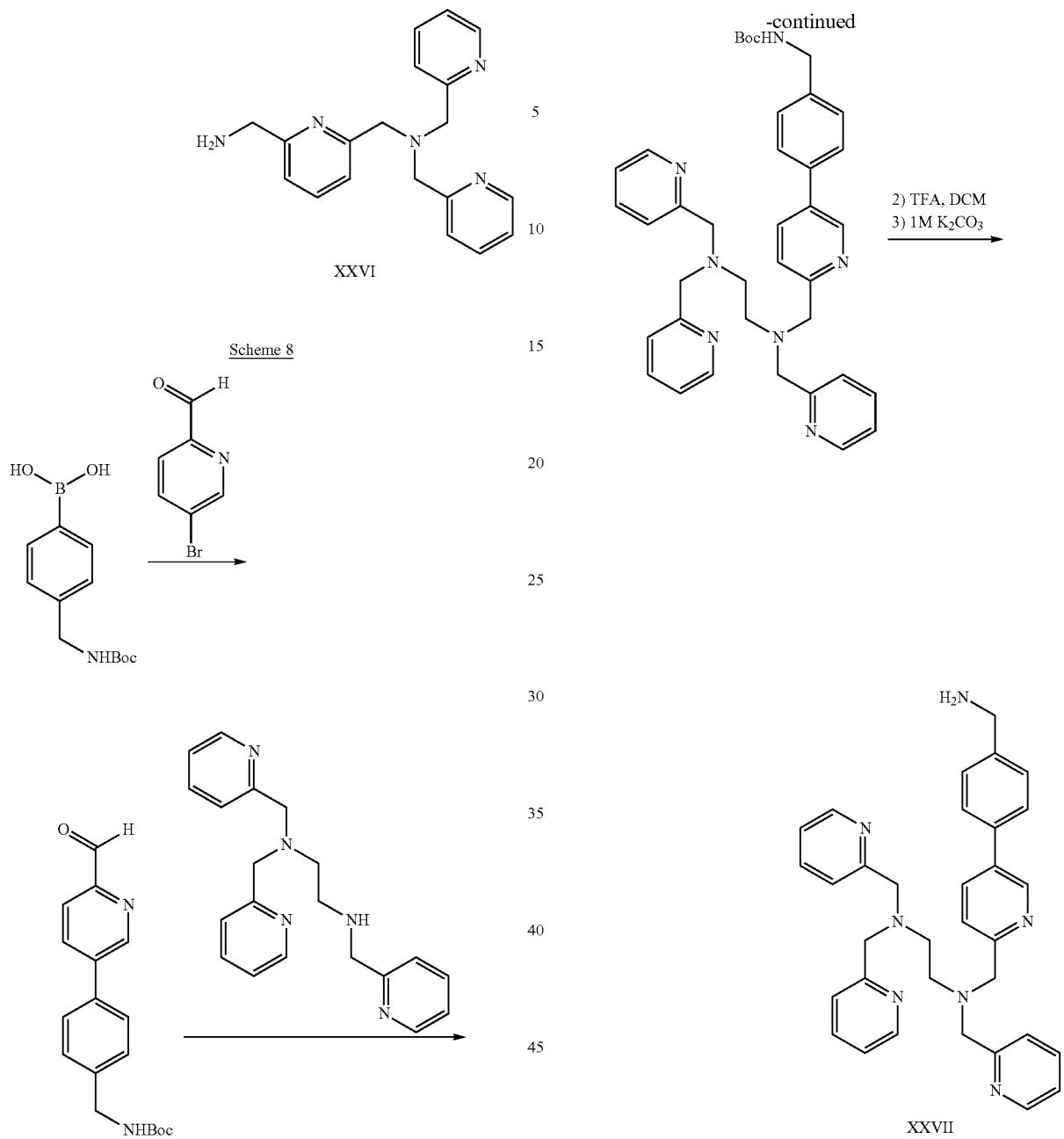
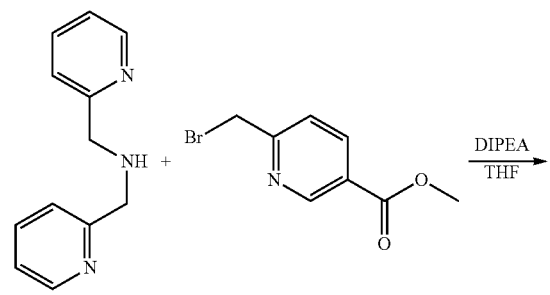

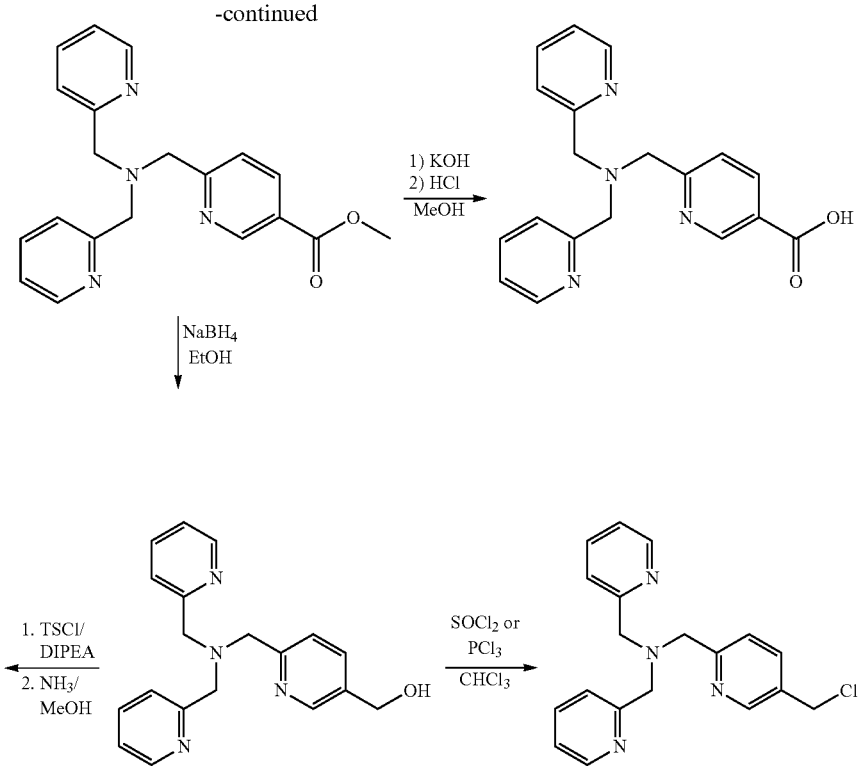
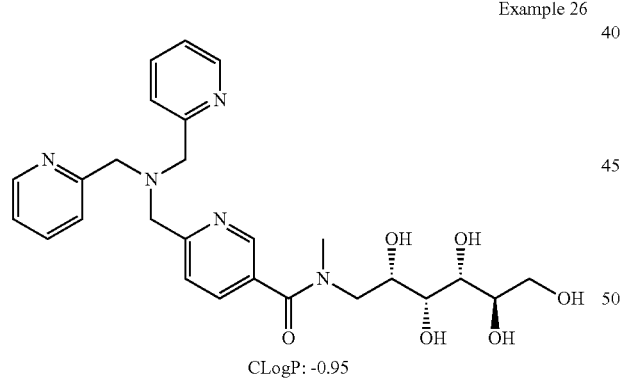
Scheme 10
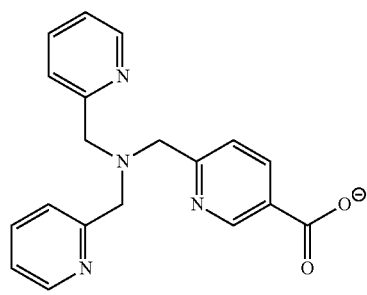
Example 26
CLogP: -0.95
Example 13
CLogP: -3.3
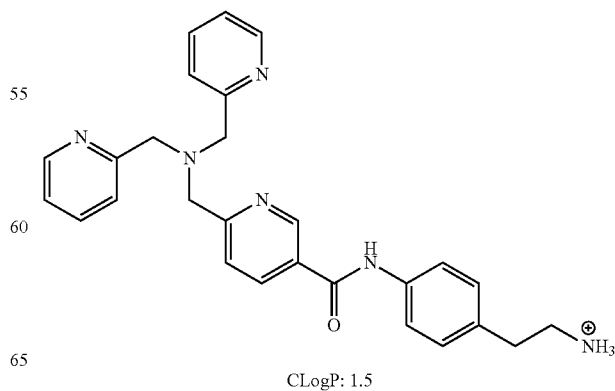
Example 14
CLogP: 0.3
Example 17
CLogP: 1.5

Example 29
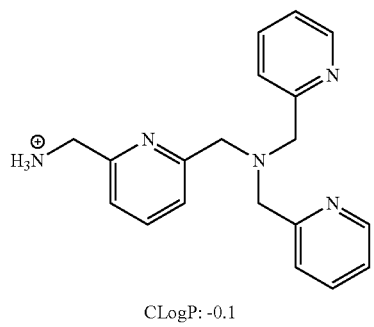
CLogP: -0.1
Example 51
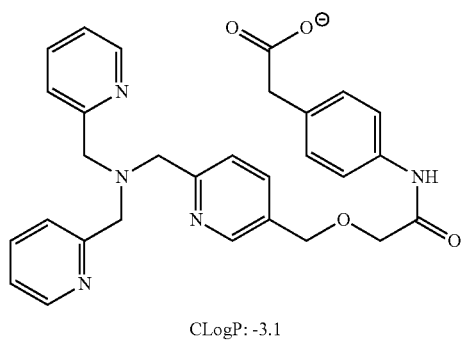
CLogP: -3.1
Example 52
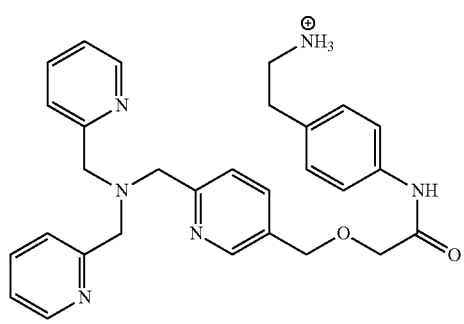
CLogP: 0.8
Example 53
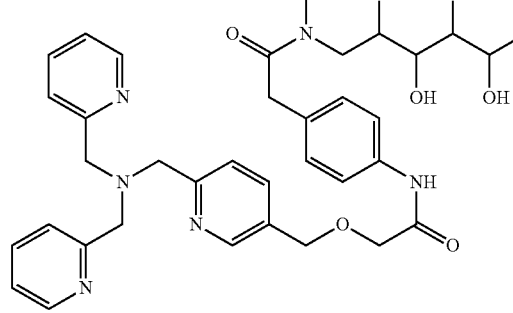
CLogP: -0.4
Example 64
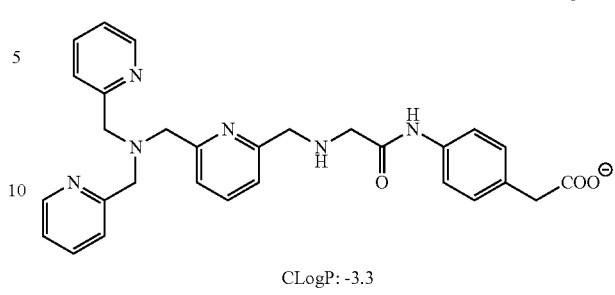
CLogP: -3.3
Scheme 11
Example 37
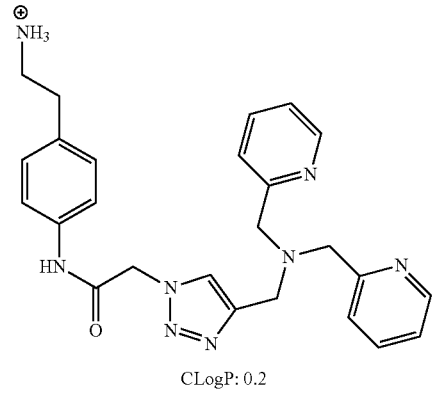
CLogP: 0.2
Example 69
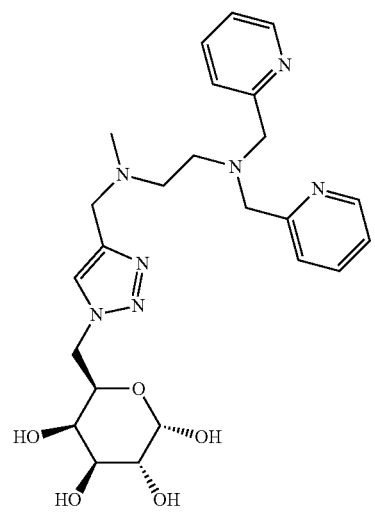
CLogP: -2.0

Example 71
CLogP: -5.2
Scheme 12
Example 44
CLogP: 0.27
Example 85
CLogP: 0.9
Example 86
CLogP: -0.5
Example 87
CLogP: 1.3
Example 88
CLogP: 0.0
Example 81
Example 89
CLogP: 1.3
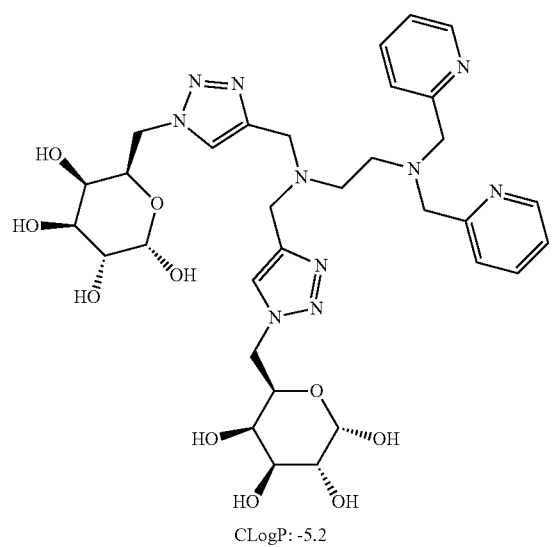

-continued
Example 90
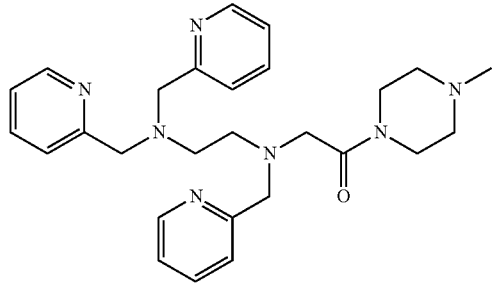
CLogP: 1.8
Example 91
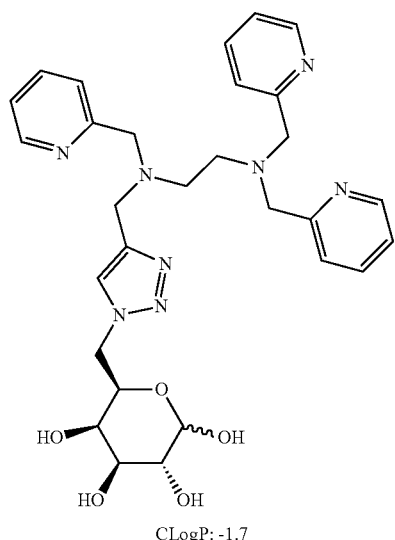
CLogP: -1.7
Scheme 13
Example 83
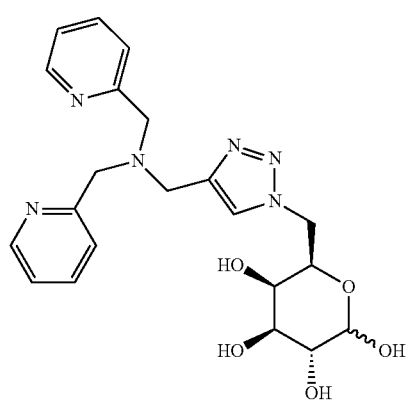
CLogP: -2.6
-continued
Example 84
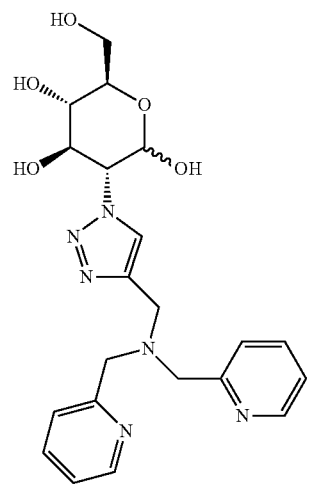
CLogP: -2.4
Example 94
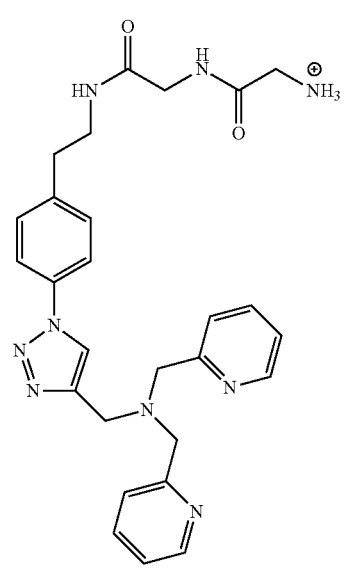
CLogP: -0.2
Example 95
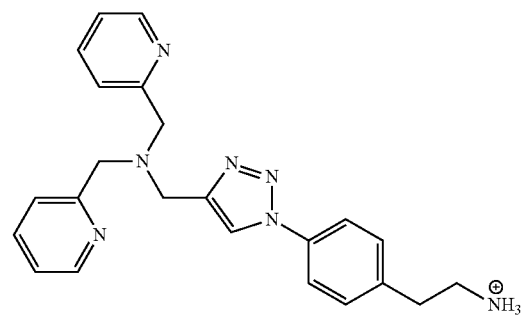
CLogP: 1.3

Example 96
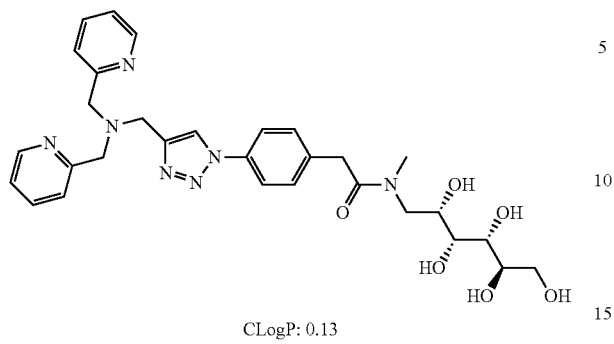
CLogP: 0.13
Example 101
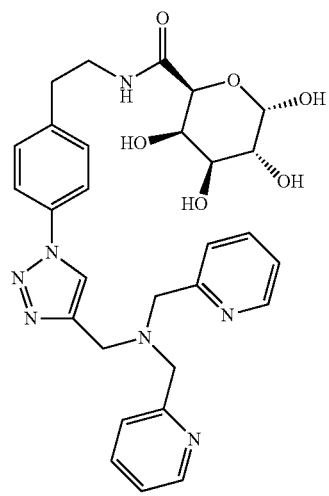
CLogP: -1.1
Example 104
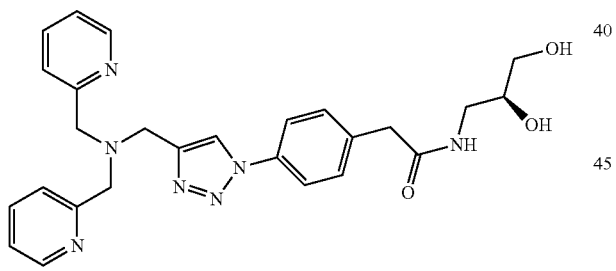
CLogP: 0.14
Example 98
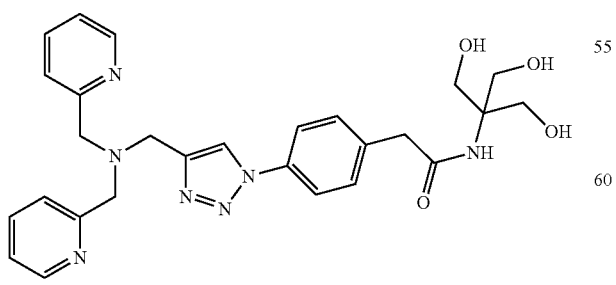
CLogP: 1.0
Scheme 14
Example 55
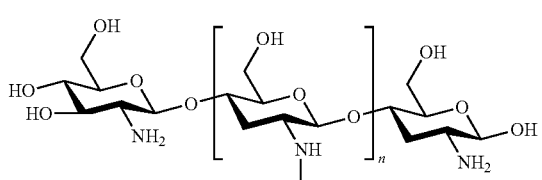
Example 57
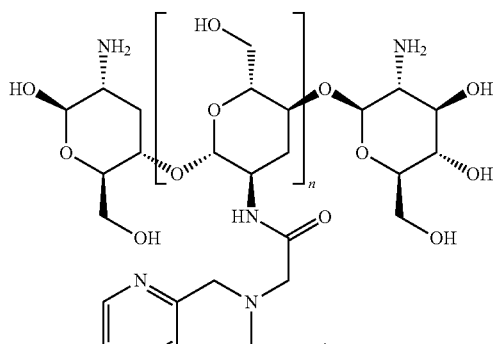
Example 56
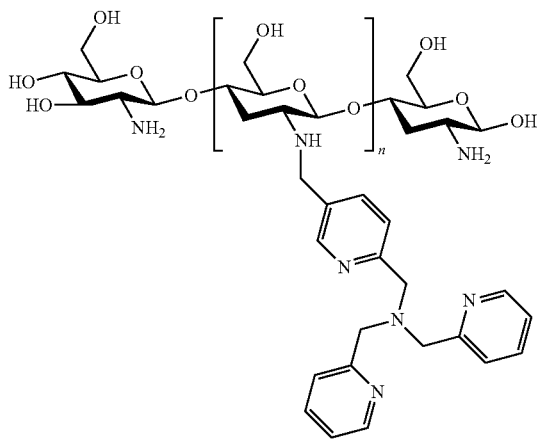

Scheme 15
Example 39
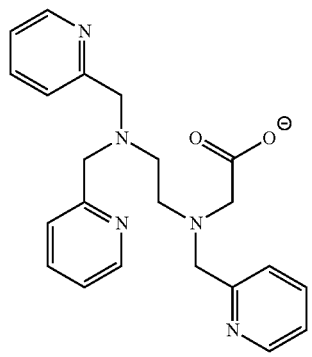
CLogP: -1.6
Example 21
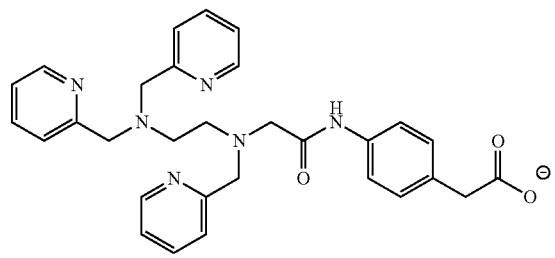
CLogP: -2.0
Example 22
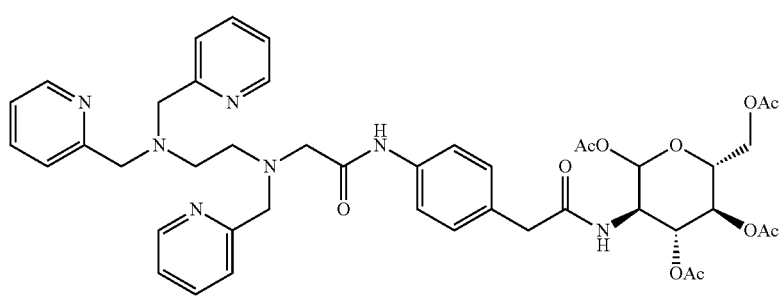
CLogP: 2.1
Example 9
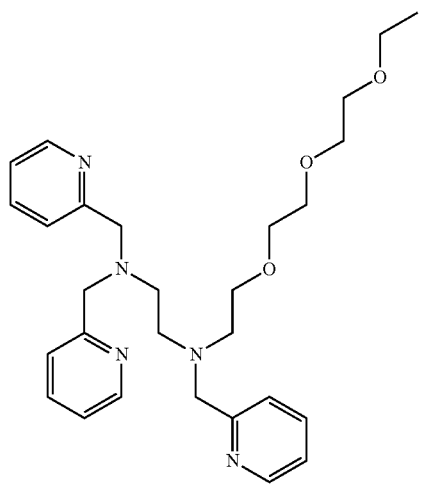
CLogP: 1.8
Example 23
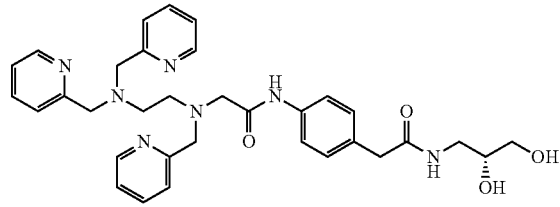
CLogP: 0.7
Example 27
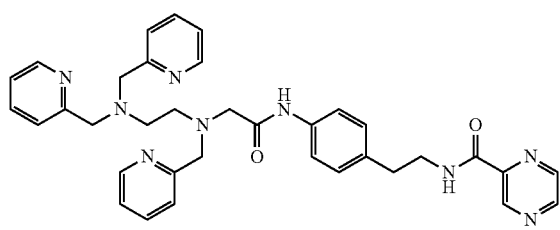
CLogP: 2.2
Example 24
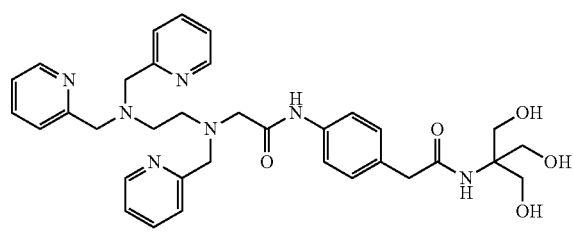
CLogP: 1.6

Example 25
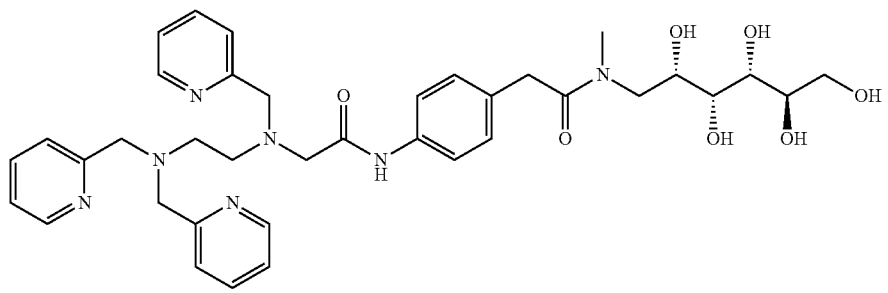
CLogP: 0.7
Example 40
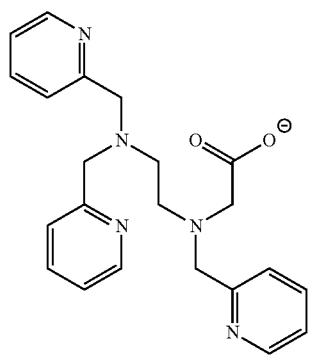
CLogP: -1.6
Example 41
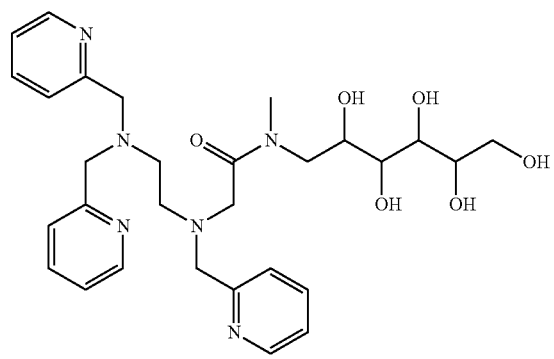
CLogP: 0.6
Example 42
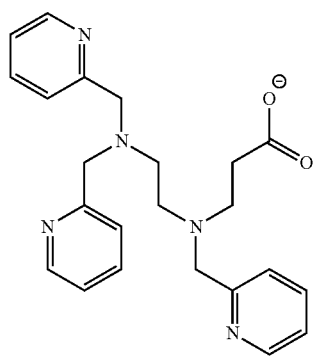
CLogP: -1.5
Example 43
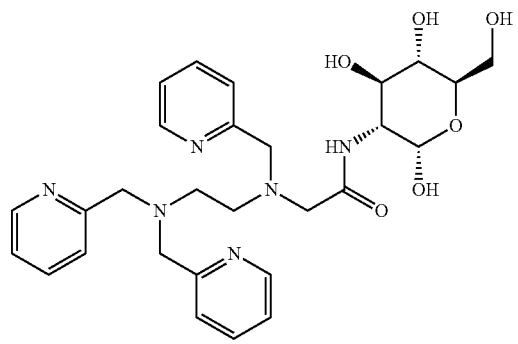
CLogP: 0.0
Example 108
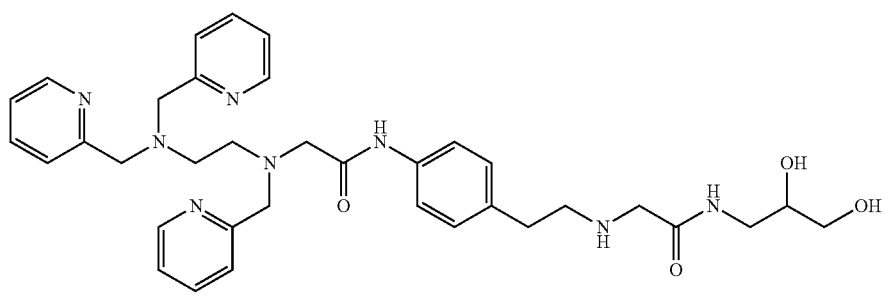
CLogP: 1.0

Scheme 16
Example 102
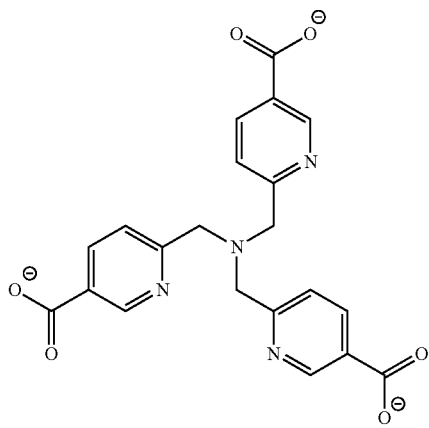
CLogP: -11.85
Example 99
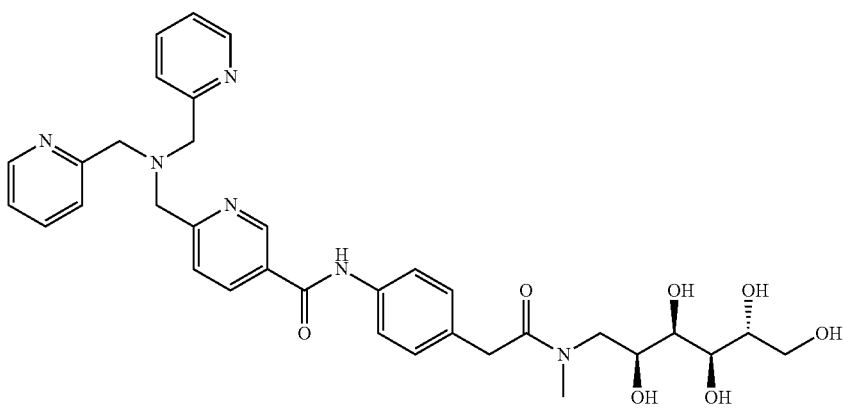
CLogP: 0.34
Example 100
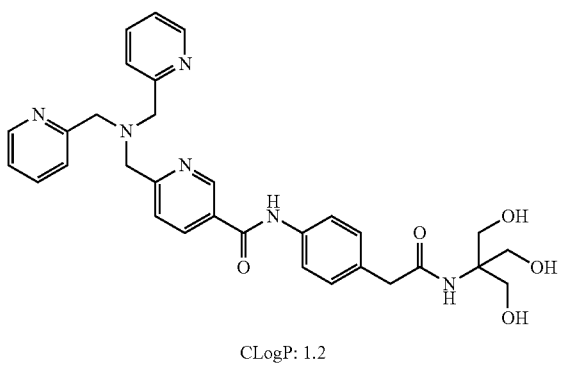
CLogP: 1.2
Example 97
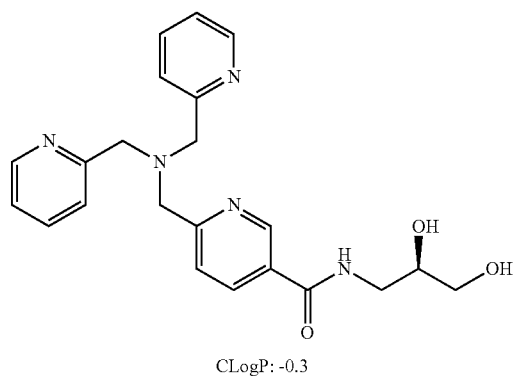
CLogP: -0.3

Example 105
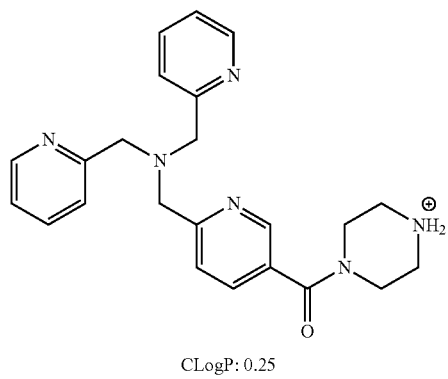
CLogP: 0.25
Example 106
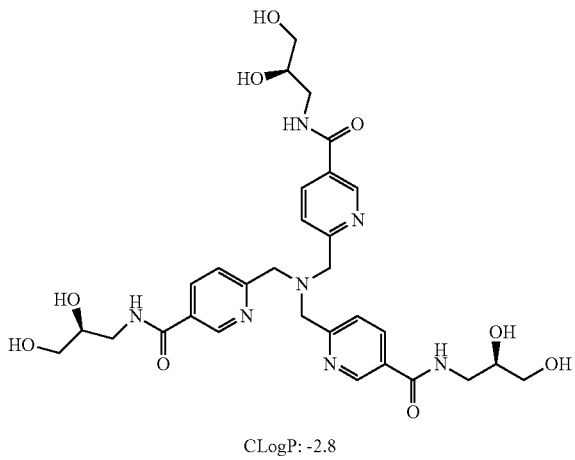
CLogP: -2.8
Scheme 17
Example 54
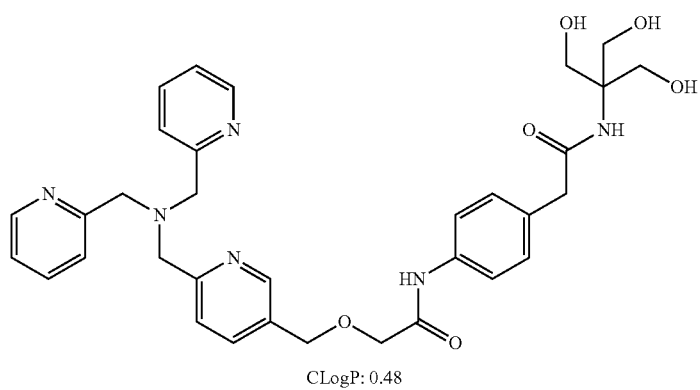
CLogP: 0.48
Example 83
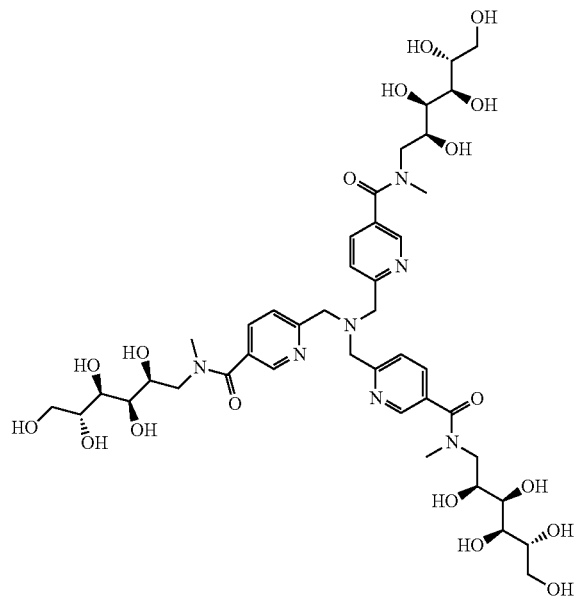
CLogP: -6.7

-continued
Example 107
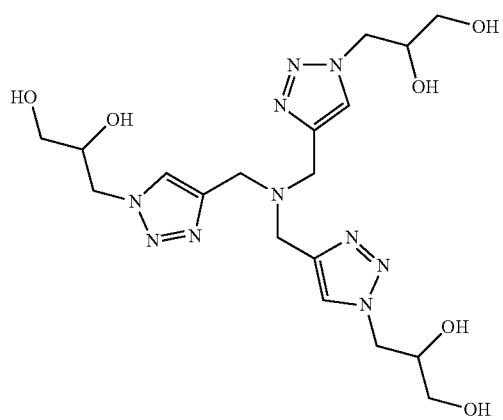
CLogP: -5.2
Example 103
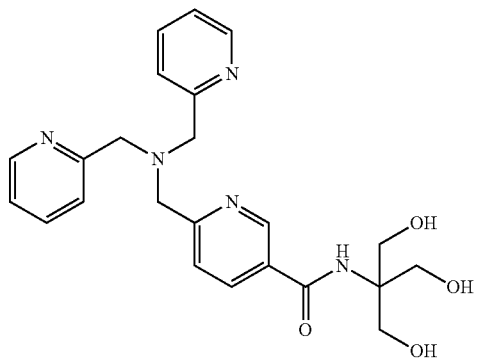
CLogP: 0.3
Example 111
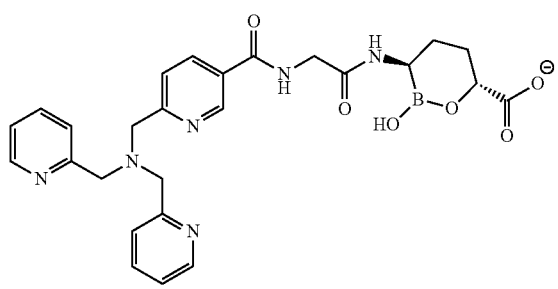
CLogP: -3.3
Example 112
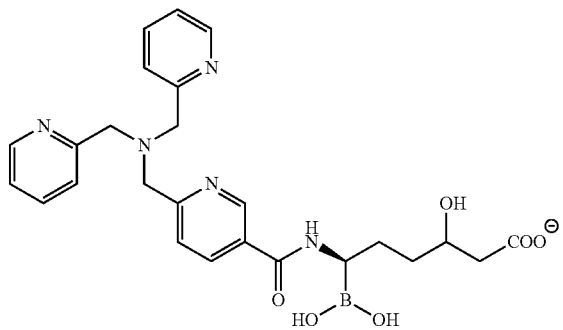
CLogP: -5.1
Example 110
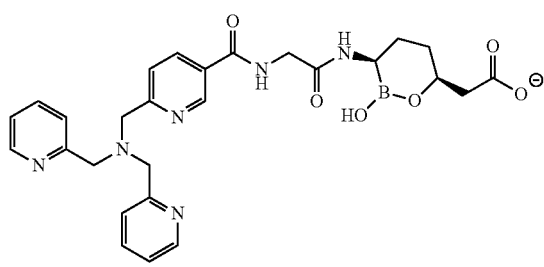
CLogP: -3.3
Example 113
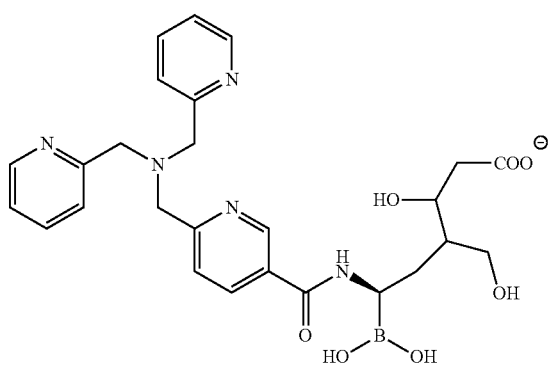
CLogP: -6.1

Example 109
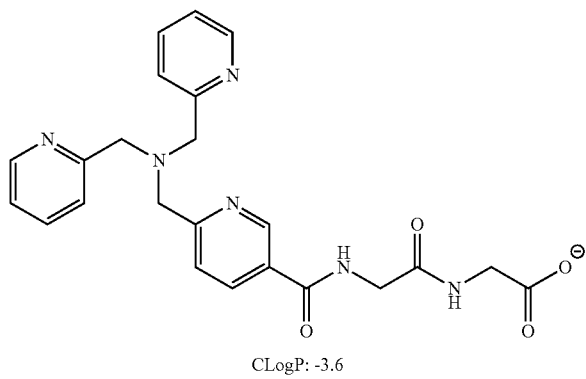
CLogP: -3.6
Scheme 18
Example 114
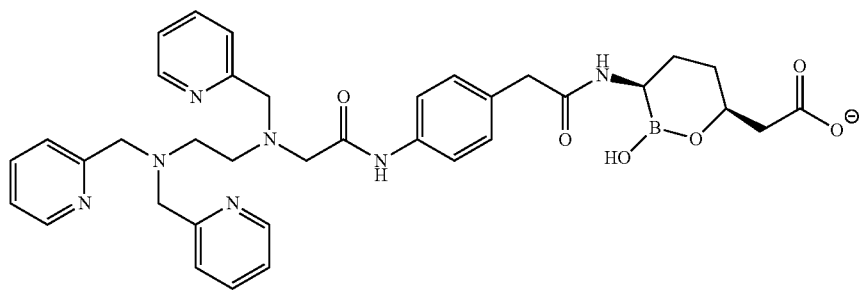
CLogP: -1.8
Example 115
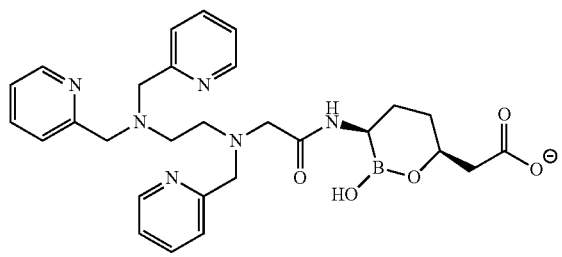
CLogP: -2.1
Example 116
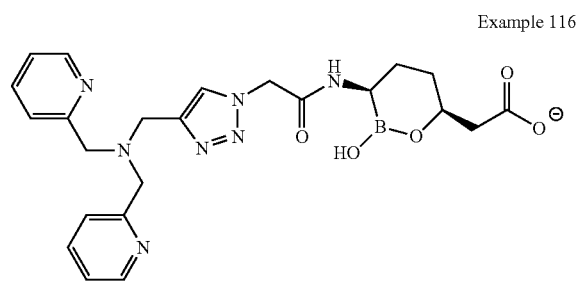
CLogP: -3.8
Example 117
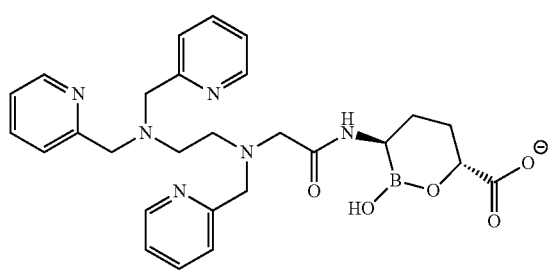
CLogP: -2.1
Example 118
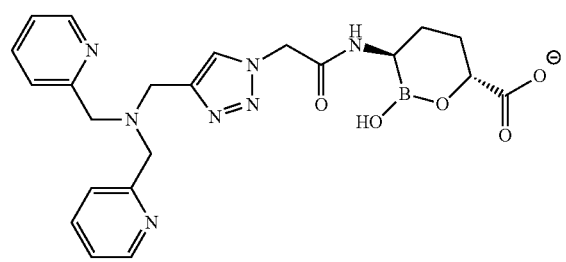
CLogP: -3.8

-continued
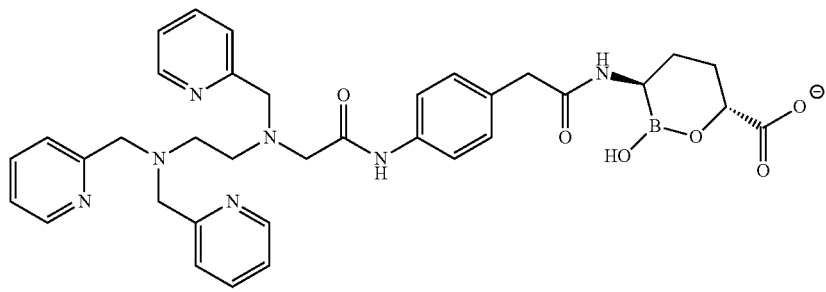
CLogP: -1.8
Example 119
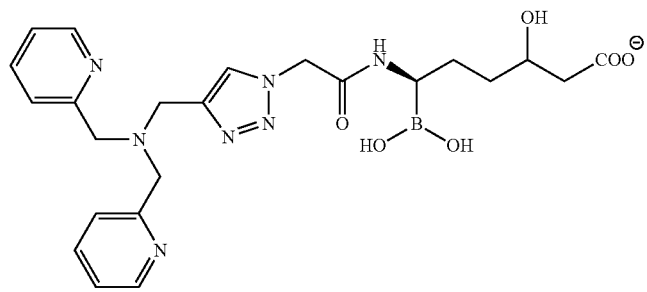
CLogP: -6.5
Example 120
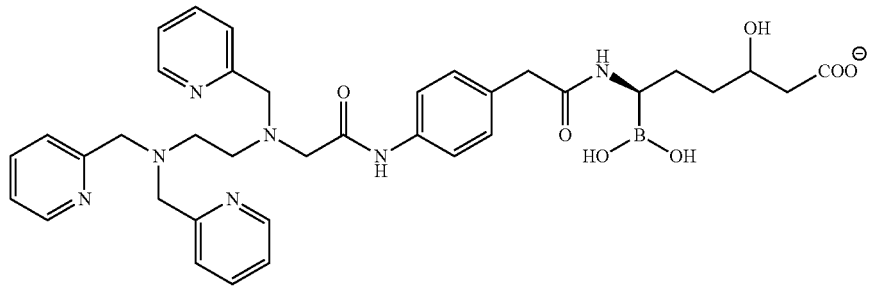
CLogP: -4.4
Example 121
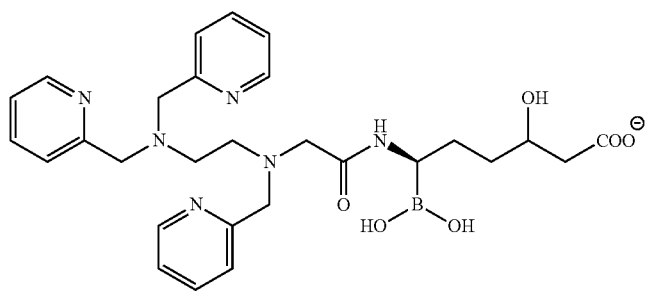
CLogP: -4.8
Example 122

Example 123
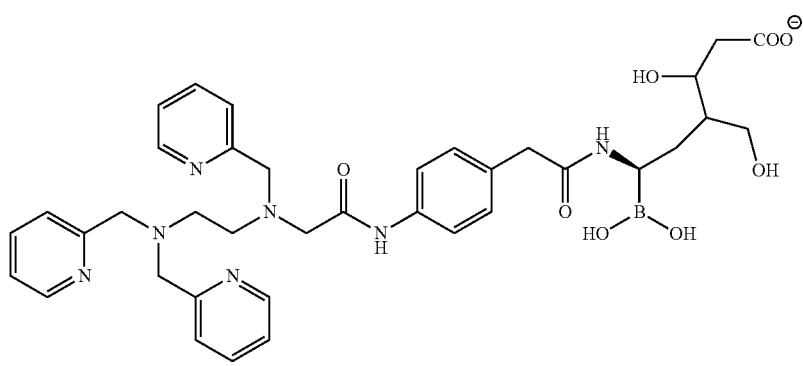
CLogP: -5.3
Example 124a
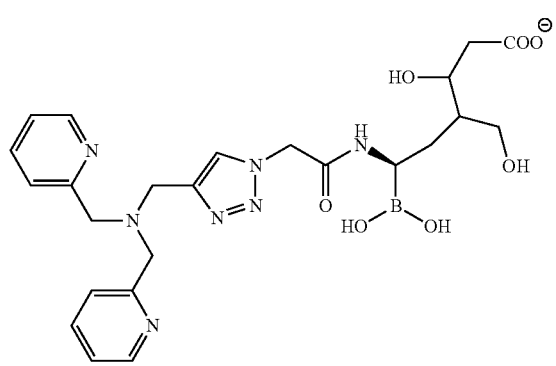
CLogP: -7.5
Example 124b
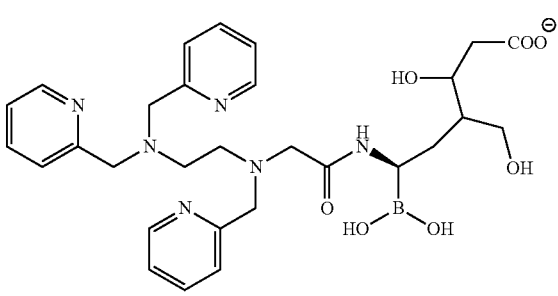
CLogP: -5.7
Scheme 19
Example 125
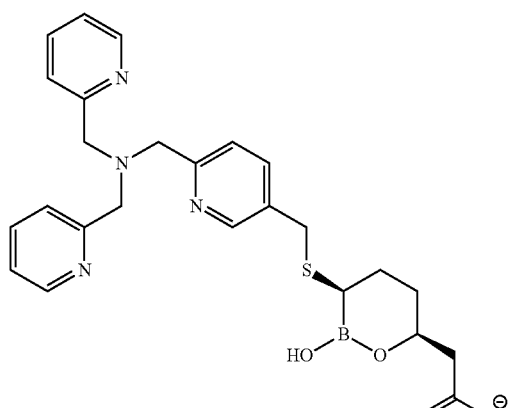
CLogP: 1.1
Example 126
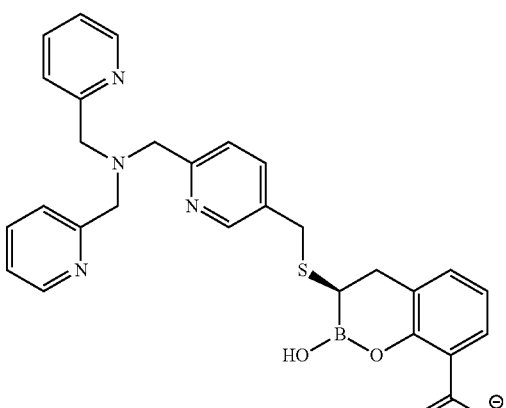
CLogP: -2.0

-continued
Example 127
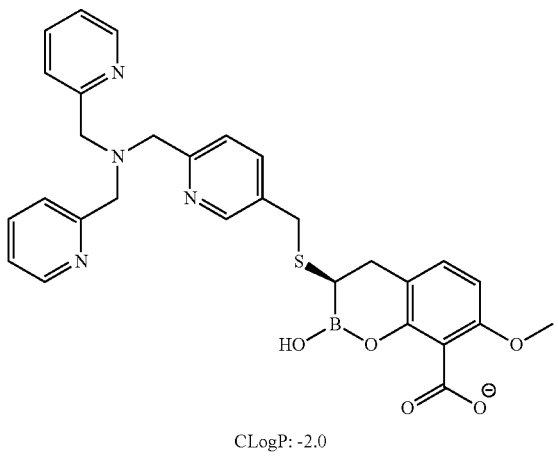
CLogP: -2.0
Example 128
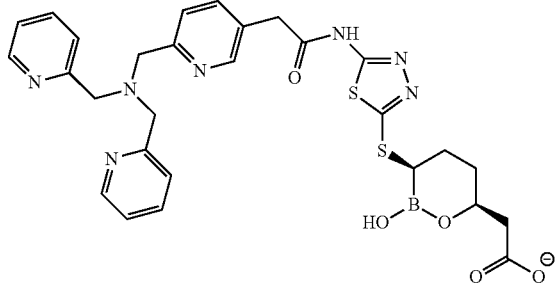
CLogP: -2.8
Example 129
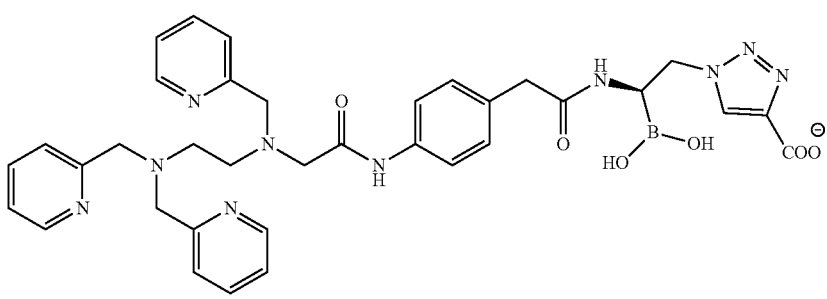
CLogP: -5.0
Example 130
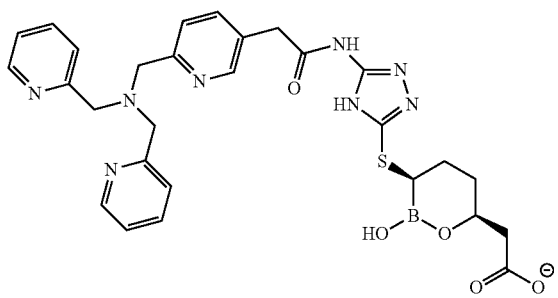
CLogP: -3.1
Example 131
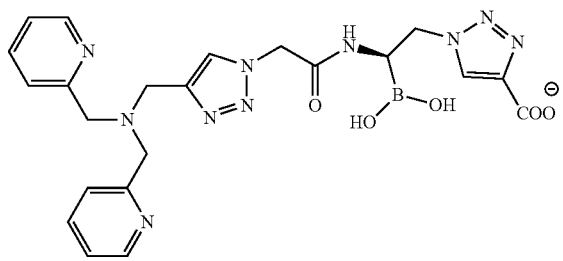
CLogP: -7.1
Example 132
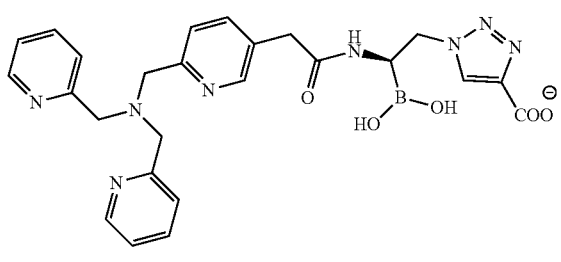
CLogP: -6.7
Example 133
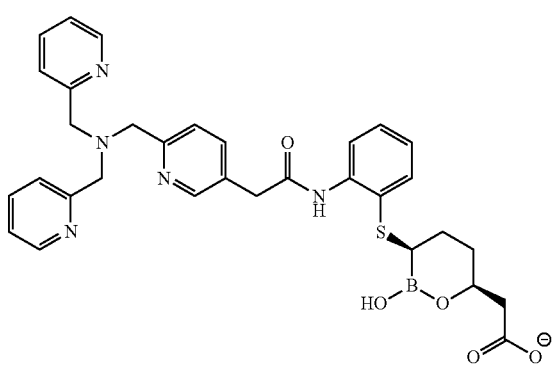
CLogP: -1.8

-continued
Example 134
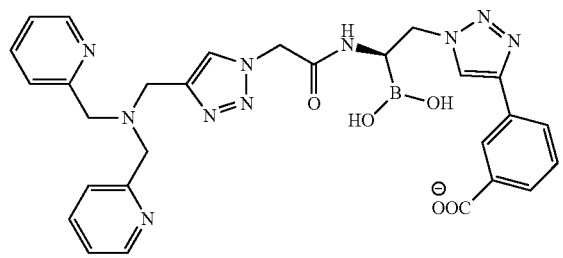
CLogP: -5.0
Example 135
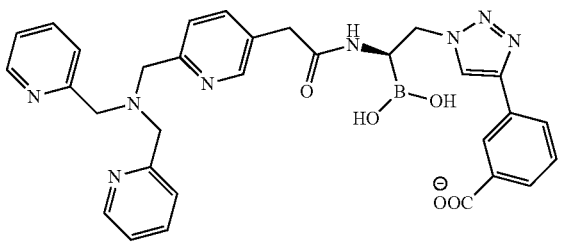
CLogP: -4.6
Scheme 20
Example 136
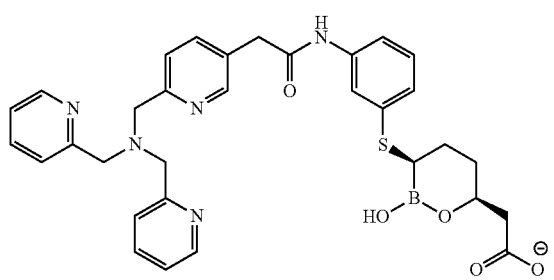
CLogP: -1.6
Example 137
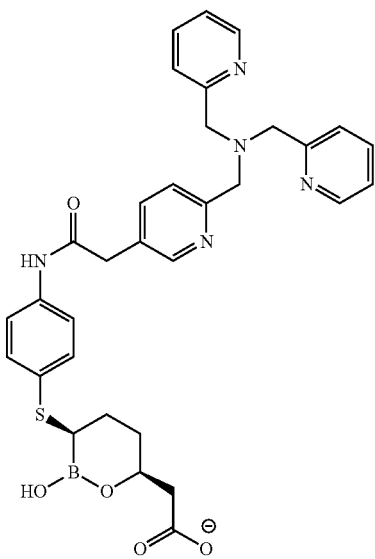
CLogP: -1.6
Example 138
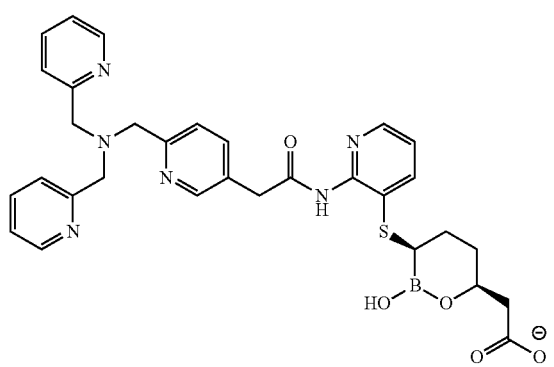
CLogP: -2.3
Example 139
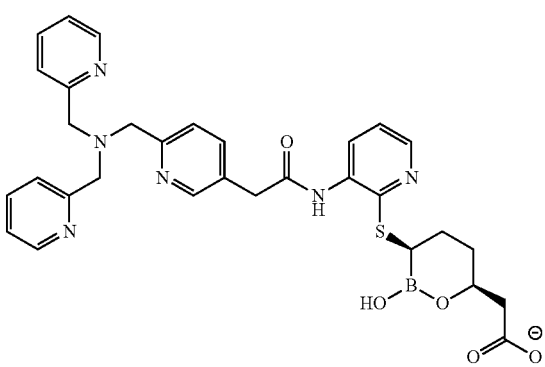
CLogP: -1.9

Example 140
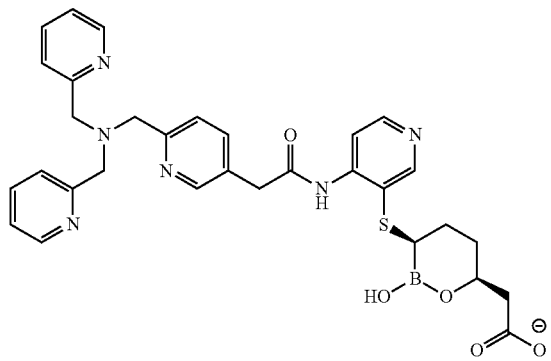
CLogP: -2.3
Example 143
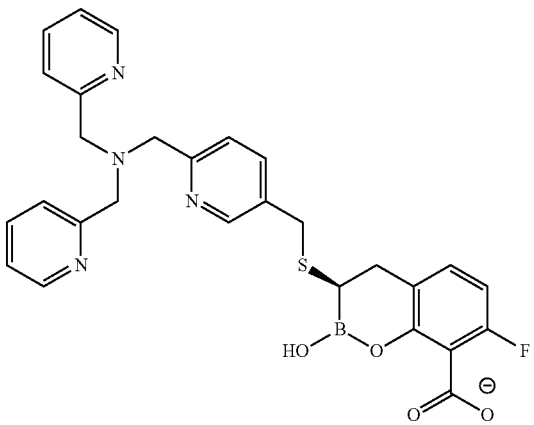
CLogP: -1.9
Example 141
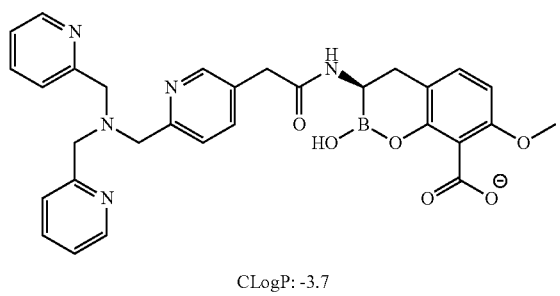
CLogP: -3.7
Example 142
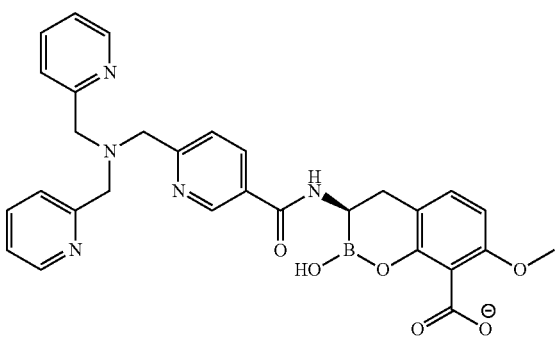
CLogP: -2.96
Example 144
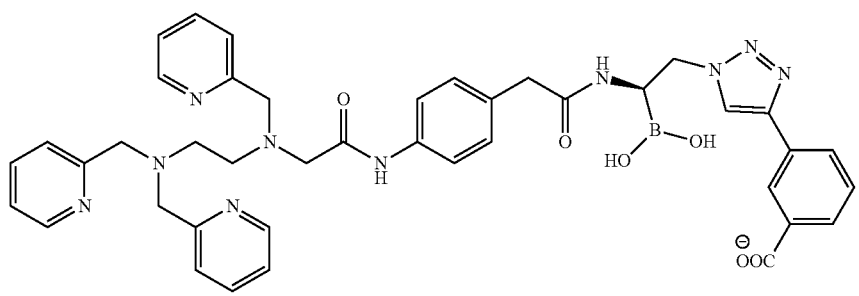
CLogP: -2.95

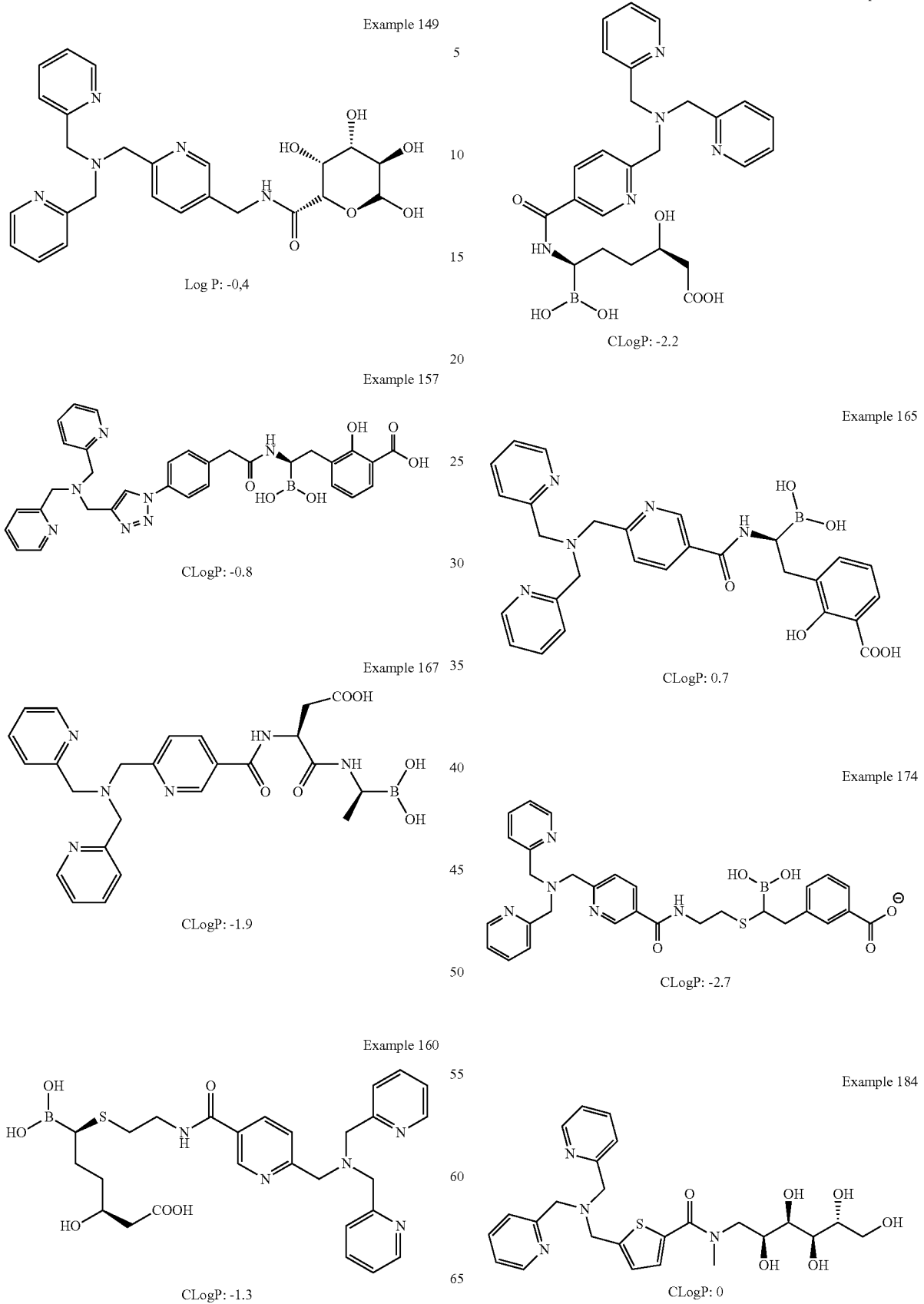

Example 191

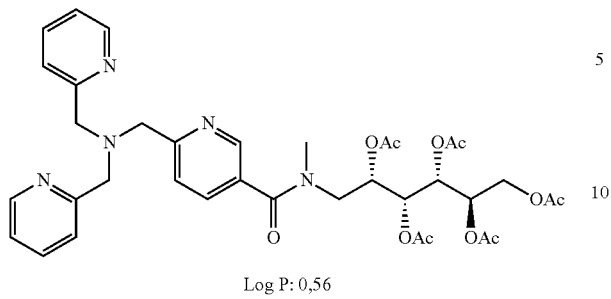

Log P: 0,56

Example 192

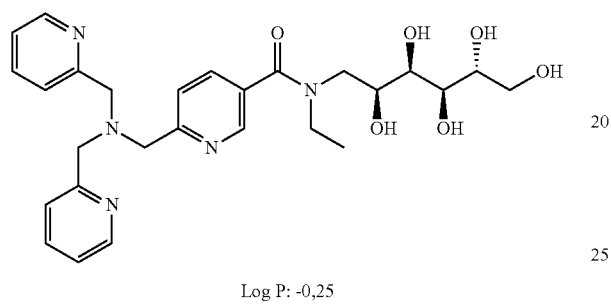

Log P: -0,25

In an embodiment, the present invention may be illustrated by the experimental results for the structures in Scheme 21. TPA N,N,N-(tris(2-pyridy-methyl) amine) is a commercially available ligand know from the prior art as a selective, lipophilic zinc chelator, analogous with TPEN. None of the latter two are useful as drugs since they tend to pass eukaryotic cell membranes and cause interference with some of the 6000 intracellular enzymes dependent on zinc. In Examples 97 and 26, a 2,3-dihydroxy-propyl-amino-carbonyl group and a pentahydroxy-hexyl-methylamino carbonyl group are covalently attached to the TPA ligand, respectively. The MIC values stay the same, but throughout the series of 3 compounds, log P drops to a negative value while the $EC_{50}$ in hepG2 cells increases dramatically from 10 µM, which is well below the effective MIC concentration for TPA, to the non-toxic compound Example 26, as illustrated in Examples 201 and 211.

Scheme 22

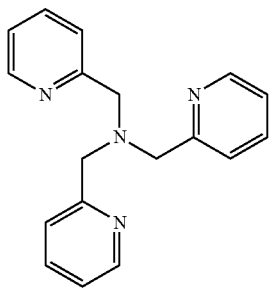

TPA

Log P: 2,7
hepG2 $EC_{50}$: 10 µM
MIC*: 1/0, 125 mg/L
at 50 µM TPA

Example 97

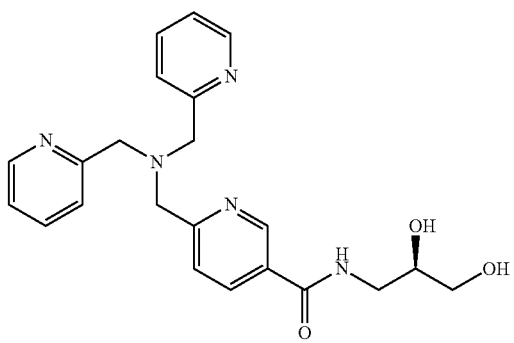

Log P: 0,79
hepG2 $EC_{50}$: 130,6 µM
MIC*: 2/0, 125 mg/L at
50 µM of Ex. 97

Example 26

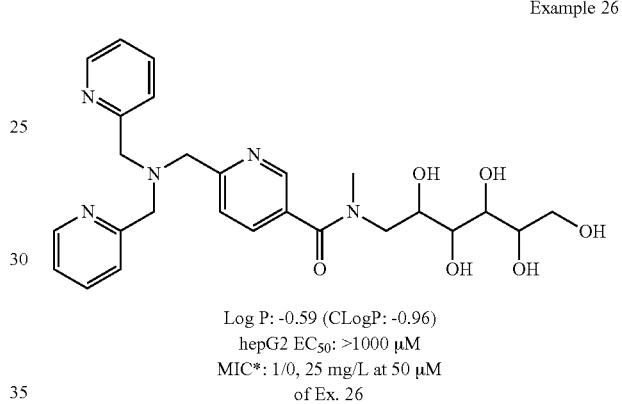

Log P: -0.59 (CLogP: -0.96)
hepG2 $EC_{50}$: >1000 µM
MIC*: 1/0, 25 mg/L at 50 µM
of Ex. 26

* The numbers given at each side of the slash are the MIC value for meropenem in the two clinically isolated resistant strains P.aeruginosa harboring the MBL VIM-2, and K.pneumoniae, harboring the MBL NDM-1, in the presence of 50 µM inhibitor. In the absence of the inhibitor, the MIC value for meropenem is 32-64 mg/L.

Another important parameter of the compounds according to the invention is shelf life stability. A pre-requisite for a drug candidate to be developed is that it can be stored without changes in the chemical structure of the active pharmaceutical ingredient, API. Typical linkers that may be subjected to hydrolytic or enzymatic cleavage are linkers comprising acetal bonds consisting of oxygen, nitrogen or sulfur atoms, ester or carbamate bonds. Even amide bonds, especially those in peptides may be susceptible to cleavage, especially cleavage by proteolytic enzymes. In the general formula Q-[-L-W]$_x$ chelating agents Q are linked to the hydrophilic group W through a linker L. Cleavage of L could lead to liberation of the more lipophilic chelating agent W potentially harming the organism hosting the infection through entry into the eukaryotic cells.

In Carbohydrate Research, Vol. 346, No. 1, 2011, Benoist, E. et al. describes chelating agents comprising a bis-2-pyridyl-methylamino group combined with a triazole group, providing 4-pod ligands attached to a water-soluble group W. The intended use is in nuclear radio imaging using PET and SPECT. No suggestion for use against bacteria or infectious diseases is given. A structural feature of L in this technology is an amino-acetal linker having an inherent ability for cleavage in a biological system, conditionally releasing the chelator that may enter eukaryotic cells, exerting toxic effects as described in the prior art.

It has now been found that when a zinc chelator is attached to a non-peptidic side chain W as herein described, the compounds are more stable in solution compared to the peptidic compounds which are described in WO 2015/049546. This is shown when Example 195, included in the present invention as an example for comparison, is compared to Example 26 (as illustrated by Example 110 in the present application). However, since Example 195 still has excellent MIC values and demonstrates a very high $EC_{50}$ value in eukaryotic cell toxicity, peptidic compounds may still be useful, e.g. as lyophilized drug products.

With respect to stability, in one embodiment of the present invention the compounds comprise an N-alkylated amide bond, represented by the following formula:

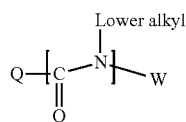

In this formula, Q and W are as herein defined, and "lower alkyl" is any straight-chained or branched $C_{1-6}$ alkyl group, preferably a $C_{1-4}$ alkyl group, e.g. a $C_{1-3}$ alkyl group. This principle is well known in the prior art for peptides (e.g. as described by Schönauer et al, in *J. Med. Chem.* (2016), 59, 5695-5705, by Chatterjee et al in *Nature America* (2012), 7(3), 432-445, and by Ovadia et al in *Molecular Pharmaceutics* (2011), 8, 479-487), but not described in relation to synthetic antibacterial agents. Each of Examples 25, 26, 41, 69, 185, 187, 189 and 190 in the present invention have an N-alkylated amide bond as a structural feature and these represent one set of preferred compounds.

The compounds according to the invention may be used alone or in adjuvant combinations with drugs affecting the respective disease. In the case of the therapy of bacterial, parasitic or viral infection in a host organism, the compounds may be used synergistically together with any antibacterial agent used therapeutically. The host organism may be any living organism having an undesired invasion or infection by a target organism. In general, the biological target may thus be present in any living organism, consisting of or comprising living cells, more preferably a warm-blooded animal, e.g. a mammal.

Typically, a combination of a state of the art β-lactam antibiotic, such as a carbapenem, and a compound as herein described may be used according to the invention. The state of the art β-lactam antibiotic may be combined with or replaced by any combination of one or more antibacterial agents known in the prior art, e.g. tetracyclines, quinolones, rifamycins, sulfonamides, trimethoprim, aminoglycosides, macrolides, chloramphenicolo, oxazolidinones, glycopeptides, cycloserine, isoniazide, daptomycin, cyclosporine, phenazines or derivatives thereof.

Although not wishing to be bound by any theory relating to their mechanism of action, an advantage with the present technology compared to the prior art (e.g. compared to the APC agents such as EDTA and DTPA) is that the compounds of the present invention inhibit bacterial enzymes irreversibly (this is supported by Examples 204, 207, 208 and 209). A further advantage is that the resistance frequency when these are co-administered with conventional antibacterial agents is remarkably low (this is supported by Example 205). At 50 mg/L, for example, the compound tested in Example 205 repeatedly shows zero remaining colonies when used in combination with sub-clinical concentrations of meropenem. The ability to use a conventional antibacterial agent (e.g. a β-lactam antibiotic) at sub-clinical concentrations is particularly advantageous. Use of any of the compounds herein described in combination with an antibacterial agent at sub-clinical concentrations (for example, at a concentration of less than 10 mg/L, less than 8 mg/L, less than 4 mg/L, or less than 2 mg/L) represents a preferred embodiment of the invention. Typically antibacterial agents, such as meropenem, may be used in the clinic at concentrations of 4-8 mg/L. Example 205A indicates that resistance frequency is zero at a meropenem concentration of 2 mg/L. Example 205B shows that resistance frequency is also dependent on the concentration of the adjuvant, at doses at least less than 10 times the concentrations showing toxicity.

Another way to disturb the zinc homeostasis in bacteria is to induce an increase of zinc in the periplasmic space of bacteria or in other relevant compartments. In a further embodiment the zinc chelates of the present invention may thus be employed to transfer zinc into these compartments. For this purpose the compounds are pre-chelated with a suitable molar amount of $Zn^{2+}$, usually in a ratio 1:1 between the chelator and the zinc ion. Such compounds carrying zinc ions form a further aspect of the invention. The zinc chelates of the compounds of the invention can be prepared using known methods, e.g. as described by Yang et al. in Inorg. Chem. (2000), 39, 2397-2404. For example, the zinc chelates can be obtained by mixing a methanol solution of the compound of the invention (the ligand) with a methanol solution of $ZnCl_2$ in a 1:1 molar ratio between the ligand and zinc, and collecting the resulting solid. The zinc chelates can be formulated and used as described in the prior art, e.g. by Prakash, V.; Suresh, M. S. in *Research Journal of Pharmaceutical, Biological and Chemical Sciences* (2013), 4(4), 1536-1550.

In a further embodiment of the invention, the compounds herein described can also be used diagnostically in vitro. The growing problem related to β-lactamases, e.g. the carbapenemases like MBLs in multi-resistant gram-negative pathogens, leading to life-threatening infections, has generated a need for rapid and accurate detection methods to guide treatment decisions. There are commercial test kits available on the market based on combinations of chelating agents like dipicoylamine (DPA) or EDTA, and a suitable β-lactam antibiotic. The total MBL detection kit (ROSCO) is an inhibitor-based dish test for detection of MBLs. The kit is based on use of EDTA and DPA in combination with imipenem or meropenem. Another example from the prior art is a test that may demonstrate discrimination between MBL-, KPC- and OXA-48-producing bacteria, e.g. as described by Teethaisong et al. in *Journal of Applied Microbiology* (2016), 121, 408-414. This uses meropenem ±EDTA or PBA (phenyl-boronic acid) to discriminate between KPC and MBL producers, and temocillin with an increase in zone diameter equal or less than 10 mm in combination with lack of synergy with meropenem ±EDTA or PBA as a positive test for OXA-48. Temocillin is not hydrolyzed by MBLs, as described by Pollini et al., in *Antimicrob Agents Chemother.* (2013) 57(1), 410-6. In this example, fluorescent agar plates using the dye resazurin are used, as described by Sener et al., *J. Clin. Microbiol.* (2011), 49, 1124-1127. The OXA-48-producing strain is identified using the known effect of temocillin against these pathogens.

However, many strains are now producing D carbapenemases and MBLs, e.g. as described by Porres-Osante et al., *Diagnostic Microbiology and Infectious Disease* (2014), 79(3), 399-400. Thus there is a medical need to be able to distinguish between all Ambler classes of lactamase-producing bacteria.

However, one deficiency of the disk test kits in the prior art is that they may show low specificity and false positive predictive values (PPV) for some of the clinically most relevant bacteria, like *Pseudomonas aeruginosa* and *Acinetobacter baumannii*, e.g. as described by F. Hansen et al., in *Diagnostic Microbiology and Infectious Disease* (2014), 79, 486-488. EDTA is an unspecific chelating agent that may induce false results; DPA is a very weak chelating agent with a $pK_d$<8. Thus, there is a need for test kits improving the performance of commercial kits.

Since the compounds of the present invention show a strong and selective inhibitory effect on gram negative bacteria harboring MBL, they can be used to verify in simple dish tests if a bacterium is harboring MBL. As a non-limiting example, the compound of Example 26 has a strong selective inhibiting effect as an adjuvant on resistant clinical isolates of gram-negative bacteria harboring MBLs together with a carbapenem (e.g. meropenem), e.g. *Pseudomonas aeruginosa, Klebsiella pneumoniae* or *E. Coli*. However, the compound of Example 26 does not show activity against strains producing *Klebsiella pneumoniae* carbapenemases (KPC). Thus disks comprising the compound of Example 26 alone (Disk A), and disks comprising the compound of Example 26 plus a carbapenem (Disk B) can be used to decide if the strains are resistant to carbapenems and are MBL-positive. The compound of Example 115 shows activity against both MBL and KPC-based bacteria. Thus the kit may further comprise disks comprising the compound of Example 115 alone (Disk C) and disks comprising the compound of Example 115 plus a carbapenem (Disk D). As well-known from prior art, a disk comprising temocillin may be used to identify OXA-48 producers. In experiment (i), when agar plates comprising the bacterial isolates are incubated with Disk A and then A+B, unchanged zone diameters indicate bacterial isolates without MBL. In experiment (ii), incubated plates with the same isolate with Disk C and then C+D, unchanged zone diameters indicate bacterial isolates without MBL or KPC. Unchanged zone diameters in experiment (i) but increased zone diameter in experiment (ii) indicates bacterial isolates with KPC, not MBL. In experiment (iii), increase in zone diameter equal to or less than 10 mm combined with unchanged zone diameters in experiment (i) and (ii) indicates the presence of an OXA-48 producer.

Advantages with the present technology compared to the prior art are that the compounds of the present invention, e.g. that of Example 26, are much stronger MBL inhibitors than DPA used in, for example, the ROSCO kit, enabling use of much lower concentrations of the adjuvant. Furthermore, the compounds of Examples 110 and 115 and other Examples in Schemes 17-20 are the first compounds to our knowledge that inhibit both MBL and KPC as adjuvants together with a carbapenem.

In a further embodiment the compounds of the invention are also useful against biofilm. Biofilms comprise extracellular polymeric substances (EPS) that are natural hydrophilic carbohydrate polymers, forming extracellularly in a host organism. Since a key feature of the compounds of the invention is their low log P, they interact particularly well with EPS. Since the compounds of the invention show high efficacy against multidrug-resistant gram-negative species producing MBL, they can be used to reduce and/or prevent biofilm formation in infections caused by, for example, *Acinetobacter baumannii, Pseudomonas aeruginosa, Klebsiella pnemoniae* and *E. coli* and other species producing MBL. The zinc chelators according to the invention may also be used against biofilm formation with gram-positive bacteria, e.g. variants of *Staphylococcus epidermidis* and methicillin-resistant *S. aureus* (MRSA). These species have been shown to be inhibited by zinc chelators of the APC class and TPEN, because of their zinc-dependent adhesion molecules mandatory for the biofilm formation, e.g. as described by Conrady et al., *PNAS* (2008), 105 (49), 19456-19461. As shown in the present specification, the compounds herein show high metal chelating selectivity and low toxicity rendering them promising drug candidates.

The administration of the compounds according to the invention to a mammal may be by any suitable method known in the medicinal arts, including intravenous, intracerebral, oral, parenteral, topical, subcutaneous administration or by inhalation. In the case of antibacterial adjuvants, an especially attractive administration regime for a selective zinc chelator with low toxicity having adjuvant effect is continuous systemic administration of the adjuvant combined with administration of the respective antibacterial agent. In the case of sepsis caused by resistant gram-negative bacteria, the adjuvant may be intravenously continuously infused, while an antibacterial agent, e.g. a carbapenem, e.g. meropenem or imipenem is administered as approved by the respective regulatory authorities. Continuous intravenous infusion of a compound according to the present invention may also be used simultaneously with other administration routes of antibacterial agents, e.g. by inhalation of a micronized formulation, by oral intake of a tableted antibiotic agent, or by topical administration of the drug.

When used as an antibacterial agent or as an adjuvant to an antibacterial agent or formulation comprising such, the compounds may be administered in a single dose to be taken at regular intervals, e.g. once or twice a day, once every 48 hours, or once every 72 hours. Sustained formulations may be given at longer intervals, e.g. 1 to 2 times a month or every three months. The precise dosage of the active compounds to be administered, the number of daily or monthly doses and the length of the course of treatment will depend on a number of factors, including the age of the patient and their weight, but can readily be determined by those skilled in the art.

The compositions may be formulated according to techniques and procedures well known in the literature and may comprise any of the known carriers, diluents or excipients. For example, the compositions/formulations which can be used in the present invention which are suitable for parenteral administration conveniently may comprise sterile aqueous solutions and/or suspensions of pharmaceutically active ingredients preferably made isotonic with the blood of the recipient generally using sodium chloride, glycerin, glucose, mannitol, sorbitol and the like. In addition, the composition may contain any of a number of adjuvants, such as buffers, preservatives, dispersing agents, agents that promote rapid onset of action or prolonged duration of action.

The compositions and formulations may be combined with one or more typical antioxidants, e.g. ascorbic acid, ascorbyl palmitate, ascorbyl stearate, BHA, BHT, citric acid, gum guaiac, lecithin, lecithin citrate, monoglyceride citrate, onoisopropyl citrate, propyl gallate, EDTA, tartaric acid or any combination thereof.

Compositions/formulations suitable for oral administration may be in sterile purified stock powder form, preferably covered by an envelope or envelopes which may contain any of a number or adjuvants such as buffers, preservative agents, agents that promote prolonged or rapid release. Compositions/formulations for use in the present invention suitable for local or topical administration may comprise the therapeutic agent mixed with known suitable ingredients such as paraffin, vaseline, cetanol, glycerol and the like, to form suitable ointments or creams.

As will be understood, any of the compounds herein described may be provided in the form of a pharmaceutically acceptable salt. The compounds according to the invention may be converted into a salt thereof, particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

Any of the compounds herein described may be provided in the form of a prodrug. The term "prodrug" refers to a derivative of an active compound which undergoes a transformation under the conditions of use, for example within the body, to release an active drug. A prodrug may, but need not necessarily, be pharmacologically inactive until converted into the active drug. As used herein, the term "prodrug" extends to any compound which under physiological conditions is converted into any of the active compounds herein described.

Suitable prodrugs include compounds which are hydrolyzed under physiological conditions to the desired molecule. Prodrugs may typically be obtained by masking one or more functional groups in the parent molecule which are considered to be, at least in part, required for activity using a progroup. By "progroup" as used herein is meant a group which is used to mask a functional group within an active drug and which undergoes a transformation, such as cleavage, under the specified conditions of use (e.g. administration to the body) to release a functional group and hence provide the active drug. Progroups are typically linked to the functional group of the active drug via a bond or bonds that are cleavable under the conditions of use, e.g. in vivo. Cleavage of the progroup may occur spontaneously under the conditions of use, for example by way of hydrolysis, or it may be catalyzed or induced by other physical or chemical means, e.g. by an enzyme, or by exposure to a change in pH, etc. Where cleavage is induced by other physical or chemical means, these may be endogenous to the conditions of use, for example pH conditions at a target site, or these may be supplied exogenously.

A wide variety of progroups suitable for masking functional groups in active compounds to provide prodrugs are well known in the art. For example, a hydroxy functional group may be masked as an ester, a phosphate ester, or a sulfonate ester which may be hydrolyzed in vivo to provide the parent hydroxy group. An amide functional group may be hydrolyzed in vivo to provide the parent amino group. A carboxyl group may be masked as an ester or amide which may be hydrolyzed in vivo to provide the parent carboxyl group. Other examples of suitable progroups will be apparent to those of skill in the art.

In one embodiment, the compounds of the invention have a hydroxy functional group that can be derivatized to produce suitable prodrugs. For example, the hydroxy group can be converted to an alkyl or aryl ester, a phosphate ester, a sulfonate ester, etc.

The compounds of the invention may contain one or more chiral centers and may therefore exist in different stereoisomeric forms. The term "stereoisomer" refers to compounds which have identical chemical constitution but which differ in respect of the spatial arrangement of the atoms or groups. Examples of stereoisomers are enantiomers and diastereomers. The term "enantiomers" refers to two stereoisomers of a compound which are non-superimposable mirror images of one another. The term "diastereoisomers" refers to stereoisomers with two or more chiral centres which are not mirror images of one another. The invention is considered to extend to diastereomers and enantiomers, as well as racemic mixtures.

The compounds herein described may be resolved into their enantiomers and/or diastereomers. For example, where these contain only one chiral center, these may be provided in the form of a racemate or racemic mixture (a 50:50 mixture of enantiomers) or may be provided as pure enantiomers, i.e. in the R- or S-form. Any of the compounds which occur as racemates may be separated into their enantiomers by methods known in the art, such as column separation on chiral phases or by recrystallization from an optically active solvent. Those compounds with at least two asymmetric carbon atoms may be resolved into their diastereomers on the basis of their physical-chemical differences using methods known per se, e.g. by chromatography and/or fractional crystallization, and where these compounds are obtained in racemic form, they may subsequently be resolved into their enantiomers.

Also provided herein is a pharmaceutical composition comprising a compound according to the invention together with at least one pharmaceutically acceptable diluent or carrier.

Compositions comprising the MBL inhibitors are preferably formulated prior to administration. The active ingredients in such compositions may comprise from 0.05% to 99% by weight of the formulation. Appropriate dosages may depend on the compound to be used, precise condition to be treated, age and weight of the patient, etc. and may be routinely determined by the skilled practitioner according to principles well known in the art. By way of example, representative dosages may include 1 to 200 or 1-100 mg/kg, e.g. 5 to 70, 5-50, or 10 to 70 or 10 to 50 mg/kg.

By "pharmaceutically acceptable" is meant that the ingredients must be compatible with other ingredients of the composition as well as physiologically acceptable to the recipient. Pharmaceutical compositions according to the present invention may be formulated according to techniques and procedures well known in the art and widely described in the literature and may comprise any of the known carriers, diluents or excipients. Other ingredients may of course also be included, according to techniques well known in the art, e.g. stabilisers, preservatives, etc. The formulations may be in the form of sterile aqueous solutions and/or suspensions of the pharmaceutically active ingredients, aerosols, ointments and the like. The formulations may also be in a sustained release form e.g. microparticles, nanoparticles, emulsions, nano-suspensions, lipid particles or oils. As discussed herein, the compounds of the invention may also be used in formulations of ZnO nanoparticles described, for example, by Pati et al. in Nanomedicine (2014), 10(6), 1195-1208.

Further, an important aspect of formulation of antibacterial agents is in the form of films, patches or folios having the MBL inhibitor coated on the surface; these form a further aspect of the invention.

EXAMPLES

The invention will be described in more detail in the following non-limiting examples and with reference to the accompanying figures, in which:

FIG. 8 shows the zinc restorability of the NDM VIM-2 after in vitro incubation with the compound of Example 26 compared to incubation with standards TPEN and EDTA;

GENERAL PROCEDURES

Figure 1:
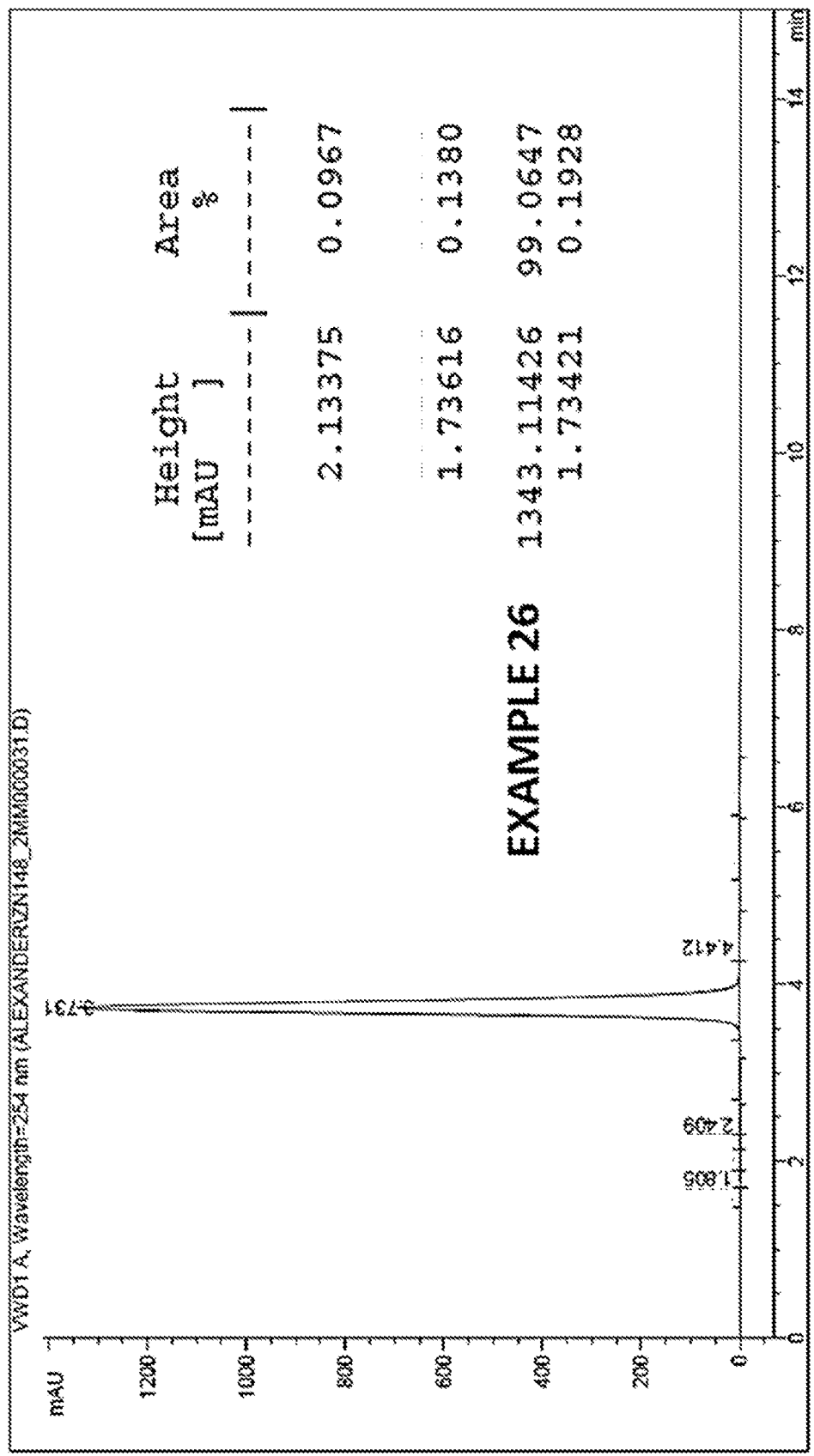
FIG. 1 shows the HPLC purity of the compound of Example 26.

All reagents and solvents used are of commercial grade and were used without further purifications prior to use. NMR ($^1H$, $^{13}C$) spectra were recorded on a Bruker AVI-600 MHz, AVII-400 MHz, a DPX-300 MHz or a DPX-200 MHz spectrometer. Coupling constants (J) are reported in hertz, and chemical shifts are reported in parts per million (ppm) relative to $CDCl_3$ (7.26 ppm for $^1H$ and 77.16 ppm for $^{13}C$) and [$D_6$]DMSO (2.50 ppm for $^1H$ and 39.52 ppm for $^{13}C$). IR spectra were obtained on a Perkin-Elmer Spectrum BX series FT-IR spectrometer and only selected peaks are reported. Mass spectra were recorded at 70 eV on Waters Prospec Q spectrometer using EI, ES or CI as the methods of ionization. High resolution mass spectra were recorded on Waters Prospec Q spectrometer using EI or ESI as the methods of ionization.

Example 1—Synthesis of tert-butyl (4-(2-azidoacetamido)phenethyl)carbamate

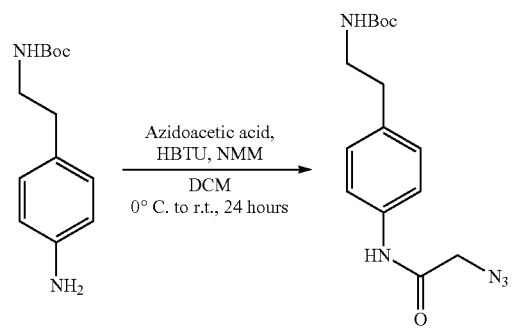 [SMILES: CC(C)(C)OC(=O)NCCc1ccc(N)cc1 ; CC(C)(C)OC(=O)NCCc1ccc(NC(=O)CN=[N+]=[N-])cc1]

Tert-butyl (4-aminophenethyl)carbamate (2.33 g, 9.89 mmol, 1.0 eq) was dissolved in DCM (100 mL) and mixed with HBTU (3.75 g, 9.89 mmol, 1.0 eq) and cooled to 0° C. using an ice bath. Azidoacetic acid (1.0 g, 9.89 mmol, 1.0 eq) was added to the stirring mixture followed by NMM (2.18 mL, 19.79 mmol, 2.0 eq). The mixture was stirred 1 hour at 0° C. and 23 hours at room temperature. The mixture was then diluted with 0.5 M $NaHCO_3$ (100 mL) and the organic phase was separated. The aqueous phase was then extracted two times with 50 mL DCM, the combined organic phases dried over $MgSO_4$, filtered and concentrated in vacuo. The crude material was further purified using column chromatography on $SiO_2$ with 50-100% EtOAc in heptane as eluent. This gave a pale yellow solid.

Example 2—Synthesis of tert-butyl (4-(2-bromoacetamido)phenethyl)carbamate

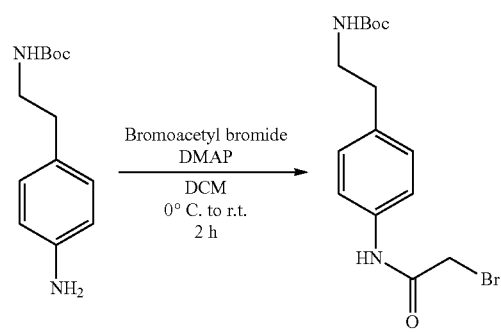 [SMILES: CC(C)(C)OC(=O)NCCc1ccc(N)cc1 ; CC(C)(C)OC(=O)NCCc1ccc(NC(=O)CBr)cc1]

Tert-butyl (4-aminophenethyl)carbamate (4.5 g, 21.83 mmol, 1.0 eq) was dissolved in DCM (150 mL) and cooled to 0° C. using an ice bath. DMAP (1.6 eq) was added in one portion to the stirring mixture followed by dropwise addition of bromoacetyl bromide (1.2 eq) in 50 mL DCM. The mixture was stirred for 30 minutes at 0° C. and then 1.5 hours at room temperature before it was concentrated in vacuo. The crude material was purified using column chromatography on $SiO_2$ with 75-100% EtOAc in heptane as eluent. This gave a colorless solid which was used directly in the next example.

Example 3—Synthesis of tert-butyl (4-(2-((2-(bis(pyridin-2-ylmethyl)amino) ethyl)(pyridin-2-ylmethyl)amino)acetamido)phenethyl)carbamate

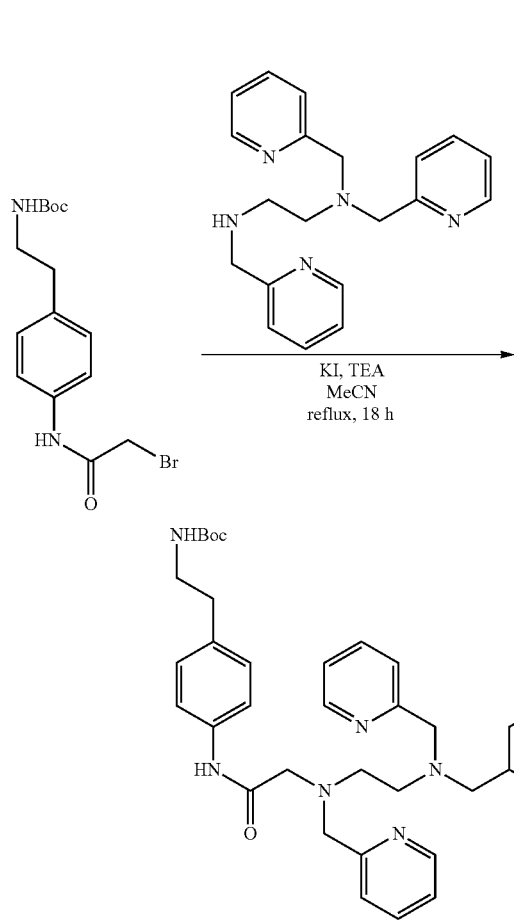

The tert-butyl (4-(2-bromoacetamido)phenethyl)carbamate prepared in Example 2 (3.57 g, 9.99 mmol, 1.0 eq) was dissolved in acetonitrile (350 mL). Potassium iodide (1.0 g, 6 mmol, 0.6 eq) and TEA (13.3 mL, 100 mmol, 10 eq) was then added, followed by N1,N1,N2-tris(pyridin-2-ylmethyl)ethane-1,2-diamine (4.0 g, 12 mmol, 1.2 eq) dissolved in 50 mL acetonitrile. The mixture was heated to reflux and stirred overnight. After cooling the mixture to room temperature, it was filtered on a glass filter to remove inorganic salts. The solution was then concentrated in vacuo to give a red-brown oil. This crude oil was further purified by column chromatography on neutral $Al_2O_3$ with 0-5% MeOH in DCM as eluent. This gave the title product as a red oil.

$^1$H NMR (600 MHz, $CDCl_3$) δ 10.40 (s, 1H), 8.51-8.48 (m, 1H), 8.47-8.44 (m, 2H), 7.59 (d, J=8.4 Hz, 2H), 7.57-7.49 (m, 3H), 7.39 (d, J=7.8 Hz, 2H), 7.14-7.10 (m, 4H), 7.10-7.06 (m, 2H), 3.72 (s, 6H), 3.33 (d, J=6.8 Hz, 2H), 3.27 (s, 2H), 2.81-2.71 (m, 4H), 2.68 (t, J=6.4 Hz, 2H), 1.40 (s, 9H). $^{13}$C NMR (151 MHz, $CDCl_3$) δ 169.92 (s), 159.14 (s), 158.18 (s), 155.93 (s), 149.55 (s), 149.08 (s), 136.94 (s), 136.59 (s), 136.47 (s), 134.40 (s), 129.17 (s), 123.15 (s), 123.11 (s), 122.56 (s), 122.11 (s), 119.99 (s), 61.01 (s), 60.47 (s), 58.70 (s), 52.09 (s), 51.59 (s), 43.50 (s), 41.90 (s), 35.66 (s), 28.48 (s). HRMS: (TOF MS ES+): calculated for $C_{35}H_{43}N_7O_3$ [M+H]$^+$: 610.3505, found 610.3511.

Example 4—Synthesis of tert-butyl (2-(bis(pyridin-2-ylmethyl)amino)ethyl)carbamate

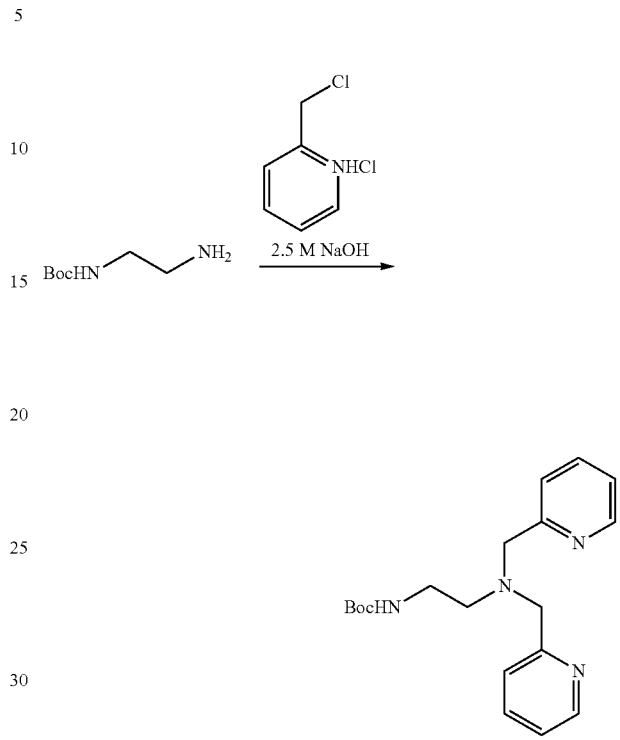

Tert-butyl (2-aminoethyl)carbamate (75.0 g, 465.3 mmol, 1.0 eq) was suspended in 1.5 L dest. $H_2O$. Chloromethyl pyridine hydrochloride (168 g 1.0 mol, 2.2 eq) was then added to the stirring suspension followed by ice cold 5 M NaOH (1.5 L). The suspension became dark red and slightly hot. The mixture was stirred at room temperature overnight. The deep red solution was then extracted with DCM (3×750 mL) and the combined organic phases were dried over $K_2CO_3$, filtered and concentrated in vacuo to yield a deep red oil which needed no further purification. NMR were in accordance with published data. See Kikuchi et al., *Inorg. Chem.*, 2009, 48 (16), pp 7630-7638.

Example 5—Synthesis of N1,N1-bis(pyridin-2-ylmethyl)ethane-1,2-diamine

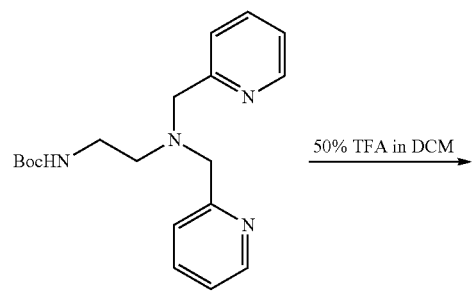

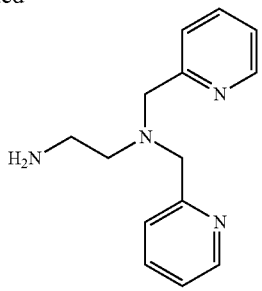

The tert-butyl (2-(bis(pyridin-2-ylmethyl)amino)ethyl) carbamate prepared in Example 4 was dissolved in 600 mL DCM and cooled to 0° C. in an ice bath. Trifluoroacetic acid (600 mL) was then added slowly to the stirring mixture at 0° C. After complete addition, the mixture was allowed to warm to room temperature and stirred for an additional 18 hours. The mixture was concentrated in vacuo, dissolved in 2M NaOH (500 mL) and extracted three times with DCM (3×500 mL). The combined organic phases were dried over $K_2CO_3$, filtered and concentrated in vacuo to give 92 grams (379 mmol, 82% yield over two steps) as a deep red oil which needed no further purification. NMR were in accordance with published data. See Kikuchi et al., *Inorg. Chem.*, 2009, 48 (16), pp 7630-7638.

Example 6—Synthesis of N1,N1,N2-tris(pyridin-2-ylmethyl)ethane-1,2-diamine 500 mg 4 Å molecular sieves and 2-pyridinecarboxaldehyde (196 µL, 2.06 mmol, 1.0 eq). The mixture was placed under nitrogen atmosphere and heated to reflux for 90-120 minutes before it was cooled to room temperature. Then $NaBH_4$ (243 mg, 6.42 mmol) was added with the aid of absolute ethanol (4 mL). The mixture was stirred at room temperature for 16 hours before it was concentrated under reduced pressure. The crude mixture was suspended in DCM (25 mL) and washed with 1M NaOH (3×25 mL). The organic phase was concentrated under reduced pressure and further purified by column chromatography on neutral alumina using 1-5% MeOH in DCM as eluent to afford the titled compound as a pale yellow oil (315 mg, 46%).

1H NMR (600 MHz, DMSO) δ 8.50-8.42 (m, 3H), 7.77-7.66 (m, 3H), 7.54 (d, J=7.8 Hz, 2H), 7.34 (d, J=7.8 Hz, 1H), 7.25-7.17 (m, 3H), 3.75 (s, 4H), 3.70 (s, 2H), 2.67-2.58 (m, 4H). 13C NMR (151 MHz, DMSO) δ 160.84 (s), 159.88 (s), 149.16 (d, J=3.2 Hz), 136.82 (d, J=12.1 Hz), 123.10 (s), 122.47 (s), 122.20 (s), 122.10 (s), 60.45 (s), 54.92 (s), 54.06 (s), 46.89 (s).

Example 7—Synthesis of N1-(prop-2-yn-1-yl)-N1,N2,N2-tris(pyridin-2-ylmethyl)ethane-1,2-diamine

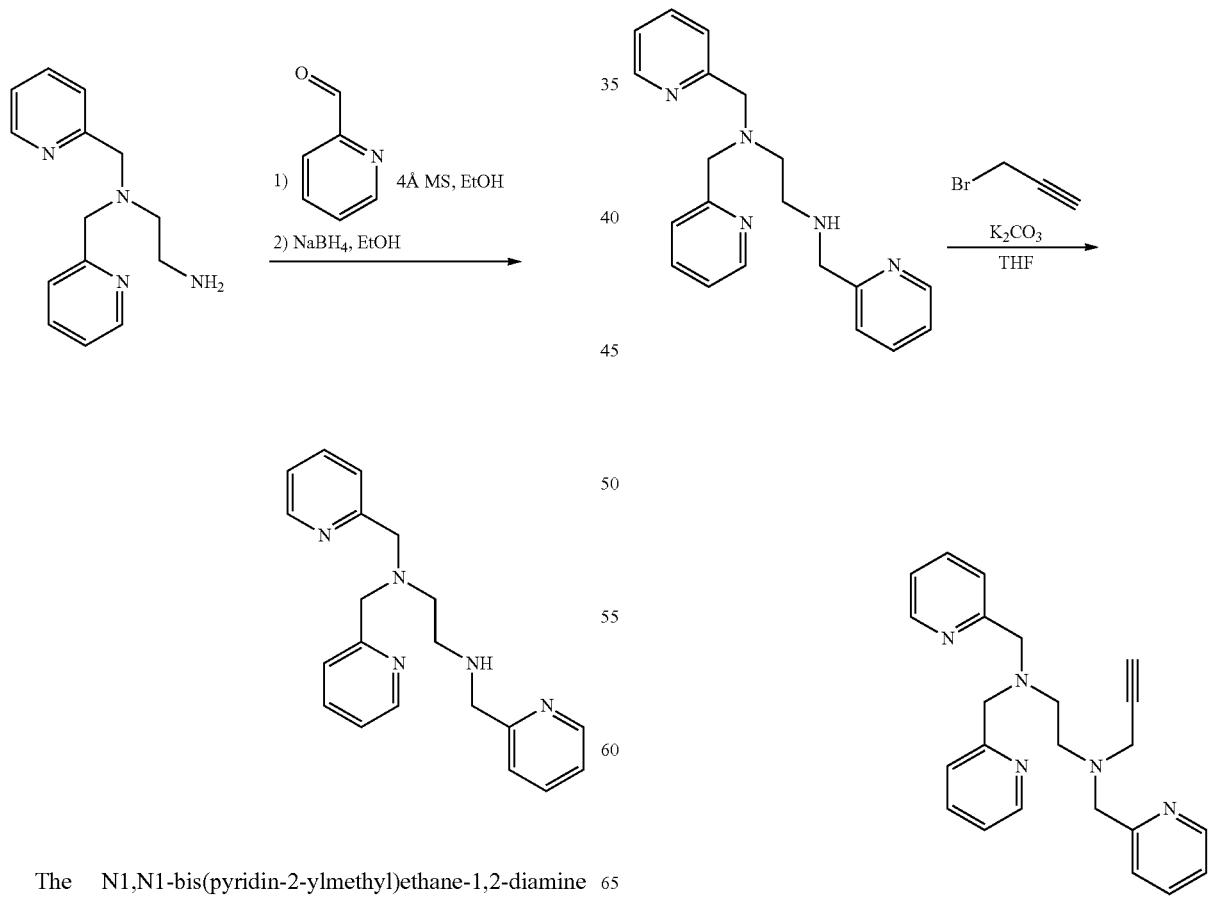

The N1,N1-bis(pyridin-2-ylmethyl)ethane-1,2-diamine prepared in Example 5 (500 mg, 2.06 mmol, 1.0 eq) was dissolved in absolute ethanol (10 mL), followed by about The N1,N1,N2-tris(pyridin-2-ylmethyl)ethane-1,2-diamine prepared in Example 6 (943 mg, 2.83 mmol, 1.0 eq) was dissolved in THF (7 mL), mixed with K₂CO₃ (1.56 g, 11.32 mmol, 4.0 eq) and cooled to 0° C. Propagyl bromide solution (80% in toluene) (3.15 µL, 2.83 mmol, 1.0 eq) was then added and the flask was sealed with a rubber septum. The mixture was stirred for 1 hour at 0° C. followed by 15 hours at room temperature. The mixture was then filtered through a pad of K₂CO₃ with the aid of DCM (100 mL). The liquid was concentrated in vacuo and purified by column chromatography on a neutral Al₂O₃ column using 50-100% DCM in EtOAc as eluent. This afforded the titled compound in 508 mg (48%) as an orange oil.

¹H NMR (400 MHz, DMSO-d6) δ 8.66-8.27 (m, 3H), 7.87-7.58 (m, 3H), 7.49 (d, J=7.8 Hz, 2H), 7.34 (d, J=7.8 Hz, 1H), 7.28-7.15 (m, 3H), 3.75 (s, 4H), 3.68 (s, 2H), 3.32 (d, J=2.1 Hz, 2H), 3.10 (t, J=2.1 Hz, 1H), 2.82-2.55 (m, 4H). ¹³C NMR (101 MHz, DMSO) δ 159.21, 158.83, 148.68, 136.39, 122.55, 122.52, 122.07, 122.01, 78.93, 75.72, 59.84, 59.45, 51.44, 50.55, 42.02.

Example 8—Synthesis of N-(4-(2-aminoethyl)phenyl)-2-((2-(bis(pyridin-2-yl methyl)amino)ethyl)(pyridin-2-ylmethyl)amino)acetamide

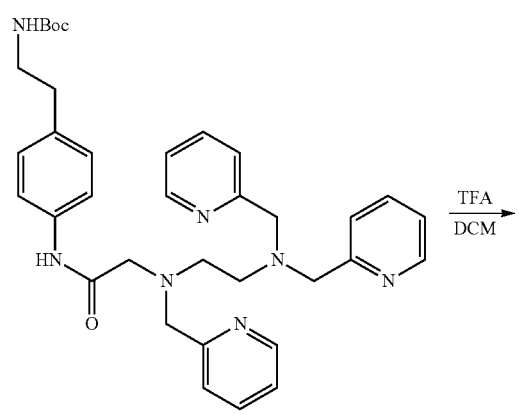

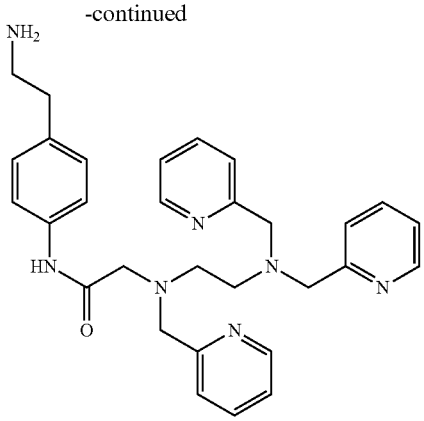

The carbamate prepared in Example 3 (135 mg, 0.22 mmol, 1.0 eq) was dissolved in DCM (10 mL) and cooled to 0° C. TFA (1.0 mL, 13.06 mmol, 59 eq) was added dropwise to the stirring solution over 5 minutes. The mixture was allowed to warm to room temperature and was then stirred an additional 2 hours at room temperature. The mixture was then concentrated under reduced pressure, dissolved in DCM (20 mL) and washed with 1M K₂CO₃ (3×20 mL). The organic phase was dried over K₂CO₃, filtered and concentrated under reduced pressure to give 70 mg (62%) of the title compound as a pale green oil.

¹H NMR (600 MHz, CDCl3) δ 10.39 (s, 1H), 8.54-8.51 (m, 1H), 8.50-8.46 (m, 2H), 7.63-7.59 (m, 2H), 7.59-7.52 (m, 3H), 7.41 (d, J=7.8 Hz, 2H), 7.17-7.07 (m, 6H), 3.75-3.72 (m, 6H), 3.29 (s, 2H), 2.95 (t, J=6.9 Hz, 2H), 2.79 (t, J=6.5 Hz, 2H), 2.74-2.67 (m, 4H), 2.16 (s, 2H). ¹³C NMR (151 MHz, CDCl3) δ 169.94 (s), 159.27 (s), 158.31 (s), 149.66 (s), 149.18 (s), 136.82 (s), 136.66 (s), 136.54 (s), 135.34 (s), 129.29 (s), 123.23 (s), 123.17 (s), 122.62 (s), 122.18 (s), 119.99 (s), 61.09 (s), 60.59 (s), 58.80 (s), 52.20 (s), 51.68 (s), 43.77 (s), 39.68 (s). HRMS: (TOF MS ES+): Calculated for C₃₀H₃₅N₇O [M+H]⁺: 510.2981, found: 510.2987.

Example 9—Synthesis of N1-(2-(2-(2-ethoxyethoxy)ethoxy)ethyl)-N1,N2,N2-tris(pyridin-2-ylmethyl)ethane-1,2-diamine

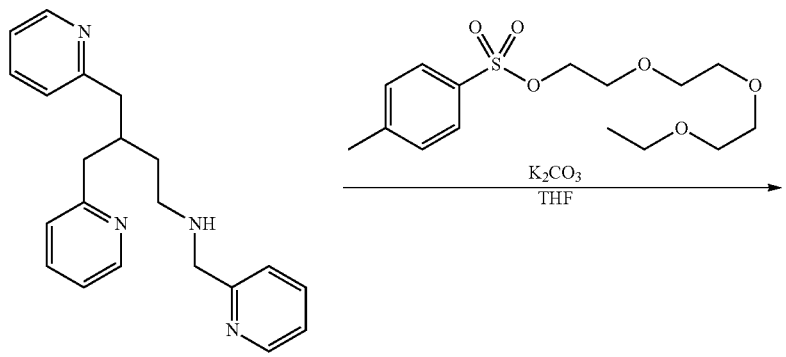

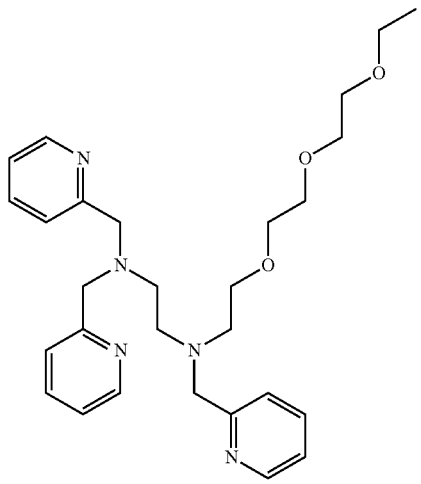

The amine prepared in Example 6 (568 mg, 1.70 mmol, 1.0 eq) was dissolved in THF (10 mL). K₂CO₃ (470 mg, 3.40 mmol, 2.0 eq) was added along with the tosylate (623 mg, 1.87 mmol, 1.1 eq). The mixture was heated to reflux and stirred for 16 hours. The mixture was then cooled to room temperature, concentrated under reduced pressure and purified by column chromatography on neutral alumina using 0-5% MeOH in DCM as eluent to afford 468 mg (56%) of the titled compound as a pale orange oil.

$^1$H NMR (400 MHz, DMSO-d6) δ 8.64-8.30 (m, 3H), 7.84-7.59 (m, 3H), 7.59-7.44 (m, 2H), 7.37 (d, J=7.8 Hz, 1H), 7.31-7.08 (m, 3H), 3.87-3.64 (m, 6H), 3.62-3.34 (m, 12H), 2.74-2.54 (m, 6H), 1.14-0.99 (m, 3H). $^{13}$C NMR (101 MHz, DMSO) δ 159.81, 159.40, 148.64, 148.49, 136.35, 136.17, 122.46, 121.96, 121.80, 69.81, 69.73, 69.67, 69.16, 68.95, 65.48, 60.58, 60.04, 53.49, 52.22, 51.63, 15.07. HRMS: (ES+): Calculated for $C_{28}H_{40}N_5O_3$ [M+H]$^+$: 493.3126. Found: 494.3127.

Example 10—Synthesis of tert-butyl N-(2-(bis(pyridin-2-ylmethyl)amino)ethyl)-N-(pyridin-2-ylmethyl)glycinate

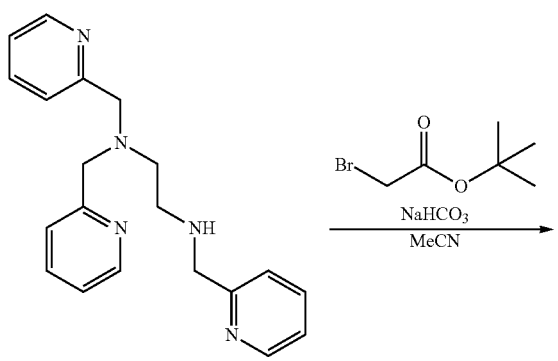

-continued

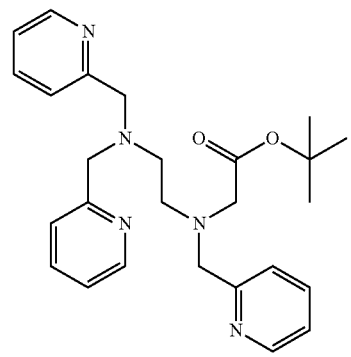

The amine prepared in Example 6 (1 g, 3 mmol, 1.0 eq) was dissolved in MeCN (10 mL) along with NaHCO₃ (0.5 g, 6 mmol, 2 eq). Tert-butyl bromoacetate (0.5 mL, 3.4 mmol, 1.1 eq) was then added and the mixture heated to reflux for 16 hours. The mixture was cooled to room temperature, mixed with Et₂O (10 mL) and filtered. The remaining solids were washed with Et₂O (2×10 mL) and DCM (10 mL). The combined organic phases were concentrated under reduced pressure to give a dark red oil. The crude material was purified using column chromatography by neutral alumina eluting with 1-2.5% MeOH in DCM. This gave 894 mg (67%) of the titled product as a red oil.

$^1$H NMR (400 MHz, CDCl₃) δ 8.55-8.43 (m, 3H), 7.60 (td, J=7.7, 1.8 Hz, 2H), 7.55 (td, J=7.7, 1.8 Hz, 1H), 7.49 (d, J=7.8 Hz, 2H), 7.44 (d, J=7.8 Hz, 1H), 7.16-7.05 (m, 3H), 3.89 (s, 2H), 3.80 (s, 4H), 3.28 (s, 2H), 2.88 (dd, J=8.1, 5.9 Hz, 2H), 2.77-2.65 (m, 2H), 1.42 (s, 9H). $^{13}$C NMR (101 MHz, CDCl₃) δ 170.82, 159.98, 149.13, 136.46, 123.00, 122.95, 121.99, 80.99, 60.91, 60.83, 56.42, 52.86, 52.23, 28.35. HRMS: (ES+): Calculated for $C_{26}H_{34}N_5O_2$ [M+H]$^+$: 448.2707. Found: 448.2706.

Example 11—Synthesis of ethyl N-(2-(bis(pyridin-2-ylmethyl)amino)ethyl)-N-(pyridin-2-ylmethyl) glycinate

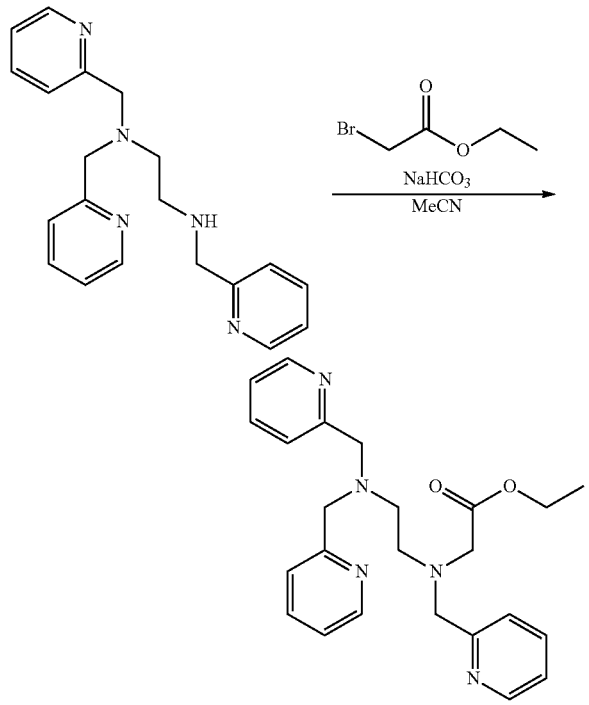

The amine prepared in Example 6 (2 g, 6 mmol, 1.0 eq) was dissolved in MeCN (20 mL) along with NaHCO$_3$ (1 g, 12 mmol, 2 eq). Ethyl bromoacetate (1 mL, 6.5 mmol, 1.1 eq) was then added and the mixture heated to reflux for 16 hours. The mixture was cooled to room temperature, mixed with Et$_2$O (10 mL) and filtered. The remaining solids were washed with Et$_2$O (2×10 mL) and DCM (10 mL). The combined organic phases were concentrated under reduced pressure to give a dark red oil. The crude material was purified using column chromatography by neutral alumina eluting with 1-5% MeOH in DCM. This gave 768 mg (31%) of the title product as a red oil.

$^1$H NMR (400 MHz, DMSO-d6) δ 8.65-8.30 (m, 3H), 7.84-7.58 (m, 3H), 7.46 (d, J=7.8 Hz, 2H), 7.36 (d, J=7.8 Hz, 1H), 7.28-7.12 (m, 2H), 4.03 (q, J=7.1 Hz, 2H), 3.79 (s, 2H), 3.71 (s, 4H), 3.35 (app. s, 2H), 2.77 (t, J=6.7 Hz, 2H), 2.57 (t, J=6.7 Hz, 2H), 1.14 (t, J=7.1 Hz, 3H). $^{13}$C NMR (101 MHz, DMSO) δ 170.84, 159.31, 159.29, 148.69, 148.61, 136.40, 136.36, 122.56, 122.53, 122.03, 59.91, 59.70, 54.64, 51.80, 51.21, 14.11. HRMS: (APCI+): Calculated for C$_{24}$H$_{30}$N$_5$O$_2$ [M+H]$^+$: 420.2394. Found: 420.2393.

Example 12—Synthesis of methyl 6-((bis(pyridin-2-ylmethyl)amino)methyl)nicotinate

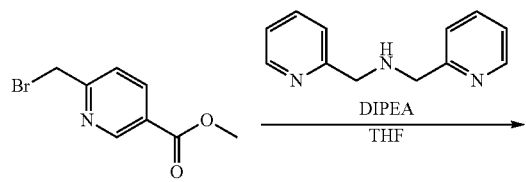

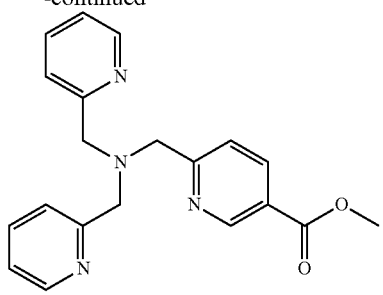

The nicotinate (1 g, 4.34 mmol, 1.0 eq) was suspended in THF (50 mL). Dipicolylamine (935 μL, 5.21 mmol, 1.2 eq) and DIPEA (1.23 mL, 7.38 mmol, 1.7 eq) was added to the pink mixture. A precipitate began forming on the side of the flask after about 2 hours. The reaction mixture was stirred at room temperature for an additional 22 hours before the slurry was filtered through a plug of celite with the aid of THF. The yellow filtrate was concentrated under reduced pressure to give a pale orange semisolid. This was suspended in Et$_2$O (50 mL) and filtered through celite with the aid of an additional 25 mL Et$_2$O. The filtrate was concentrated under reduced pressure to about 30 mL where a white precipitate began to form. The flask was placed in the freezer (−20° C.) to facilitate further precipitation. The crystals formed were filtered off to give 860 mg (57%) the title compound as a white powder. $^1$H NMR and $^{13}$C NMR were in accordance with reported data. See K. J. Humphreys, K. D. Karlin, S. E. Rokita, *J. Am. Chem. Soc.* 2002, 124, 6009-6019.

Example 13—Synthesis of 6-((bis(pyridin-2-ylmethyl)amino)methyl)nicotinic acid

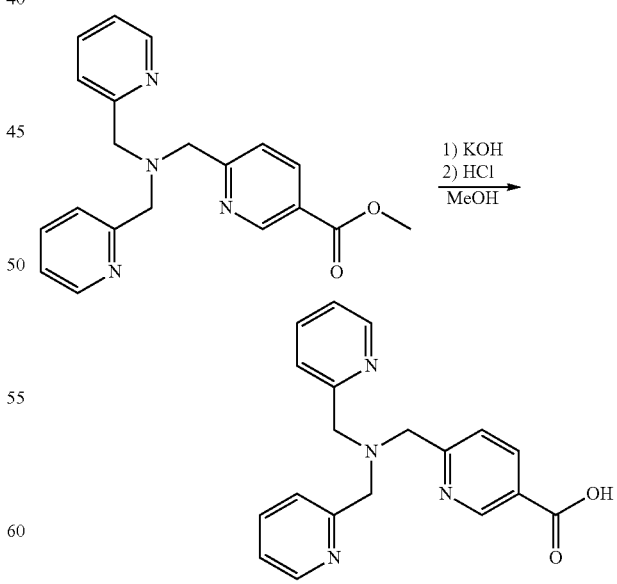

The ester prepared in Example 12 (200 mg) was dissolved in MeOH (0.65 mL) and 2M KOH solution (0.45 mL) was added. The mixture was stirred for 2 hours at room temperature before 1M HCl (0.97 mL) was added and the

Example 14—Synthesis of (6-((bis(pyridin-2-ylmethyl)amino)methyl)pyridin-3-yl) methanol

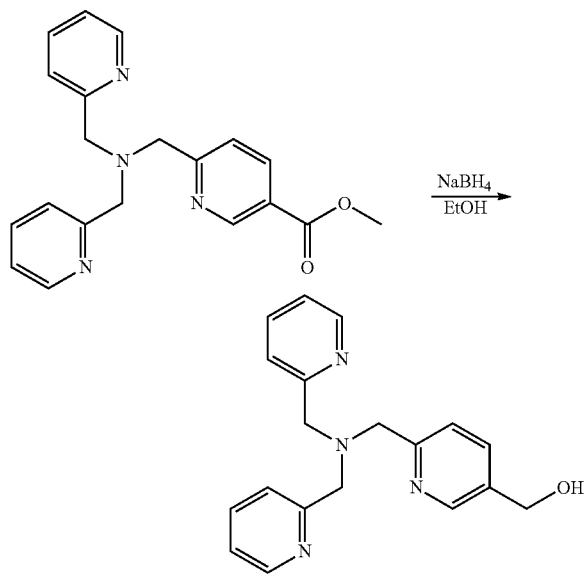

The ester prepared in Example 12 (330 mg, 0.95 mmol, 1.0 eq) was dissolved in absolute ethanol (10 mL) and placed under argon. NaBH$_4$ pellets (250 mg, 6.95 mmol, 7.0 eq) was added to the stirring mixture and the slurry was heated to 50° C. for 48 hours. The mixture was then quenched by the addition of NH$_4$Cl solution and concentrated under reduced pressure to give a white sticky solid. The crude material was suspended in 1M K$_2$CO$_3$ (25 mL) and extracted with DCM (3×25 mL). The combined organic phases were dried over K$_2$CO$_3$, filtered and concentrated under reduced pressure to give 221 mg (69%) of the title product as a pale yellow oil. NMR was in accordance with published data. See K. J. Humphreys, K. D. Karlin, S. E. Rokita, *J. Am. Chem. Soc.* 2002, 124, 6009-6019.

mixture was concentrated under reduced pressure to a sticky solid. The crude material was suspended in MeOH (1.5 mL) and filtered first through a paper filter and then through a syringe filter. The filtrate was concentrated under reduced pressure to give 197 mg (>99%) of the titled compound as a foamy white solid. NMR was in accordance with the reported data (Natsuho Yamamoto et al, *J. Med. Chem.*, (2012), 11013-11021.

Example 15—Synthesis of 1-(5-(chloromethyl)pyridin-2-yl)-N,N-bis(pyridin-2-yl methyl)methanamine

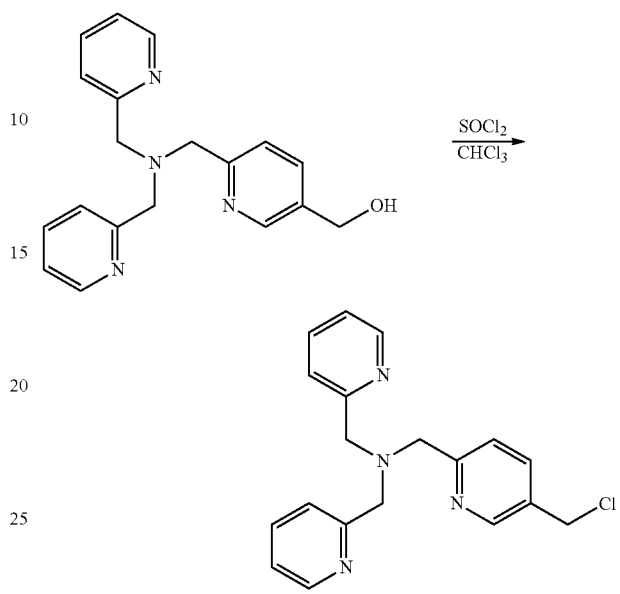

The alcohol prepared in Example 14 (500 mg, 1.5 mmol, 1.0 eq) was dissolved in CHCl$_3$ (15 mL) and cooled to 0° C. before SOCl$_2$ (1 mL, 13.8 mmol, 9 eq) was added dropwise. The mixture was stirred for 30 minutes at 0° C. before it was warmed to room temperature and stirred for an additional 16 hours. The solution was then concentrated under reduced pressure to give a dark green paste. The crude material was dissolved in DCM (25 mL) and washed with 1M K$_2$CO$_3$ (3×25 mL). The organic phase was dried over K$_2$CO$_3$, filtered and concentrated under reduced pressure. The material was further purified by column chromatography using neutral Al$_2$O$_3$ as stationary phase and EtOAc as mobile phase to give 395 mg (74%) the title compound as a pale yellow solid. NMR was in accordance with published data. See K. J. Humphreys, K. D. Karlin, S. E. Rokita, *J. Am. Chem. Soc.* 2002, 124, 6009-6019.

Example 16—Synthesis of tert-butyl 4-(6-((bis(pyridin-2-ylmethyl)amino)methyl) nicotinamido)phenethylcarbamate

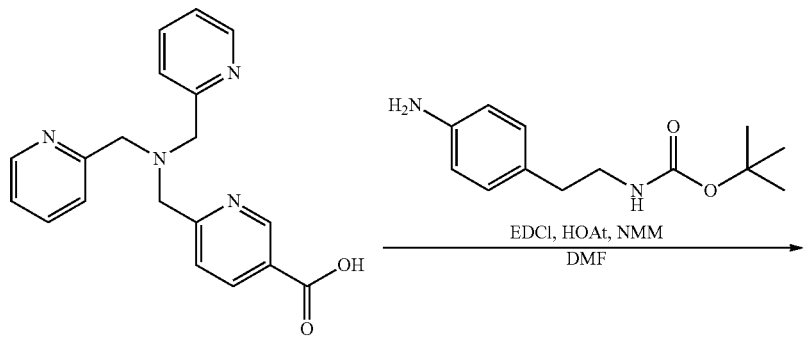

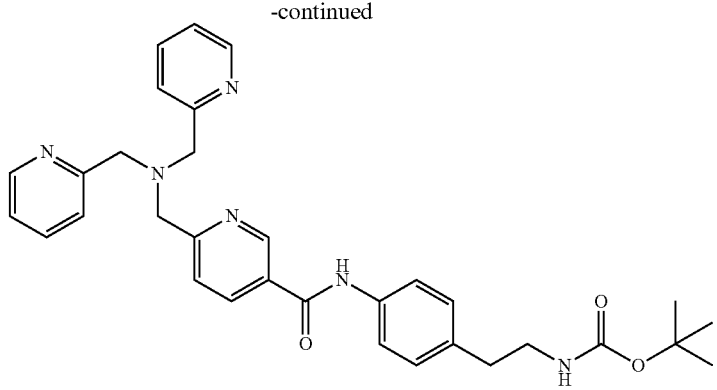

The 6-((bis(pyridin-2-ylmethyl)amino)methyl)nicotinic acid prepared in Example 13 was dissolved in 20 mL dry DMF at room temperature and filtered into a 50 mL round bottomed flask prior to reaction to remove the insoluble salts. To this solution was added tert-butyl 4-aminophenethylcarbamate (1.76 g, 7.45 mmol, 1.5 eq.), followed by EDCl (1.428 g, 7.45 mmol, 1.5 eq.), HOAt (1.014 g, 7.45 mmol, 1.5 eq.) and NMM (0.821 mL, 7.45 mmol, 1.5 eq.). The reaction mixture was stirred at room temperature for 16 h and then concentrated under reduced pressure. The residual crude mixture was dissolved in 100 mL CHCl$_3$, transferred into a separation funnel and washed with 100 mL sat. aq. K$_2$CO$_3$ solution and 100 mL brine. The organic phase was separated, dried oved Na$_2$SO$_4$, filtered and concentrated under reduced pressure. Purification of the product was performed by column chromatography on neutral Al$_2$O$_3$ using 1% MeOH in DCM giving the product with minor impurities, followed by C18-SPE using gradient elution (10% MeOH to 90% MeOH in H$_2$O) affording 1.697 g (3.07 mmol, 62%) of the product as a yellow oil.

$^1$H NMR (300 MHz, MeOH) δ 8.96 (d, J=1.8 Hz, 1H), 8.46-8.39 (m, 2H), 8.23 (dd, J=8.2, 2.3 Hz, 1H), 7.76 (td, J=7.7, 1.5 Hz, 3H), 7.62 (dd, J=13.5, 8.1 Hz, 4H), 7.24 (ddd, J=7.3, 5.0, 1.1 Hz, 2H), 7.17 (d, J=8.5 Hz, 2H), 3.89 (s, 2H), 3.85 (s, 4H), 3.24 (t, J=7.3 Hz, 2H), 2.72 (t, J=7.3 Hz, 2H), 1.40 (s, 9H). $^{13}$C NMR (101 MHz, MeOD) δ 166.10, 163.40, 159.85, 158.28, 149.56, 148.92, 138.55, 137.76, 137.41, 137.15, 130.88, 130.16, 124.83, 124.14, 123.81, 122.23, 79.86, 61.10, 60.84, 42.95, 36.59, 28.79. APCI-HRMS e/z calc. for C$_{32}$H$_{36}$N$_6$O$_3$: 552.2849, found: 553.2920 [M+H].

Example 17—Synthesis of N-(4-(2-aminoethyl) phenyl)-6-((bis(pyridin-2-ylmethyl) amino)methyl) nicotinamide

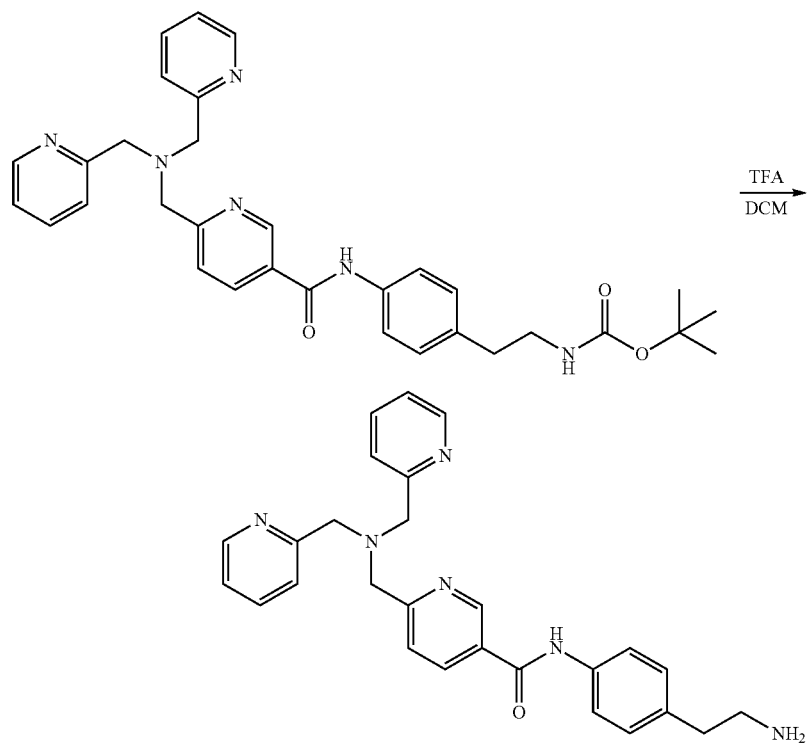

The tert-butyl 4-(6-((bis(pyridin-2-ylmethyl)amino) methyl)-nicotinamido) phenethylcarbamate (1.697 g, 3.07 mmol, 1 eq.) prepared in Example 16 was dissolved in 10 mL DCM at room temperature. To this solution was added TFA (5 mL) and the mixture stirred at room temperature until TLC (Al$_2$O$_3$, 5% MeOH in DCM) or NMR indicated full conversion. The mixture was then concentrated under reduced pressure, the residue dissolved in a mixture of CHCl$_3$/dest. H$_2$O/sat. aq. K$_2$CO$_3$ (100 mL/10 mL/100 mL) and transferred into a separation funnel. The organic phase was separated, the aq. phase extracted twice with 50 mL CHCl$_3$ and the combined organics washed with 100 mL brine, dried over K$_2$CO$_3$/Na$_2$SO$_4$, filtered and concentrated under reduced pressure to afford N-(4-(2-aminoethyl)phenyl)-6-((bis(pyridin-2-ylmethyl)amino)methyl)nicotinamide in quantitative yield.

$^1$H NMR (300 MHz, MeOH) δ 8.97 (d, J=1.7 Hz, 1H), 8.45 (ddd, J=5.0, 1.7, 0.9 Hz, 2H), 8.26 (dd, J=8.2, 2.3 Hz, 1H), 7.80 (td, J=7.6, 1.6 Hz, 3H), 7.68 (d, J=7.8 Hz, 2H), 7.62 (d, J=8.5 Hz, 2H), 7.28 (ddd, J=7.4, 5.0, 1.2 Hz, 2H), 7.23 (d, J=8.5 Hz, 2H), 3.94 (s, J=4.3 Hz, 2H), 3.90 (s, 4H), 2.88 (t, J=6.7 Hz, 2H), 2.76 (t, J=6.9 Hz, 2H). $^{13}$C NMR (101 MHz, MeOD) δ 163.55, 159.96, 149.62, 148.93, 138.69, 137.51, 131.02, 130.19, 124.99, 124.32, 123.92, 122.54, 79.46, 61.24, 60.96, 44.03, 39.22. APCI-HRMS e/z calc. for C$_{27}$H$_{28}$N$_6$O: 452.2325, found: 453.2396 [M+H].

Example 18—Synthesis of methyl 2-(4-aminophenyl)acetate hydrochloride

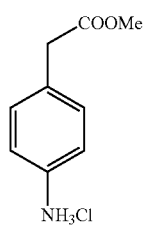

2-(4-aminophenyl)acetic acid (5.176 g, 34.2 mmol, 1 eq.) was suspended in 100 mL methanol and cooled to 0° C. in an ice bath. To this mixture SOCl$_2$ (2.89 mL, 41.07 mmol, 1.2 eq.) was added dropwise over a period of 10 minutes. The mixture was stirred at 0° C. for another 30 minutes, 1 h at room temperature and then refluxed for 14 h. The reaction mixture was then concentrated under reduced pressure to afford the title compound as a pale brown solid in quantitative yield that was taken to the next step without further purification. $^1$H NMR was in accordance with published data. See Threadgill et al., Bioorganic & Medicinal Chemistry, 2003, 11, 4189-4206.

Example 19—Synthesis of methyl 2-(4-(2-bromoacetamido)phenyl)acetate or methyl 2-(4-(2-chloroacetamido)phenyl)acetate

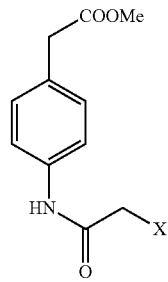

X = Cl or Br

Methyl 2-(4-aminophenyl)acetate hydrochloride prepared in Example 18 (6.89 g, 34.2 mmol, 1 eq.) was suspended in 100 mL DCM and cooled to 0° C. in an ice bath. A solution of DMAP (7.51 g, 61.56 mmol, 1.8 eq.) and NMM (3.75 mL, 34.2 mmol, 1 eq.) in 50 mL DCM was added dropwise over 30 minutes via a dropping funnel, followed by dropwise addition of bromoacetyl bromide or chloroacetyl chloride (1.8 eq.) over 30 minutes at 0° C. The mixture was stirred at 0° C. for another 30 minutes and at room temperature for 12 h. The mixture was then washed with 0.1 M HCl (3×50 mL) and brine (50 mL) and the organic phase dried over anhydrous MgSO$_4$, filtered and concentrated under reduced pressure. The product was isolated via column chromatography on SiO$_2$ using isocratic elution with a 3:1 mixture of n-heptane and EtOAc to afford methyl 2-(4-(2-bromoacetamido)phenyl)acetate or methyl 2-(4-(2-chloroacetamido) phenyl)acetate in 82% (Br) or 73% (Cl) yield as white solids which could be used directly in the next step. Optional additional purification could be obtained by recrystallization from EtOAc.

Example 20—Synthesis of methyl 2-(4-(2-((2-(bis(pyridin-2-yl methyl)amino)ethyl)(pyridin-2-ylmethyl)amino)acetamido)phenyl)acetate Example 21—Synthesis of 2-(4-(2-((2-(bis(pyridin-2-ylmethyl)amino)ethyl)(pyridin-2-yl methyl)amino)acetamido)phenyl)acetic acid

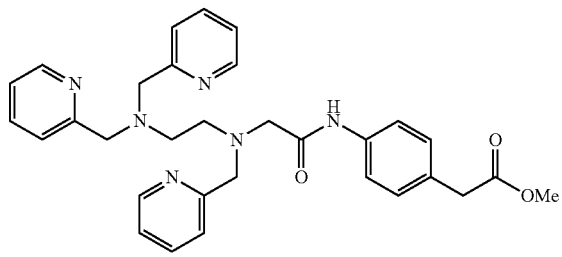 [SMILES: COC(=O)Cc1ccc(NC(=O)CN(CCN(Cc2ccccn2)Cc2ccccn2)Cc2ccccn2)cc1]

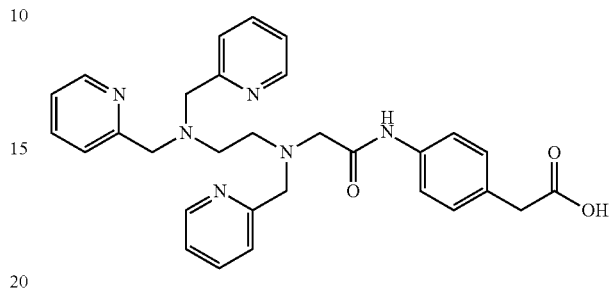

N1,N1,N2-tris(pyridin-2-ylmethyl)ethane-1,2-diamine described in Example 6 (1 eq.) was dissolved in 50 mL CH$_3$CN at room temperature. To this solution was added K$_2$CO$_3$ (4 eq.) and KI (0.6 eq.), followed by methyl 2-(4-(2-bromoacetamido)phenyl)acetate or methyl 2-(4-(2-chloroacetamido)phenyl)acetate prepared in example 18 (1.1 eq.). The mixture was heated to reflux for 16 h until TLC indicated full conversion of the amine. The mixture was then passed through a pad of celite using CH$_3$CN as eluent and concentrated under reduced pressure. The product was isolated via column chromatography on neutral Al$_2$O$_3$ using 1-2% MeOH in DCM as eluent to afford the titled compound in 76% yield as a brown oil. $^1$H NMR (400 MHz, DMSO-d6) δ 10.29 (s, 1H), 8.52 (dd, J=4.8, 0.8 Hz, 1H), 8.44 (dd, J=4.8, 0.9 Hz, 2H), 7.71 (td, J=7.6, 1.8 Hz, 1H), 7.64 (td, J=7.6, 1.8 Hz, 2H), 7.56 (d, J=8.5 Hz, 2H), 7.41 (d, J=7.8 Hz, 2H), 7.33 (d, J=7.7 Hz, 1H), 7.29-7.23 (m, 1H), 7.22-7.16 (m, 4H), 3.75 (s, 2H), 3.69 (s, 4H), 3.62 (s, 2H), 3.61 (s, 3H), 3.28 (s, 2H), 2.76 (t, J=6.4 Hz, 2H), 2.61 (t, J=6.4 Hz, 2H). $^{13}$C NMR (101 MHz, DMSO-d6) δ 171.74, 169.46, 158.98, 158.53, 149.03, 148.72, 137.41, 136.66, 136.35, 129.64, 129.17, 123.07, 122.75, 122.39, 122.05, 119.11, 60.16, 59.65, 58.15, 51.74, 51.65, 51.14, 30.67.

Methyl 2-(4-(2-((2-(bis(pyridin-2-ylmethyl)amino)ethyl)(pyridin-2-ylmethyl)amino)acetamido)phenyl)acetate prepared in example 20 (922 mg, 1.7 mmol, 1 eq.) was dissolved in 10 mL THF at 0° C. To this solution was added LiOH.H$_2$O (144 mg, 3.4 mmol, 2.0 eq.) in 7 mL dest. H$_2$O and the solution stirred at 0° C. until TLC indicated full conversion (Al$_2$O$_3$, 5% MeOH in DCM). The mixture was then concentrated under reduced pressure to remove the THF, and the residual aq. solution adjusted to pH 7 with 0.5 M HCl. The solvent was removed under reduced pressure to afford the product in quantitative yield.

$^1$H NMR (600 MHz, DMSO) δ 10.20 (s, 1H), 8.51 (dd, J=4.7, 0.7 Hz, 1H), 8.44 (dd, J=4.8, 0.8 Hz, 2H), 7.71 (td, J=7.6, 1.8 Hz, 1H), 7.65 (td, J=7.6, 1.8 Hz, 2H), 7.45 (t, J=9.3 Hz, 2H), 7.42 (t, J=9.4 Hz, 2H), 7.33 (d, J=7.7 Hz, 1H), 7.27-7.23 (m, 1H), 7.23-7.18 (m, 2H), 7.15 (d, J=8.4 Hz, 2H), 3.74 (s, 2H), 3.68 (s, 4H), 3.26 (s, 2H), 3.22 (s, 2H), 2.75 (t, J=6.5 Hz, 2H), 2.60 (t, J=6.5 Hz, 2H). $^{13}$C NMR (151 MHz, DMSO) δ 174.40, 169.17, 158.98, 158.57, 149.04, 148.76, 136.69, 136.45, 136.00, 134.36, 129.43, 123.09, 122.79, 122.43, 122.14, 118.65, 60.20, 59.65, 58.18, 51.76, 51.13, 44.97.

Example 22a—Synthesis of (3R,4R,5S,6R)-6-(acetoxymethyl)-3-(2-(4-(2-((2-(bis(pyridin-2-ylmethyl)amino)ethyl)(pyridin-2-ylmethyl)amino)acetamido)phenyl)acetamido) tetrahydro-2H-pyran-2,4,5-triyl triacetate

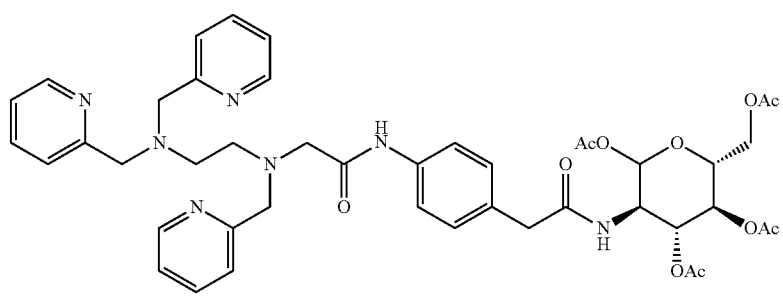 [SMILES: CC(=O)OC[C@H]1OC(OC(C)=O)[C@H](NC(=O)Cc2ccc(NC(=O)CN(CCN(Cc3ccccn3)Cc3ccccn3)Cc3ccccn3)cc2)[C@@H](OC(C)=O)[C@@H]1OC(C)=O]

The acid prepared in Example 21 (220.8 mg, 0.442 mmol, 1 eq.) was suspended in 5 mL dry CH$_3$CN under N$_2$ atmosphere cooled to 0° C. in ice bath. HATU (168 mg, 0.442 mmol, 1.05 eq.), 1,3,4,6-tetra-O-acetyl-β-D-glucosamine hydrochloride (170 mg, 0.442 mmol, 1.05 eq.) and NMM (139 μL, 3 eq.) was then added to the mixture. The mixture was stirred at 0° C. for 1 h, then at room temperature for 16 h and was concentrated under reduced pressure. The residue was dissolved in a minimum amount of 5% MeOH in DCM and passed through a plug of neutral Al$_2$O$_3$ eluting with 10% MeOH in DCM. The resulting solution was concentrated under reduced pressure and the product isolated via column chromatography on neutral Al$_2$O$_3$ using 1-5% MeOH in DCM as eluent to afford 168.8 mg (48%) of the product as a yellow foamy semi solid.

$^1$H NMR (400 MHz, CDCl$_3$) δ 10.53 (s, 1H), 8.47 (dd, J=5.0, 1.6 Hz, 1H), 8.44 (dd, J=4.9, 0.8 Hz, 2H), 7.62 (d, J=8.5 Hz, 2H), 7.53 (ddd, J=15.9, 7.9, 1.8 Hz, 3H), 7.36 (d, J=7.8 Hz, 2H), 7.08 (ddd, J=8.4, 7.4, 4.7 Hz, 6H), 6.26 (d, J=9.3 Hz, 1H), 5.68 (d, J=8.8 Hz, 1H), 5.16 (dd, J=10.5, 9.4 Hz, 1H), 5.02 (t, J=9.6 Hz, 1H), 4.24-4.11 (m, 2H), 4.04 (dd, J=12.5, 2.2 Hz, 1H), 3.76-3.69 (m, 7H), 3.38 (s, 2H), 3.29 (s, J=10.6 Hz, 2H), 2.81-2.73 (m, 2H), 2.73-2.63 (m, 2H), 2.01 (s, 3H), 1.95 (s, 3H), 1.92 (s, 3H), 1.85 (s, 3H). $^{13}$C NMR (101 MHz, CDCl$_3$) δ 171.39, 170.66, 170.64, 170.04, 169.32, 169.23, 158.93, 158.07, 149.52, 149.09, 137.76, 136.63, 136.49, 129.96, 129.50, 123.17, 122.60, 122.17, 120.17, 92.33, 72.77, 72.24, 68.09, 61.74, 60.82, 60.33, 58.70, 52.99, 51.96, 51.44, 43.27, 20.74, 20.71, 20.57, 20.53. APCI-HRMS e/z calc. for C$_{44}$H$_{51}$N$_7$O$_{11}$: 853.3647, found 854.3726 [M+H].

Example 22b—Synthesis of 2-((2-(bis(pyridin-2-ylmethyl)amino)ethyl)(pyridin-2-ylmethyl)amino)-N-(4-(2-oxo-2-(((3R,4R,5S,6R)-2,4,5-trihydroxy-6-(hydroxymethyl)tetrahydro-2H-pyran-3-yl)amino)ethyl)phenyl)acetamide

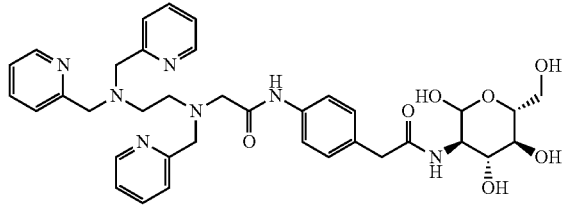 [SMILES: O=C(CN(CCN(Cc1ccccn1)Cc1ccccn1)Cc1ccccn1)Nc1ccc(CC(=O)N[C@H]2C(O)O[C@H](CO)[C@@H](O)[C@@H]2O)cc1]

The title compound can be obtained from Example 22a as described in Example 81.

Example 23—Synthesis of (R)-2-((2-(bis(pyridin-2-ylmethyl)amino)ethyl)(pyridin-2-yl methyl)amino)-N-(4-(2-(2,3-dihydroxypropylamino)-2-oxoethyl)phenyl)acetamide

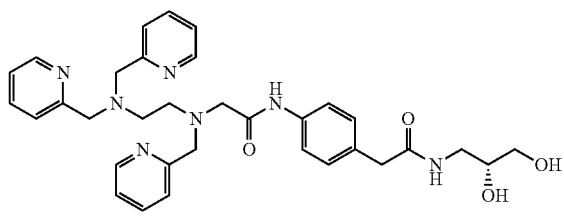 [SMILES: O=C(Cc1ccc(NC(=O)CN(CCN(Cc2ccccn2)Cc2ccccn2)Cc2ccccn2)cc1)NC[C@@H](O)CO]

The acid prepared in Example 21 (124.3 mg, 0.237 mmol, 1 eq.) was dissolved in 2 mL dry DMF under N$_2$ atmosphere at room temperature. (R)-3-Amino-1,2-propanediol (32 mg, 0.355 mmol, 1.5 eq.), EDCl (68 mg, 0.355 mmol, 1.5 eq.), HOAt (48 mg, 0.355 mmol, 1.5 eq.) and NMM (39 μL, 1.5 eq.) were then added and the mixture was stirred at room temperature for 16 h. The reaction mixture was concentrated under reduced pressure and the product isolated via chromatography on reversed phase silica-C18 using 20-75% MeOH in H$_2$O affording 61 mg (50%) of the title product as a yellow glassy oil.

$^1$H NMR (400 MHz, MeOD) δ 8.51 (d, J=4.8 Hz, 1H), 8.43 (d, J=4.9 Hz, 2H), 7.75 (t, J=7.7 Hz, 1H), 7.70 (t, J=7.7 Hz, 2H), 7.56 (dd, J=19.5, 8.1 Hz, 4H), 7.39 (d, J=7.7 Hz, 1H), 7.34-7.22 (m, 5H), 3.81 (s, 2H), 3.77 (s, 4H), 3.75-3.70 (m, 1H), 3.56 (s, 2H), 3.54-3.48 (m, 2H), 3.42 (dd, J=13.8, 4.8 Hz, 1H), 3.33 (s, 2H), 3.26 (dd, J=13.8, 6.7 Hz, 1H), 2.83 (t, J=6.4 Hz, 2H), 2.73 (t, J=6.4 Hz, 2H). $^{13}$C NMR (101 MHz, MeOD) δ 174.60, 172.23, 160.20, 159.47, 150.20, 149.50, 138.58, 138.53, 138.15, 132.84, 130.57, 125.00, 124.88, 124.02, 123.79, 121.38, 71.96, 65.05, 62.08, 61.27, 59.78, 53.72, 53.10, 43.56, 43.26. APCI-HRMS e/z calc. for C$_{33}$H$_{39}$N$_7$O$_4$: 597.3064, found 598.3135 [M+H].

Example 24—Synthesis of 2-((2-(bis(pyridin-2-ylmethyl)amino)ethyl)(pyridin-2-yl methyl)amino)-N-(4-(2-(1,3-dihydroxy-2-(hydroxymethyl)propan-2-ylamino)-2-oxoethyl)phenyl)acetamide

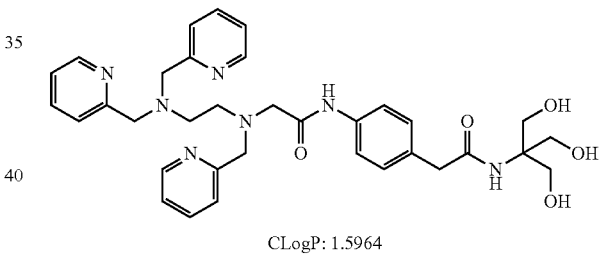

CLogP: 1.5964

The acid prepared in Example 21 (185.4 mg, 0.354 mmol, 1 eq.) was dissolved in 3 mL dry DMF under N$_2$ atmosphere at room temperature. Tris-(hydroxymethyl)-aminomethane (Trizma base, 64 mg, 0.53 mmol, 1.5 eq.), EDCl (101 mg, 0.53 mmol, 1.5 eq.), HOAt (72 mg, 0.53 mmol, 1 eq.) and NMM (58 μL, 1.5 eq.) were then added and mixture was stirred at room temperature for 16 h. The reaction mixture was concentrated under reduced pressure and the product isolated via chromatography on reversed phase silica-C18 using 10-90% MeOH in H$_2$O affording 59.2 mg (27%) of the title product as a yellow glassy oil.

$^1$H NMR (400 MHz, MeOD) δ 8.49 (d, J=4.4 Hz, 1H), 8.42 (d, J=4.5 Hz, 2H), 7.71 (dt, J=20.2, 7.6 Hz, 3H), 7.59 (d, J=7.7 Hz, 2H), 7.52 (d, J=7.8 Hz, 2H), 7.37 (d, J=7.7 Hz, 1H), 7.32 (d, J=7.9 Hz, 2H), 7.26 (dd, J=13.2, 7.0 Hz, 3H), 3.80 (s, 2H), 3.77 (s, 6H), 3.75 (s, 4H), 3.61 (s, 2H), 3.32 (s, 2H), 2.82 (t, J=6.1 Hz, 2H), 2.71 (t, J=6.1 Hz, 2H). $^{13}$C NMR (101 MHz, MeOD) δ 175.00, 172.18, 160.17, 159.43, 150.20, 149.51, 138.56, 138.49, 138.18, 132.73, 130.73, 124.97, 124.86, 123.99, 123.77, 121.36, 63.56, 62.54, 62.06, 61.23, 59.73, 53.65, 53.06, 49.00, 43.74. APCI-HRMS e/z calc. for C$_{34}$H$_{41}$N$_7$O$_5$: 627.3169, found 628.3236 [M+H].

Example 25—Synthesis of 2-(4-(2-((2-(bis(pyridin-2-ylmethyl)amino)ethyl)(pyridin-2-yl methyl)amino)acetamido)phenyl)-N-methyl-N-(2,3,4,5,6-pentahydroxyhexyl)acetamide

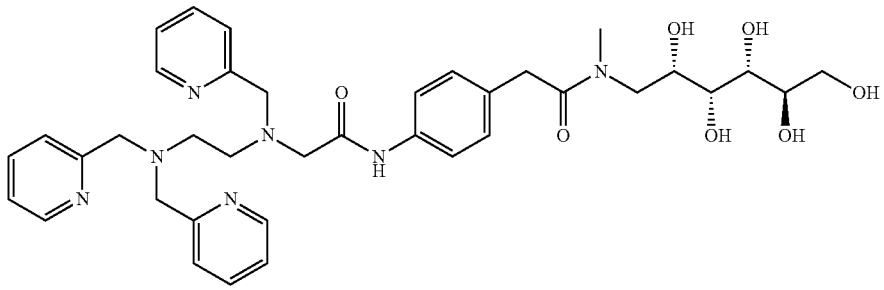 [SMILES: CN(C[C@H](O)[C@@H](O)[C@H](O)[C@H](O)CO)C(=O)Cc1ccc(NC(=O)CN(CCN(Cc2ccccn2)Cc2ccccn2)Cc2ccccn2)cc1]

The acid prepared in Example 21 (203.2 mg, 0.387 mmol, 1 eq.) was dissolved in 2 mL dry DMF under N₂ atmosphere at room temperature. N-Methyl-D-glucamine (113 mg, 0.581 mmol, 1.5 eq.), EDCl (111 mg, 0.581 mmol, 1.5 eq.), HOAt (79 mg, 0.581 mmol, 1.5 eq.) and NMM (64 μL, 1.5 eq.) was then added and the mixture stirred at room temperature for 30 min, then heated to 50° C. for 12 h. The reaction mixture was concentrated under reduced pressure and the product isolated via chromatography on reverse phase silica-C18 using 10-90% MeOH in H₂O affording 109.6 mg (40%) of the product as a yellow oil. The product appears as a syn/anti mixture regarding the amide bond.
¹H NMR (600 MHz, MeOD) δ 8.48-8.45 (m, 1H), 8.39 (d, J=4.1 Hz, 2H), 7.71 (td, J=7.7, 1.3 Hz, 1H), 7.67 (tt, J=7.7, 2.1 Hz, 2H), 7.55 (dd, J=11.3, 8.5 Hz, 2H), 7.50 (d, J=8.0 Hz, 2H), 7.35 (d, J=7.8 Hz, 1H), 7.24 (dd, J=14.8, 8.0 Hz, 5H), 4.05-3.98 (m, 1H), 3.94-3.78 (m, 2H), 3.78-3.74 (m, 4H), 3.72 (s, 5H), 3.70-3.60 (m, 4H), 3.44 (ddd, J=8.0, 5.2, 1.4 Hz, 1H), 3.28 (d, J=3.1 Hz, 2H), 3.15, 3.00 (2×s, 3H), 2.79 (t, J=6.5 Hz, 2H), 2.68 (t, J=6.5 Hz, 2H). ¹³C NMR (201 MHz, MeOD) δ 174.65, 174.54, 172.19, 172.16, 160.14, 159.46, 150.23, 149.54, 138.61, 138.54, 138.03, 137.93, 132.89, 132.22, 130.54, 130.45, 125.00, 124.89, 124.02, 123.81, 121.45, 121.34, 74.09, 73.74, 73.07, 73.01, 72.82, 72.32, 71.54, 71.24, 64.77, 64.74, 62.03, 61.20, 59.69, 54.12, 53.59, 53.03, 52.72, 49.00, 41.07, 40.65, 38.31, 34.81. APCI-HRMS e/z calc. for C₃₇H₄₇N₇O₇: 701.3537, found 702.3607 [M+H]

Example 26—Synthesis of 6-((bis(pyridin-2-ylmethyl)amino)methyl)-N-methyl-N-((2S,3R,4R,5R)-2,3,4,5,6-pentahydroxyhexyl)nicotinamide

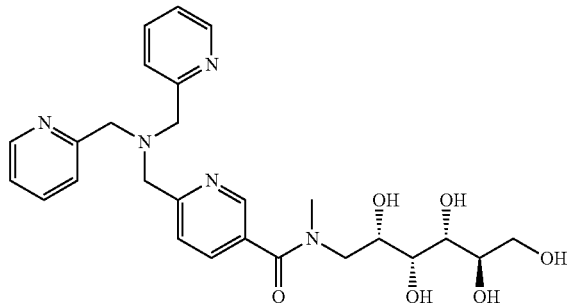 [SMILES: CN(C[C@H](O)[C@@H](O)[C@H](O)[C@H](O)CO)C(=O)c1ccc(CN(Cc2ccccn2)Cc2ccccn2)nc1]

The 6-((bis(pyridin-2-ylmethyl)amino)methyl)nicotinic acid prepared in Example 13 (194 mg, 0.58 mmol, 1 eq.) was dissolved in 5 mL dry DMF at room temperature. N-Methyl-D-glucamine (170 mg, 0.87 mmol, 1.5 eq.), EDCl (167 mg, 0.87 mmol, 1.5 eq.), HOAt (118 mg, 0.87 mmol, 1.5 eq.) and NMM (96 μL, 0.87 mmol, 1.5 eq.) was then added. Upon addition of the HOAt the mixture turned from colorless to yellow. The mixture was heated to 50° C. for 16 h with stirring and then concentrated under reduced pressure. The product was isolated via chromatography on reverse phase silica-C18 using 10-90% MeOH in H₂O affording 99 mg (33%) of product as a yellow glassy oil. The product appears as a syn/anti mixture regarding the amide bond.
¹H NMR (300 MHz, MeOH) δ 8.57 (d, J=11.3 Hz, 1H), 8.44 (d, J=4.7 Hz, 2H), 7.89 (dd, J=20.9, 7.9 Hz, 1H), 7.79 (t, J=7.7 Hz, 2H), 7.72 (d, J=7.6 Hz, 1H), 7.67 (d, J=7.9 Hz, 2H), 7.34-7.22 (m, 2H), 4.08 (dt, J=18.6, 6.6 Hz, 1H), 3.87 (s, J=3.1 Hz, 6H), 3.84-3.46 (m, 7H), 3.14, 3.07 (2×s, 3H). ¹³C NMR (101 MHz, MeOD) δ 170.57, 169.95, 160.31, 159.73, 158.51, 148.12, 147.03, 146.52, 137.21, 136.23, 135.55, 131.20, 130.93, 123.50, 122.84, 122.60, 122.43, 72.52, 72.02, 71.59, 71.51, 70.97, 70.24, 70.10, 69.65, 63.27, 59.88, 59.73, 59.60, 59.43, 53.78, 51.00, 38.54, 32.37. APCI-HRMS e/z calc. for C₂₆H₃₃N₅O₆: 511.2431, found 512.2503 [M+H]

Example 27—Synthesis of N-(4-(2-((2-(bis(pyridin-2-ylmethyl)amino)ethyl)(pyridin-2-yl methyl)amino)acetamido)phenethyl)pyrazine-2-carboxamide

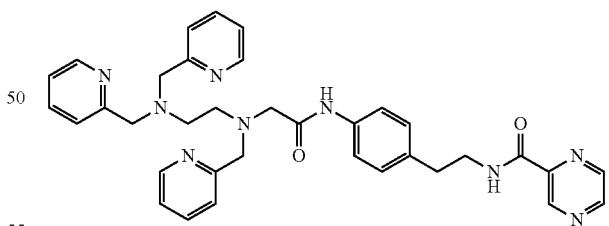

The amine prepared in Example 8 (87.7 mg, 0.172 mmol, 1 eq.) was dissolved in 6 mL acetone cooled to 0° C. in an ice bath. To this solution was added 2,3-pyrazinedicarboxylic acid anhydride (25.8 mg, 0.172 mmol, 1 eq.). The yellow solution turned into a suspension and was then stirred room temperature for 10 min. The precipitate was filtered off with suction, washed with acetone, dissolved in methanol and concentrated under reduced pressure to afford 54 mg (51%) of the title product as an orange solid.
¹H NMR (400 MHz, DMSO-d6) δ 10.23 (s, 1H), 8.92 (t, J=5.9 Hz, 1H), 8.80 (d, J=2.4 Hz, 1H), 8.76 (d, J=3.4 Hz, 1H), 8.75 (d, J=2.5 Hz, 1H), 8.51 (d, J=4.0 Hz, 1H), 8.44 (d, J=4.0 Hz, 2H), 7.71 (td, J=7.7, 1.7 Hz, 1H), 7.64 (td, J=7.7, 1.7 Hz, 2H), 7.53 (d, J=8.4 Hz, 2H), 7.42 (t, J=9.2 Hz, 2H), 7.33 (d, J=7.8 Hz, 1H), 7.28-7.15 (m, 5H), 3.76 (s, 2H), 3.72 (s, 4H), 3.49 (dd, J=14.2, 6.5 Hz, 3H), 3.28 (s, 2H), 2.81 (dt, J=13.7, 8.2 Hz, 4H), 2.65 (t, J=6.2 Hz, 2H). $^{13}$C NMR (101 MHz, DMSO-d6) δ 169.28, 166.90, 165.62, 163.12, 158.66, 158.42, 149.03, 148.75, 147.71, 146.48, 145.66, 144.90, 143.82, 143.43, 136.84, 136.72, 136.46, 134.16, 128.88, 123.13, 122.87, 122.44, 122.16, 119.27, 60.09, 59.53, 58.08, 54.89, 51.65, 51.16, 48.62, 34.30. APCI-HRMS e/z calc. for $C_{35}H_{37}N_9O_2$: 615.3070, found 616.3141 [M+H]

Example 28—Synthesis of 2-((6-((bis(pyridin-2-ylmethyl)amino)methyl)pyridin-2-yl) methyl)isoindoline-1,3-dione

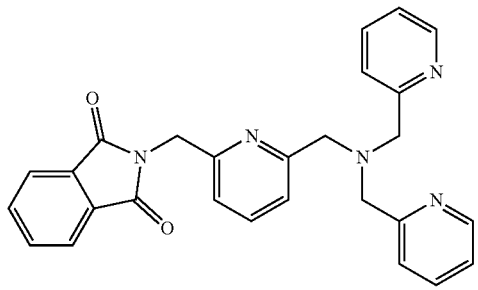 [SMILES: O=C1c2ccccc2C(=O)N1Cc1cccc(CN(Cc2ccccn2)Cc2ccccn2)n1]

The title compound was prepared according to a slightly modified published literature procedure, see Z. Guo, G.-H. Kim, J. Yoon, I. Shin, *Nat. Protocols* 2014, 9, 1245-1254. 2-((6-(chloromethyl)pyridin-2-yl)methyl)isoindoline-1,3-dione (0.842 g, 3.16 mmol, 1 eq.) was suspended in 10 mL CH₃CN at room temperature. Bis(2-pyridylmethyl)amine (0.625 mL, 3.48 mmol, 1.1 eq.) and K₂CO₃ (0.917 g, 6.63 mmol, 2.1 eq.) were added and the mixture heated to reflux for 16 h. After cooling to room temperature, the mixture was passed through a plug of celite using CH₃CN as eluent and the solution concentrated under reduced pressure. The product was isolated via column chromatography on neutral Al₂O₃ using 3-5% MeOH in DCM as eluent to afford 952 mg (66%) of a yellow oil that was pure enough for the next step. Further purification from the obtained yellow oil was achieved by addition of Et₂O and precipitation of a pale beige solid (614 mg). The NMR data obtained for the product corresponded to the reported data in the reference.

Example 29—Synthesis of 1-(6-(aminomethyl)pyridin-2-yl)-N,N-bis(pyridin-2-yl methyl)methanamine

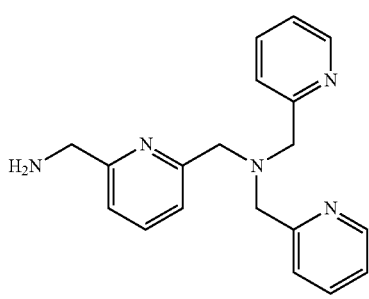 [SMILES: NCc1cccc(CN(Cc2ccccn2)Cc2ccccn2)n1]

The title compound was prepared according to a slightly modified published literature procedure from the phthalimide protected amine in example 28, see Z. Guo, G.-H. Kim, J. Yoon, I. Shin, *Nat. Protocols* 2014, 9, 1245-1254. The 2-((6-((bis(pyridin-2-ylmethyl)amino)methyl)pyridin-2-yl) methyl)isoindoline-1,3-dione prepared in Example 28 (0.499 g, 1.11 mmol, 1 eq.) was dissolved in 10 mL MeOH at room temperature. Hydrazine hydrate solution (35%, 1.11 mL, 12.24 mmol, 11 eq.) was added and the mixture was heated to reflux for 5 h until TLC (Al₂O₃, 3% MeOH in DCM) indicated full conversion of the starting material and a new spot developed that stained with ninhydrin solution. The mixture was concentrated under reduced pressure at 30° C. and the residual white solid dissolved in 150 mL CHCl₃ and washed with 100 mL H₂O. The organic phase was separated and the aqueous phase extracted with CHCl₃ (3×30 mL). The combined organics were washed with 50 mL 1 M NaOH solution and 50 mL brine, dried over anhydrous MgSO₄, filtered and concentrated under reduced pressure at 30° C. to afford a pale yellow oil. The product was isolated via column chromatography on neutral Al₂O₃ using 5-10% MeOH in DCM as eluent to afford 241 mg (68%) of the title product as a pale yellow oil. The product was directly used for the next step without prolonged storage.

$^1$H NMR (400 MHz, CD₂Cl₂) δ 8.49 (d, J=4.4 Hz, 2H), 7.69-7.55 (m, 5H), 7.41 (d, J=7.7 Hz, 1H), 7.17-7.10 (m, 3H), 3.92 (s, 2H), 3.84 (s, 4H), 3.82 (s, 2H). $^{13}$C NMR (101 MHz, CD₂Cl₂) δ 160.25, 159.46, 149.58, 137.39, 136.83, 123.45, 122.48, 121.49, 119.86, 60.77, 60.63, 48.02.

Example 30—Synthesis of methyl 2-(4-(2-((6-((bis(pyridin-2-yl methyl) amino)methyl)pyridin-2-yl) methylamino)acetamido)phenyl)acetate

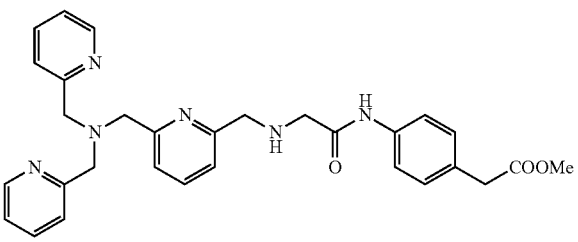 [SMILES: COC(=O)Cc1ccc(NC(=O)CNCc2cccc(CN(Cc3ccccn3)Cc3ccccn3)n2)cc1]

The amine prepared in Example 29 (214 mg, 0.67 mmol, 1 eq.) is dissolved in 10 mL CH₃CN at room temperature. To this mixture is added methyl 2-(4-(2-chloroacetamido)phenyl)acetate prepared in example 19 (170 mg, 0.7 mmol, 1.05 eq.), KI (66.7 mg, 0.402 mmol, 0.6 eq.) and K₂CO₃ (185 mg, 1.34 mmol, 2 eq.). The mixture is heated to reflux for 16 h or until all starting material has been consumed as evident by a TLC analysis. The mixture is then passed through a plug of celite using CH₃CN as solvent. The solution is concentrated under reduced pressure and the product can be isolated via column chromatography on neutral Al₂O₃ or reverse phase C18 silica using an appropriate solvent system.

Example 31—Synthesis of (1-(((3aR,5R,5aS,8aS, 8bR)-2,2,7,7-Tetramethyltetrahydro-5H-bis([1,3] dioxolo)[4,5-b:4',5'-d]pyran-5-yl)methyl)-1H-1,2,3-triazol-4-yl)methanol

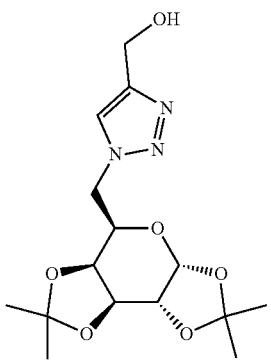

To a solution of 6-azido-6-deoxy-1,2:3,4-di-O-isopropylidene-α-D-galactose (286 mg, 1.0 mmol) in 3 mL acetonitrile, propargyl alcohol (0.12 mL, 2.1 mmol) was added, followed by copper(I)iodide (40.5 mg, 0.21 mmol). The reaction was stirred over night at room temperature. After removal of solvent, the product was purified on a silica column, eluting with a gradient 3:1 ethyl acetate/heptane to pure ethyl acetate. Fractions containing pure product were collected and the solvent removed under reduced pressure to afford 247.7 mg product (73%) which was used directly in the next example.

Example 32—Synthesis of (1-(((3aR,5R,5aS,8aS, 8bR)-2,2,7,7-Tetramethyltetrahydro-5H-bis([1,3] dioxolo)[4,5-b:4',5'-d]pyran-5-yl)methyl)-1H-1,2,3-triazol-4-yl)methyl methanesulfonate

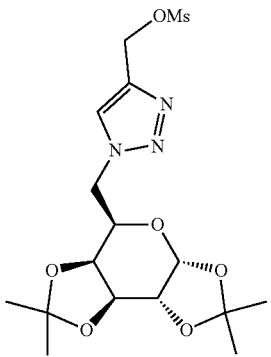

The parent alcohol described in Example 31 (246.3 mg, 0.722 mmol) was dissolved in 5 mL DCM and cooled to 0° C. Triethylamine (0.15 mL, 1.08 mmol) was added, followed by methanesulfonyl chloride (0.07 mL, 0.9 mmol) and the reaction stirred at room temperature for 1 h. The reaction mixture was immediately loaded onto a plug of silica and eluted with ethyl acetate. Removal of solvent gave quantitative conversion to crude product, which was used in the subsequent step (Example 34) without further purification.

Example 33—Synthesis of $N^1,N^1,N^2$-Tris(pyridin-2-ylmethyl)-$N^2$-((1-(((3aR,5R,5aS,8aS,8bR)-2,2,7,7-tetramethyltetrahydro-5H-bis([1,3]dioxolo)[4,5-b:4', 5'-d]pyran-5-yl)methyl)-1H-1,2,3-triazol-4-yl) methyl)ethane-1,2-diamine

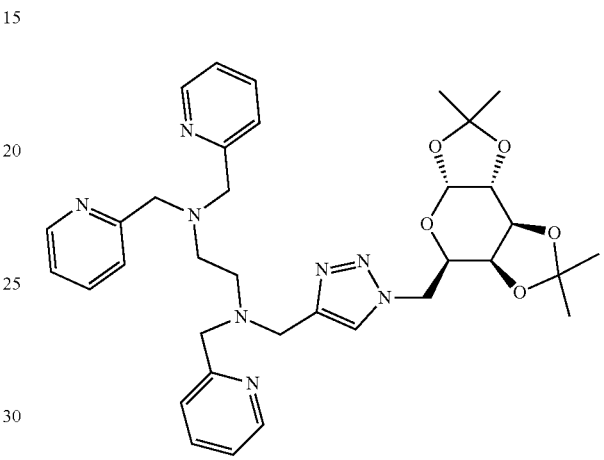

To an ice cold solution of $N^1,N^1,N^2$-tris(pyridin-2-ylmethyl)ethane-1,2-diamine described in Example 6 (241.2 mg, 0.723 mmol) in 10 mL acetonitrile, $K_2CO_3$ (208 mg, 1.50 mmol) was added, and subsequently a solution of (1-(((3aR,5R,5aS,8aS,8bR)-2,2,7,7-tetramethyltetrahydro-5H-bis([1,3]dioxolo) [4,5-b:4',5'-d]pyran-5-yl)methyl)-1H-1,2,3-triazol-4-yl)methyl methanesulfonate as described in Example 32 (0.722 mmol) in 5 mL acetonitrile was then added dropwise, after which the mixture was allowed to warm to room temperature to further react overnight. After filtration through celite and subsequent removal of solvent under reduced pressure, the crude product was purified on an alumina column, with a 1%-1.5% gradient of methanol in DCM as eluent. Further purification of the resulting brown oil was achieved by way of dry column vacuum chromatography on Bondesil C18-OH material, using a stepwise elution from 30% to 70% methanol in water. Evaporation of solvents gave the product as an orange gum (93.8 mg, 20%).

$^1$H NMR (400 MHz, methanol-$d_4$) δ 8.40 (m, 3H), 7.90 (s, 1H), 7.69-7.76 (m, 3H), 7.50-7.56 (m, 3H), 7.24-7.27 (m, 3H), 5.41 (d, J=4.9 Hz, 1H), 4.67 (dd, J=2.5 Hz, 7.9 Hz, 1H), 4.61 (dd, J=3.2 Hz, 14.2 Hz, 1H), 4.46 (dd, J=9.3 Hz, 14.2 Hz, 1H), 4.35 (dd, J=2.5 Hz, 4.9 Hz, 1H), 4.30 (dd, J=1.9 Hz, 7.9 Hz, 1H), 4.19 (ddd, J=1.9 Hz, 3.2 Hz, 9.3 Hz, 1H), 3.76 (s, 6H), 3.68 (s, 2H), 2.66-2.72 (m, 4H), 1.47 (s, 3H), 1.36 (s, 3H), 1.29 (s, 3H), 1.21 (s, 3H). $^{13}$C NMR (100 MHz, methanol-$d_4$) δ 160.7, 149.39, 149.37, 145.3, 138.64, 138.60, 126.0, 124.9, 124.8, 123.73, 123.69, 110.9, 110.0, 97.7, 72.6, 72.2, 71.8, 68.8, 61.5, 60.8, 53.4, 52.7, 51.8, 50.2, 26.3, 26.2, 25.1, 24.6.

Example 34—Synthesis of tert-butyl (4-(2-(4-(bromomethyl)-1H-1,2,3-triazol-1-yl)acetamido)phenethyl)carbamate

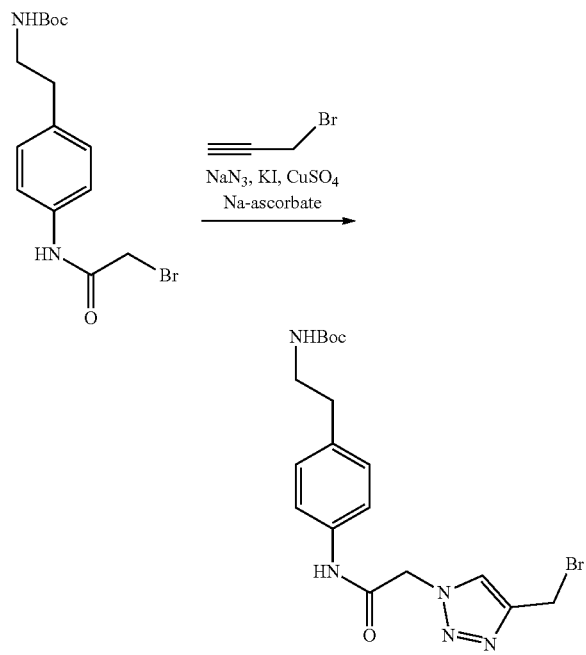

Tert-butyl (4-(2-bromoacetamido)phenethyl)carbamate (1 eq) is suspended in a mixture of tert-butanol and water or another appropriate solvent mixture, and mixed with potassium iodide (0.1-1.0 eq) and copper sulfate (0.1-1.0 eq). Propagyl bromide solution (1.0-100 eq) is then added to the stirring mixture and it is stirred for 1-72 hours at a temperature between 20-100° C. or until all starting material is consumed as monitored by TLC or HPLC. The reaction mixture is then diluted with water and extracted with an appropriate organic solvent (e.g. DCM) three times. The combined organic phases are dried over MgSO$_4$, filtered and concentrated in vacuo. If further purification is necessary, the crude material is purified by column chromatography using an appropriate combination of stationary phase and solvent mixture or recrystallization from an appropriate solvent or solvent mixture.

Example 35—Synthesis of tert-butyl (4-(2-(4-(hydroxymethyl)-1H-1,2,3-triazol-1-yl)acetamido)phenethyl)carbamate

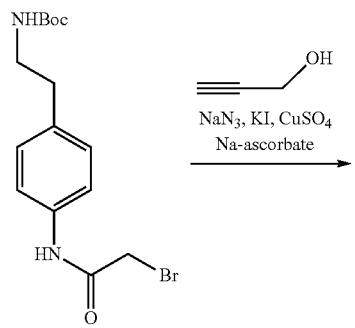

-continued

Tert-butyl (4-(2-bromoacetamido)phenethyl)carbamate as described in Example 2 (1 eq) is suspended in a mixture of tert-butanol and water or another appropriate solvent mixture, and mixed with potassium iodide (0.1-1.0 eq) and copper sulfate (0.1-1.0 eq). Propargyl alcohol solution (1.0-100 eq) is then added to the stirring mixture and it is stirred for 1-72 hours at a temperature between 20-100° C. or until all starting material is consumed as monitored by TLC or HPLC. The reaction mixture is then diluted with water and extracted with an appropriate organic solvent (e.g. DCM) three times. The combined organic phases are dried over MgSO$_4$, filtered and concentrated in vacuo. If further purification is necessary, the crude material is purified by column chromatography using an appropriate combination of stationary phase and solvent mixture or recrystallization from an appropriate solvent or solvent mixture.

Example 36—Synthesis of tert-butyl (4-(2-(4-((bis(pyridin-2-ylmethyl)amino)methyl)-1H-1,2,3-triazol-1-yl)acetamido)phenethyl)carbamate

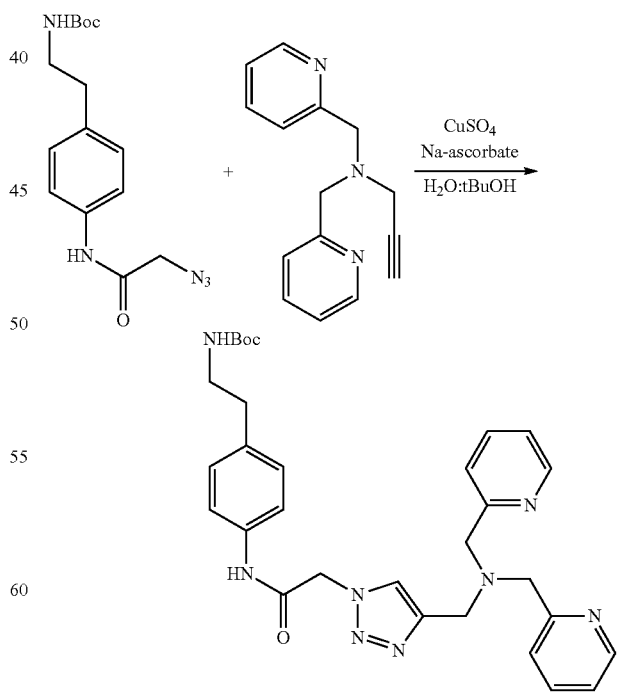

Tert-butyl (4-(2-azidoacetamido)phenethyl)carbamate as prepared in Example 1 (1 eq) is suspended in a mixture of tert-butanol and water or another appropriate solvent mixture, and mixed with copper sulfate (0.1-1.0 eq). N,N-bis(pyridin-2-ylmethyl)prop-2-yn-1-amine (1.0-100 eq) is then added to the stirring mixture and it is stirred for 1-72 hours at a temperature between 20-100° C. or until all starting material is consumed as monitored by TLC or HPLC. The reaction mixture is then either diluted with water and extracted with an appropriate organic solvent (e.g. DCM) three times, the combined organic phases dried over $K_2SO_4$, filtered and concentrated in vacuo or directly purified by column chromatography using an appropriate combination of stationary phase and solvent mixture or recrystallization from an appropriate solvent or solvent mixture to give the titled compound.

Example 37—Synthesis of N-(4-(2-aminoethyl)phenyl)-2-(4-((bis(pyridin-2-ylmethyl) amino)methyl)-1H-1,2,3-triazol-1-yl)acetamide

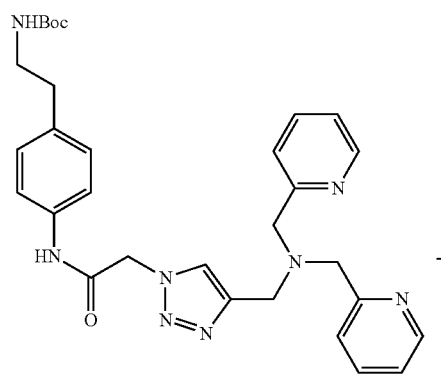

The carbamate prepared in Example 36 is dissolved in DCM and cooled to 0° C. Trifluoroacetic acid (5-100 eq) is then added slowly to the stirring mixture and the solution is kept cold using an ice bath. The mixture is left at 0° C. until all trifluoroacetic acid is added, then stirred at room temperature until all starting material is consumed. The mixture is then concentrated in vacuo, dissolved in 2M NaOH and extracted three times with an appropriate solvent (e.g. DCM). The combined organic phases are dried over $K_2CO_3$, filtered and concentrated in vacuo. If further purification is needed, the material can be subjected to column chromatography using an appropriate combination of stationary phase and eluent, preparative HPLC, recrystallization or combinations thereof.

Example 38—Synthesis of 2-((bis(pyridin-2-ylmethyl)amino)methyl)tetrahydro-2H-pyran-2,3,4,5-tetraol

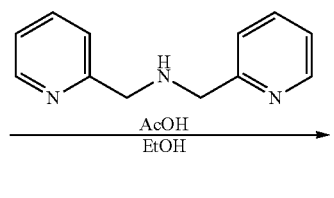

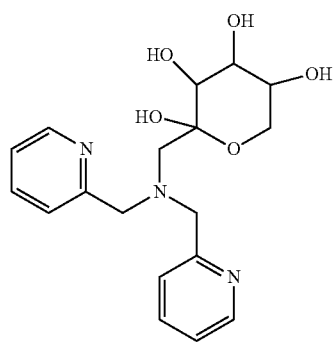

Dipicolylamine (1.0 eq) and D-glucose (1.0-10.0 eq) are suspended in absolute ethanol. Glacial acetic acid (3.0-20.0 eq) is then added and the mixture is stirred at a temperature between room temperature and reflux for 1-72 hours or until all starting material has been consumed. The mixture is then cooled to room temperature and purified by extraction, column chromatography, recrystallization, preparative HPLC or combinations thereof.

Example 39—Synthesis of N-(2-(bis(pyridin-2-ylmethyl)amino)ethyl)-N-(pyridin-2-yl methyl)glycine

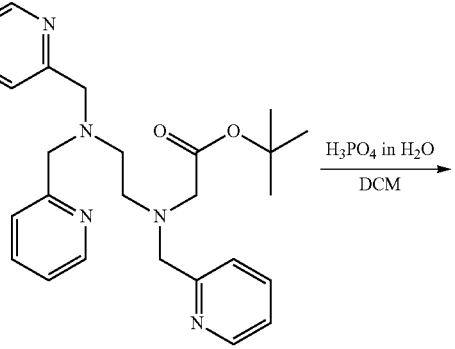

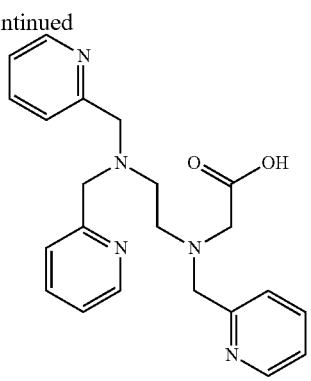

The ester prepared in Example 10 is dissolved in DCM and stirred rapidly. H₃PO₄ (85%) is then added and the mixture is stirred at room temperature for 1-72 hours or until all starting material has been consumed. The organic solvent is then removed in vacuo and the aqueous phase is neutralized with NaHCO₃ or K₂CO₃ to pH 7. The solution is then concentrated under reduced pressure, the solids washed with absolute ethanol and filtered to remove inorganic salts. The ethanolic solution is then concentrated under reduced pressure to give the titled acid.

Example 40—Synthesis of N-(2-(bis(pyridin-2-ylmethyl)amino)ethyl)-N-(pyridin-2-yl methyl)glycine

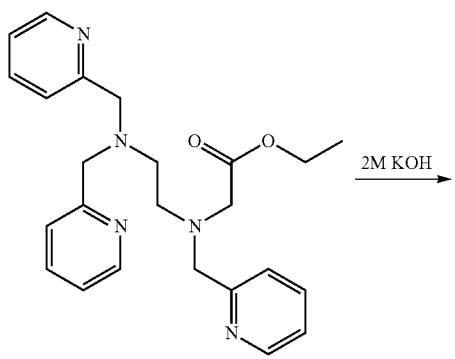

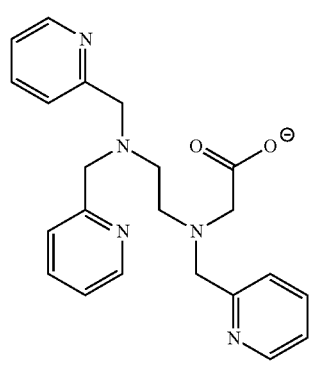

The ester prepared in Example 11 is suspended in 2M KOH and is stirred at room temperature for 1-72 hours or until all starting material has been consumed. The aqueous phase is neutralized with 1M HCl until pH 7. The solution is then concentrated under reduced pressure, the solids washed with absolute ethanol and filtered to remove inorganic salts. The ethanolic solution is then concentrated under reduced pressure to give the titled acid.

Example 41—Synthesis of 2-((2-(bis(pyridin-2-ylmethyl)amino)ethyl)(pyridin-2-yl methyl)amino)-N-methyl-N-(2,3,4,5,6-pentahydroxyhexyl)acetamide

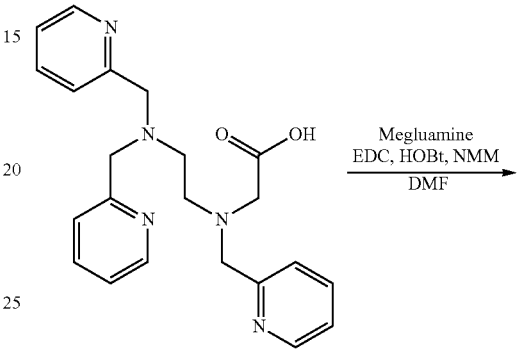

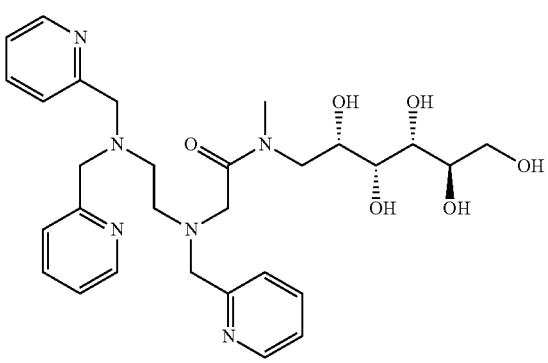

The acid described in Example 40 is dissolved in an appropriate solvent (e.g. DMF, DCM or EtOH) and cooled to 0° C. before megluamine (1.0-10.0 eq). A coupling agent (e.g. HBTU, HATU, CDI, EDC, DCC, COMU) (1.0-10.0 eq) and additive if necessary (HOAt, Oxyma) (0.5-20.0 eq) is then added. The mixture is stirred for 0-15 minutes before the base (e.g. NMM or DIPEA) (1.0-40.0 eq) is added. The mixture is stirred for 0-72 hours at 0° C. and an additional 1-72 hours at room temperature or until all starting material is consumed. The mixture is then either first diluted with 1M K₂CO₃ and extracted repeatedly with EtOAc, the organic phases pooled, dried over K₂CO₃, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 42—Synthesis of 3-((2-(bis(pyridin-2-ylmethyl)amino)ethyl)(pyridin-2-yl methyl)amino)propanoic acid

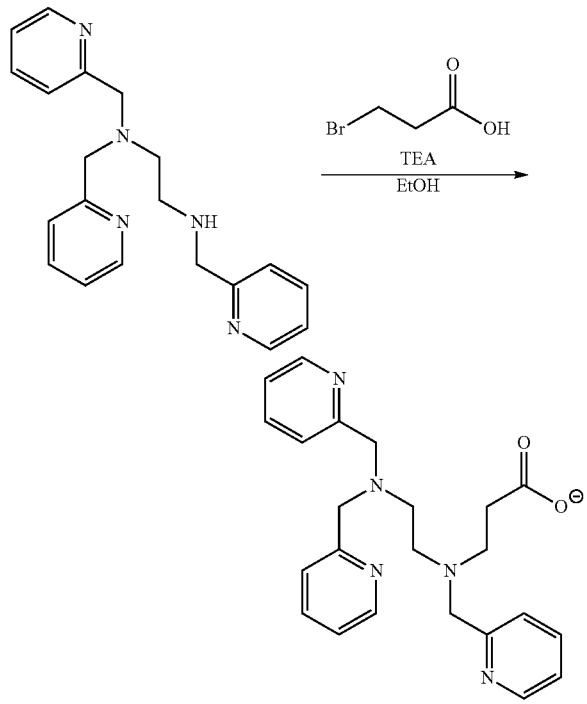

The amine prepared in Example 6 (1.0 eq) is dissolved in an appropriate solvent (e.g. EtOH (abs)) and mixed with 3-bromopropionic acid (1.1-5.0 eq) and TEA (1.2-10.0 eq). The mixture is heated to reflux and stirred for 1-72 hours or until all starting material has been consumed. The mixture is then concentrated under reduced pressure to an absolute minimum amount of solvent, filtered and diluted with Et$_2$O. The mixture is then filtered again and the remaining solution is concentrated under reduced pressure. The crude material is then purified by column chromatography using an appropriate combination of stationary phase and eluent, preparative HPLC, recrystallization or combinations thereof.

Example 43—Synthesis of 2-((2-(bis(pyridin-2-ylmethyl)amino)ethyl)(pyridin-2-yl methyl)amino)-N-((2S,3R,4R,5S,6R)-2,4,5-trihydroxy-6-(hydroxymethyl)tetrahydro-2H-pyran-3-yl)acetamide

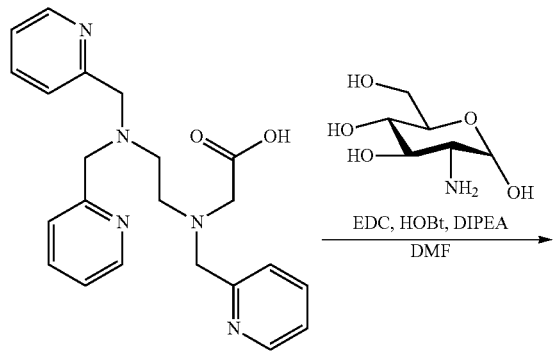

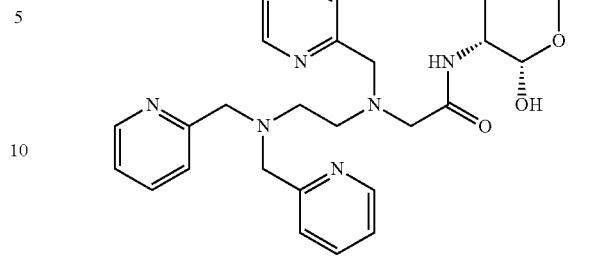

The acid described in Example 40 is dissolved in an appropriate solvent (e.g. DMF, DCM or EtOH) and cooled to 0° C. before D-glucosamine hydrochloride (1.0-10.0 eq) is added. A coupling agent (e.g. HBTU, HATU, CDI, EDC, DCC, COMU) (1.0-10.0 eq) and additive if necessary (HOAt, Oxyma) (0.5-20.0 eq) is then added. The mixture is stirred for 0-15 minutes before the base (e.g. NMM or DIPEA) (1.0-40.0 eq) is added. The mixture is stirred for 0-72 hours at 0° C. and an additional 1-72 hours at room temperature or until all starting material is consumed. The mixture is then either first diluted with 1M K$_2$CO$_3$ and extracted repeatedly with EtOAc, the organic phases pooled, dried over K$_2$CO$_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 44—Synthesis of 3-((2-(bis(pyridin-2-ylmethyl)amino)ethyl)(pyridin-2-yl methyl)amino)-N-((2S,3R,4R,5S,6R)-2,4,5-trihydroxy-6-(hydroxymethyl)tetrahydro-2H-pyran-3-yl)propanamide

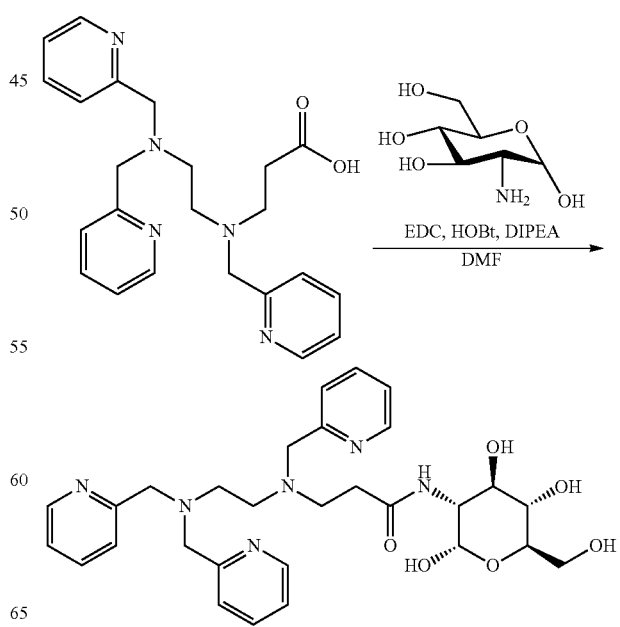

The acid described in Example 42 is dissolved in an appropriate solvent (e.g. DMF, DCM or EtOH) and cooled to 0° C. before D-glucosamine hydrochloride (1.0-10.0 eq) is added. A coupling agent (e.g. HBTU, HATU, CDI, EDC, DCC, COMU) (1.0-10.0 eq) and additive if necessary (HOAt, Oxyma) (0.5-20.0 eq) is then added. The mixture is stirred for 0-15 minutes before the base (e.g. NMM or DIPEA) (1.0-40.0 eq) is added. The mixture is stirred for 0-72 hours at 0° C. and an additional 1-72 hours at room temperature or until all starting material is consumed. The mixture is then either first diluted with 1M K$_2$CO$_3$ and extracted repeatedly with EtOAc, the organic phases pooled, dried over K$_2$CO$_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 45—Synthesis of tert-butyl (4-(((6-((bis(pyridin-2-ylmethyl)amino)methyl) pyridin-3-yl)methyl)amino)phenethyl)carbamate

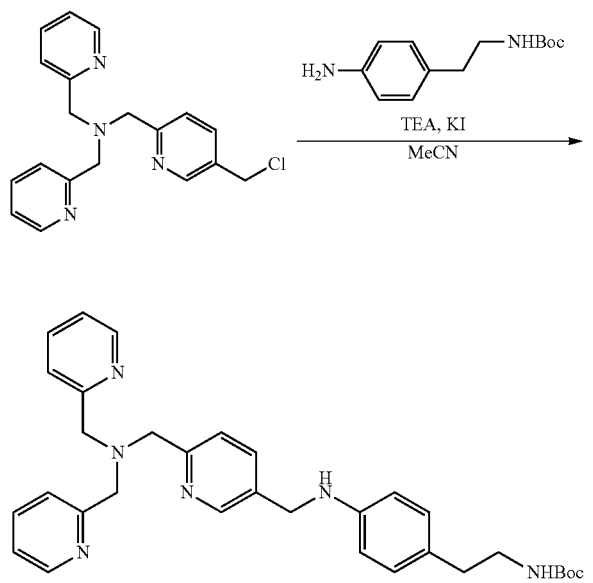 [SMILES: "MeCN" ; ClCc1ccc(CN(Cc2ccccn2)Cc2ccccn2)nc1 ; CC(C)(C)OC(=O)NCCc1ccc(N)cc1 ; CC(C)(C)OC(=O)NCCc1ccc(NCc2ccc(CN(Cc3ccccn3)Cc3ccccn3)nc2)cc1]

The chloride described in Example 15 (1.0 eq) is dissolved in an appropriate solvent (e.g. MeCN) and mixed with KI (0.1-5.0 eq) and TEA (1.0-20.0 eq). The aniline (0.5-10.0 eq) is then added. The mixture is heated to reflux and stirred for 1-72 hours or until all starting material has been consumed. The mixture is then cooled to room temperature and concentrated under reduced pressure. The crude material is then either suspended in 1M K$_2$CO$_3$ and extracted with DCM three times, the organic phases pooled, dried over K$_2$CO$_3$, filtered and concentrated under reduced pressure or directly subjected to column chromatography using an appropriate combination of stationary phase and mobile phase (e.g. neutral alumina with 0-5% MeOH in DCM). If further purification is necessary the compound can be subjected to preparative HPLC, recrystallization or combinations thereof.

Example 46—Synthesis of 6-((bis(pyridin-2-ylmethyl)amino)methyl)nicotinaldehyde

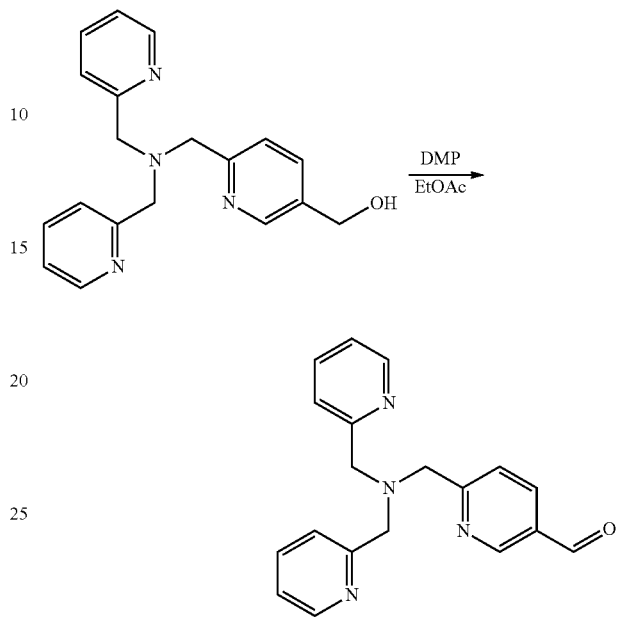

The alcohol prepared in Example 14 is dissolved in EtOAc. A mild oxidating agent (e.g. DMP, IBX or TEMPO/H$_2$O$_2$) is then added and the mixture is stirred for 1-72 hours at a temperature between 20° C. and reflux or until all starting material is consumed. The mixture is then cooled to room temperature and then either first diluted with 1M K$_2$CO$_3$ and extracted repeatedly with EtOAc, the organic phases are pooled, dried over K$_2$CO$_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 47—Synthesis of tert-butyl (4-(((6-((bis(pyridin-2-ylmethyl) amino)methyl)pyridin-3-yl)methyl)amino)phenethyl)carbamate

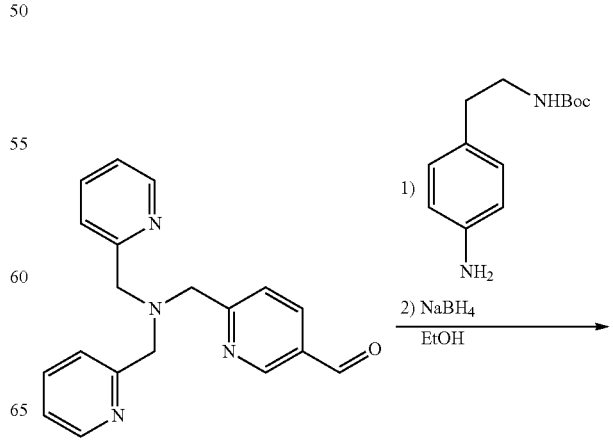

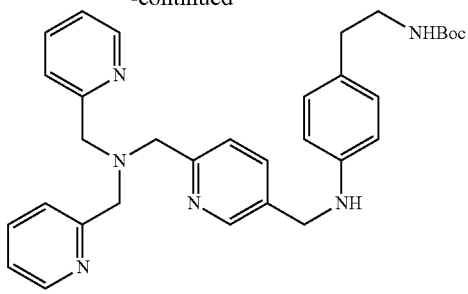

The aldehyde described in Example 46 (1.0 eq) is dissolved in absolute ethanol under argon and the aniline (0.5-5.0 eq) is added. 3 Å or 4 Å molecular sieves can be added in order to increase ratio or yield of the imine formation. The mixture is heated to reflux for 1-72 hours or until all starting material has been consumed. The mixture is then cooled to room temperature and $NaBH_4$ (1-20 eq) is added. The mixture is stirred for 1-72 hours at 20-78° C. before $NH_4Cl$-solution is added. The mixture is then concentrated under reduced pressure, suspended in 1M $K_2CO_3$ and extracted with DCM three times. The combined organic phases are dried over $K_2CO_3$, filtered and concentrated under reduced pressure. The crude material can then be further purified by column chromatography using an appropriate combination of stationary phase and eluent, preparative HPLC, recrystallization or combinations thereof.

Example 48—Synthesis of methyl 2-(4-((((6-((bis (pyridin-2-ylmethyl)amino)methyl) pyridin-3-yl) methyl)amino)phenyl)acetate

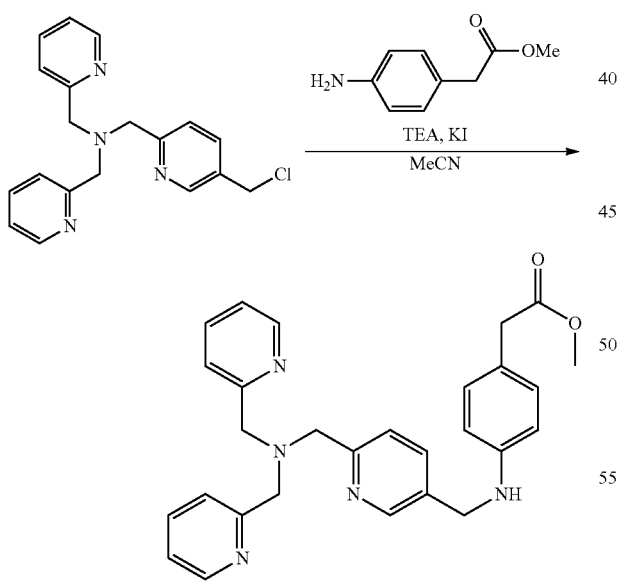

The chloride described in Example 15 (1.0 eq) is dissolved in an appropriate solvent (e.g. MeCN) and mixed with KI (0.1-5.0 eq) and TEA (1.0-20.0 eq). The aniline (0.5-10.0 eq) is then added. The mixture is heated to reflux and stirred for 1-72 hours or until all starting material has been consumed. The mixture is then cooled to room temperature and concentrated under reduced pressure. The crude material is then either suspended in 1M $K_2CO_3$ and extracted with DCM three times, the organic phases pooled, dried over $K_2CO_3$, filtered and concentrated under reduced pressure or directly subjected to column chromatography using an appropriate combination of stationary phase and mobile phase (e.g. neutral alumina with 0-5% MeOH in DCM). If further purification is necessary the compound can be subjected to preparative HPLC, recrystallization or combinations thereof.

Example 49—Synthesis of tert-butyl (4-(2-((6-((bis (pyridin-2-ylmethyl)amino)methyl) pyridin-3-yl) methoxy)acetamido)phenethyl)carbamate

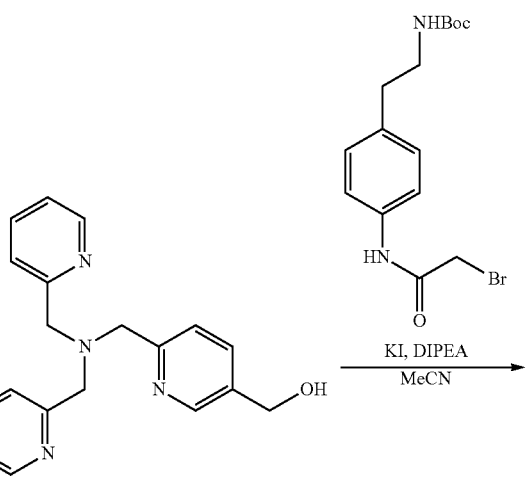

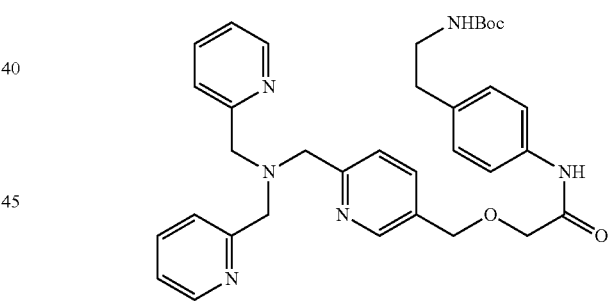

The alcohol prepared in Example 14 (1.0 eq) is dissolved in an appropriate solvent (e.g. MeCN) and mixed with KI (0.1-5.0 eq) and a base (e.g. DIPEA) (1.0-20.0 eq). The bromo amide described in Example 2 (0.5-10.0 eq) is then added. The mixture is heated to reflux and stirred for 1-72 hours or until all starting material has been consumed. The mixture is then cooled to room temperature and concentrated under reduced pressure. The crude material is then either suspended in 1M $K_2CO_3$ and extracted with DCM three times, the organic phases pooled, dried over $K_2CO_3$, filtered and concentrated under reduced pressure or directly subjected to column chromatography using an appropriate combination of stationary phase and mobile phase (e.g. neutral alumina with 0-5% MeOH in DCM). If further purification is necessary the compound can be subjected to preparative HPLC, recrystallization or combinations thereof.

Example 50—Synthesis of methyl 2-(4-(2-((6-((bis(pyridin-2-ylmethyl)amino)methyl) pyridin-3-yl)methoxy)acetamido)phenyl)acetate

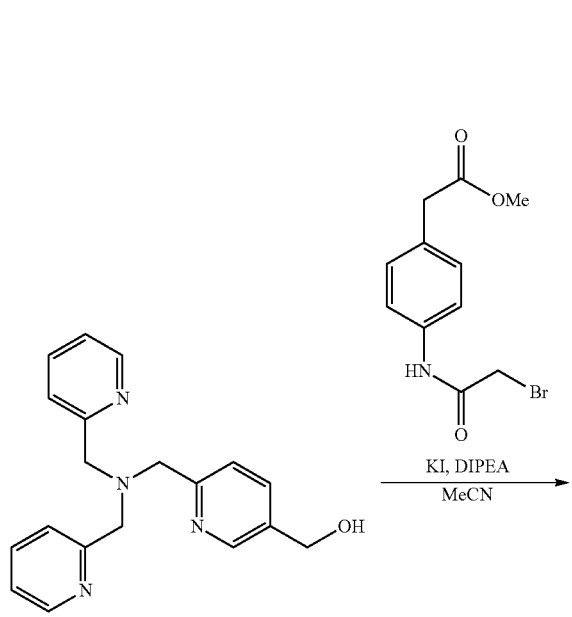

The alcohol prepared in Example 14 (1.0 eq) is dissolved in an appropriate solvent (e.g. MeCN) and mixed with KI (0.1-5.0 eq) and a base (e.g. DIPEA) (1.0-20.0 eq). The chloroamide described in example 18 (0.5-10.0 eq) is then added. The mixture is heated to reflux and stirred for 1-72 hours or until all starting material has been consumed. The mixture is then cooled to room temperature and concentrated under reduced pressure. The crude material is then either suspended in 1M $K_2CO_3$ and extracted with DCM three times, the organic phases pooled, dried over $K_2CO_3$, filtered and concentrated under reduced pressure or directly subjected to column chromatography using an appropriate combination of stationary phase and mobile phase (e.g. neutral alumina with 0-5% MeOH in DCM). If further purification is necessary the compound can be subjected to preparative HPLC, recrystallization or combinations thereof.

Example 51—Synthesis of 2-(4-(2-((6-((bis(pyridin-2-ylmethyl)amino)methyl)pyridin-3-yl)methoxy)acetamido)phenyl)acetic acid

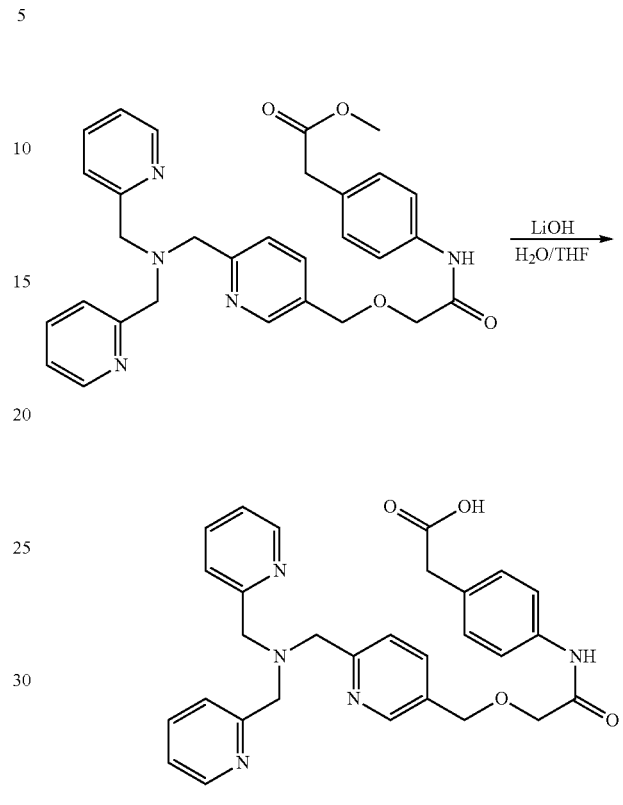

The ester described in Example 50 is dissolved in THF and placed under argon and 2M LiOH solution is added at 0° C. The mixture is stirred for 0-72 hours at 0° C. and 0-72 hours at room temperature before 1M HCl is to neutralize the mixture to pH 7. The mixture is then concentrated under reduced pressure and the crude material is suspended in MeOH and filtered. The filtrate is concentrated under reduced pressure and used directly without any further purification.

Example 52—Synthesis of N-(4-(2-aminoethyl)phenyl)-2-((6-((bis(pyridin-2-yl methyl)amino)methyl)pyridin-3-yl)methoxy)acetamide

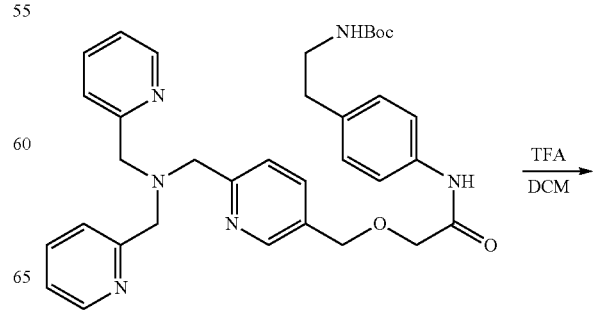

-continued

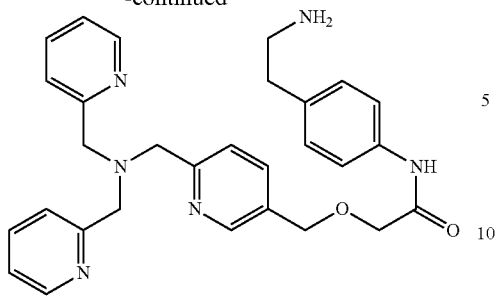

The carbamate described in Example 49 is dissolved in DCM under argon and cooled to 0° C. TFA (1-200 eq) is then added slowly to the stirring mixture and it is stirred for 0-72 hours at 0° C. and 0-72 hours at room temperature. The mixture is then concentrated under reduced pressure, suspended in 1M $K_2CO_3$ and extracted three times with DCM. The combined organic phases are dried over $K_2CO_3$, filtered and concentrated under reduced pressure. The crude material can then be further purified by column chromatography using an appropriate combination of stationary phase and eluent, preparative HPLC, recrystallization or combinations thereof.

Example 53—Synthesis of 2-(4-(2-((6-(((bis(pyridin-2-ylmethyl)amino)methyl)pyridin-3-yl)methoxy) acetamido)phenyl)-N-methyl-N-(2,3,4,5,6-pentahydroxyhexyl)acetamide

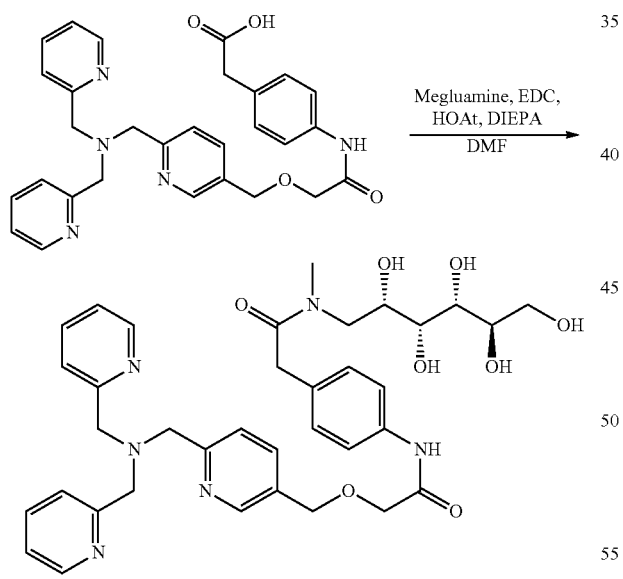

The acid described in Example 51 is dissolved in an appropriate solvent (e.g. DMF, DCM or EtOH) and cooled to 0° C. before megluamine (1.0-10.0 eq) is added. A coupling agent (e.g. HBTU, HATU, CDI, EDC, DCC, COMU) (1.0-10.0 eq) and additive if necessary (HOAt, Oxyma) (0.5-20.0 eq) is then added. The mixture is stirred for 0-15 minutes before the base (e.g. NMM or DIPEA) (1.0-40.0 eq) is added. The mixture is stirred for 0-72 hours at 0° C. and an additional 1-72 hours at room temperature or until all starting material is consumed. The mixture is then either first diluted with 1M $K_2CO_3$ and extracted repeatedly with EtOAc, the organic phases pooled, dried over $K_2CO_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 54—Synthesis of 2-((6-(((bis(pyridin-2-ylmethyl)amino)methyl)pyridin-3-yl) methoxy)-N-(4-(2-((1,3-dihydroxy-2-(hydroxymethyl)propan-2-yl)amino)-2-oxoethyl)phenyl)acetamide

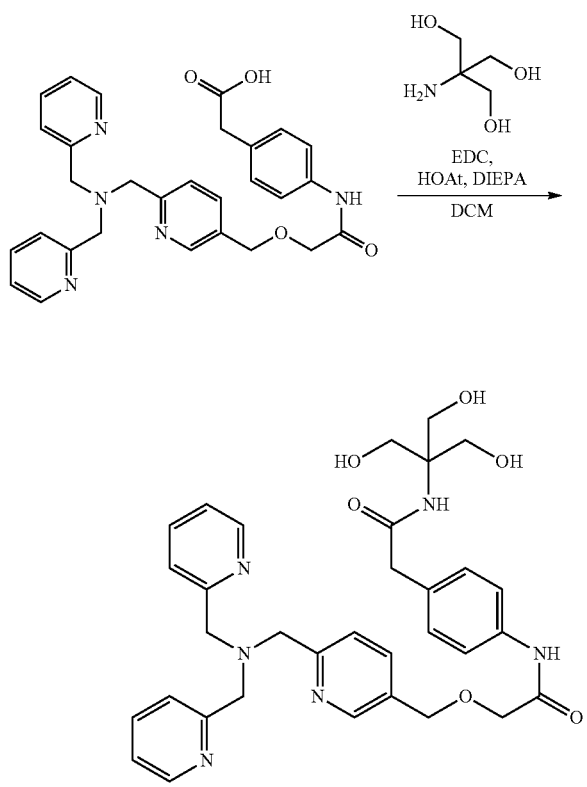

The acid described in Example 51 is dissolved in an appropriate solvent (e.g. DMF, DCM or EtOH) and cooled to 0° C. before Tris(hydroxymethyl)aminomethane hydrochloride (1.0-10.0 eq) is added. A coupling agent (e.g. HBTU, HATU, CDI, EDC, DCC, COMU) (1.0-10.0 eq) and additive if necessary (HOAt, Oxyma) (0.5-20.0 eq) is then added. The mixture is stirred for 0-15 minutes before the base (e.g. NMM or DIPEA) (1.0-40.0 eq) is added. The mixture is stirred for 0-72 hours at 0° C. and an additional 1-72 hours at room temperature or until all starting material is consumed. The mixture is then either first diluted with 1M $K_2CO_3$ and extracted repeatedly with EtOAc, the organic phases pooled, dried over $K_2CO_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 55—Synthesis of Chitosan Functionalized Zinc Chelators by Amide Bond Formation

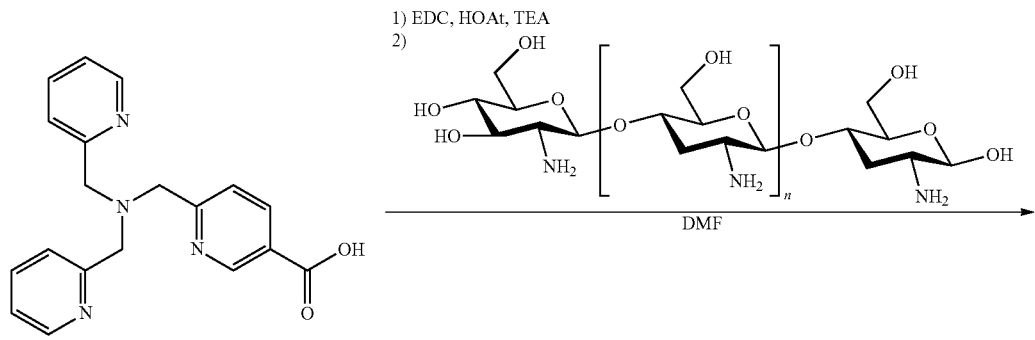

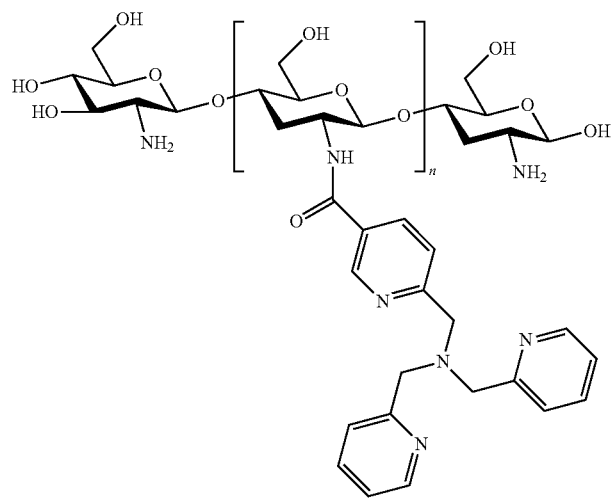

The acid described in Example 13 (1.0-100 eq) is dissolved in an appropriate solvent (e.g. DMF, DCM or EtOH) and cooled to 0° C. a coupling agent (e.g. HBTU, HATU, CDI, EDC, DCC, COMU) (1.0-200.0 eq) an additive if necessary (HOAt, Oxyma) (0.5-400.0 eq) and a base (e.g. NMM or DIPEA) (2.0-800.0 eq) is added. The mixture is stirred for 0-1 hours at 0° C. and an additional 0-1 hours at room temperature before chitosan is added (1.0 eq). The mixture is then stirred at room temperature for 1-72 hours or until all of the starting material has been consumed. The mixture is then concentrated under reduced pressure. The crude material can then be further purified by column chromatography using an appropriate combination of stationary phase and eluent, preparative HPLC, recrystallization or combinations thereof.

Example 56—Synthesis of Chitosan Functionalized Zinc Chelators by Reductive Amination

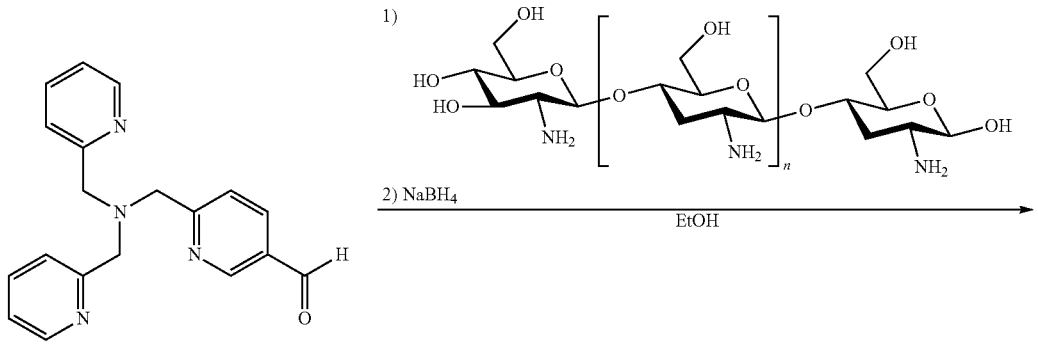

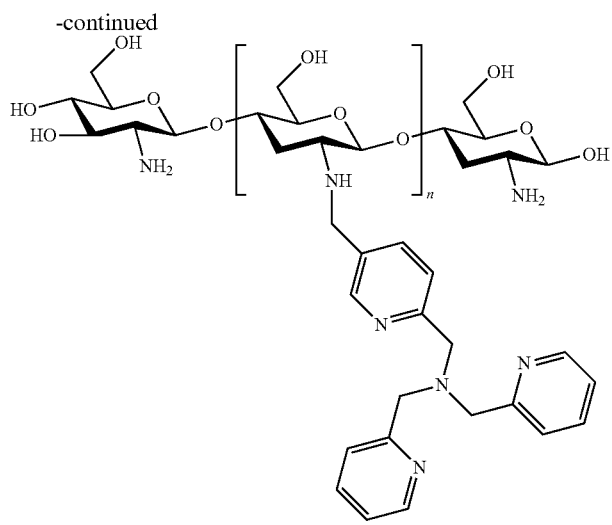

The aldehyde described in Example 46 (1.0-100 eq) is dissolved in an appropriate solvent (e.g. EtOH) and cooled to 0° C. before chitosan is added (1.0 eq). The mixture is then stirred at a temperature between 20-80° C. for 1-72 hours or until all of the starting material has been consumed. The mixture is then cooled to room temperature before NaBH$_4$ (3-300 eq) is added and the mixture is stirred for an additional 1-72 hours at room temperature. 1M K$_2$CO3 or NH$_4$Cl is then added slowly to quench the reaction. The mixture is then concentrated under reduced pressure. The crude material can then be further purified by column chromatography using an appropriate combination of stationary phase and eluent, preparative HPLC, recrystallization or combinations thereof.

Example 57—Synthesis of Chitosan Functionalized Zinc Chelators by Amide Bond Formation 2

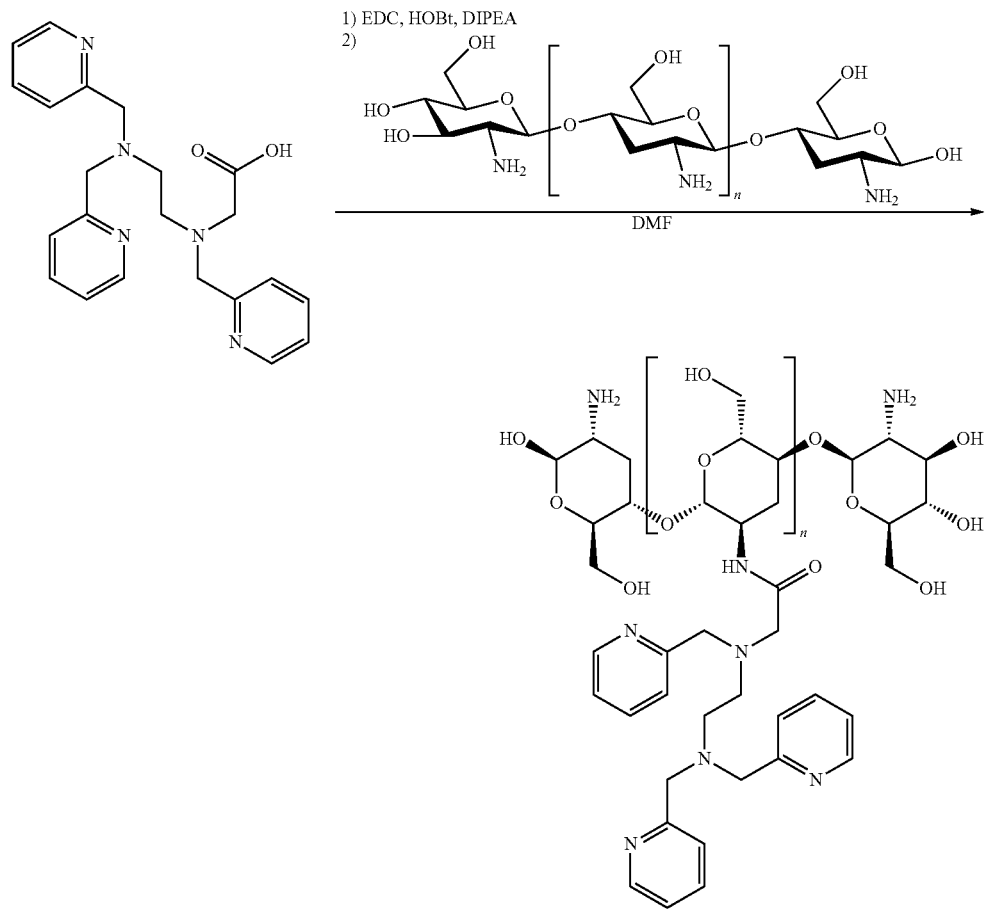

The acid described in Example 40 (1.0-100 eq) is dissolved in an appropriate solvent (e.g. DMF, DCM or EtOH) and cooled to 0° C. a coupling agent (e.g. HBTU, HATU, CDI, EDC, DCC, COMU) (1.0-200.0 eq) an additive if necessary (HOAt, Oxyma) (0.5-400.0 eq) and a base (e.g. NMM or DIPEA) (2.0-800.0 eq) is added. The mixture is stirred for 0-1 hours at 0° C. and an additional 0-1 hours at room temperature before chitosan is added (1.0 eq). The mixture is then stirred at room temperature for 1-72 hours or until all of the starting material has been consumed. The mixture is then concentrated under reduced pressure. The crude material can then be further purified by column chromatography using an appropriate combination of stationary phase and eluent, preparative HPLC, recrystallization or combinations thereof.

Example 58—Synthesis of 2-((2-(bis(pyridin-2-ylmethyl)amino)ethyl)(pyridin-2-yl methyl)amino)ethan-1-ol

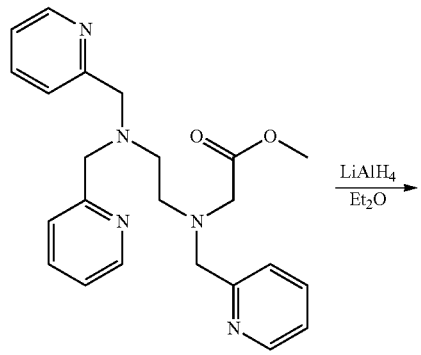

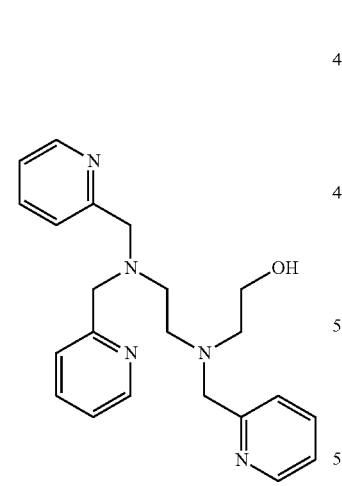

The ester prepared in Example 11 (1.0 eq) is dissolved in an appropriate solvent (e.g. absolute ethanol) and placed under argon. LiAlH₄ pellets or solution (1.0-10.0 eq) is added to the stirring mixture and the slurry is stirred at a temperature between −20-80° C. for 1-78 hours or until all starting material has been consumed. The mixture is then quenched by the addition of NH₄Cl solution and concentrated under reduced pressure. The mixture is then either first diluted with 1M $K_2CO_3$ and extracted repeatedly with EtOAc, the organic phases pooled, dried over $K_2CO_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 59—Synthesis of 2-((2-(bis(pyridin-2-ylmethyl)amino)ethyl)(pyridin-2-yl methyl)amino)acetaldehyde

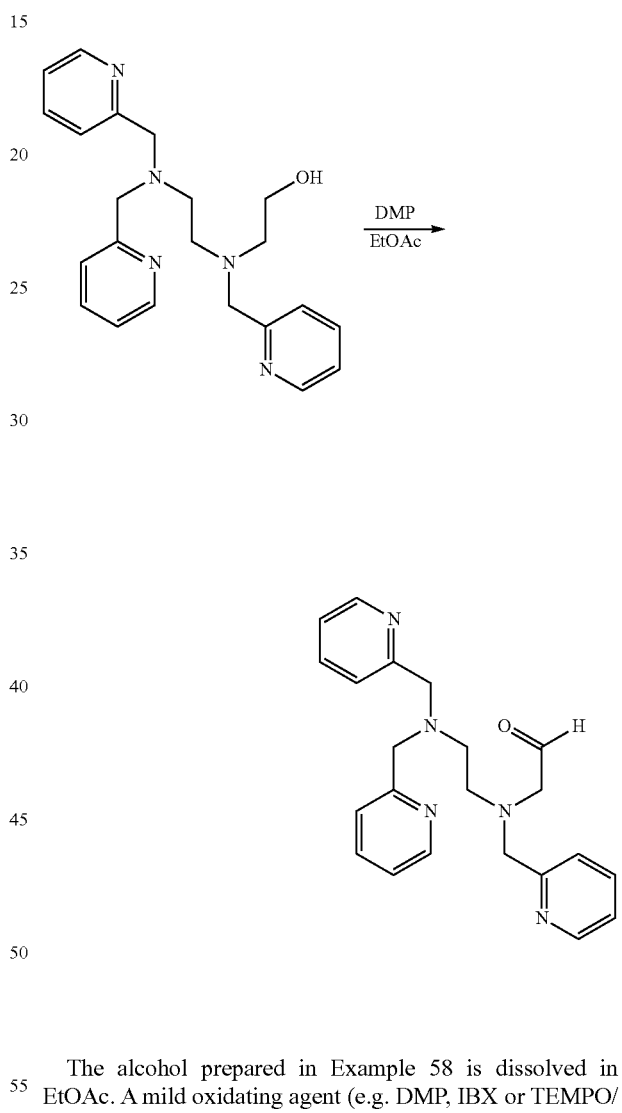

The alcohol prepared in Example 58 is dissolved in EtOAc. A mild oxidating agent (e.g. DMP, IBX or TEMPO/$H_2O_2$) is then added and the mixture is stirred for 1-72 hours at a temperature between 20° C. and reflux or until all starting material is consumed. The mixture is then cooled to room temperature and then either first diluted with 1M $K_2CO_3$ and extracted repeatedly with EtOAc, the organic phases pooled, dried over $K_2CO_3$, filtered and concentrated under reduced pressure, or concentrated under reduced pressure directly. The crude material can then be further purified by column chromatography using an appropriate combination of stationary phase and eluent, preparative HPLC, recrystallization or combinations thereof.

Example 60—Synthesis of Chitosan Functionalized Zinc Chelators by Reductive Amination 2

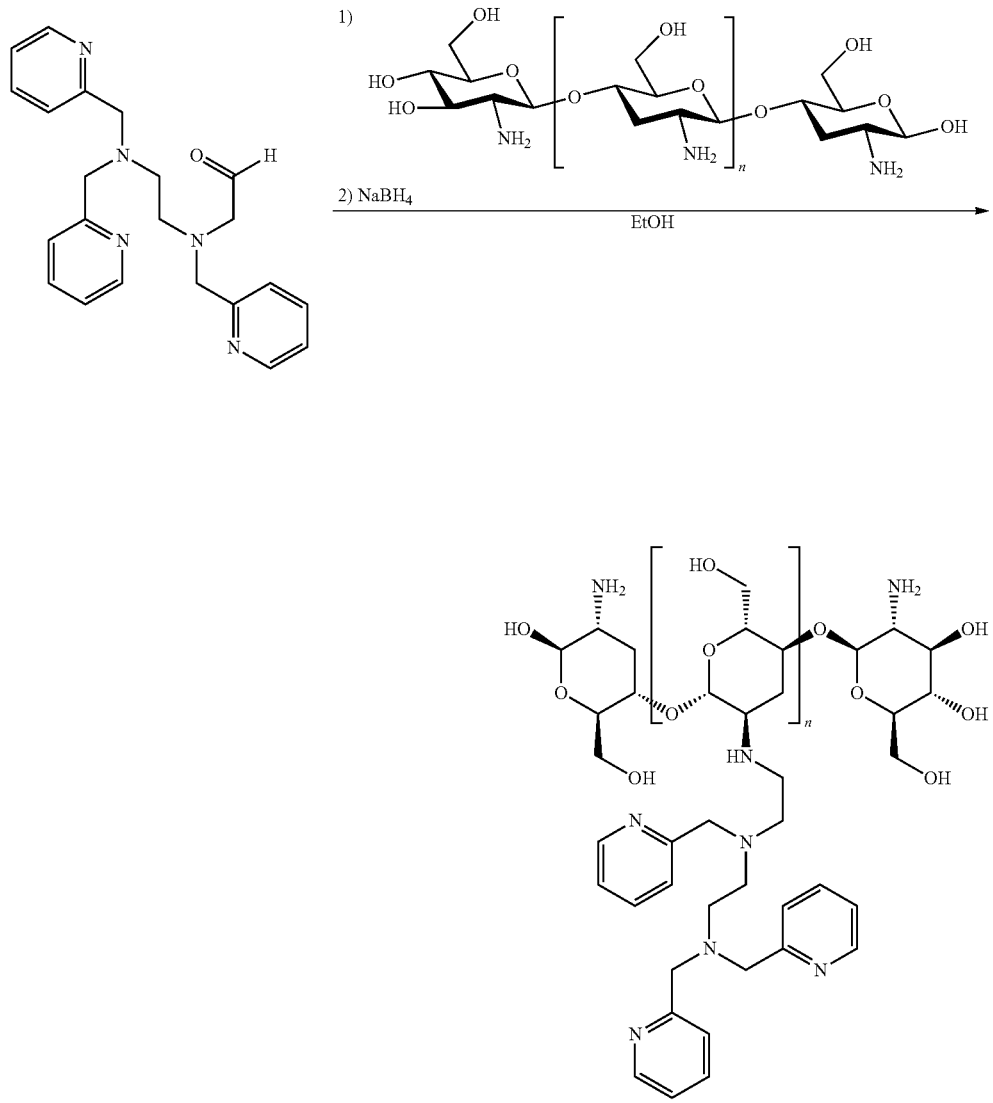

The aldehyde described in Example 59 (1.0-100 eq) is dissolved in an appropriate solvent (e.g. EtOH) and cooled to 0° C. before chitosan is added (1.0 eq). The mixture is then stirred at a temperature between 20-80° C. for 1-72 hours or until all of the starting material has been consumed. The mixture is then cooled to room temperature before $NaBH_4$ (3.0-300.0 eq) is added and the mixture is stirred for an additional 1-72 hours at room temperature. 1M $K_2CO_3$ or $NH_4Cl$ is then added slowly to quench the reaction. The mixture is then concentrated under reduced pressure. The crude material can then be further purified by column chromatography using an appropriate combination of stationary phase and eluent, preparative HPLC, recrystallization or combinations thereof.

Example 61—Synthesis of 2-isothiocyanato-N,N-bis(pyridin-2-ylmethyl)ethan-1-amine

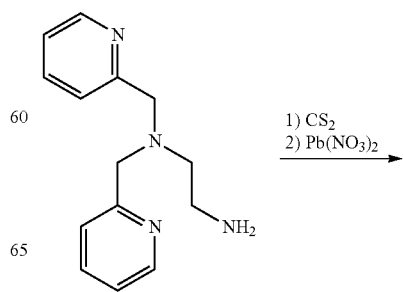

Example 63—Synthesis of methyl 2-(4-(2-((6-((bis(pyridin-2-yl methyl)amino)methyl)pyridin-2-yl)methylamino)acetamido)phenyl)acetate

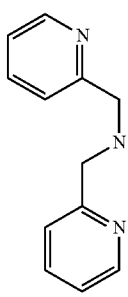

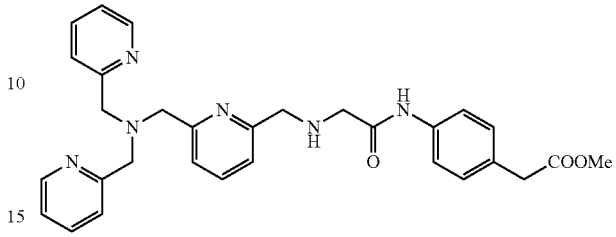

The amine prepared in Example 5 is dissolved in an appropriate solvent (e.g. DCM, DMF or MeCN) under argon before CS$_2$ is added. The mixture is then heated to reflux and stirred for 1-72 hours or until all starting material has been consumed. The mixture is then cooled to room temperature and Pb(NO$_3$)$_2$ is added. The mixture is stirred at room temperature for 1-72 hours or until full product conversion is observed either by TLC, HPLC, NMR or GC. The mixture is then concentrated under reduced pressure. The crude material can then be further purified by column chromatography using an appropriate combination of stationary phase and eluent, preparative HPLC, recrystallization or combinations thereof.

The amine prepared in Example 29 (1 eq.) is dissolved in 10 mL CH$_3$CN at room temperature. To this mixture is added methyl 2-(4-(2-chloroacetamido)phenyl)acetate prepared in Example 19 (1.05 eq.), KI (0.6 eq.) and K$_2$CO$_3$ (2 eq.). The mixture is heated to reflux for 16 h until TLC control reveals full conversion of the amine. The mixture is then passed through a plug of celite using CH$_3$CN and the solution is concentrated under reduced pressure. The product isolated via column chromatography on an appropriate stationary phase using an appropriate solvent mixture as eluent.

Example 62—Synthesis of 2-isocyanato-N,N-bis(pyridin-2-ylmethyl)ethan-1-amine

Example 64—Synthesis of 2-(4-(2-((6-((bis(pyridin-2-ylmethyl)amino)methyl)pyridin-2-yl)methylamino)acetamido)phenyl)acetic acid

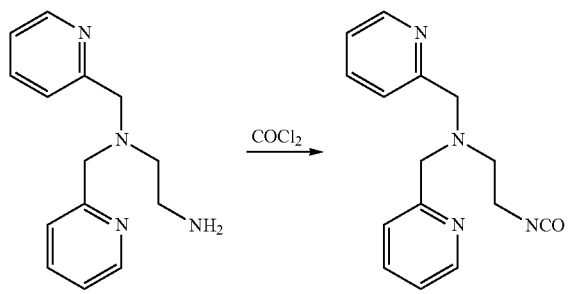

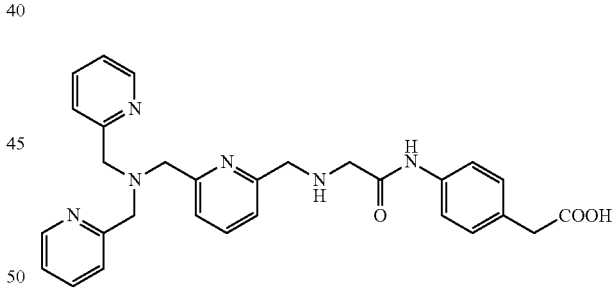

The amine prepared in Example 5 is dissolved in an appropriate solvent (e.g. DCM, DMF or MeCN) under argon and cooled to 0° C. before COCl$_2$ is added. The mixture is then stirred at 0° C. for 0-2 hours before the mixture is then heated to reflux and stirred for 1-72 hours or until all starting material has been consumed. The mixture is then concentrated under reduced pressure. The crude material can then be further purified by column chromatography using an appropriate combination of stationary phase and eluent, preparative HPLC, recrystallization or combinations thereof.

Methyl 2-(4-(2-((6-((bis(pyridin-2-ylmethyl)amino)methyl)pyridin-2-yl)methylamino) acetamido)phenyl)acetate prepared in Example 63 (1 eq.) is dissolved in an appropriate amount of THF cooled to 0° C. in an ice bath. To this solution is added LiOH.H$_2$O (2.0 eq.) in an appropriate amount of distilled H$_2$O and the solution is stirred at 0° C. until TLC indicates full conversion. The mixture is then concentrated under reduced pressure to remove the THF, and the residual aq. solution adjusted to pH 7 with 0.5 M HCl. The water is removed under reduced pressure to afford the product acid.

Example 65—Synthesis of 2,2'-((2-(Bis(pyridin-2-ylmethyl)amino)ethyl)azanediyl) diacetic acid

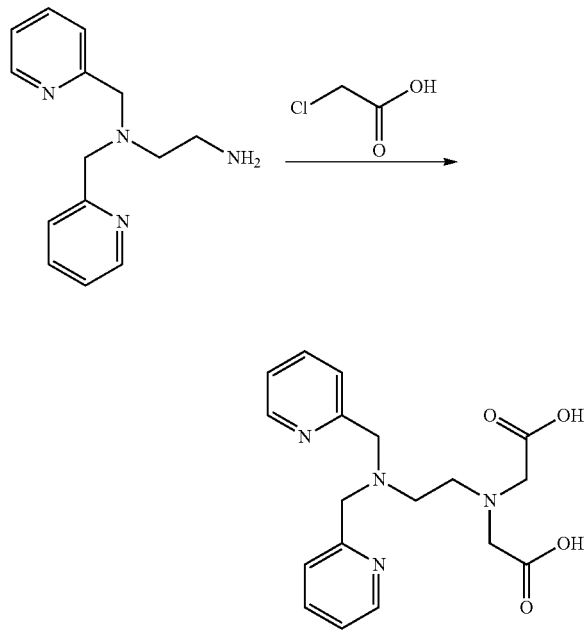

Chloroacetic acid (2 mmol), dissolved in 2 mL water, is neutralized by an equimolar amount of sodium hydroxide in 2 mL water, and $N^1,N^1$-bis(pyridin-2-ylmethyl)ethane-1,2-diamine as described in Example 5 (1 mmol) is added. After heating to reflux, more sodium hydroxide is added dropwise (2.1 mmol in 2 mL water) and the solution kept on reflux for 1 h. After neutralization with 4M HCl (aq.) and further addition to acidic pH, the compound is purified using a pH-gradient on a strong cation exchange column, or by crystallization from methanol-pyridine mixture.

Example 66—Synthesis of 4-(2-(Bis(pyridin-2-ylmethyl)amino)ethyl)morpholine-2,6-dione

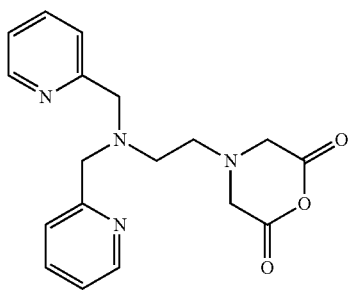 [SMILES: O=C1CN(CCN(Cc2ccccn2)Cc2ccccn2)CC(=O)O1]

2,2'-((2-(Bis(pyridin-2-ylmethyl)amino)ethyl)azanediyl) diacetic acid (described in Example 65) is heated to reflux in excess acetic anhydride and an appropriate solvent. After removal of volatiles, the crude product is used as is for subsequent steps, or purified by crystallization/precipitation methods from appropriate solvents or solvent mixtures.

Example 67—Synthesis of (2S,3R,4S,5R,6R)-6-((4-(((2-(Bis(pyridin-2-ylmethyl)amino)ethyl)(pyridin-2-ylmethyl)amino)methyl)-1H-1,2,3-triazol-1-yl)methyl)tetrahydro-2H-pyran-2,3,4,5-tetraol

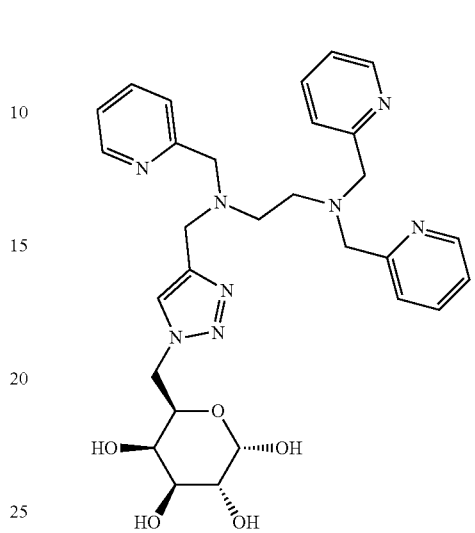

Treatment of $N^1,N^1,N^2$-Tris(pyridin-2-ylmethyl)-$N^2$-((1-(((3aR,5R,5aS,8aS,8bR)-2,2,7,7-tetramethyltetrahydro-5H-bis([1,3]dioxolo) [4,5-b:4',5'-d]pyran-5-yl)methyl)-1H-1,2,3-triazol-4-yl)methyl)ethane-1,2-diamine as described in Example 33 with 50% trifluoracetic acid in water for 1 h-24 h affords, after removal of solvents, the title compound. The crude product may be further purified with reversed phase chromatographic methods, or cation exchange materials, or combinations thereof.

Example 68a—Synthesis of $N^1$-methyl-$N^2,N^2$-bis(pyridin-2-ylmethyl)-$N^1$-((1-(((3aR,5R,5aS,8aS,8bR)-2,2,7,7-tetramethyltetrahydro-5H-bis([1,3]dioxolo)[4,5-b:4',5'-d]pyran-5-yl)methyl)-1H-1,2,3-triazol-4-yl)methyl)ethane-1,2-diamine

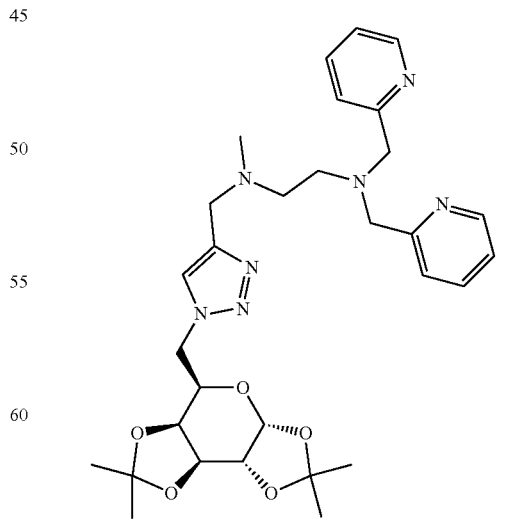

To a solution of N-methyl-N',N'-bis(pyridin-2-ylmethyl)ethane-1,2-diamine as described in the literature (G. Berggren et al, *Dalton Trans.*, (2009), 10044-10054) 2 mmol) in 30 mL acetonitrile or other suitable non-nucleophilic solvents, K₂CO₃ (4 mmol) is added and the mixture is then cooled down on an ice bath. A solution of (1-(((3aR,5R,5aS,8aS,8bR)-2,2,7,7-tetramethyltetrahydro-5H-bis([1,3]dioxolo)[4,5-b:4',5'-d]pyran-5-yl)methyl)-1H-1,2,3-triazol-4-yl)methyl methanesulfonate as described in Example 32 (2 mmol) in the same solvent is then added dropwise, and the mixture is allowed to heat to room temperature to further react for 4 h-48 h. After filtration and removal of solvent, product may be further purified using either chromatography on alumina, silica or reversed phase materials, and/or with SPE methods, both cationic exchange and reversed phase packing materials.

Example 68b—Synthesis of (2S,3R,4S,5R,6R)-6-((4-(((2-(Bis(pyridin-2-yl methyl)amino)ethyl)(methyl)amino)methyl)-1H-1,2,3-triazol-1-yl)methyl)tetrahydro-2H-pyran-2,3,4,5-tetraol

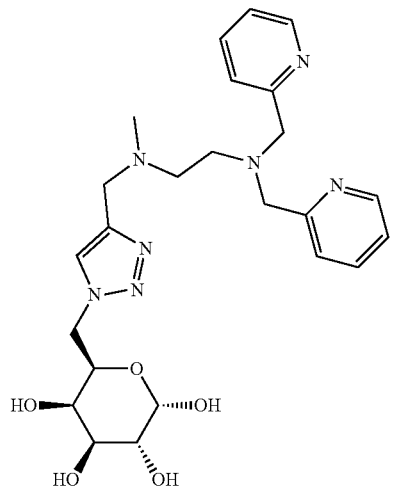 [SMILES: CN(CCN(Cc1ccccn1)Cc1ccccn1)Cc1cn(C[C@H]2O[C@H](O)[C@H](O)[C@@H](O)[C@H]2O)nn1]

Treatment of the compound as described in Example 68a with 50% trifluoracetic acid in water for 1 h-24 h affords, after removal of solvents, the title compound. The crude product may be further purified with reversed phase chromatographic methods, or cation exchange materials, or combinations thereof.

Example 69—Synthesis of 2-((2-(bis(pyridin-2-ylmethyl)amino)ethyl)(methyl)amino)-N-methyl-N-((2S,3R,4R,5R)-2,3,4,5,6-pentahydroxyhexyl)acetamide

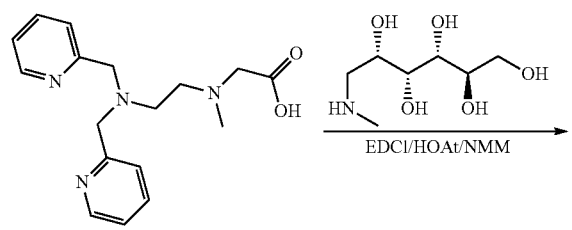

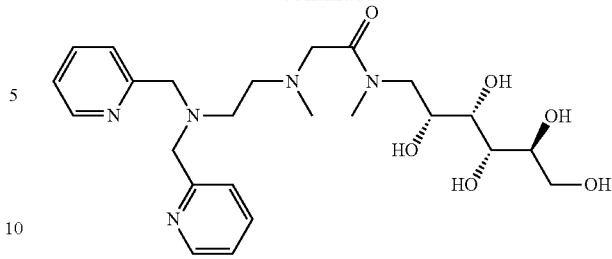

The title compound was prepared as described below for Example 96e.

Example 70—Synthesis of N¹,N¹-Bis(pyridin-2-ylmethyl)-N²,N²-bis((1-(((3aR,5R,5aS,8aS,8bR)-2,2,7,7-tetramethyltetrahydro-5H-bis([1,3]dioxolo)[4,5-b:4',5'-d]pyran-5-yl)methyl)-1H-1,2,3-triazol-4-yl)methyl)ethane-1,2-diamine

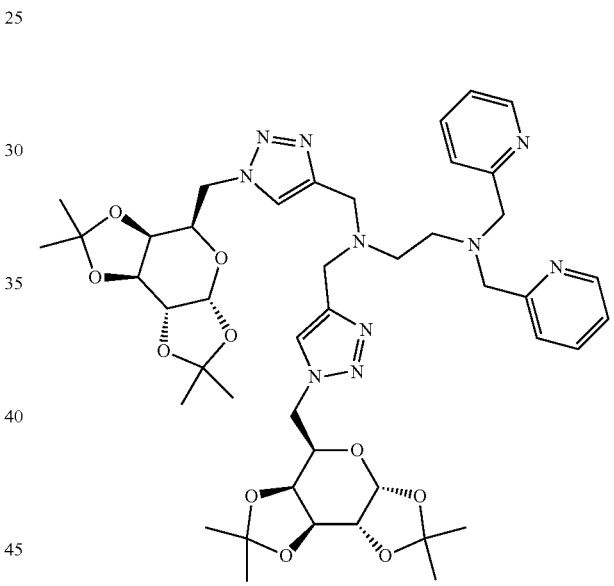

To a solution of N¹,N-bis(pyridin-2-ylmethyl)ethane-1,2-diamine as described in Example 5 (2 mmol) in 30 mL acetonitrile or other suitable non-nucleophilic solvents, K₂CO₃ (8 mmol) is added and the mixture was then cooled down on an ice bath. A solution of (1-(((3aR,5R,5aS,8aS,8bR)-2,2,7,7-tetramethyltetrahydro-5H-bis([1,3]dioxolo)[4,5-b:4',5'-d]pyran-5-yl)methyl)-1H-1,2,3-triazol-4-yl)methyl methanesulfonate as described in Example 32 (4 mmol) in the same solvent is then added dropwise, and the mixture is allowed to heat to room temperature to further react for 4 h-48 h. After filtration and removal of solvent, product may be further purified using either chromatography on alumina, silica or reversed phase materials, and/or with SPE methods, both cationic exchange and reversed phase packing materials.

Example 71—Synthesis of (2S,2'S,3R,3'R,4S,4'S, 5R,5'R,6R,6'R)-6,6'-(((((2-(Bis(pyridin-2-ylmethyl) amino)ethyl)azanediyl)bis(methylene))bis(1H-1,2,3-triazole-4,1-diyl))bis(methylene))bis(tetrahydro-2H-pyran-2,3,4,5-tetraol)

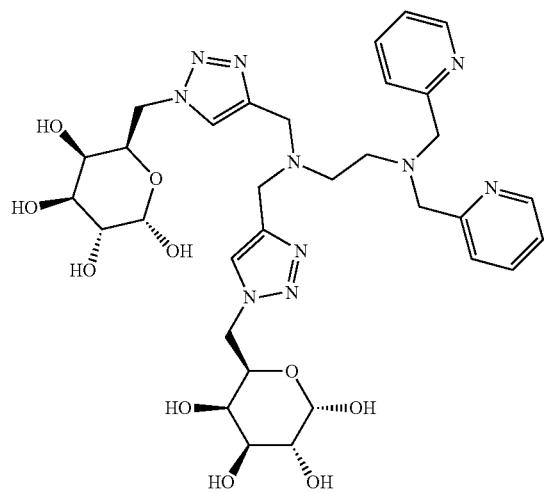 [SMILES: O[C@@H]1[C@@H](O)[C@@H](O)O[C@H](Cn2cc(CN(CCN(Cc3ccccn3)Cc3ccccn3)Cc3cn(C[C@H]4O[C@H](O)[C@H](O)[C@@H](O)[C@H]4O)nn3)nn2)[C@@H]1O]

Treatment of $N^1,N^1$-Bis(pyridin-2-ylmethyl)-$N^2,N^2$-bis((1-(((3aR,5R,5aS,8aS,8bR)-2,2,7,7-tetramethyltetrahydro-5H-bis([1,3]dioxolo) [4,5-b:4',5'-d]pyran-5-yl)methyl)-1H-1,2,3-triazol-4-yl)methyl)ethane-1,2-diamine as described in Example 70 with 50% trifluoracetic acid in water for 1 h-24 h affords, after removal of solvents, the title compound. The crude product may be further purified with reversed phase chromatographic methods, or cation exchange materials, or combinations thereof.

Example 72—Synthesis Of Bis-Pentaacetylated Gluconate According To A Published Literature Procedure Described By I.-H. Paik, D. Tapriyal, R. M. Enick, A. D. Hamilton, Angew. Chem. Int. Ed. 2007, 46, 3284-3287

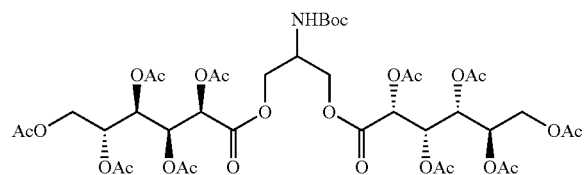 [SMILES: CC(=O)OC[C@@H](OC(C)=O)[C@@H](OC(C)=O)[C@H](OC(C)=O)[C@@H](OC(C)=O)C(=O)OCC(COC(=O)[C@H](OC(C)=O)[C@@H](OC(C)=O)[C@H](OC(C)=O)[C@@H](COC(C)=O)OC(C)=O)NC(=O)OC(C)(C)C]

A solution of pentaacetylated gluconic acid (2.08 eq.) in anhydrous DCM is treated with EDCl (2.2 eq.) and pyridine (3.4 eq.). N-Boc-serinol (1.0 eq.) is added into the reaction mixture followed by addition of DMAP (catalytic amount). The reaction mixture is stirred for 12 hours and is poured into saturated aq. ammonium chloride solution. The organic phase is separated and extracted with DCM, dried over MgSO$_4$ and concentrated under reduced pressure to give a sticky solid. Flash column chromatography on silica eluting with 2% methanol/DCM gives N-Boc-protected bis-acetylated gluconate ester as a colorless dense oil.

Example 73—Boc-Deprotection of Bis-Pentaacetylated Gluconate According to a Published Literature Procedure Described by I.-H. Paik, D. Tapriyal, R. M. Enick, A. D. Hamilton, Angew. Chem. Int. Ed. 2007, 46, 3284-3287

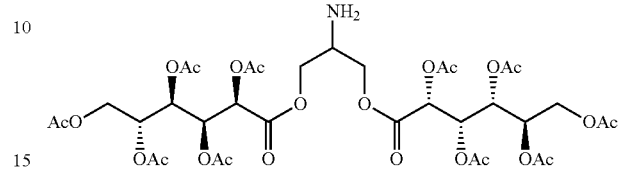

To a solution of N-Boc-protected bis-acetylated gluconate ester prepared in Example 72 in anhydrous dichloromethane is added large excess trifluoroacetic acid (50-100 eq.) slowly dropwise at room temperature. The reaction mixture is stirred for 3 hours and concentrated under reduced pressure and completely dried under high vacuum to afford the deprotected bis-pentaacetylated gluconate amine.

Example 74—General Procedure for the Coupling of Chelator-Linker-Acid or Chelator-Acids to the Bis-Pentaacetylated Gluconate Amine

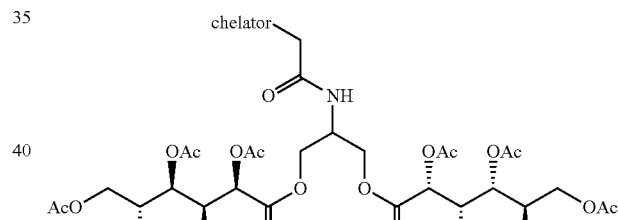

The chelator-linker acid or chelator-acid prepared in e.g. Example 13 or 21 (1 eq.) is dissolved in an appropriate solvent (e.g., but not limited to DMF, CH$_3$CN, EtOAc, CH$_2$Cl$_2$). To this mixture is added the coupling reagent (e.g., but not limited to HATU, COMU, PyBOP, EDCl), (1-1.5 eq.), optional activator (e.g., but not limited to HOAt, HOBt), (1-1.5 eq.) and appropriate non-nucleophilic base (e.g., but not limited to NMM, DIPEA), (2-3 eq.) at a temperature between 0° C. and room temperature. The amine in Example 73 (1-1.2 eq.) is added. Alternatively, an activated acid can be employed (1 eq.) and the amine in example 73 (1-1.2 eq.) and base (1-1.2 eq.) are added to the mixture. The reaction mixture is stirred at a temperature between 0° C. and reflux until full conversion of the acid or active ester indicated by TLC. The solvent is removed under reduced pressure and the product isolated via column chromatography on an appropriate stationary phase using an appropriate solvent mixture as eluent.

Example 75—General Procedure for the Synthesis of Alkyladenosines with Halo Chelators According to an Appropriately Modified Literature Procedure Described by V. E. Oslovsky, M. S. Drenichev, S. N. Mikhailov, Nucleosides, Nucleotides and Nucleic Acids 2015, 34, 475-499

Example 76—Synthesis of Amides from N2-(1-Carboxyethyl)-Guanosine 5'-Monophosphate According to an Appropriately Modified Literature Procedure Described in D. Festring, A. Brockhoff, W. Meyerhof, T. Hofmann, J. Agric. Food Chem. 2011, 59, 8875-8885

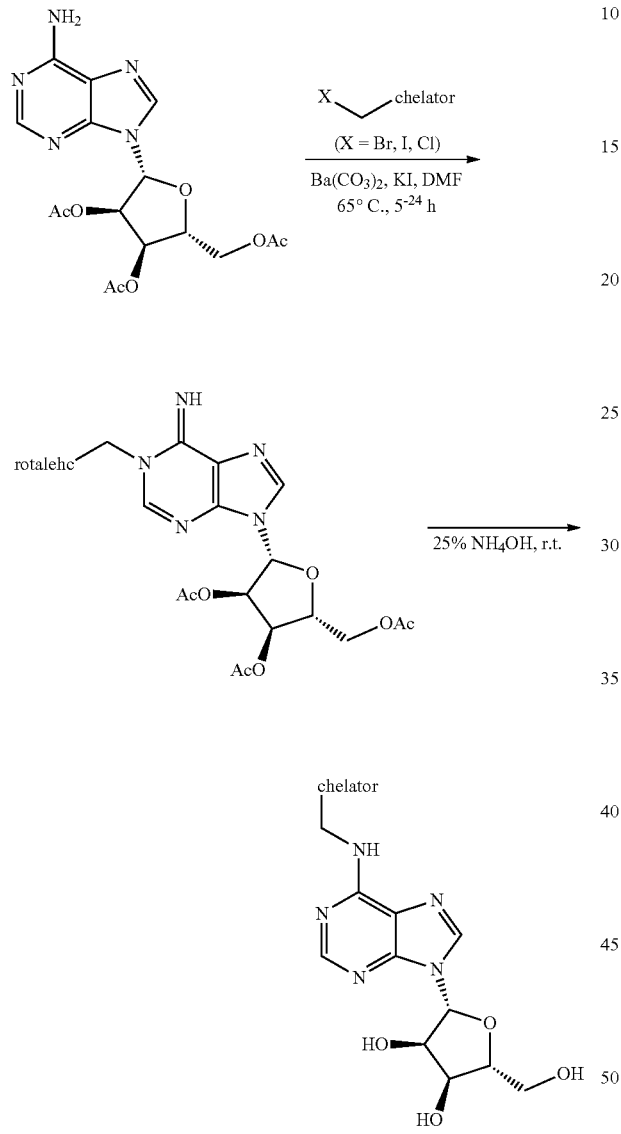

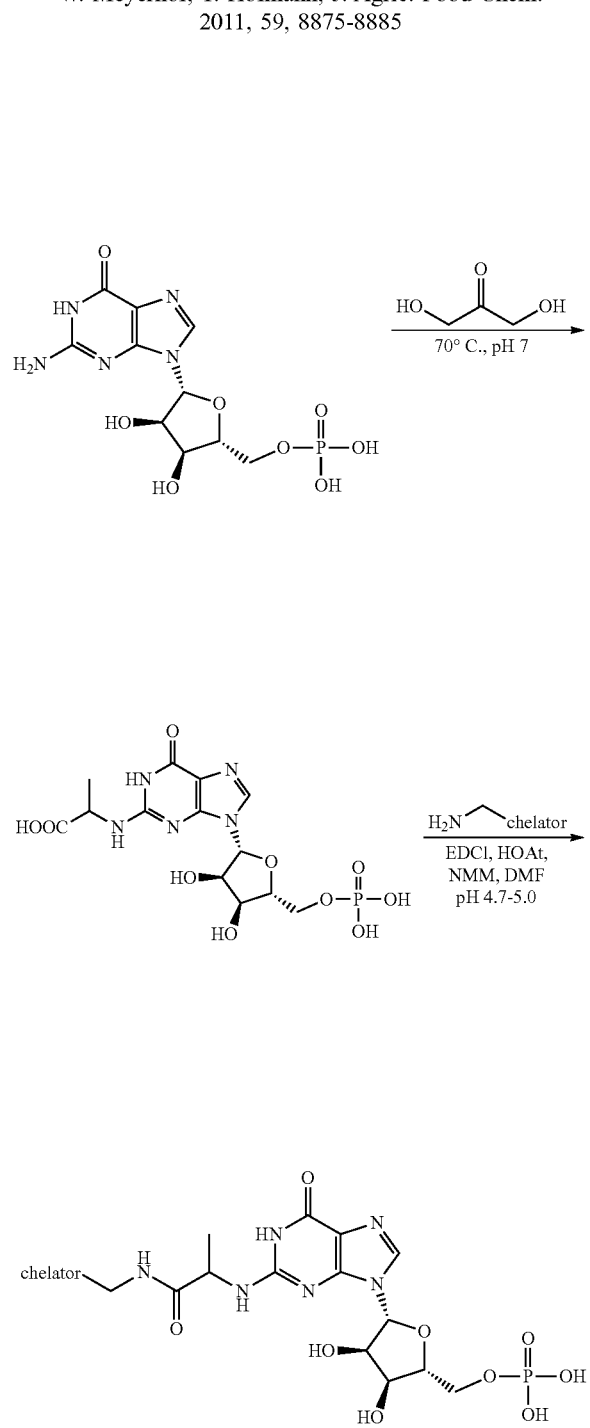

To a solution of triacetyladenosine (1 eq.) in DMF barium carbonate (2.5 eq.), potassium iodide (2 eq.) and the chelator-chloride prepared in Example 15 (2 eq.) are added, and the mixture is stirred at 65° C. for 24 hours. Then the mixture is cooled to room temperature, diluted with ethyl acetate and filtered through celite from $BaCO_3$. Celite is washed with ethyl acetate and the combined filtrate evaporated in vacuum to the volume ca. 2 mL. Then 25% aqueous ammonia is added, and the mixture is left to stay at r.t. during a week. The mixture is evaporated under reduced pressure, evaporated with EtOH, and the product is isolated via column chromatography, prep. HLPC, crystallization or distillation using the appropriate conditions.

A mixture of guanosine 5'-monophosphate (1 eq.) and 1,3-dihydroxyacetone dimer (1.5 eq.)) in phosphate buffer (1 mol/L, pH 7.0; 5 mL) is heated for 24 h at 70° C. The crude mixture is diluted with water and purified via column chromatography, prep. HLPC, crystallization or distillation using the appropriate conditions. A solution of the carboxyethyl (1 eq.), EDCl (5 eq.) and the chelator amine, e.g. the amine prepared in Example 29 (20 eq.) in H₂O or an alternative appropriate solvent is adjusted to pH 5 with 1M HCl or 1M NaOH. The mixture stirs at room temperature maintaining pH 5 until full conversion is detected. The product is isolated and purified via column chromatography, prep. HLPC, crystallization or distillation using the appropriate conditions.

Example 77—General Procedure for the N-Acylation of Guanosine with Activated Chelator Acid According to an Appropriately Modified Literature Procedure, See: Y. Fan, B. L. Gaffney, R. A. Jones, Org. Lett. 2004, 6, 2555-2557

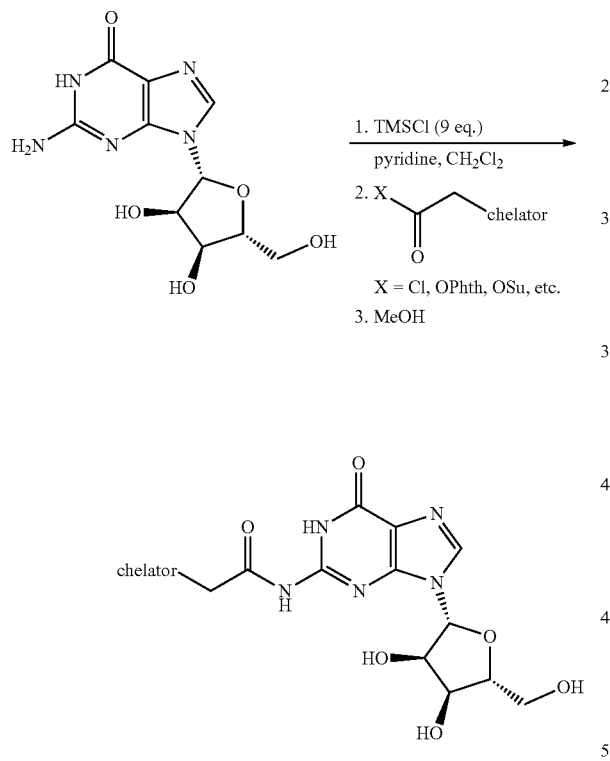

To dried guanosine hydrate (1 eq.) in dry dichloromethane under N₂ cooled in an ice bath, TMSCl (9 eq.) is added over 2 min, and the mixture allowed to stir for 2 h at room temperature. The flask is then cooled again in an ice bath, and the activated chelator acid, e.g. the activated version of the acid described in example 13 (1.1 eq.) dissolved in an appropriate solvent is added over 10 min. The mixture is stirred at a temperature between 0° C. and room temperature until full conversion (TLC, Ninhydrine). Methanol in excess is then added, and the solution is stirred at room temperature until complete desilylation. The mixture is evaporated, and the product is isolated via column chromatography, prep. HLPC, crystallization or distillation using the appropriate conditions.

Example 78—General Procedure for the Synthesis of 5' Esterificated Nucleosides Using the Chelator-Acids According to Appropriately Adopted Literature Procedures, See: W. Wei, W.-K. Shi, P.-F. Wang, X.-T. Zeng, P. Li, J.-R. Zhang, Q. Li, Z.-P. Tang, J. Peng, L.-Z. Wu, M.-Q. Xie, C. Liu, X.-H. Li, Y.-C. Wang, Z.-P. Xiao, H.-L. Zhu, Bioorg. Med. Chem. 2015, 23, 6602-6611; E. Hernindez-Vazquez, V. Chagoya, Med. Chem. Res. 2014, 24, 2325-2335

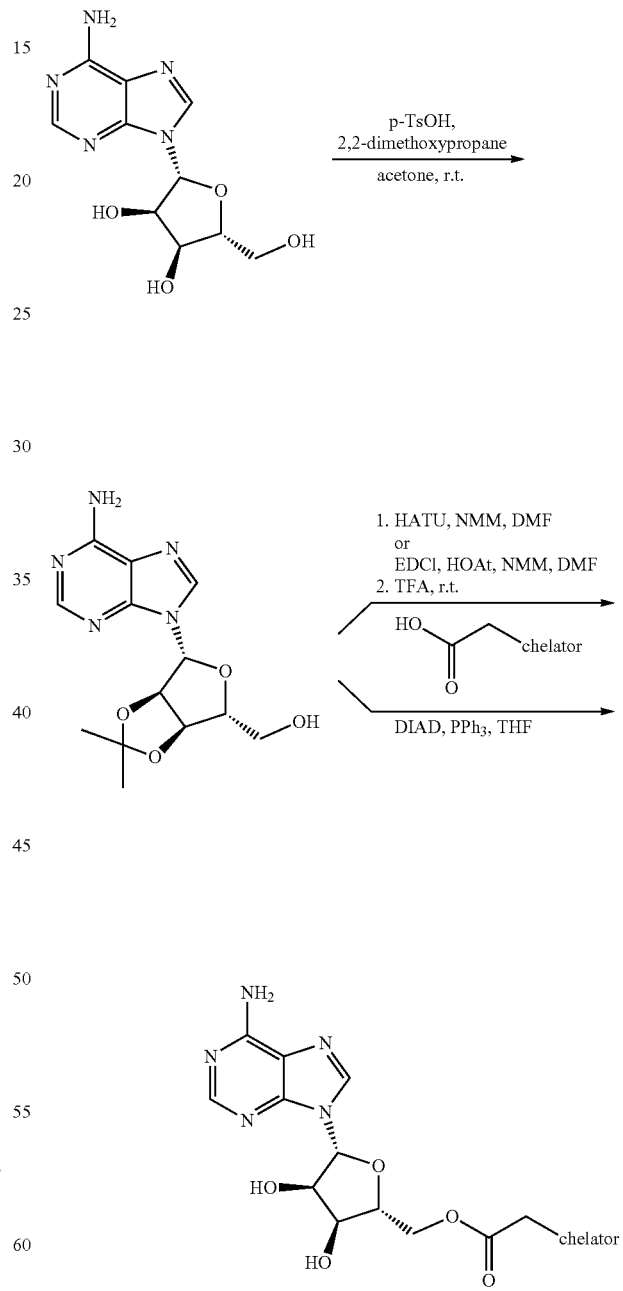

To a suspension of nucleoside (1 eq.) and β-toluensulfonic acid (1.1 eq.) in dry acetone, 2,2-dimethoxypropane (4 eq.) is added. After 3 days of vigorous stirring, the solution is neutralized with a saturated solution of Na₂CO₃ and then extracted with chloroform. The organic layers are joined and dried using Na₂SO₄. The solvent is removed under reduced pressure and the remainder solid is suspended with ether and washed with cold water obtaining a crude product that is purified and isolated via column chromatography, prep. HLPC, crystallization or distillation using the appropriate conditions. The 2',3'-O-isopropylidenadenosine prepared above (1 eq.) and the chelator-acid, e.g. the one described in Example 13, (1 eq.) are dissolved in an appropriate dry solvent (e.g., but not limited to DMF, CH₃CN, EtOAc, CH₂Cl₂) at room temperature. To this mixture is added the coupling reagent (e.g., but not limited to HATU, COMU, PyBOP, EDCl), (1-1.5 eq.), optional activator (e.g., but not limited to HOAt, HOBt), (1-1.5 eq.) and appropriate non-nucleophilic base (e.g., but not limited to NMM, DIPEA), (2-3 eq.) at a temperature between 0° C. and room temperature. The mixture is stirred for 1 h-20 h until full conversion and worked up by extraction, celite filtration, or direct concentration under reduced pressure, followed by purification and isolation via column chromatography, prep. HLPC, crystallization or distillation using the appropriate conditions.

Example 79—General Procedure for the Synthesis of Chelator Functionalized Guanosine Triphosphates According to an Appropriately Modified Literature Procedure, See: S. Masuda, T. Tomohiro, S. Yamaguchi, S. Morimoto, Y. Hatanaka, Bioorg. Med. Chem. Lett. 2015, 25, 1675-1678

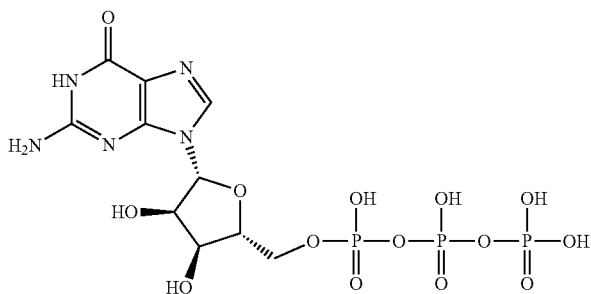
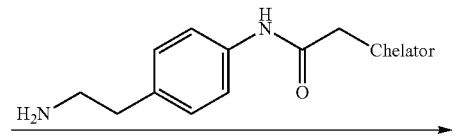
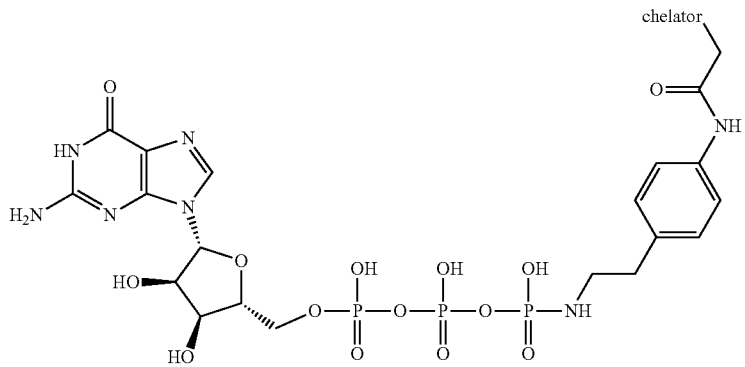

A solution of the chelator-amine described in Example 8 in water (50 mM) or a mixture of water and e.g. methanol, DMF, acetonitrile, THF is added to a buffered solution (pH 6.8) of ATP (50 mM). An aqueous solution of EDCl and a buffered solution (pH 6.8) of NEt3 (600 mM) are added at room temperature and the mixture is stirred for 1-8 h. The mixture is then concentrated under reduced pressure and the product isolated and purified via column chromatography using the appropriate stationary phase and eluent, prep. HPLC, crystallization or distillation.

Example 80—General Procedure for the Synthesis of Chelator Functionalized Adenosine Monophosphates According to an Appropriately Modified Literature Procedure, See: H. Fu, B. Han, Y.-F. Zhao, Chem. Commun. 2003, 134-135

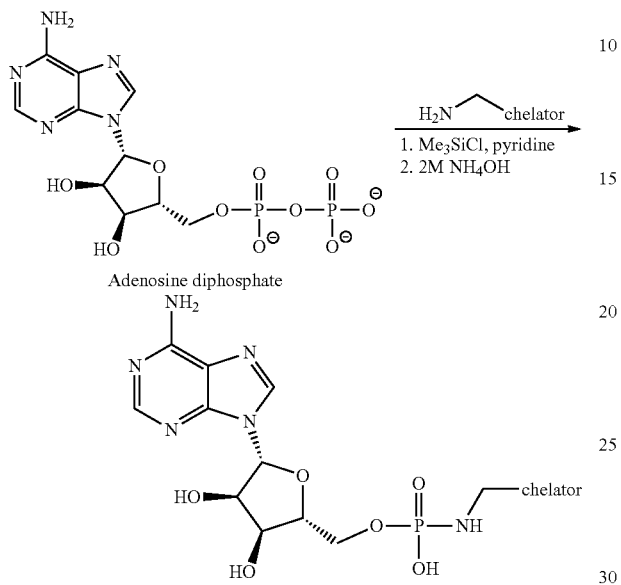

Under nitrogen atmosphere at room temperature trimethylsilyl chloride (10 eq.) is added dropwise to a mixture of ADP (adenosine 5A-diphosphate disodium salt) and a chelator-amine, e.g. the amine described in example 29 (2 eq.) in pyridine and stirred for two days. The solvent is removed under reduced pressure, the residue hydrolyzed in 2 M $NH_3$ (aq), and extracted with diethyl ether four times, and the remaining solution is evaporated to dryness. The product is isolated via column chromatography, prep. HLPC, crystallization or distillation using the appropriate conditions.

Example 81—General Procedure for the Acetate-Deprotection of the Coupled Products Prepared in the Previous Example According to an Appropriately Modified Literature Procedure, See: L. Zeng, G. Xu, P. Gao, M. Zhang, H. Li, J. Zhang, Eur. J. Med. Chem. 2015, 93, 109-120

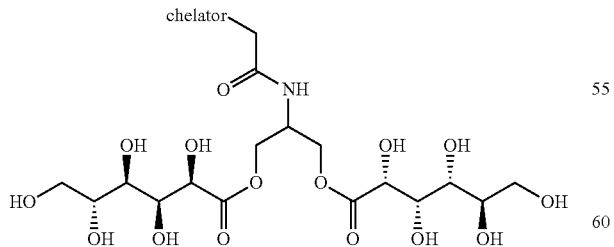

$CH_3ONa$ (15 eq.) is added to a solution of the bis-pentaacetylated gluconate amide prepared in example 74 (1 eq.) in methanol at 0° C. The mixture was stirred at 0° C. for 4 h and its pH was adjusted to 7 with 4 mol/L HCl in EtOAc. The reaction mixture was subject to evaporation to remove solvent and purified and isolated via column chromatography, prep. HLPC, crystallization or distillation using the appropriate conditions.

Example 82—General Procedure for the Reaction of Poly-Phosphateguanidine Salts Linked to a Chelator-Linker-Alcohol Using an Appropriately Modified Literature Procedure, See: C. J. McKinlay, R. M. Waymouth, P. A. Wender, J. Am. Chem. Soc. 2016, 138, 3510-3517

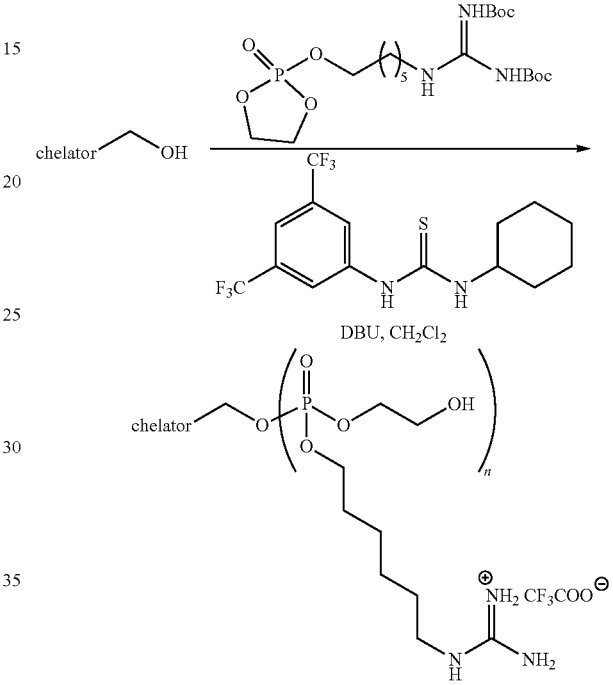

Example 83a—1-(pyridin-2-yl)-N-(pyridin-2-ylmethyl)-N-((1-(((3aR,5R,5aS,8aS,8bR)-2,2,7,7-tetramethyltetrahydro-5H-bis([1,3]dioxolo)[4,5-b:4',5'-d]pyran-5-yl)methyl)-1H-1,2,3-triazol-4-yl)methyl)methanamine

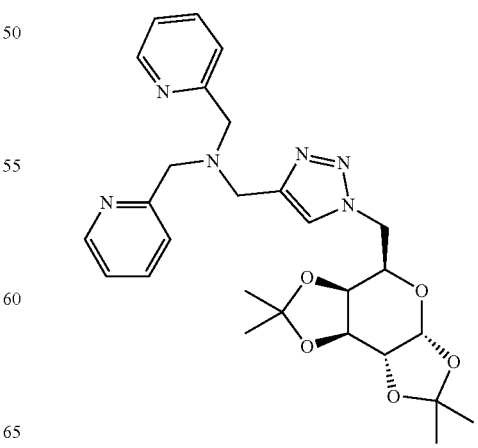

The title compound was prepared by reacting the product from Example 32 with di-(2-pyridyl-methyl)amine (DPA) as described in Example 68a.

Example 83b—(3R,4S,5R,6R)-6-((4-((bis(pyridin-2-ylmethyl)amino)methyl)-1H-1,2,3-triazol-1-yl)methyl)tetrahydro-2H-pyran-2,3,4,5-tetraol

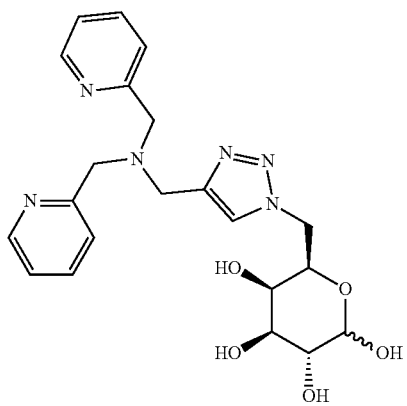 [SMILES: OC1O[C@H](Cn2cc(CN(Cc3ccccn3)Cc3ccccn3)nn2)[C@H](O)[C@H](O)[C@H]1O]

The title compound was prepared by deprotecting the product from Example 83a as described in Example 68b.

Example 84—(3R,4R,5S,6R)-3-(4-((bis(pyridin-2-ylmethyl)amino)methyl)-1H-1,2,3-triazol-1-yl)-6-(hydroxymethyl)tetrahydro-2H-pyran-2,4,5-triol

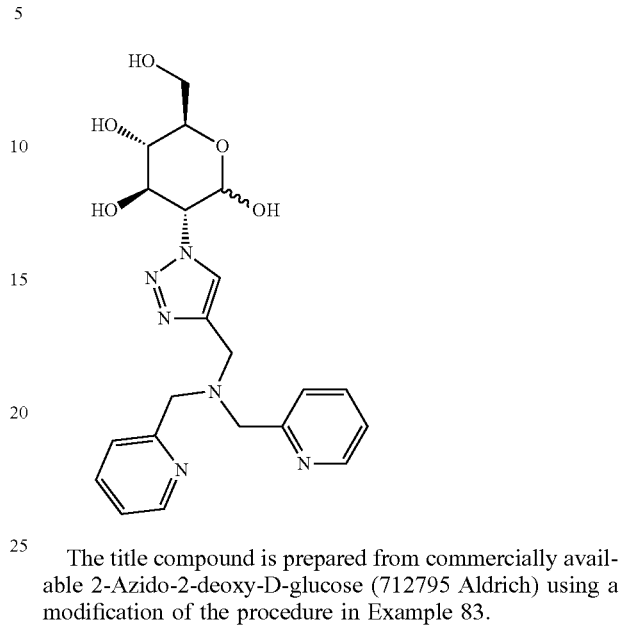

The title compound is prepared from commercially available 2-Azido-2-deoxy-D-glucose (712795 Aldrich) using a modification of the procedure in Example 83.

Example 85-6,6',6''-(nitrilotris(methylene))tris(N-methyl-N-((2S,3R,4R,5R)-2,3,4,5,6-pentahydroxyhexyl)nicotinamide)

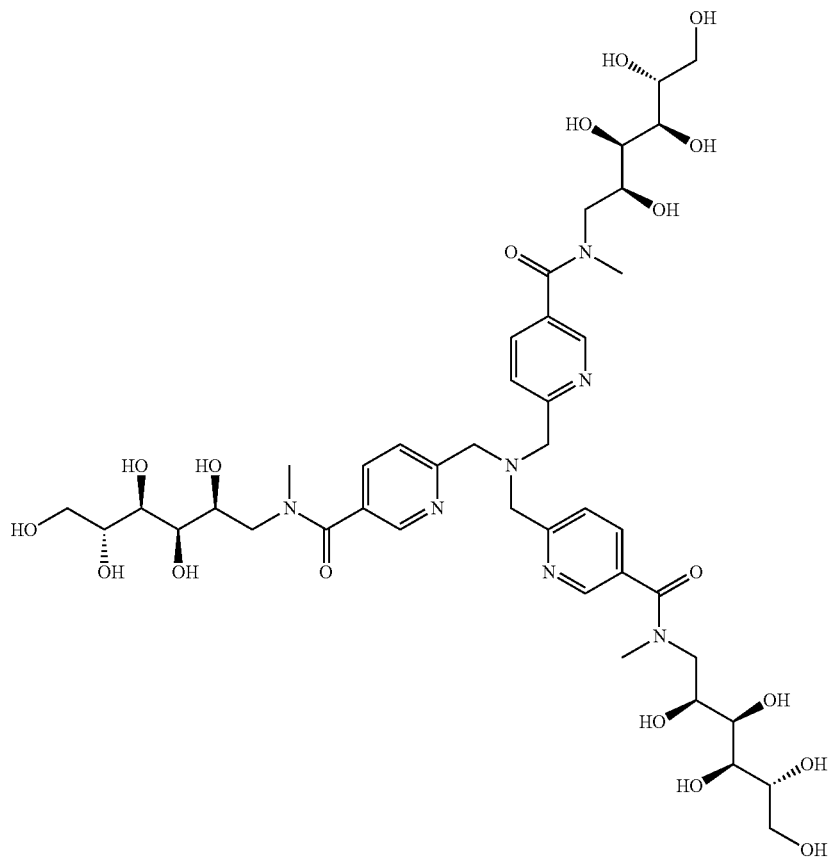 [SMILES: CN(C[C@H](O)[C@@H](O)[C@H](O)[C@H](O)CO)C(=O)c1ccc(CN(Cc2ccc(C(=O)N(C)C[C@H](O)[C@@H](O)[C@H](O)[C@H](O)CO)cn2)Cc2ccc(C(=O)N(C)C[C@H](O)[C@@H](O)[C@H](O)[C@H](O)CO)cn2)nc1]

The title compound can be prepared using modifications of the methods described in Example 106.

Examples 86-94

The compounds given in Schemes 10-20 above can be prepared using modifications of the methods described above.

Example 95a—tert-Butyl (4-(4-((bis(pyridin-2-ylmethyl)amino)methyl)-1H-1,2,3-triazol-1-yl)phenethyl)carbamate

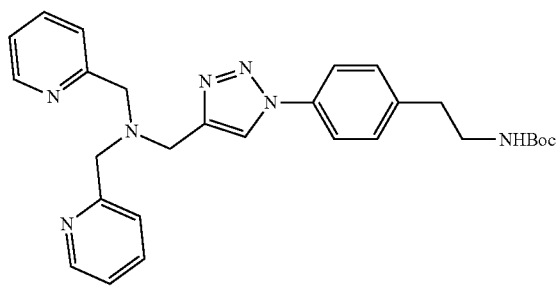 [SMILES: CC(C)(C)OC(=O)NCCc1ccc(-n2cc(CN(Cc3ccccn3)Cc3ccccn3)nn2)cc1]

Sodium ascorbate (10.15 g, 51.24 mmol) and CuSO$_4$.5H$_2$O (6.40 g, 25.62 mmol) was mixed rapidly in 60 mL water, and the resulting yellow solution transferred to a flask containing N-propargyl-di(2-picolyl)amine (6.08 g, 25.62 mmol), prepared as described by Simmons et al., Inorg. Chem., 2013, 52, 5838-5850, dissolved in 60 mL tert-butanol. After rapid stirring, the resulting green solution was transferred to a flask containing tert-butyl 4-azidophenethylcarbamate (5.60 g, 21.35 mmol), prepared according to Murai et al., Eur. J. Org. Chem., 2013, 2428-2433, and allowed to stir for 15 h. The reaction mixture was diluted with ethyl acetate, and washed with 1:1 water/brine. The water phase was then alkalized to pH 9-10 and extracted with ethyl acetate. Combined organic extracts was washed with a 0.025 M EDTA/0.5 M NaHCO$_3$ mixture and dried over sodium sulfate. Filtration and subsequent removal of solvent under reduced pressure gave a crude product as a brown oil which could be purified on neutral alumina, gradient 0-1% methanol in dichloromethane, giving the product as a thick orange oil. Purification was performed on three combined batches of different sizes, with a combined yield of 14.09 g (73%). $^1$H NMR (400 MHz, DMSO-d$_6$) δ 8.73 (s, 1H), 8.51 (m, 2H), 7.83-7.77 (m, 4H), 7.63 (d, J=7.9 Hz, 2H), 7.41 (m, 2H), 7.27 (m, 2H), 6.92 (br t, NH, 1H), 3.89 (s, 2H), 3.85 (s, 4H), 3.19 (m, 2H), 2.78 (t, J=7.3 Hz, 2H), 1.37 (s, 9H). MS (ESI, positive mode) m/z 500.5 [M+H]$^+$.

Example 95b—2-(4-(4-((Bis(pyridin-2-ylmethyl)amino)methyl)-1H-1,2,3-triazol-1-yl)phenyl)ethan-1-amine

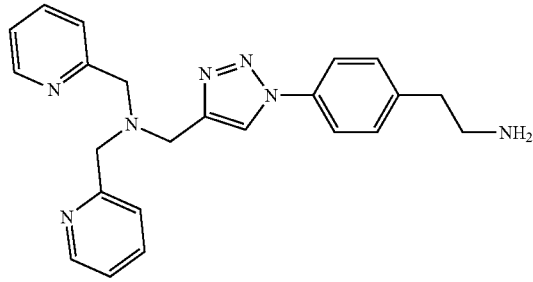 [SMILES: NCCc1ccc(-n2cc(CN(Cc3ccccn3)Cc3ccccn3)nn2)cc1]

To a solution of tert-butyl (4-(4-((bis(pyridin-2-ylmethyl)amino)methyl)-1H-1,2,3-triazol-1-yl)phenethyl)carbamate (12.70 g, 25.4 mmol) in 96 mL dioxane, 4 M HCl in dioxane (46 mL) was added slowly. After stirring under Ar overnight, the volatiles were removed under reduced pressure. The crude product was redissolved in 50 mL saturated NaHCO$_3$ solution (aq.) and extracted with 250 mL dichloromethane. This first extract contained product in a rather low purity. Repeated extractions with 100 mL dichloromethane (>10 repetitions) afforded, after removal of solvent under reduced pressure, pure product as an orange, thick oil (8.98 g, 88.5%). $^1$H NMR (400 MHz, DMSO-d$_6$) δ 8.70 (s, 1H), 8.50 (m, 2H), 7.82-7.75 (m, 4H), 7.63 (d, J=7.6 Hz, 2H), 7.42 (m, 2H), 7.25 (m, 2H), 3.86 (s, 2H), 3.82 (s, 4H), 2.83 (m, 2H), 2.73 (m, 2H), 1.74 (br, 2H). MS (ESI, positive mode) m/z 400.4 [M+H]$^+$.

Example 96—2-(4-(4-((bis(pyridin-2-ylmethyl)amino)methyl)-1H-1,2,3-triazol-1-yl)phenyl)-N-methyl-N-((2S,3R,4R,5R)-2,3,4,5,6-pentahydroxyhexyl)acetamide Example 96a—Ethyl 2-(4-(4-((bis(pyridin-2-ylmethyl)amino)methyl)-1H-1,2,3-triazol-1-yl)phenyl)acetate

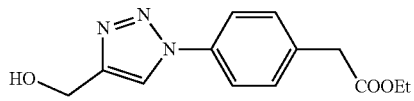 [SMILES: CCOC(=O)Cc1ccc(-n2cc(CO)nn2)cc1]

To a solution of ethyl 4-azidophenylacetate (5.00 g, 24.4 mmol), prepared according to Rao et al.,[3] in 58 mL acetonitrile, propargyl alcohol (2.73 g, 48.7 mmol) and copper(I) iodide (0.928 g, 4.87 mmol) was added. After stirring for 24 h, volatiles were removed under reduced pressure and the crude product purified using column chromatography on silica, using a gradient of ethyl acetate in dichloromethane. Removal of solvent gave the product as a yellow solid (6.14 g, 96%). $^1$H NMR (400 MHz, DMSO-d$_6$) δ 8.66 (s, 1H), 7.86 (m, 2H), 7.48 (m, 2H), 5.33 (t, J=5.6 Hz, 1H), 4.61 (d, J=5.6 Hz, 2H), 4.11 (q, J=7.12 Hz, 2H), 3.78 (s, 2H), 1.21 (t, J=7.1 Hz, 3H). MS (ESI, positive mode) m/z 262.3 [M+H]$^+$.

Example 96b—Ethyl 2-(4-{4-[(methanesulfonyloxy)methyl]-1H-1,2,3-triazol-1-yl}phenyl)acetate

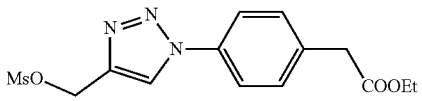

Ethyl 2-(4-(4-(hydroxymethyl)-1H-1,2,3-triazol-1-yl)phenyl)acetate (6.100 g, 23.35 mmol) was dissolved in 58 mL dichloromethane and kept on an ice bath. Triethylamine (3.544 g, 35.02 mol) was added, followed by methanesulfonyl chloride (3.209 g, 28.02 mmol). The reaction mixture was kept stirring on ice bath for 3 h, after which volatiles were removed under reduced pressure. Purification of the crude product on a silica column, using a gradient of 5%-10% ethyl acetate in dichloromethane, gave, after removal of solvent, the product as a colourless solid (5.11 g, 64%). $^1$H NMR (400 MHz, DMSO-$d_6$) δ 8.99 (s, 1H), 7.87 (m, 2H), 7.51 (m, 2H), 5.44 (s, 2H), 4.11 (q, J=7.12 Hz, 2H), 3.79 (s, 2H), 3.29 (s, 3H), 1.21 (t, J=7.1 Hz, 3H).

Example 96c—Ethyl 2-[4-(4-{[bis(pyridin-2-ylmethyl)amino]methyl}-1H-1,2,3-triazol-1-yl)phenyl]acetate

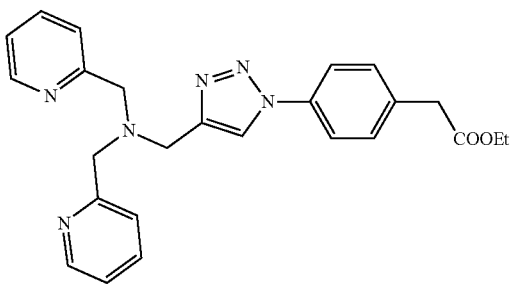 [SMILES: CCOC(=O)Cc1ccc(-n2cc(CN(Cc3ccccn3)Cc3ccccn3)nn2)cc1]

Di-(2-picolyl)amine (2.83 g, 14.2 mmol) was dissolved in acetonitrile. Potassium carbonate (3.93 g, 28.4 mmol) was added and the mixture was cooled down on an ice bath. Ethyl 2-(4-{4-[(methanesulfonyloxy)methyl]-1H-1,2,3-triazol-1-yl}phenyl)acetate (4.82 g, 14.2 mmol), dissolved in acetonitrile (total volume of acetonitrile in the reaction was 310 mL), was subsequently added dropwise, and after removal of the ice bath, allowed to react at room temperature for 12 hours. Filtration through celite, and with subsequent wash of the celite with dichloromethane, gave, after removal of solvents, a crude product as a dark orange thick oil. Purification on a silica column, using a gradient of methanol in dichloromethane, with additional ammonia added to the mobile phase, gave the product as a dark orange oil. Purification was performed on three combined batches of different sizes, with a combined yield of 6.02 g (80%). $^1$H NMR (400 MHz, DMSO-$d_6$) δ 8.75 (s, 1H), 8.50 (m, 2H), 7.87 (m, 2H), 7.78 (td, J=7.6 Hz, 1.9 Hz, 2H), 7.63 (d, J=7.9 Hz, 2H), 7.49 (m, 2H), 7.25 (m, 2H), 4.11 (q, J=7.1 Hz, 2H), 3.86 (s, 2H), 3.82 (s, 4H), 3.78 (s, 2H), 1.20 (t, J=7.1 Hz, 3H). MS (ESI, positive mode) m/z 443.2 [M+H]$^+$.

Example 96d 2-(4-(4-((bis(pyridin-2-ylmethyl)amino)methyl)-1H-1,2,3-triazol-1-yl) phenyl)acetic acid

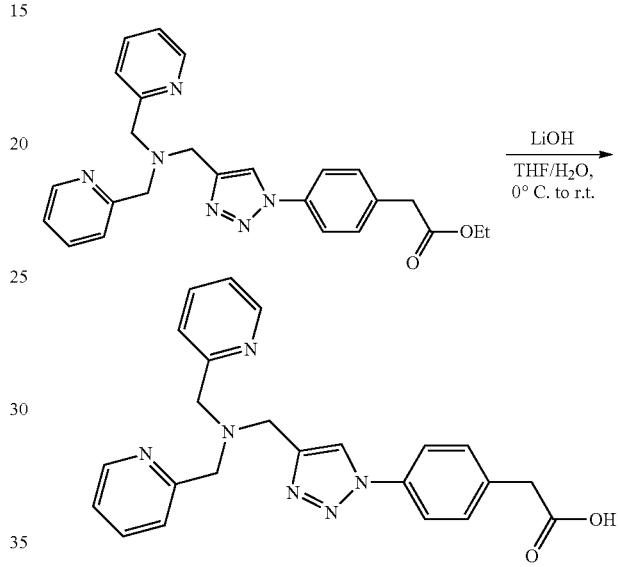

Ethyl 2-(4-(4-((bis(pyridin-2-ylmethyl)amino)methyl)-1H-1,2,3-triazol-1-yl)phenyl)acetate (323.1 mg, 0.73 mmol, 1.0 eq.) from Example 96a was dissolved in 10 mL THF and cooled to 0° C. in an ice bath. A solution of LiOH hydrate (61 mg, 1.46 mmol, 2.0 eq.) in 5 mL dest. H$_2$O was added and the solution stirred at 0° C. until TLC (Alumina, 5% MeOH/CH$_2$Cl$_2$) indicated full conversion. The THF was removed under reduced pressure and the residual aqueous solution was adjusted to pH=6 using 4 N HCl. The solvent was removed under reduced pressure affording the product in quantitative yield, used in the next step without further purification.

Example 96e—2-(4-(4-((bis(pyridin-2-ylmethyl)amino)methyl)-1H-1,2,3-triazol-1-yl) phenyl)-N-methyl-N-((2S,3R,4R,5R)-2,3,4,5,6-pentahydroxyhexyl)acetamide

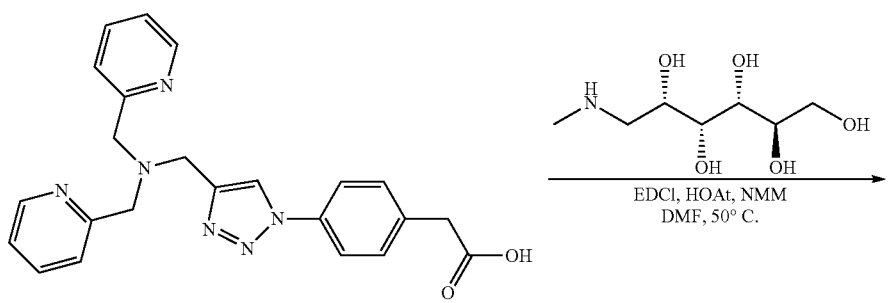

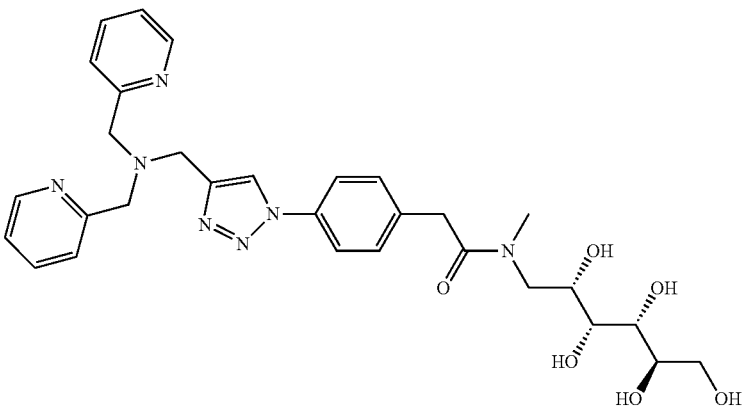

2-(4-(4-((bis(pyridin-2-ylmethyl)amino)methyl)-1H-1,2,3-triazol-1-yl)phenyl) acetic acid from example 96d (302 mg, 0.73 mmol, 1.0 eq.) was dissolved in 3 mL dry DMF at room temperature. N-Methyl-D-Glucamine (213 mg, 1.059 mmol, 1.5 eq.), EDCl (209.9 mg, 1.095 mmol, 1.5 eq.), HOAt (149 mg, 1.095 mmol, 1.5 eq.) and NMM (120 µL, 1.095 mmol, 1.5 eq.) were then added. The mixture was heated to 50° C. for 16 h with stirring and then concentrated under reduced pressure. Purification of the product was achieved by way of dry column vacuum chromatography on C18 material, using a stepwise elution from 10% to 90% methanol in water affording 321.1 mg (0.542 mmol, 74%) of product as a pale yellow foam. The product appears as a syn/anti mixture regarding the amide bond. $^1$H NMR (400 MHz, MeOD) δ 8.50-8.39 (m, 3H), 7.78 (dd, J=13.8, 7.2 Hz, 4H), 7.69 (d, J=7.8 Hz, 2H), 7.47 (d, J=8.0 Hz, 2H), 7.32-7.20 (m, 2H), 4.08-3.96 (m, 2H), 3.93 (s, 2H), 3.87 (s, 5H), 3.83-3.57 (m, 6H), 3.46 (dd, J=13.3, 6.5 Hz, 1H), 3.19, 3.02 (2×s, 3H). $^{13}$C NMR (101 MHz, MeOD) δ 174.01, 173.91, 160.20, 149.49, 146.06, 138.69, 138.29, 137.62, 137.13, 137.04, 131.81, 131.70, 124.99, 123.82, 123.51, 121.66, 121.54, 74.11, 73.69, 73.11, 73.04, 72.76, 72.22, 71.61, 71.24, 64.77, 64.75, 60.63, 54.09, 52.73, 40.92, 40.49, 38.25, 34.79. APCI-HRMS e/z calc. for $C_{30}H_{37}N_7O_6$: 591.2805, found: 592.2878 [M+H].

Example 97—(R)-6-((bis(pyridin-2-ylmethyl)amino)methyl)-N-(2,3-dihydroxypropyl)nicotinamide

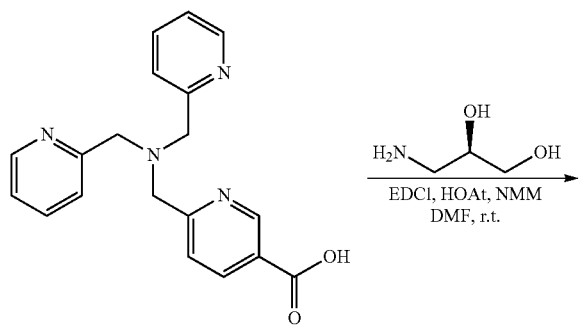

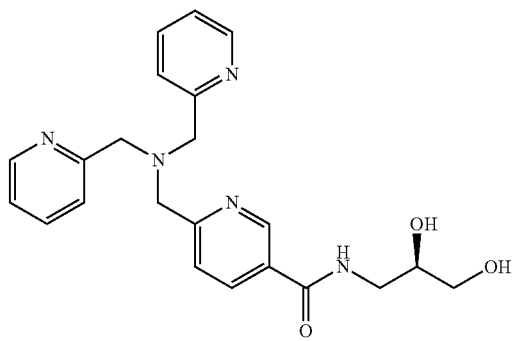

The 6-((bis(pyridin-2-ylmethyl)amino)methyl)nicotinic acid from example 13 (135.7 mg, 0.406 mmol, 1.0 eq.) was dissolved in 3 mL dry DMF at room temperature. (R)-3-aminopropane-1,2-diol (55 mg, 0.609 mmol, 1.5 eq.), EDCl (117 mg, 0.609 mmol, 1.5 eq.), HOAt (83 mg, 0.609 mmol, 1.5 eq.) and NMM (67 µL, 0.609 mmol, 1.5 eq.) were then added and the mixture stirred at room temperature for 16 h. The reaction mixture was concentrated under reduced pressure and the purification of the product was achieved by way of dry column vacuum chromatography on C18 material, using a stepwise elution from 10% to 90% methanol in water affording 61 mg (0.162 mmol, 40%) of product. $^1$H NMR (300 MHz, MeOH) δ 8.88 (dd, J=2.2, 0.6 Hz, 1H), 8.44 (ddd, J=5.0, 1.6, 0.9 Hz, 2H), 8.17 (dd, J=8.2, 2.3 Hz, 1H), 7.78 (ddd, J=11.4, 8.7, 5.2 Hz, 3H), 7.66 (d, J=7.8 Hz, 2H), 7.27 (ddd, J=7.4, 5.0, 1.2 Hz, 2H), 3.91 (s, 2H), 3.88 (s, 4H), 3.86-3.78 (m, 1H), 3.61-3.51 (m, 3H), 3.41 (dd, J=13.7, 7.0 Hz, 1H). $^{13}$C NMR (101 MHz, MeOD) δ 168.32, 163.39, 159.94, 149.59, 148.72, 138.68, 137.26, 130.28, 124.97, 124.30, 123.90, 71.95, 65.22, 61.25, 60.95, 44.12. APCI-HRMS e/z calc. for $C_{22}H_{25}N_5O_3$: 407.1957, found 408.2029 [M+H]

Example 98—2-(4-(4-((bis(pyridin-2-ylmethyl)amino)methyl)-1H-1,2,3-triazol-1-yl)phenyl)-N-(1,3-dihydroxy-2-(hydroxymethyl)propan-2-yl)acetamide

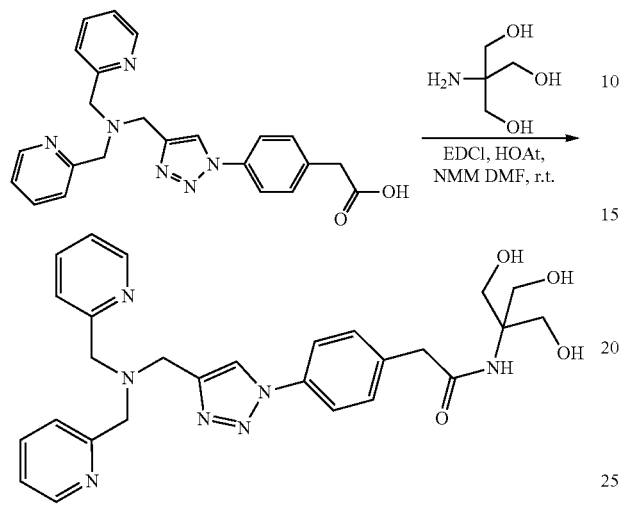

2-(4-(4-((bis(pyridin-2-ylmethyl)amino)methyl)-1H-1,2,3-triazol-1-yl)phenyl)acetic acid from example 96d (132.5 mg, 0.3199 mmol, 1.0 eq.) was dissolved in 2 mL dry DMF at room temperature. 2-amino-2-(hydroxymethyl)propane-1,3-diol (58 mg, 0.479 mmol, 1.5 eq.), EDCl (91.6 mg, 0.479 mmol, 1.5 eq.), HOAt (65 mg, 0.479 mmol, 1.5 eq.) and NMM (53 μL, 0.479 mmol, 1.5 eq.) were then added. The mixture was stirred at room temperature for 16 h and then concentrated under reduced pressure. Purification of the product was achieved by way of dry column vacuum chromatography on C18 material, using a stepwise elution from 10% to 90% methanol in water affording 76.3 mg (0.147 mmol, 46%) of product. $^1$H NMR (400 MHz, MeOD) δ 8.45 (s, 1H), 8.43 (d, J=3.7 Hz, 2H), 7.78 (t, J=7.9 Hz, 4H), 7.68 (d, J=7.8 Hz, 2H), 7.51 (d, J=7.8 Hz, 2H), 7.25 (t, J=5.7 Hz, 2H), 3.92 (s, 2H), 3.86 (s, 4H), 3.75 (s, 6H), 3.68 (s, 2H). $^{13}$C NMR (101 MHz, MeOD) δ 174.24, 160.15, 149.47, 146.05, 138.67, 138.03, 137.17, 131.78, 124.96, 123.81, 123.47, 121.54, 63.68, 62.49, 60.62, 49.96, 43.54. APCI-HRMS e/z calc. for $C_{27}H_{31}N_7O_4$: 517.2438, found: 518.2509 [M+H].

Example 99—6-((bis(pyridin-2-ylmethyl)amino)methyl)-N-(4-(2-(methyl((2S,3R,4R,5R)-2,3,4,5,6-pentahydroxyhexyl)amino)-2-oxoethyl)phenyl)nicotinamide

Example 99a—Methyl 2-(4-(6-((bis(pyridin-2-ylmethyl)amino)methyl) nicotinamido)phenyl)acetate

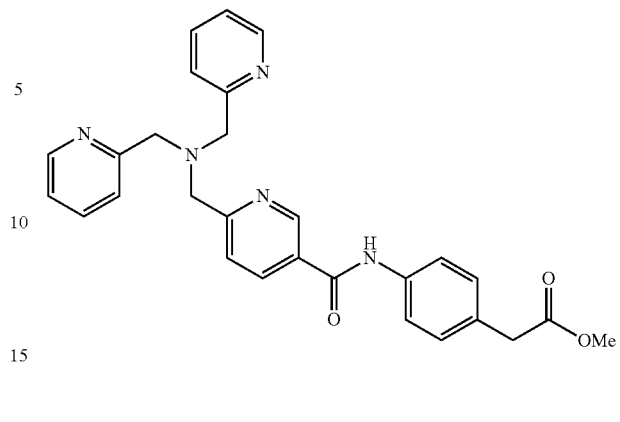

The 6-((bis(pyridin-2-ylmethyl)amino)methyl)nicotinic acid from example 13 (976.3 mg, 2.92 mmol, 1.0 eq.) was dissolved in 20 mL dry DMF, cooled to 0° C. in an ice bath. Methyl 2-(4-aminophenyl)acetate hydrochloride (883 mg, 4.38 mmol, 1.5 eq.), EDCl (839 mg, 4.38 mmol, 1.5 eq.) and HOAt (596 mg, 4.38 mmol, 1.5 eq.) were added, followed by NMM (740 μL, 6.71 mmol, 2.3 eq.) dropwise over a period of 30 min at 0° C. The mixture was allowed to warm to room temperature and stirred for 16 h and was concentrated under reduced pressure. The residue was dissolved in 100 mL CHCl$_3$ and transferred into a separation funnel. The organic phase was washed with a mixture of sat. aq. K2CO3 solution and H2O (50 mL each) followed by brine (50 mL). The organic phase was separated, dried over Na2SO4, filtered and concentrated under reduced pressure and the product purified by dry column vacuum chromatography on C18 material, using a stepwise elution from 10% to 90% methanol in water affording 723.9 mg (1.5 mmol, 51%) of product as a yellow oil. $^1$H NMR (200 MHz, MeOD) δ 8.97 (d, J=2.0 Hz, 1H), 8.49-8.41 (m, 2H), 8.27 (dd, J=8.2, 2.3 Hz, 1H), 7.81 (td, J=7.5, 1.8 Hz, 3H), 7.73-7.61 (m, 4H), 7.28 (ddd, J=6.5, 4.8, 2.3 Hz, 4H), 3.94 (s, 2H), 3.90 (s, 4H), 3.68 (s, 3H), 3.65 (s, 2H). $^{13}$C NMR (101 MHz, MeOD) δ 173.93, 166.05, 161.46, 157.71, 157.66, 149.15, 148.63, 140.22, 138.46, 137.69, 132.12, 131.28, 130.80, 125.48, 124.72, 124.52, 122.21, 60.53, 60.17, 52.47, 41.08. APCI-HRMS e/z calc. for $C_{28}H_{27}N_3O_3$: 481.2114, found: 482.2184 [M+H].

Example 99b—2-(4-(6-((bis(pyridin-2-ylmethyl)amino)methyl)nicotinamido) phenyl)acetic acid

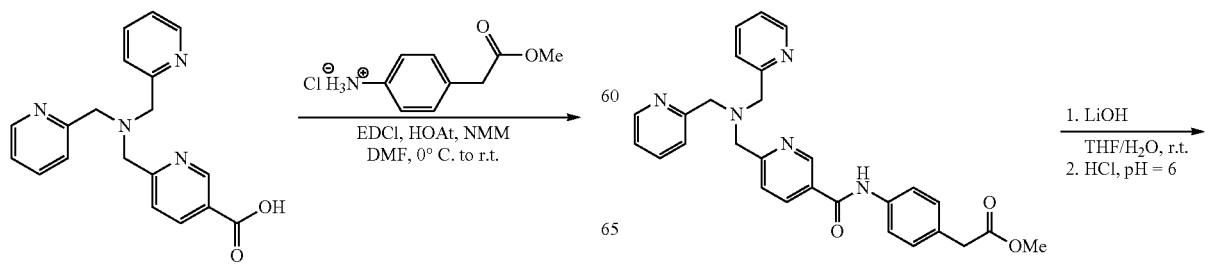

-continued

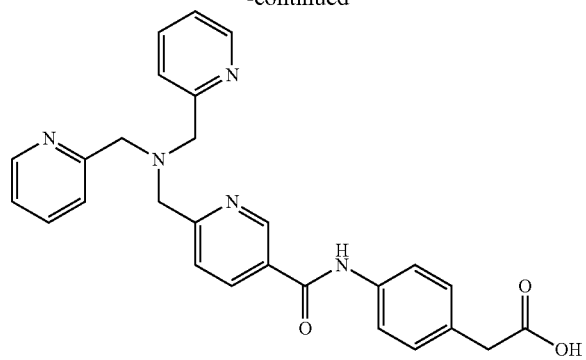

Methyl 2-(4-(6-((bis(pyridin-2-ylmethyl)amino)methyl)nicotinamido)phenyl)acetate from example 99a (287.7 mg, 0.59 mmol, 1.0 eq.) was dissolved in 10 mL THF and cooled to 0° C. in an ice bath. A solution of LiOH hydrate (49.5 mg, 1.18 mmol, 2.0 eq.) in 10 mL dest. $H_2O$ was added and the solution stirred at 0° C. until TLC (Alumina, 5% MeOH in $CH_2Cl_2$) indicated full conversion. The THF was removed under reduced pressure and the residual aqueous solution was adjusted to pH=6 using 4 N HCl. The solvent was removed under reduced pressure affording the product in quantitative yield which was used in the next step without further purification.

Example 99d—6-((bis(pyridin-2-ylmethyl)amino)methyl)-N-(4-(2-(methyl((2S,3R,4R,5R)-2,3,4,5,6-pentahydroxyhexyl)amino)-2-oxoethyl)phenyl)nicotinamide

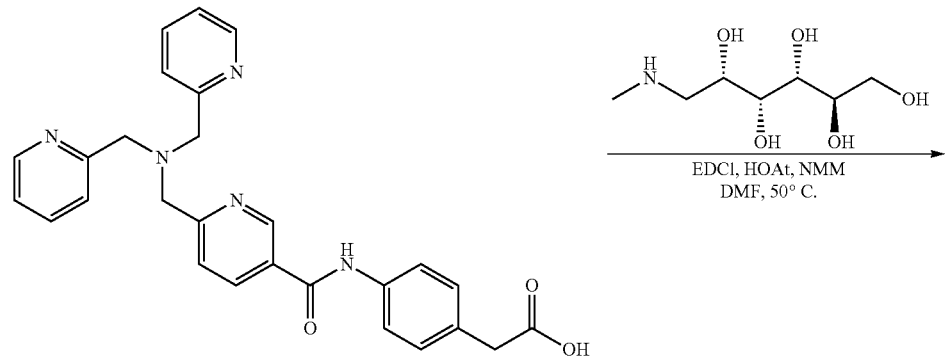

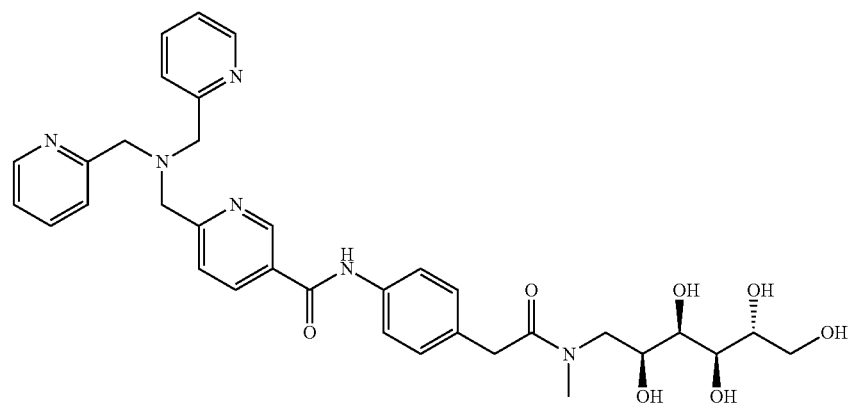

The 2-(4-(6-((bis(pyridin-2-ylmethyl)amino)methyl)nicotinamido)phenyl)acetic acid from example 99b (276 mg, 0.59 mmol, 1.0 eq.) was dissolved in 2.5 mL dry DMF at room temperature. N-Methyl-D-Glucamine (173 mg, 0.885 mmol, 1.5 eq.), EDCl (169 mg, 0.885 mmol, 1.5 eq.), HOAt (120 mg, 0.885 mmol, 1.5 eq.) and NMM (98 μL, 0.885 mmol, 1.5 eq.) were then added. The mixture was heated to 50° C. for 16 h with stirring and then concentrated under reduced pressure. Purification of the product was achieved by way of dry column vacuum chromatography on C18 material, using a stepwise elution from 10% to 90% methanol in water affording 207.4 mg (0.322 mmol, 54%) of product as a white foam. The product appears as a syn/anti mixture regarding the amide bond. $^1$H NMR (400 MHz, MeOD) δ 9.00-8.93 (m, 1H), 8.44 (dd, J=4.9, 0.7 Hz, 2H), 8.25 (dd, J=8.2, 1.7 Hz, 1H), 7.79 (td, J=7.7, 1.8 Hz, 3H), 7.65 (dd, J=16.4, 7.7 Hz, 4H), 7.27 (dd, J=9.5, 4.5 Hz, 4H), 4.06-3.97 (m, 1H), 3.93 (s, 2H), 3.89 (s, 4H), 3.82-3.58 (m, 7H), 3.43 (ddd, J=7.9, 5.1, 1.4 Hz, 1H), 3.15, 3.00 (2×s, 3H). $^{13}$C NMR (101 MHz, MeOD) δ 174.60, 174.50, 166.30, 163.54, 163.52, 159.93, 149.60, 148.94, 138.66, 138.32, 138.22, 137.51, 133.40, 132.71, 130.98, 130.55, 130.45, 124.95, 124.28, 123.89, 122.40, 122.30, 74.12, 73.78, 73.09, 73.04, 72.80, 72.33, 71.56, 71.24, 64.76, 64.74, 61.21, 60.94, 54.14, 52.71, 41.09, 40.66, 38.29, 34.82. ESI-HRMS e/z calc. for $C_{34}H_{40}N_6O_7$: 644.2958, found: 707.2166 [(M−H)Zn]$^+$.

Example 100—6-((bis(pyridin-2-ylmethyl)amino)methyl)-N-(4-(2-(1,3-dihydroxy-2-(hydroxymethyl)propan-2-ylamino)-2-oxoethyl)phenyl)nicotinamide

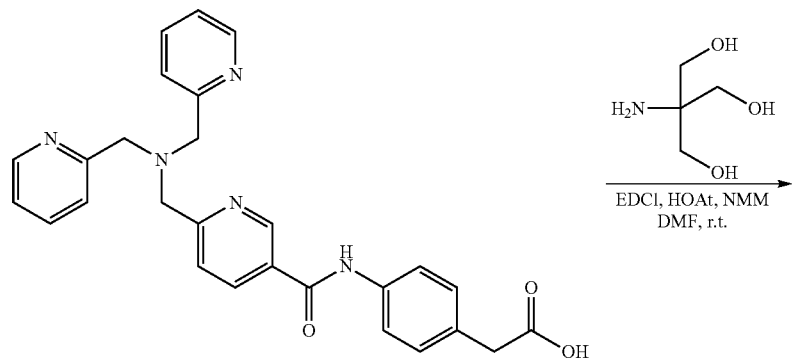

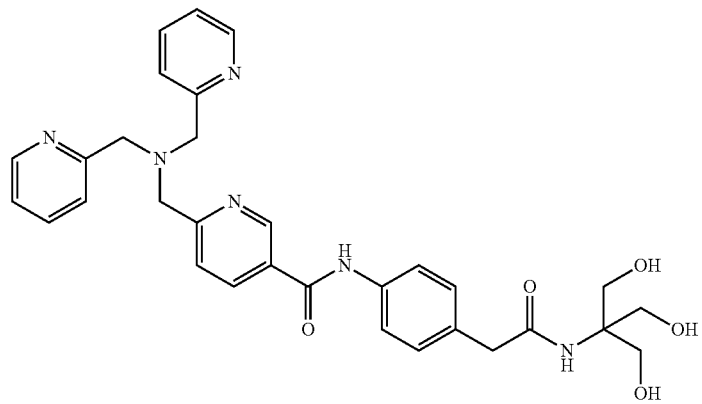

The 2-(4-(6-((bis(pyridin-2-ylmethyl)amino)methyl) nicotinamido)phenyl)acetic acid from Example 99b (99.5 mg, 0.213 mmol, 1.0 eq.) was dissolved in 3 mL dry DMF at room temperature. 2-amino-2-(hydroxymethyl)propane-1,3-diol (38.7 mg, 0.3195 mmol, 1.5 eq.), EDCl (61 mg, 0.3195 mmol, 1.5 eq.), HOAt (43 mg, 0.3195 mmol, 1.5 eq.) and NMM (35 µL, 0.3195 mmol, 1.5 eq.) were then added. The mixture was stirred at room temperature for 16 h and then concentrated under reduced pressure. Purification of the product was achieved by way of dry column vacuum chromatography on C18 material, using a stepwise elution from 10% to 90% methanol in water affording 91.4 mg (0.16 mmol, 75%) of product. $^1$H NMR (400 MHz, MeOD) δ 8.97 (s, 1H), 8.45 (s, 2H), 8.26 (d, J=8.2 Hz, 1H), 7.79 (t, J=7.8 Hz, 3H), 7.66 (t, J=8.2 Hz, 4H), 7.30 (dd, J=13.2, 6.6 Hz, 4H), 3.94 (s, 2H), 3.89 (s, 4H), 3.72 (s, 6H), 3.58 (s, 2H). $^{13}$C NMR (101 MHz, MeOD) δ 174.99, 166.34, 163.56, 159.94, 149.61, 148.94, 138.69, 138.50, 137.52, 133.28, 131.00, 130.75, 124.97, 124.31, 123.91, 122.33, 63.58, 62.51, 61.23, 60.95, 43.73. APCI-HRMS e/z calc. for $C_{31}H_{34}N_6O_5$: 570.2591, found: 571.2664 [M+H].

Example 101—(2S,3R,4S,5R,6S)—N-(4-(4-((Bis (pyridin-2-ylmethyl)amino)methyl)-1H-1,2,3-triazol-1-yl)phenethyl)-3,4,5,6-tetrahydroxytetrahydro-2H-pyran-2-carboxamide Example 101a—(3aR,5S,5aR,8aS,8bR)—N-(4-(4-((Bis(pyridin-2-ylmethyl)amino)methyl)-1H-1,2,3-triazol-1-yl)phenethyl)-2,2,7,7-tetramethyltetrahydro-5H-bis([1,3]dioxolo)[4,5-b:4',5'-d]pyran-5-carboxamide

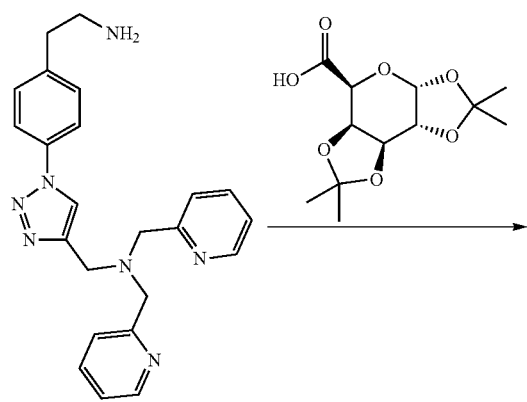

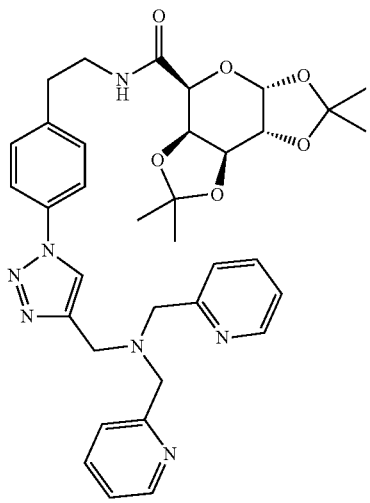

To an ice-cooled flask under nitrogen, containing 2-(4-(4-((Bis(pyridin-2-ylmethyl)amino)methyl)-1H-1,2,3-triazol-1-yl)phenyl)ethan-1-amine (207.5 mg, 0.519 mmol) from Example 95b 1,2:3,4-di-O-isopropylidene-αiD-galacturonide (141.3 mg, 0.515 mmol) and HATU (201.5 mg, 0.530 mmol), dissolved in 3 mL DMF, N-methylmorpholine (0.07 mL, 0.6 mmol) was added. After stirring for 30 min, the flask was left at room temperature and stirred overnight. Solvent was removed under reduced pressure and the crude product loaded onto a plug of Bondesil C-18 OH SPE material. The product was eluted using portion-wise additions of methanol/water mixtures, ranging from 50% to 75% methanol. Pure fractions were collected and removal of solvent gave the title compound as a pale yellow film (195.1 mg, 57.8%). $^1$H NMR (400 MHz, methanol-$d_4$) δ (app. dt, J=1.8 Hz, 7.8 Hz, 2H), 7.75 (m, 2H), 7.70 (d, J=7.8 Hz, 2H), 7.46 (m, 2H), 7.27 (m, 2H), 5.61 (d, J=4.9 Hz, 1H), 4.69 (dd, J=7.8 Hz, 2.5 Hz, 1H), 4.58 (dd, J=7.8 Hz, 2.1 Hz, 1H), 4.41 (dd, J=4.9 Hz, 2.5 Hz, 1H), 4.23 (d, J=2.1 Hz, 1H), 3.93 (s, 2H), 3.87 (s, 4H), 3.57 (m, 1H), 3.47 (m, 1H), 2.91 (app. t, J=7.2 Hz, 2H), 1.47 (s, 3H), 1.38 (s, 3H), 1.34 (s, 3H), 1.32 (s, 3H). $^{13}$C NMR (100 MHz, methanol-$d_4$) δ 136.8, 131.4, 125.0, 123.9, 123.5, 121.5, 110.6, 110.3, 97.8, 73.0, 72.1, 72.0, 70.0, 60.6, 50.0, 41.3, 36.0, 26.34, 26.26, 25.0, 24.5. MS (APCI, positive mode) m/z 656.3 [M+H]$^+$, HR-MS (APCI, pos. mode) m/z 656.3191 calculated for $C_{35}H_{42}N_7O_6$, found m/z 656.3189.

Example 101b—(2S,3R,4S,5R,6S)—N-(4-(4-((Bis(pyridin-2-ylmethyl)amino)methyl)-1H-1,2,3-triazol-1-yl)phenethyl)-3,4,5,6-tetrahydroxytetrahydro-2H-pyran-2-carboxamide

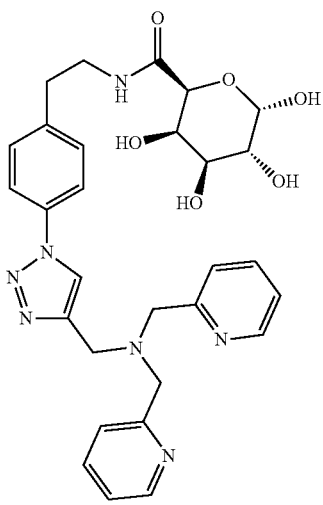 [SMILES: O=C(NCCc1ccc(-n2cc(CN(Cc3ccccn3)Cc3ccccn3)nn2)cc1)[C@H]1O[C@H](O)[C@H](O)[C@@H](O)[C@H]1O]

From the doubly isopropylidene protected sugar in Example 101a (186.6 mg, 0.285 mmol), the deprotected product was obtained by stirring in room temperature with 20 mL trifluoroacetic acid and 15 mL water for 4 h. The volatile materials were removed after repeated additions of 10 mL toluene followed by evaporation on a rotary evaporator between each addition. The crude product was loaded onto a small SPE cartridge with C18 material and eluted with a methanol in water gradient, going from 25% to 45%. Only limited retention was observed on this material. Final purification was achieved after removal of eluent and re-loading the material onto a cartridge containing strong cationic exchange SPE material, using 1:1 methanol/water and a pH-gradient from pH 3 to pH 10 with formic acid and ammonia as additives to elute the product. The product eluted at pH 9, and removal of solvent under reduced pressure afforded the title compound as a colourless oil or foam (128.9 mg, 78.6%). The NMR spectra have a very complex appearance overall due to presence of a and 3 anomers, and also additional minor peaks, likely from furanose forms. For 8H below 6 ppm, peaks from the sugar moiety are reported with shift only. In the multiplicity edited HSQC spectrum, 20 methine resonances, some of which are partly overlapping, are clearly visible. However, we have only reported $\delta_C$ data for resonances clearly visible in the 1D spectrum. $^1$H NMR (400 MHz, DMSO-$d_6$) δ 8.46-8.43 (m, 3H), 7.80 (app. dt, J=1.8 Hz, 7.7 Hz, 2H), 7.75 (m, 2H), 7.70 (d, J=7.8 Hz, 2H), 7.47 (m, 2H), 7.28 (m, 2H), 5.24, 5.14, 4.49, 4.41, 4.36, 4.21, 4.15, 4.10, 4.08, 4.02, 3.94 (s, 2H), 3.91, 3.87 (s, 4H), 3.83, 3.76, 3.53 (m, 2.8H (methylene overlapping with sugar resonances), 2.92 (m, 2H). $^{13}$C NMR (100 MHz, DMSO-$d_6$) δ 174.8, 172.1, 171.3, 160.2, 149.5, 145.94, 145.93, 141.74, 141.69, 138.8, 136.8, 131.44, 131.43, 131.36, 131.34, 125.0, 123.9, 123.5, 121.66, 121.64, 121.62, 98.7, 94.4, 76.6, 74.7, 73.2, 72.4, 71.6, 70.9, 70.0, 60.6, 50.0, 41.47, 41.44, 41.37, 36.1, 36.0.

Compound 102 given in Schemes 10-20 above can be prepared using modifications of the methods described above.

Example 103—6-((bis(pyridin-2-ylmethyl)amino)methyl)-N-(1,3-dihydroxy-2-(hydroxymethyl)propan-2-yl)nicotinamide

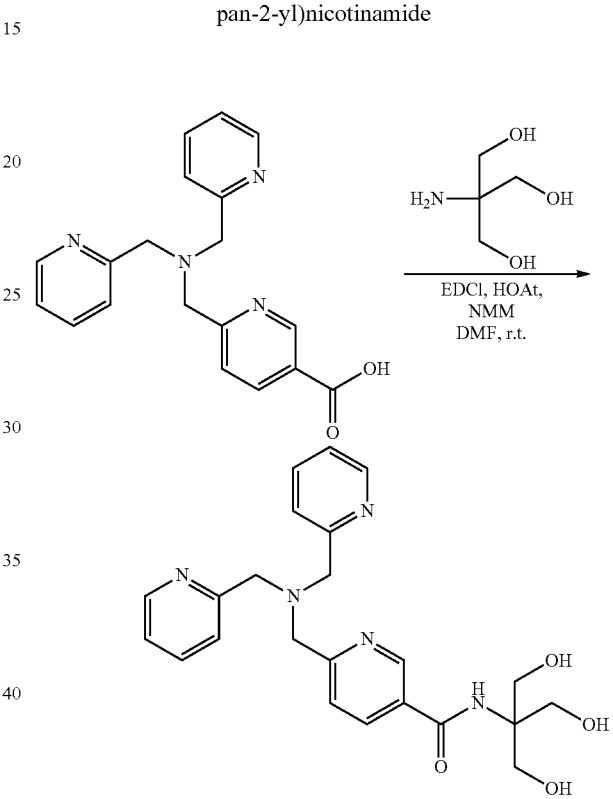

The 6-((bis(pyridin-2-ylmethyl)amino)methyl)nicotinic acid from Example 13 (121 mg, 0.363 mmol, 1.0 eq.) was dissolved in 3 mL dry DMF at room temperature. 2-amino-2-(hydroxymethyl)propane-1,3-diol (66 mg, 0.545 mmol, 1.5 eq.), EDCl (104 mg, 0.545 mmol, 1.5 eq.), HOAt (74 mg, 0.545 mmol, 1.5 eq.) and NMM (60 µL, 0.545 mmol, 1.5 eq.) were added and the mixture stirred at room temperature for 16 h. The reaction mixture was concentrated under reduced pressure and the purification of the product was achieved by way of dry column vacuum chromatography on C18 material, using a stepwise elution from 10% to 90% methanol in water affording 97.2 mg (0.222 mmol, 61%) of product. $^1$H NMR (300 MHz, MeOH) δ 8.92-8.81 (m, 1H), 8.44 (ddd, J=5.0, 1.6, 0.8 Hz, 2H), 8.15 (dd, J=8.2, 2.3 Hz, 1H), 7.78 (ddd, J=14.2, 10.1, 5.0 Hz, 3H), 7.66 (d, J=7.8 Hz, 2H), 7.27 (ddd, J=7.4, 5.0, 1.2 Hz, 2H), 3.90 (s, 2H), 3.87 (s, 6H), 3.87 (s, 4H). $^{13}$C NMR (101 MHz, MeOD) δ 168.80, 163.25, 159.93, 149.59, 148.78, 138.67, 137.36, 131.11, 124.94, 124.16, 123.89, 64.23, 62.38, 61.15, 60.89. APCI-HRMS e/z calc. for $C_{23}H_{27}N_5O_4$: 437.2063, found 438.2134 [M+H]

Example 104—(S)-2-(4-(4-((bis(pyridin-2-ylmethyl)amino)methyl)-1H-1,2,3-triazol-1-yl)phenyl)-N-(2,3-dihydroxypropyl)acetamide

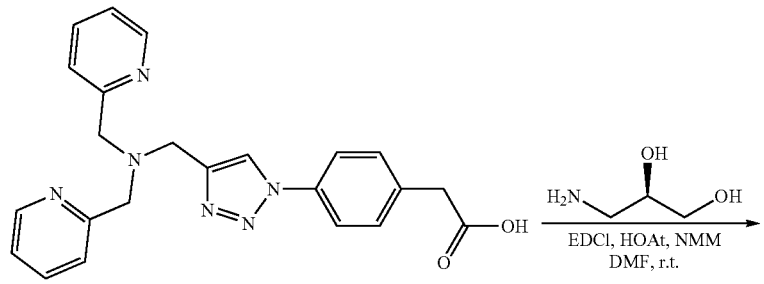

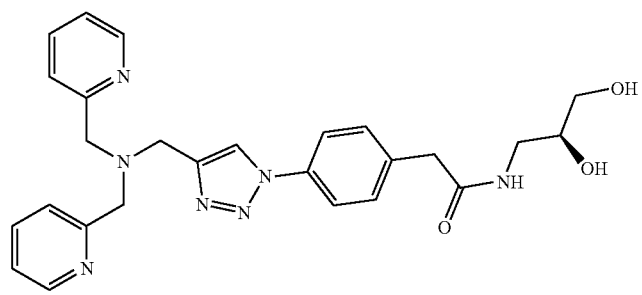

2-(4-(4-((bis(pyridin-2-ylmethyl)amino)methyl)-1H-1,2,3-triazol-1-yl)phenyl) acetic acid from Example 96d (152 mg, 0.367 mmol, 1.0 eq.) was dissolved in 2 mL dry DMF at room temperature. (R)-3-aminopropane-1,2-diol (50 mg, 0.55 mmol, 1.5 eq.), EDCl (105 mg, 0.55 mmol, 1.5 eq.), HOAt (75 mg, 0.55 mmol, 1.5 eq.) and NMM (60 µL, 0.55 mmol, 1.5 eq.) were then added. The mixture was stirred at room temperature for 16 h and then concentrated under reduced pressure. Purification of the product was achieved by way of dry column vacuum chromatography on C18 material, using a stepwise elution from 10% to 90% methanol in water affording 126.8 mg (0.26 mmol, 71%) of product. $^1$H NMR (300 MHz, MeOH) δ 8.46 (s, 1H), 8.43 (ddd, J=5.0, 1.6, 0.8 Hz, 2H), 7.84-7.71 (m, 4H), 7.69 (t, J=7.7 Hz, 2H), 7.49 (d, J=8.6 Hz, 2H), 7.25 (ddd, J=7.3, 5.0, 1.2 Hz, 2H), 3.92 (s, 2H), 3.86 (s, 4H), 3.80-3.66 (m, 1H), 3.62 (s, 2H), 3.50 (d, J=0.6 Hz, 1H), 3.48 (d, J=1.5 Hz, 1H), 3.40 (dd, J=13.8, 4.8 Hz, 1H), 3.24 (dd, J=13.8, 6.8 Hz, 1H). $^{13}$C NMR (101 MHz, CDCl$_3$) δ 173.80, 160.12, 149.46, 146.03, 138.67, 138.03, 137.16, 131.60, 124.94, 123.80, 123.45, 121.53, 71.93, 65.07, 60.58, 43.62, 43.10. APCI-HRMS e/z calc. for C$_{26}$H$_{29}$N$_7$O$_3$: 487.2332, found: 488.2403 [M+H].

Example 105—(6-((bis(pyridin-2-ylmethyl)amino)methyl)pyridin-3-yl)(piperazin-1-yl)methanone Example 105a—tert-Butyl 4-(6-((bis(pyridin-2-ylmethyl)amino)methyl) nicotinoyl)piperazine-1-carboxylate

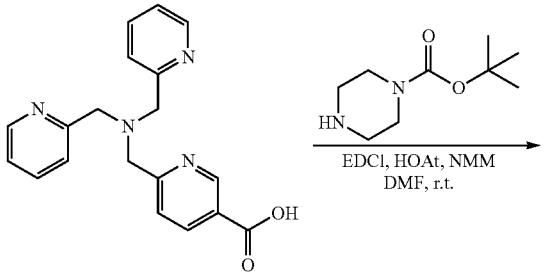

-continued

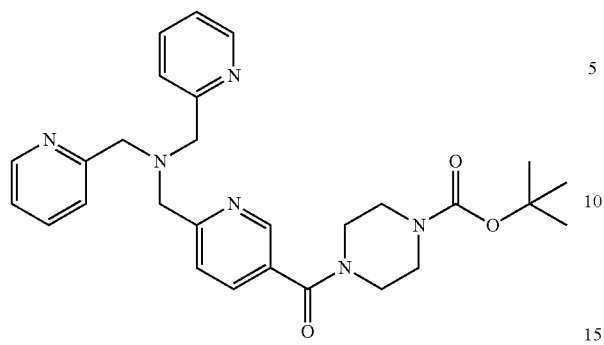

The 6-((bis(pyridin-2-ylmethyl)amino)methyl)nicotinic acid from Example 13 (179.5 mg, 0.537 mmol, 1.0 eq.) was dissolved in 3 mL dry DMF at room temperature. Tert-butyl piperazine-1-carboxylate (150 mg, 0.806 mmol, 1.5 eq.), EDCl (134 mg, 0.806 mmol, 1.5 eq.), HOAt (109.6 mg, 0.806 mmol, 1.5 eq.) and NMM (89 μL, 0.806 mmol, 1.5 eq.) were added and the mixture was stirred at room temperature for 16 h. The reaction mixture was concentrated under reduced pressure and the purification of the product was achieved by way of dry column vacuum chromatography on C18 material, using a stepwise elution from 10% to 90% methanol in water affording 244 mg (0.486 mmol, 91%) of product. $^1$H NMR (300 MHz, MeOH) δ 8.52 (dd, J=2.1, 0.7 Hz, 1H), 8.44 (ddd, J=4.9, 1.6, 0.9 Hz, 2H), 7.80 (ddd, J=9.4, 7.9, 2.0 Hz, 3H), 7.74 (d, J=7.9 Hz, 1H), 7.68 (d, J=7.8 Hz, 2H), 7.27 (ddd, J=7.4, 5.0, 1.2 Hz, 2H), 3.91 (s, 2H), 3.89 (s, 4H), 3.82-3.62 (m, 2H), 3.46 (s, 6H), 1.46 (s, 9H). $^{13}$C NMR (101 MHz, MeOH) δ 169.81, 162.16, 159.99, 156.19, 149.59, 148.15, 138.64, 137.18, 131.40, 124.97, 124.38, 123.87, 81.71, 61.32, 61.02, 28.59. APCI-HRMS e/z calc. for $C_{28}H_{34}N_6O_3$: 502.2692, found 503.2765 [M+H]

Example 105b—(6-((bis(pyridin-2-ylmethyl)amino)methyl)pyridin-3-yl)(piperazin-1-yl) methanone

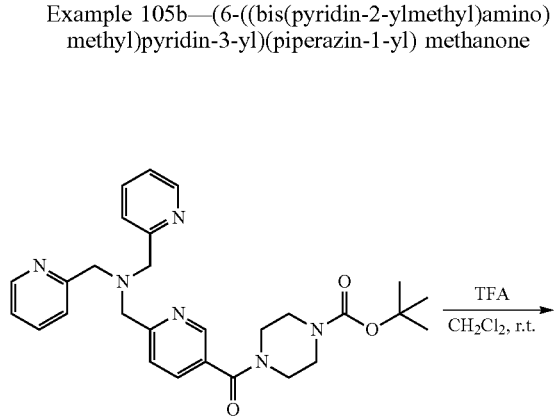

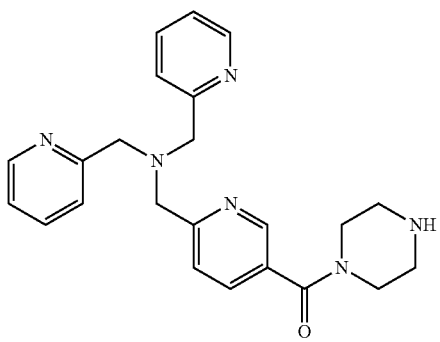

The tert-butyl 4-(6-((bis(pyridin-2-ylmethyl)amino)methyl)nicotinoyl)piperazine-1-carboxylate prepared in the previous reaction (233.5 mg, 0.465 mmol, 1.0 eq.) was dissolved in 10 mL $CH_2Cl_2$ at room temperature. To this solution was added TFA (2.84 mL, 80 eq.) and the mixture stirred at room temperature until NMR indicated full conversion. The mixture was concentrated under reduced pressure, the residue dissolved in dest. $H_2O$, neutralized with sat. aq. $K_2CO_3$ solution and concentrated under reduced pressure. Purification of the product was achieved by way of dry column vacuum chromatography on C18 material, using a stepwise elution from 10% to 90% methanol in water affording 79.6 mg (0.35 mmol, 76%) of product. $^1$H NMR (300 MHz, MeOH) δ 8.50 (dd, J=2.1, 0.7 Hz, 1H), 8.44 (ddd, J=5.0, 1.7, 0.9 Hz, 2H), 7.79 (ddd, J=9.6, 6.2, 2.3 Hz, 3H), 7.75-7.70 (m, 1H), 7.67 (d, J=7.8 Hz, 2H), 7.27 (ddd, J=7.4, 5.0, 1.2 Hz, 2H), 3.90 (s, 2H), 3.89 (s, 4H), 3.72 (s, J=15.5 Hz, 2H), 3.40 (s, J=18.3 Hz, 2H), 2.84 (d, J=17.0 Hz, 4H). $^{13}$C NMR (101 MHz, MeOD) δ 169.56, 162.02, 160.00, 149.58, 148.01, 138.64, 137.10, 131.57, 124.98, 124.41, 123.87, 61.36, 61.06, 45.67, 44.01. APCI-HRMS e/z calc. for $C_{23}H_{26}N_6O$: 402.2168, found 403.2240 [M+H]

Example 106-6,6',6''-nitrilotris(methylene)tris(N—((S)-2,3-dihydroxypropyl) nicotinamide)

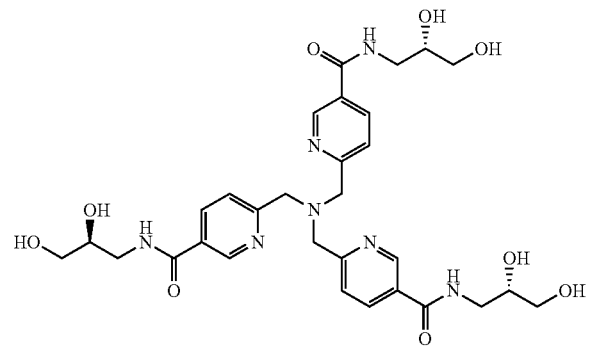 [SMILES: O=C(NC[C@H](O)CO)c1ccc(CN(Cc2ccc(C(=O)NC[C@H](O)CO)cn2)Cc2ccc(C(=O)NC[C@H](O)CO)cn2)nc1]

177

Example 106a—6,6',6"-nitrilotris(methylene)tris (N—((S)-2,3-dihydroxypropyl) nicotinamide)

178

Example 106b—6,6',6"-nitrilotris(methylene)tris (N—(((S)-2,2-dimethyl-1,3-dioxolan-4-yl) methyl) nicotinamide)

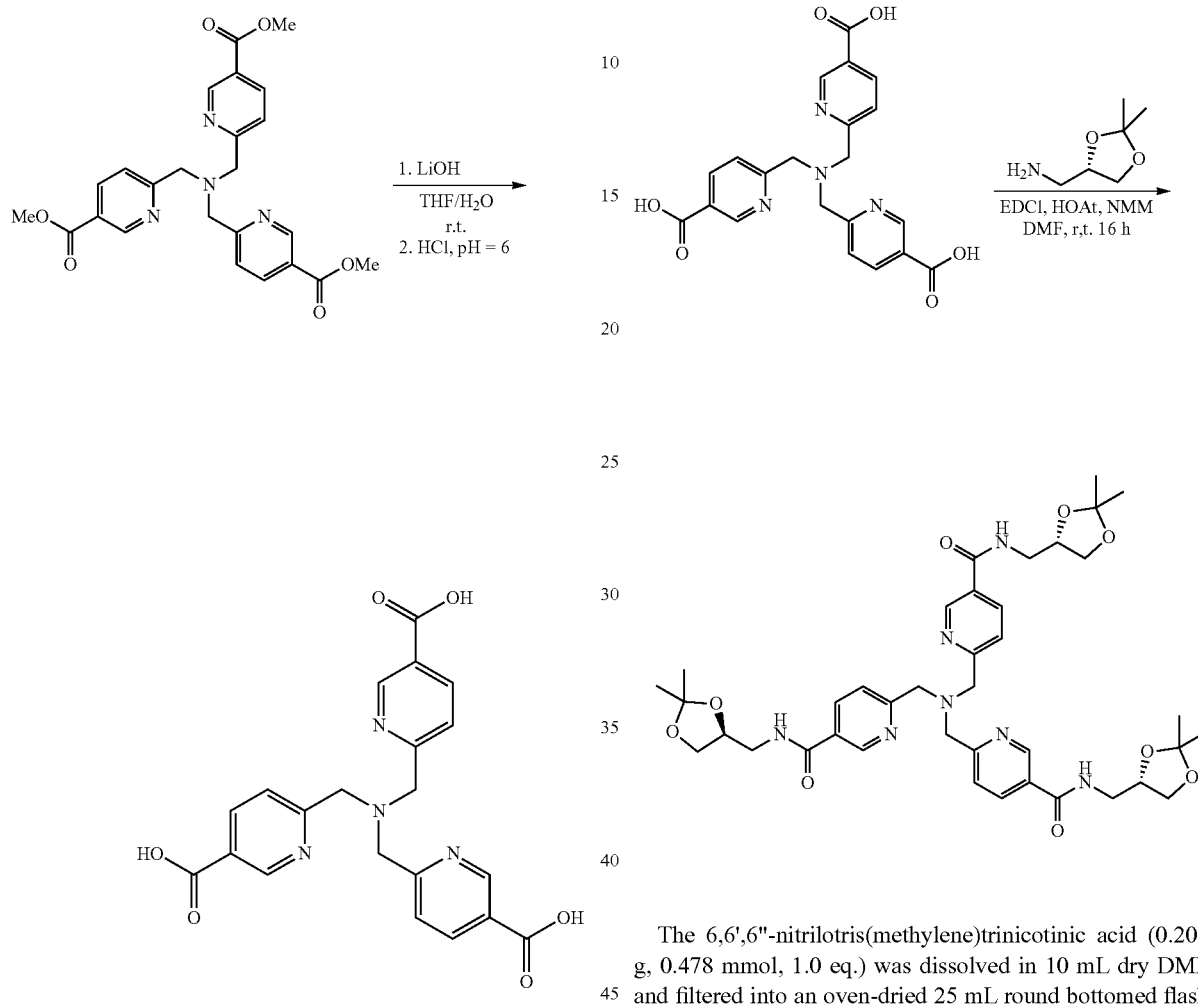

Commercially available trimethyl 6,6',6"-nitrilotris(methylene)trinicotinate (0.222 g, 0.478 mmol, 1.0 eq.) was dissolved in a mixture of 10 mL THF and 10 mL H2O at room temperature. To this solution was added LiOH.H2O (0.2 g, 4.87 mmol, 10.0 eq.) and the reaction progress monitored by TLC on alumina using 5% MeOH in CH2Cl2. Upon full conversion, the crude reaction mixture was concentrated under reduced pressure and the residue dissolved in 5 mL dest. H2O. The pH of the basic solution was adjusted to 6 with 2M HCl and the mixture concentrated under reduced pressure. The obtained 6,6',6"-nitrilotris(methylene)trinicotinic acid was used for the next reaction without further purification. $^1$H NMR (300 MHz, D$_2$O) δ 8.76 (d, J=2.0 Hz, 1H), 8.09 (dd, J=8.1, 2.0 Hz, 1H), 7.55 (d, J=8.1 Hz, 1H), 3.94 (s, 1H).

The 6,6',6"-nitrilotris(methylene)trinicotinic acid (0.202 g, 0.478 mmol, 1.0 eq.) was dissolved in 10 mL dry DMF and filtered into an oven-dried 25 mL round bottomed flask to remove insoluble salts from the neutralization in the previous reaction. To this solution (R)-3-aminopropane-1,2-diol (0.376 g, 2.87 mmol, 6.0 eq.), EDCl (0.550 g, 2.87 mmol, 6.0 eq.), HOAt (0.390 g, 2.87 mmol, 6.0 eq.) and NMM (0.316 ml, 2.87 mmol, 6.0 eq.) were added and the mixture was stirred at room temperature for 16 h. The reaction mixture was then concentrated under reduced pressure and purification of the product was achieved by way of dry column vacuum chromatography on C18 material, using a stepwise elution from 10% to 90% methanol in water affording 0.177 g (0.23 mmol, 49%) of product. 1.0H NMR (400 MHz, MeOD) β 8.87 (d, J=1.9 Hz, 3H, 8.15 (dd, J=8.2, 2.3 Hz, 3H), 7.73 (d, J=8.2 Hz, 3H), 4.31 (p, J=5.8 Hz, 3H), 4.07 (dd, J=8.5, 6.3 Hz, 3H), 3.95 (s, 6H), 3.74 (dd, J=8.5, 6.0 Hz, 3H), 3.53 (dd, J=5.5, 1.6 Hz, 6H), 1.40 (s, 9H), 1.32 (s, 9H). $^{13}$C NMR (101 MHz, MeOD) δ 168.12, 163.13, 148.77, 137.30, 130.29, 124.48, 110.56, 75.89, 68.20, 61.14, 43.51, 27.16, 25.57. APCI-HRMS e/z calc. for $C_{39}H_{51}N_7O_9$: 761.3748, found 762.3814 [M+H]

Example 106c—the title compound 6,6',6''-nitrilo-tris(methylene)tris(N—((S)-2,3-dihydroxypropyl)nicotinamide)

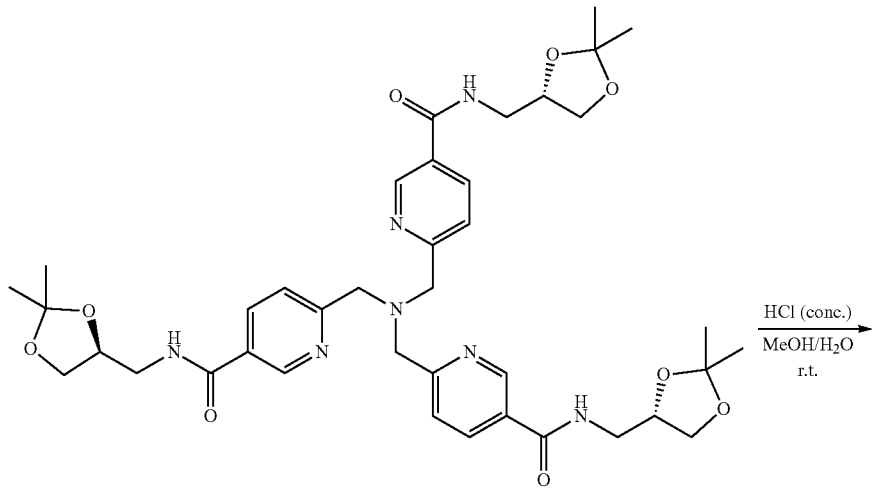

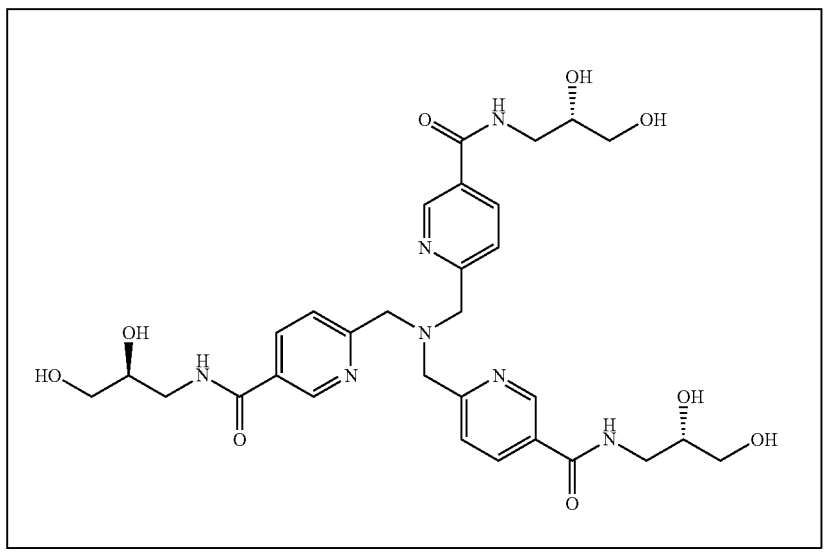

The 6,6',6''-nitrilotris(methylene)tris(N—(((S)-2,2-dimethyl-1,3-dioxolan-4-yl)methyl)nicotinamide) (50.5 mg, 0.066 mmol, 1.0 eq.) was dissolved in 1.5 mL MeOH at room temperature in a screw-capped vial. To this solution was added 1 mL of H2O and 3 drops conc. HCl. The reaction mixture was sealed and stirred at room temperature for 16 h and then concentrated under reduced pressure. The obtained crude was dissolved in 1 mL H2O, the pH adjusted to 7 with 0.1 M NaOH and concentrated under reduced pressure to dryness. The resulting semi-solid was treated with ice-cooled MeOH (2 mL) and filtered into a new flask. Removal of the solvent under reduced pressure resulted in 36.1 mg (0.056 mmol, 85%) of product. $^1$H NMR (400 MHz, D$_2$O) δ 8.61 (d, J=1.8 Hz, 3H), 7.94 (dd, J=8.2, 2.1 Hz, 3H), 7.47 (d, J=8.2 Hz, 3H), 3.93 (ddd, J=11.3, 6.7, 4.7 Hz, 3H), 3.84 (s, 5H), 3.68 (dd, J=11.8, 4.1 Hz, 3H), 3.58 (dd, J=11.9, 6.3 Hz, 3H), 3.52 (dd, J=14.0, 4.7 Hz, 3H), 3.41 (dd, J=14.0, 7.3 Hz, 3H). $^{13}$C NMR (101 MHz, D$_2$O) δ 168.05, 161.27, 146.78, 136.06, 128.24, 124.17, 70.26, 63.33, 61.10, 42.37. ESI-HRMS e/z calc. for $C_{30}H_{39}N_7O_9$: 641.2809, found 664.2701 [M+Na]

Examples 107-144

Compounds 107-144 given in Schemes 10-20 above can be prepared using modifications of the methods described above.

Example 145—(6-((bis(pyridin-2-ylmethyl)amino)methyl)pyridin-3-yl)methyl methanesulfonate

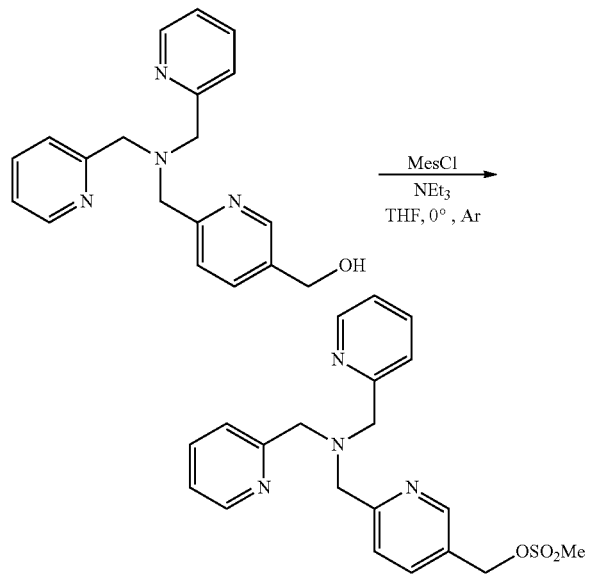

(6-((bis(pyridin-2-ylmethyl)amino)methyl)pyridin-3-yl)methanol prepared in Example 14a (2.822 g, 8.81 mmol, 1.0 eq.) was dissolved in 150 mL dry THF under Ar and cooled to 0° C. in an ice bath. To this solution was added NEt3 (2.45 mL, 17.62 mmol, 2.0 eq.), followed by a solution of mesyl chloride (1.363 mL, 17.62 mmol, 2.0 eq.) in 30 mL dry THF dropwise. A precipitate formed and the suspension was stirred at 0° C. for 30 min, until TLC (Alumina, 3% MeOH in CH2Cl2) indicated full conversion. The mixture was filtered into a new flask, concentrated under reduced pressure to a volume of ca. 100 mL at 40° C., and DMF (80 mL) was added. The remaining THF was removed under reduced pressure and the obtained solution of (6-((bis(pyridin-2-ylmethyl)amino)methyl)pyridin-3-yl)methyl methanesulfonate in DMF used in the next reaction without further treatment under assumption of quantitative conversion. $^1$H NMR (300 MHz, Chloroform-d) δ 10.59 (s, 1H), 8.70 (ddd, J=5.5, 1.6, 0.8 Hz, 2H), 8.50 (dd, J=2.2, 0.8 Hz, 1H), 8.05 (td, J=7.8, 1.7 Hz, 2H), 7.80 (d, J=7.9 Hz, 1H), 7.69 (dd, J=8.1, 2.3 Hz, 1H), 7.61-7.37 (m, 2H), 4.47 (s, 2H), 4.42 (s, 4H), 4.16 (s, 2H), 3.06 (s, 3H).

Example 146—1-(5-(azidomethyl)pyridin-2-yl)-N,N-bis(pyridin-2-ylmethyl) methanamine

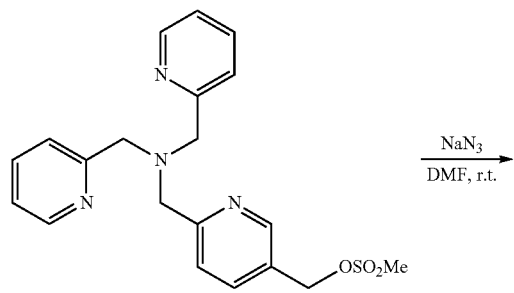

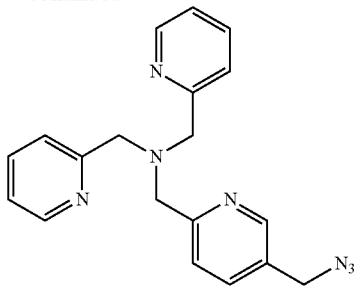

To the solution of the (6-((bis(pyridin-2-ylmethyl)amino)methyl)pyridin-3-yl)methyl methanesulfonate (3.51 g, 8.81 mmol, 1.0 eq.) in 80 mL DMF, obtained in Example 145, was added NaN3 (2.864 g, 44.04 mmol, 5.0 eq.) at room temperature. The mixture was stirred at room temperature for 20 h, then filtered into a new flask and concentrated in vacuo to a volume of approximately 30 mL. The mixture was diluted with 100 mL H2O, transferred into a separation funnel and extracted with EtOAc (2×100 mL). The combined organics were washed with sat. aq. K2CO3 solution (50 mL), brine (50 mL), dried over K2CO3, filtered and concentrated under reduced pressure. The obtained compound was used in the next reaction without further treatment.

Example 147—1-(5-(aminomethyl)pyridin-2-yl)-N,N-bis(pyridin-2-ylmethyl) methanamine hydrochloride

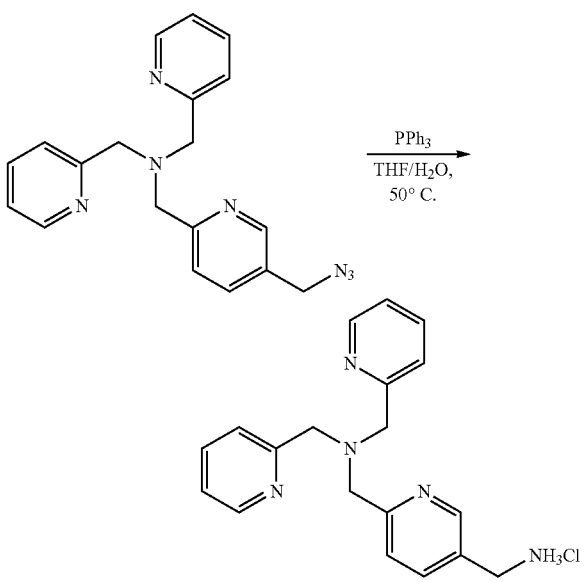

The 1-(5-(azidomethyl)pyridin-2-yl)-N,N-bis(pyridin-2-ylmethyl)methanamine, obtained in Example 146 (2.783 g, 8.06 mmol, 1.0 eq.) was dissolved in 50 mL THF. To this solution was added 5 mL dest. H2O and PPh3 (4.228 g, 16.12 mmol, 2.0 eq.) in one portion. The mixture was heated to 50° C. and stirred for 3 h until TLC (Alumina, 3% MeOH in CH2Cl2) indicated full conversion. The mixture was concentrated under reduced pressure, the residue was treated with CH2Cl2 and H2O (100 mL each) and the pH of the aqueous phase adjusted to 1 with conc. HCl with stirring. The mixture was transferred into a separation funnel, the aq. phase washed with CH2Cl2 (50 mL) and concentrated under reduced pressure to afford 2.825 g (7.93 mmol, 98%) of 1-(5-(aminomethyl)pyridin-2-yl)-N,N-bis(pyridin-2-ylmethyl)methanamine as the hydrochloride salt. $^1$H NMR (300 MHz, DMSO) δ 9.00 (s, 3H), 8.91 (d, J=1.6 Hz, 1H), 8.81 (dd, J=5.7, 0.9 Hz, 2H), 8.48 (ddd, J=9.3, 8.3, 1.5 Hz, 3H), 8.16 (d, J=7.9 Hz, 2H), 8.11 (d, J=8.2 Hz, 1H), 7.94-7.84 (m, 2H), 4.38 (s, 4H), 4.30 (s, 2H), 4.17 (d, J=5.5 Hz, 2H). $^{13}$C NMR (101 MHz, DMSO) δ 153.22, 152.46, 145.43, 142.25, 131.67, 126.96, 125.90, 125.82, 56.20, 55.59.

Example 148—(3aS,5S,5aR,8aS,8bR)—N-((6-((bis(pyridin-2-ylmethyl)amino)methyl) pyridin-3-yl)methyl)-2,2,7,7-tetramethyltetrahydro-3aH-bis[1,3]dioxolo[4,5-b:4',5'-d]pyran-5-carboxamide

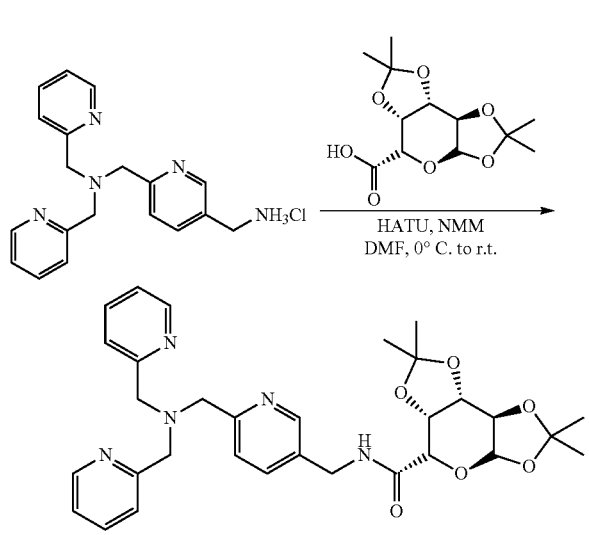

1-(5-(aminomethyl)pyridin-2-yl)-N,N-bis(pyridin-2-ylmethyl)methanamine hydrochloride from example 147 (0.276 g, 0.775 mmol, 1.0 eq.), was suspended in 5 mL dry DMF and cooled to 0° C. in an ice bath. To this suspension was added 1,2:3,4-Di-O-isopropylidene-a-D-galacturonide (0.213 g, 0.775 mmol, 1.0 eq.), HATU (0.295 g, 0.775 mmol, 1.0 eq.) and NMM (0.256 mL, 2.325 mmol, 3.0 eq.) after which the mixture turned into a solution. The mixture was stirred at 0° C. for 30 min, then at room temperature for 16 h and concentrated under reduced pressure. Purification of the product was achieved by way of dry column vacuum chromatography on C18 bondesil material, using a stepwise elution from 10% to 70% methanol in water affording 156.1 mg (0.271 mmol, 35%) of product. $^1$H NMR (400 MHz, MeOD) δ 8.42 (dd, J=7.1, 3.3 Hz, 3H), 7.77 (ddd, J=16.5, 8.3, 1.9 Hz, 3H), 7.66 (d, J=7.8 Hz, 2H), 7.60 (d, J=8.1 Hz, 1H), 7.30-7.24 (m, 2H), 5.62 (d, J=4.9 Hz, 1H), 4.71 (dd, J=7.7, 2.5 Hz, 1H), 4.63 (d, J=15.4 Hz, 1H), 4.59 (dd, J=7.8, 2.1 Hz, 1H), 4.43 (dd, J=4.9, 2.6 Hz, 1H), 4.30 (d, J=2.0 Hz, 1H), 4.25 (d, J=15.4 Hz, 1H), 3.84 (s, 6H), 1.49 (s, 3H), 1.34 (s, 3H), 1.33 (s, 3H), 1.30 (s, 3H). $^{13}$C NMR (101 MHz, MeOD) δ 171.51, 160.15, 158.85, 149.62, 148.80, 138.76, 137.99, 134.94, 124.94, 124.47, 123.95, 110.79, 110.45, 97.89, 73.28, 72.07, 72.04, 70.30, 61.21, 60.97, 40.81, 26.39, 26.29, 25.06, 24.61. APCI-HRMS e/z calc. for $C_{31}H_{37}N_5O_6$: 575.2744, found 576.2817 [M+H].

Example 149—(2S,3R,4S,5R,6R)—N-((6-((bis(pyridin-2-ylmethyl)amino)methyl)pyridin-3-yl)methyl)-3,4,5,6-tetrahydroxytetrahydro-2H-pyran-2-carboxamide

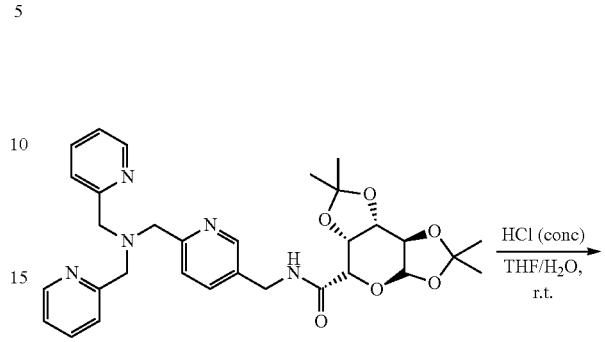

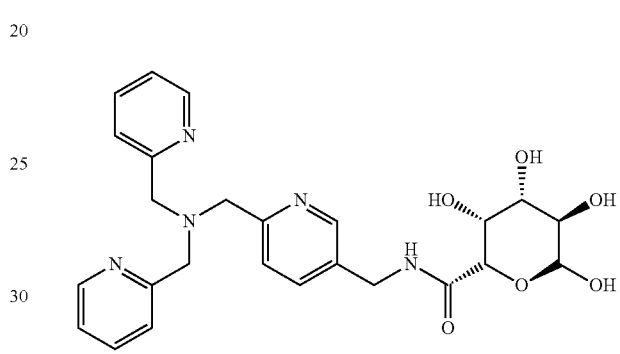

The protected starting material (0.1339 mg, 0.232 mmol, 1.0 eq.) was dissolved in 10 mL THF and 5 mL H2O at room temperature. To this solution was added 5 drops of conc. HCl and the mixture stirred at room temperature for 16 h in a tightly sealed vessel. The pH was adjusted to 9 with sat. aq. K2CO3 solution, and the mixture concentrated under reduced pressure. The residue was treated with MeOH (30 mL) and filtered into a new flask, and concentrated under reduced pressure. Purification of the product was achieved by way of dry column vacuum chromatography on C18 bondesil material, using a stepwise elution from 10% to 50% methanol in water affording 45.7 mg (0.092 mmol, 40%) of product.

Example 150—S-((6-((bis(pyridin-2-ylmethyl)amino)methyl)pyridin-3-yl)methyl) ethanethioate

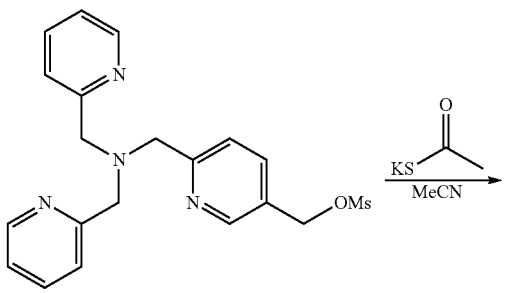

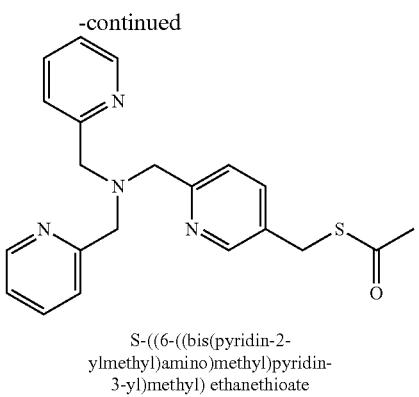

S-((6-((bis(pyridin-2-ylmethyl)amino)methyl)pyridin-3-yl)methyl) ethanethioate

The mesylate from Example 145 (64 mg, 0.16 mmol) was dissolved in 10 mL MeCN before potassium thioacetate (100 mg, 0.88 mmol) was added. The mixture was stirred for 3 hours at room temperature before it was concentrated under reduced pressure. The crude material was purified on a neutral alumina column using 0-2% MeOH in DCM as eluent giving the product. $^1$H NMR (400 MHz, Chloroform-d) δ 8.51 (ddd, J=5.0, 1.8, 1.0 Hz, 2H), 8.43 (dd, J=2.4, 0.9 Hz, 1H), 7.63 (td, J=7.6, 1.9 Hz, 2H), 7.59-7.42 (m, 4H), 7.12 (ddd, J=7.5, 4.9, 1.4 Hz, 2H), 4.04 (s, 2H), 3.89 (app. d, J=5.3 Hz, 6H), 2.33 (s, 3H).

Example 151—tert-Butyl 2-((tert-butoxycarbonyl)oxy)-3-methylbenzoate

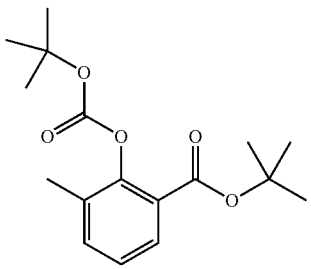 [SMILES: Cc1cccc(C(=O)OC(C)(C)C)c1OC(=O)OC(C)(C)C]

The title compound was prepared from 3-methylsalisylic acid (19.1 g, 0.1255 mol) as described in Reddy et al WO 2016/003929. Purification was done by way of dry column vacuum chromatography using silica as adsorbent, giving 9.85 g product (25.5%). $^1$H NMR (400 MHz, chloroform-d) δ 7.74 (m, 1H), 7.35 (m, 1H), 7.15 (app. t, J=7.7 Hz, 1H), 2.26 (s, 3H), 1.57 (s, 9H), 1.56 (s, 9H).

Example 152—tert-Butyl 3-(bromomethyl)-2-((tert-butoxycarbonyl)oxy)benzoate

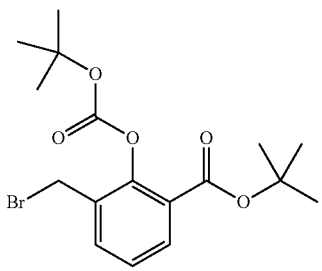 [SMILES: CC(C)(C)OC(=O)Oc1c(CBr)cccc1C(=O)OC(C)(C)C]

Free radical bromination of tert-butyl 2-((tert-butoxycarbonyl)oxy)-3-methylbenzoate (8.72 g, 28.3 mmol) was performed with N-bromosuccinimide (5.29 g, 29.7 mmol) in tetrachloromethane (100 mL) as described by Hecjer et al in WO 201614939. Azobisisobutyronitrile (463 mg, 2.82 mmol) was employed as radical initiator. After recrystallization from hexane, the product was obtained as a colourless solid (8.18 g, 74.6%).

$^1$H NMR (400 MHz, chloroform-d) δ 7.83 (dd, J=7.8 Hz, 1.7 Hz, 1H), 7.55 (dd, J=7.7 Hz, 1.7 Hz, 1H), 7.24 (app. t, J=7.8 Hz, 1H), 4.50 (s, 2H), 1.57 (s, 18H).

Example 153—Tert-Butyl 2-((Tert-Butoxycarbonyl)Oxy)-3-(((3aS,4S,6S,7aR)-3a,5,5-Trimethylhexahydro-4,6-Methanobenzo[d][1,3,2]Dioxaborol-2-yl)Methyl)Benzoate

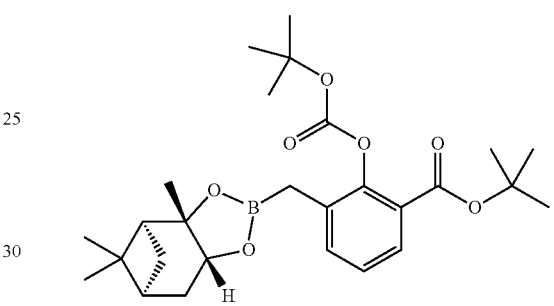

Miyaura-borylation of tert-butyl 3-(bromomethyl)-2-((tert-butoxycarbonyl)oxy)benzoate (4.71 g, 12.2 mmol) was performed as described in Reddy et al WO 2016/003929, and the title compound was obtained as a colourless oil after purification on a silica column eluted with a gradient of ethyl acetate in n-heptane (3.18 g, 53.8%). $^1$H NMR (400 MHz, chloroform-d) δ 7.70 (dd, J=7.8 Hz, 1.8 Hz, 1H), 7.40 (dd, J=7.7 Hz, 1.8 Hz, 1H), 7.14 (app. t, J=7.7 Hz, 1H), 4.25 (dd, J=8.7 Hz, 2.0 Hz, 1H), 2.31-2.24 (m, 3H), 2.19 (m, 1H), 2.02 (m, 1H), 1.90-1.81 (m, 2H), 1.554 (s, 9H), 1.548 (s, 9H), 1.38 (s, 3H), 1.27 (s, methyl overlapping with lipid impurities), 1.18 (d, J=11.0 Hz, 1H), 0.82 (s, 3H). MS (ESI, positive mode) m/z 509.3 [M+Na]$^+$, HR-MS (ESI, pos. mode) m/z 509.2681 calculated for $C_{27}H_{39}O_7$$^{11}$BNa, found m/z 509.2682.

Example 154—Tert-Butyl 2-((Tert-Butoxycarbonyl)Oxy)-3-((S)-2-Chloro-2-((3aS,4S,6S,7aR)-3a,5,5-Trimethylhexahydro-4,6-Methanobenzo[d][1,3,2]Dioxaborol-2-yl)ethyl)Benzoate

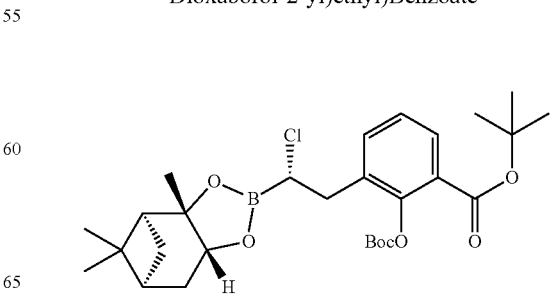

Matteson-homologation of tert-butyl 2-((tert-butoxycarbonyl)oxy)-3-(((3aS,4S,6S,7aR)-3a,5,5-trimethylhexahydro-4,6-methanobenzo[d][1,3,2]dioxaborol-2-yl)methyl)benzoate (3.03 g, 6.24 mmol) was performed as described in Reddy et al WO2016003929. Purification of the product was achieved by way of column chromatography, with silica as adsorbent and a gradient of ethyl acetate in n-heptane as eluent. After removal of solvent, the product was obtained as a pale yellow oil (2.10 g, 62.9%). $^1$H NMR (400 MHz, chloroform-d) δ 7.81 (dd, J=7.8 Hz, 1.8 Hz, 1H), 7.48 (dd, J=7.6 Hz, 1.8 Hz, 1H), 7.19 (app. t, J=7.7 Hz, 1H), 4.36 (dd, J=8.8 Hz, 1.8 Hz, 1H), 3.67 (dd, J=9.0 Hz, 6.9 Hz, 1H), 3.23 (dd, J=14.2 Hz, 6.9 Hz, 1H), 3.05 (dd, J=14.2 Hz, 9.0 Hz, 1H), 2.33 (m, 1H), 2.19 (m, 1H), 2.06 (m, 1H), 1.92-1.85 (m, 2H), 1.56 (s, 9H), 1.55 (s, 9H), 1.37 (s, 3H), 1.28 (s, 3H), 1.10 (d, J=11.0 Hz, 1H), 0.83 (s, 3H). $^{13}$C NMR (100 MHz, chloroform-d) 6164.1, 151.4, 149.1, 135.2, 132.4, 130.5, 125.7, 125.4, 87.0, 83.7, 81.6, 78.7, 51.3, 41.4 (br), 39.5, 38.4, 35.3, 35.1, 28.5, 28.3, 27.9, 27.2, 26.4, 24.1. Minor peaks from the diastereomer were visible in $^1$H and $^{13}$C spectrum. MS (ESI, positive mode) m/z 557.2 [M+Na]$^+$, HR-MS (ESI, pos. mode) m/z 557.2448 calculated for $C_{28}H_{40}{}^{35}ClO_7{}^{11}BNa$, found m/z 557.2450.

Example 155—tert-Butyl 3-((R)-2-(bis(trimethylsilyl)amino)-2-((3aS,4S,6S,7aR)-3a,5,5-trimethylhexahydro-4,6-methanobenzo[d][1,3,2]dioxaborol-2-yl)ethyl)-2-((tert-butoxycarbonyl)oxy)benzoate

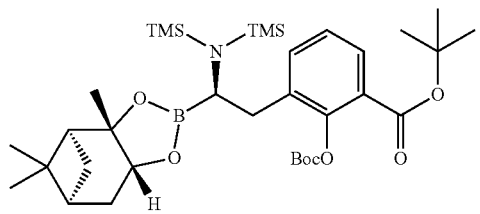

A flask containing tert-butyl 2-((tert-butoxycarbonyl)oxy)-3-((S)-2-chloro-2-((3aS,4S,6S,7aR)-3a,5,5-trimethylhexahydro-4,6-methanobenzo[d][1,3,2]dioxaborol-2-yl)ethyl)benzoate (113.5 mg, 0.212 mmol) under a nitrogen atmosphere was dissolved in 5 mL tetrahydrofuran and cooled down to −78° C. A solution of lithium bis(trimethylsilyl)amide, 1.0 M in tetrahydrofuran was added (0.21 mL, 0.21 mmol), and the solution was then allowed to reach room temperature. Stirring was continued over night, after which volatiles were removed under reduced pressure, and the resulting crude mixture used directly in the next step.

Example 156a—tert-Butyl 3-((R)-2-(2-(4-(4-((bis(pyridin-2-ylmethyl)amino)methyl)-1H-1,2,3-triazol-1-yl)phenyl)acetamido)-2-((3aS,4S,6S,7aR)-3a,5,5-trimethylhexahydro-4,6-methanobenzo[d][1,3,2]dioxaborol-2-yl)ethyl)-2-((tert-butoxycarbonyl)oxy)benzoate

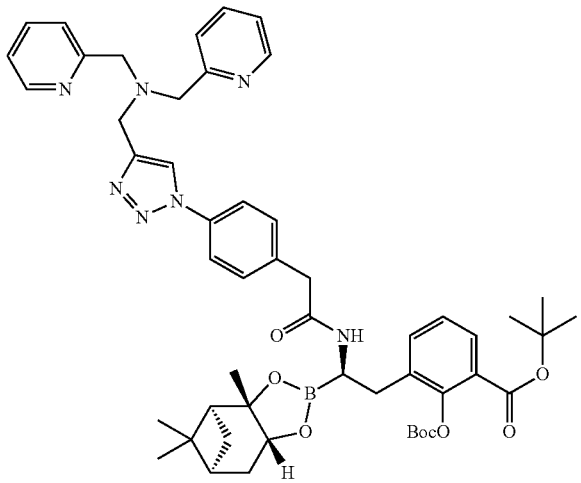

2-(4-(4-((Bis(pyridin-2-ylmethyl)amino)methyl)-1H-1,2,3-triazol-1-yl)phenyl)acetic acid (0.248 mmol) from example 96d, was dissolved in 5 mL dimethylformamide and cooled down on an ice bath. To this solution, 1-ethyl-3-(3-dimethylaminopropyl)carbodiimide hydrochloride salt (59.7 mg, 0.311 mmol) and 1-hydroxy-7-azabenzotriazole (34.4 mg, 0.253 mmol) was added, and allowed to stir on ice bath for 30 min. A solution of the bis(trimethylsilyl)amino compound, described above, in 2 mL dimethylformamide, was added (0.212 mmol assumed), followed by N-methylmorpholine (0.08 mL, 0.7 mmol). The mixture was allowed to stir over night. After being concentrated on a rotary evaporator, the reaction mixture was partitioned between dichloromethane and a mixture of 0.5 M K$_2$CO$_3$ (aq.) and saturated NaCl solution. The phases were separated and the aqueous phase extracted with more dichloromethane. The combined organic extracts were then dried over Na$_2$SO$_4$, filtered and solvents removed under reduced pressure. The crude product was loaded onto a 2 g SPE plug with C18 material. Pure product was eluted by running through 25 mL portions of methanol/water mixture, going stepwise from 70% to 90% methanol, giving after removal of solvents under reduced pressure, 70.9 mg product (36.7% over two steps). $^1$H NMR (400 MHz, chloroform-d) δ 8.55 (br d, 2H), 8.05 (s, 1H), 7.73 (dd, J=7.8 Hz, 1.8 Hz, 1H), 7.68-7.64 (m, 4H), 7.59 (br d, J=7.8 Hz, 2H), 7.34 (m, 2H), 7.27 (m, 1H), 7.17-7.10 (m, 3H), 4.31 (dd, J=8.9 Hz, 2.1 Hz, 1H), 3.96 (s, 2H), 3.90 (s, 4H), 3.62 (d, J=3.0 Hz, 2H), 2.95-2.84 (m, 3H), 2.35 (m, 1H), 2.19 (m, 1H), 2.02 (app t, J=5.5 Hz, 1H), 1.92-1.84 (m, 2H), 1.67 (s, 3H (exchanging protons)), 1.54 (s, 9H), 1.53 (s, 9H), 1.44-1.40 (m, 4H), 1.29 (s, 3H), 0.87 (s, 3H). Minor peaks from the diastereomer were visible in $^1$H spectrum. $^{13}$C NMR (100 MHz, chloroform-d) 6173.5 (only visible from HMBC), 164.0, 159.3, 152.1, 149.3, 148.8, 145.3, 136.64, 136.58, 134.9, 134.4, 130.9, 130.1, 125.9, 125.7, 123.5, 122.2, 121.3, 121.0, 84.6, 84.1, 81.8, 77.3, 59.9, 52.2, 48.8, 42.1 (only visible in HSQC spectrum), 40.1, 39.9, 38.3, 36.5, 31.4, 29.1, 28.3, 27.9, 27.5, 26.7, 24.3. MS (APCI, positive mode) m/z 912.5 [M+H]⁺, HR-MS (APCI, pos. mode) m/z 911.4862 calculated for $C_{51}H_{63}N_7O_8{}^{10}B$, found m/z 911.4863.

Example 156b—(R)-3-(2-(4-(4-((Bis(pyridin-2-ylmethyl)amino)methyl)-1H-1,2,3-triazol-1-yl)phenyl)acetamido)-2-hydroxy-3,4-dihydro-2H-benzo[e][1,2]oxaborinine-8-carboxylic acid hydrochloride

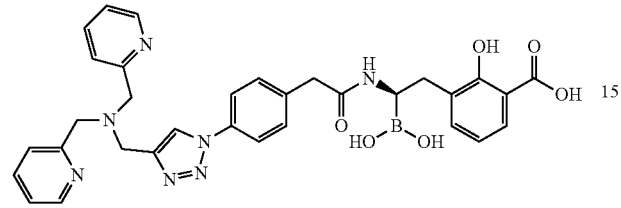

Global deprotection and cyclisation was achieved by treatment of a solution of the triply protected precursor (64.1 mg, 0.0703 mmol) in 2 mL dioxane with 1 mL 4 M HCl in dioxane. After heating to reflux for 2 h, a solid precipitate was formed, which after cooling was collected by way of suction filtration. This gave after drying an ochre powder (58.3 mg, >100%), containing an unknown amount of HCl. Purification was attempted using SPE plugs with respectively cation exchange, anion exchange and reverse phase (C18) materials, without any success. Chromatographic purity of the precipitate was 80%, using a hybrid C18 reversed phase column with high pH tolerance, a methanol gradient and buffered with potassium phosphate adjusted with HCl (aq.) to pH 11.5. ¹H NMR (400 MHz, mixture trifluoroacetic acid-d and water-$d_2$) δ (uncalibrated) 8.55 (br d, J=6.0 Hz, 2H), 8.33 (app br t, J=8.0 Hz, 2H), 8.13 (s, 1H), 7.89 (d, J=8.1 Hz, 2H), 7.75 (app br t, 2H), 7.11 (m, 4H), 6.75 (d, J=8.2 Hz, 2H), 6.67 (app t, J=7.6 Hz, 1H), 4.23 (s, 4H), 3.88 (s, 2H). The remaining signals were broadened beyond identification, possibly due to the numerous equilibria exhibited by the compound. MS (ESI, negative mode, dissolved in water/methanol) m/z 648.3 (100%, "base peak", tetrahedral boron doubly esterified with methanol), 634.3 (23%, tetrahedral boron, with one methanol), 616.2 (31%, trigonal planar boron, with one methanol).

Example 157—(R)-3-(2-(2-(4-(4-((bis(pyridin-2-ylmethyl)amino)methyl)-1H-1,2,3-triazol-1-yl)phenyl)acetamido)-2-boronoethyl)benzoic acid The title compound can be prepared analogously using the methods described in Example 156.

Example 158—6-((bis(pyridin-2-ylmethyl)amino)methyl)-N-(2-mercaptoethyl) nicotinamide

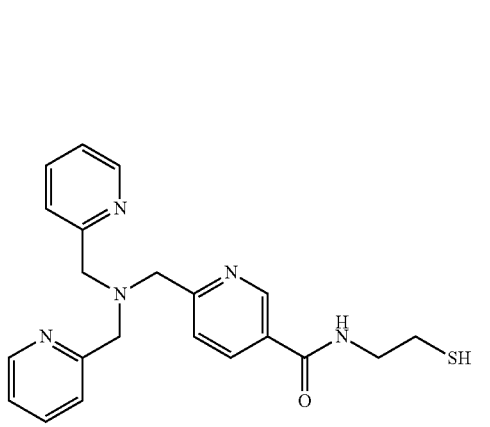

The 6-((bis(pyridin-2-ylmethyl)amino)methyl)nicotinic acid prepared in Example 13 was dissolved in 20 mL dry DMF at room temperature and filtered into a 50 mL round bottomed flask prior to reaction to remove the insoluble salts. To this solution was added 2-aminoethane-1-thiol (575 mg, 7.45 mmol, 1.5 eq.), followed by EDCl (1.428 g, 7.45 mmol, 1.5 eq.), HOAt (1.014 g, 7.45 mmol, 1.5 eq.) and NMM (0.821 mL, 7.45 mmol, 1.5 eq.). The reaction mixture was stirred at room temperature for 16 h and then concentrated under reduced pressure. The residual crude mixture was dissolved in 100 mL CHCl₃, transferred into a separation funnel and washed with 100 mL sat. aq. K₂CO₃ solution and 100 mL brine. The organic phase was separated, dried oved Na₂SO₄, filtered and concentrated under reduced pressure. Purification of the product was performed by column chromatography on neutral Al₂O₃ using 1% MeOH in DCM giving the product with minor impurities, followed by C18-SPE using gradient elution (10% MeOH to 90% MeOH in H₂O) affording the product as a yellow oil without visible impurities, that was used without further purification.

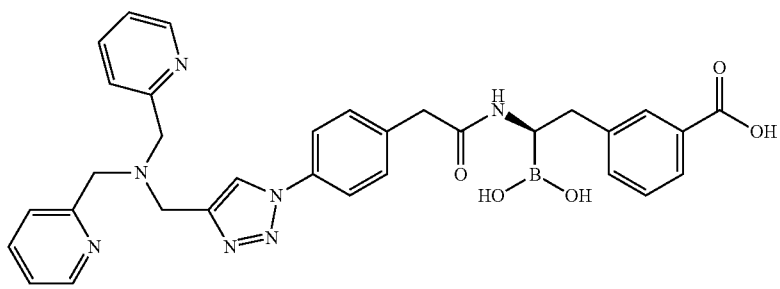 [SMILES: O=C(Cc1ccc(-n2cc(CN(Cc3ccccn3)Cc3ccccn3)nn2)cc1)N[C@@H](Cc1cccc(C(=O)O)c1)B(O)O]

Example 159—tert-Butyl (3S,6R)-6-((2-(6-((bis(pyridin-2-ylmethyl)amino)methyl) nicotinamido)ethyl)thio)-3-((tert-butyldimethylsilyl)oxy)-6-((3aS,4S,6S,7aR)-3a,5,5-trimethylhexahydro-4,6-methanobenzo[d][1,3,2]dioxaborol-2-yl)hexanoate

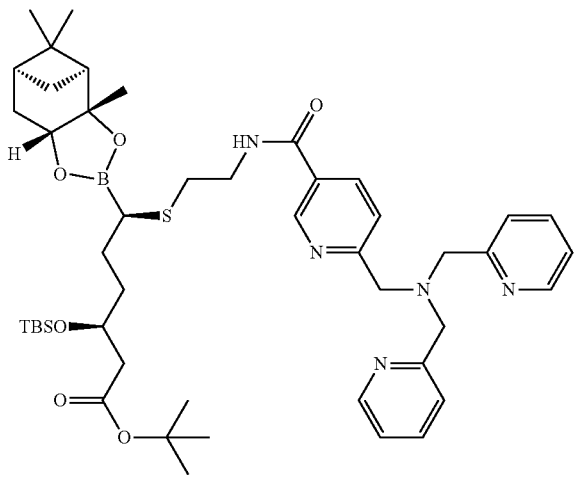 [SMILES: CC(C)(C)OC(=O)C[C@H](CC[C@H](SCCNC(=O)c1ccc(CN(Cc2ccccn2)Cc2ccccn2)nc1)B1O[C@@H]2C[C@@H]3C[C@@H](C3(C)C)[C@]2(C)O1)O[Si](C)(C)C(C)(C)C]

To a flask containing (3S,6S)-tert-butyl 3-(tert-butyldimethylsilyloxy)-6-chloro-6-[(2S,6R)-2,9,9-trimethyl-3,5-dioxa-4-boratricyclo[6.1.1.0$^{2,6}$]-decan-4-yl)hexanoate (293.8 mg, 0.570 mmol), prepared as described in Hecker et al. *J. Med. Chem.*, 2015, 58, 3682-3692, 6-((bis(Pyridin-2-ylmethyl)amino)methyl)-N-(2-mercaptoethyl)nicotinamide (298 mg, 0.757 mmol) from example 158 was added as a solution in 15 mL dichloromethane. After dropwise addition of triethylamine (0.21 mL, 1.5 mmol), the mixture was stirred at room temperature overnight. The mixture was worked up by transfer to a separatory funnel with 50 mL 0.5 M NaHCO$_3$ (aq.) and extracted twice with 50 mL ethyl acetate. The extract was washed with sat. NaCl (aq.) and dried over Na$_2$SO$_4$. Filtration and subsequent removal of solvents under reduced pressure gave a crude product which was purified initially by loading onto a plug of Bondesil-C18 OH SPE material and eluted by running through portions of methanol/water mixture, going stepwise from 50% to pure methanol. This procedure was repeated once, and final purification was achieved by loading onto a plug of strong cationic exchange SPE material, using 1:1 methanol/water and a pH-gradient from pH 3 to pH 10 with formic acid and ammonia as additives. Fractions containing product was collected and the solvent removed under reduced pressure to give the desired product (136.3 mg, 27.4%). $^1$H NMR (400 MHz, chloroform-d) δ 8.91 (m, 1H), 8.54 (m, 2H), 8.08 (dd, J=8.1 Hz, 2.3 Hz, 1H), 7.68-7.63 (m, 3H), 7.55 (d, J=7.8 Hz, 2H), 7.15 (m, 2H), 6.90-6.84 (br m, 1H), 4.30-4.26 (m, 1H), 4.08 (m, 1H), 3.93 (s, 2H), 3.88 (s, 4H), 3.66 (m, 2H), 2.83 (m, 2H), 2.41-2.27 (m, 3H), 2.23-2.12 (m, 2H), 2.03-2.00 (m, 1H), 1.89-1.79 (m, 2H), 1.76-1.57 (m, 4H), 1.42 (s, 2.5H (diastereomer)), 1.41 (s, 6.5H), 1.36 (s, 3H), 1.25 (s, 3H), 1.13 (d, J=10.9 Hz, 1H), 0.85 (s, 9H), 0.80 (s, 3H), 0.05 (s, 3H), 0.04 (s, 3H). The product appears to be a 5:2 mixture of diastereomers, most readily apparent by the split chemical shifts of the tert-butyl ester protons. $^{13}$C NMR (100 MHz, chloroform-d) δ171.1, 165.7, 162.9, 159.2, 149.3, 147.7, 136.7, 135.7, 128.8, 123.2, 122.7, 122.3, 86.4, 80.5, 78.3, 69.1, 60.3, 60.1, 51.4, 43.9, 39.5, 39.2, 38.3, 36.2, 35.6, 32.0, 28.7, 28.3, 27.1, 26.7, 26.6, 26.0 (overlapping with severely broadened resonance δ to boron, only visible in HSQC), 24.1, 18.2, −4.3, −4.5. Shifts only given for major diastereomer. MS (APCI, pos. mode) m/z 872.5 [M+H]$^+$, HR-MS (APCI, pos. mode) m/z 871.5018 calculated for C$_{47}$H$_{71}$N$_5$O$_6$SSi$^{10}$B, found m/z 871.5015.

Example 160—2-((3R,6S)-3-((2-(6-((bis(pyridin-2-ylmethyl)amino)methyl) nicotinamido)ethyl)thio)-2-hydroxy-1,2-oxaborinan-6-yl)acetic acid

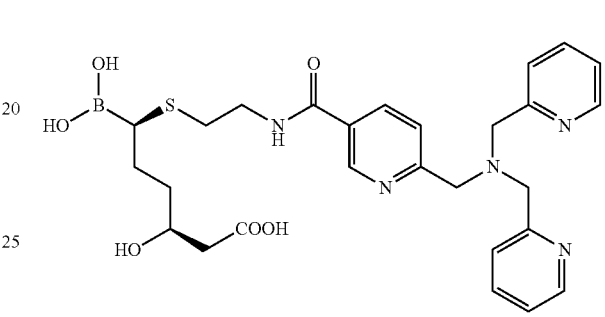

A mixture of the triply protected precursor from Example 159 (84.4 mg, 0.0967 mmol), and β-toluenesulfonic acid monohydrate (1.9 g, 10 mmol) was mixed with 20 mL acetonitrile and heated to reflux for two hours. After removal of solvent under reduced pressure, the residue was dissolved in 15 mL 0.5 M HCl (aq.) and washed with diethyl ether. The aqueous phase was loaded onto a plug of strong cationic exchange SPE material, and eluted using 1:1 methanol/water and a pH-gradient from pH 3 to pH 9 with formic acid and ammonia as additives. The acid eluted in the acidic fractions, whereas the desired product eluted at pH 9. Purity was difficult to assess by way HPLC due to presence of diastereomers (methanol in water, gradient eluted, with 0.5% trifluoroacetic acid in the eluent). $^1$H NMR (400 MHz, methanol-d$_4$) δ 8.88 (m, 1H), 8.44 (m, 2H), 8.18 (m, 1H), 7.81-7.65 (m, 5H), 7.28 (m, 2H), 4.20 (m, 1H), 3.92 (s, 2H), 3.90 (s, 4H), 3.65 (m, 1H), 3.43 (m, 1H), 2.74-2.55 (m, 3H), 2.19 (m, 1H), 2.09 (m, 1H), 1.84-1.74 (m, 2H), 1.58 (br d, 1H), 1.45 (m, 1H). Reported peaks and integrals correspond to main peaks from the edited HSQC spectrum. There are also several minor, unreported peaks; either arising from equilibrium forms and/or diasteromers of product or said forms, and possibly also from impurities. $^{13}$C NMR (100 MHz, methanol-d$_4$) δ 178.5, 168.2, 163.1, 159.8, 149.6, 148.9, 138.8, 137.3, 130.5, 125.0, 124.3, 124.0, 68.1, 61.3, 61.0, 40.8, 37.1, 35.3, 29.8, 28.9. Shifts from 1D $^{13}$C spectrum only given for the major diastereomer, as interpreted from the additional HSQC and HMBC spectra. Shift of carbon 6 to boron not visible in any spectrum. MS (ESI, neg. mode) m/z 548.2 [M−H]$^-$, HR-MS (ESI, neg. mode) m/z 547.2181 calculated for C$_{27}$H$_{31}$N$_5$O$_5$S$^{10}$B, found m/z 547.2180.

Example 161—tert-Butyl (3S,6R)-6-(bis(trimethylsilyl)amino)-3-((tert-butyldimethylsilyl)oxy)-6-((3aS,4S,6S,7aR)-3a,5,5-trimethylhexahydro-4,6-methanobenzo[d][1,3,2]dioxaborol-2-yl)hexanoate

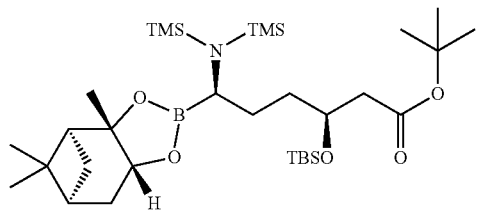 [SMILES: CC(C)(C)OC(=O)C[C@H](CC[C@@H](B1O[C@@H]2C[C@@H]3C[C@@H](C3(C)C)[C@]2(C)O1)N([Si](C)(C)C)[Si](C)(C)C)O[Si](C)(C)C(C)(C)C]

A flask containing (3S,6S)-tert-butyl 3-(tert-butyldimethylsilyloxy)-6-chloro-6-[(2S,6R)-2,9,9-trimethyl-3,5-dioxa-4-boratricyclo[6.1.1.0²,6]-decan-4-yl]hexanoate (307.9 mg, 0.598 mmol), prepared as described in Hecker et al. *J. Med. Chem.*, 2015, 58, 3682-3692, was put under a nitrogen atmosphere, dissolved in 10 mL dry tetrahydrofuran and cooled down on a dry ice/acetone bath to −78° C. Lithium bis(trimethylsilyl)amide was added (1.0 M solution in THF, 0.60 mL, 0.60 mmol), after which the cooling bath was removed and the mixture allowed to reach room temperature and stir overnight. At the end of the reaction, 5 mL dry dimethylformamide was added, and the tetrahydrofuran solvent removed under reduced pressure. The unstable product was transferred to the next reaction step as a solution in DMF without any additional purification or characterisation.

Example 162—tert-Butyl (3S,6R)-6-(6-((bis(pyridin-2-ylmethyl)amino)methyl) nicotinamido)-3-((tert-butyldimethylsilyl)oxy)-6-((3aS,4S,6S,7aR)-3a,5,5-trimethylhexahydro-4,6-methanobenzo[d][1,3,2]dioxaborol-2-yl)hexanoate

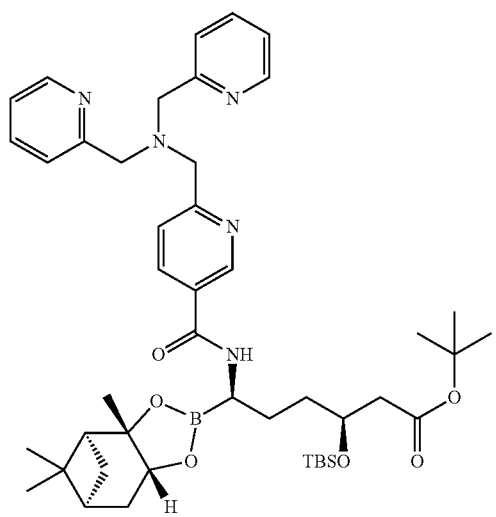 [SMILES: CC(C)(C)OC(=O)C[C@H](CC[C@H](NC(=O)c1ccc(CN(Cc2ccccn2)Cc2ccccn2)nc1)B1O[C@@H]2C[C@@H]3C[C@@H](C3(C)C)[C@]2(C)O1)O[Si](C)(C)C(C)(C)C]

To a flask containing 6-((bis(pyridin-2-ylmethyl)amino) methyl)nicotinic acid (0.718 mmol), prepared in situ by hydrolysis, neutralization and subsequent solvent removal from the corresponding methyl ester, dimethylformamide (5 mL) was added, and the resulting solution cooled down on an ice bath under nitrogen. 1-Ethyl-3-(3-dimethylaminopropyl)carbodiimide hydrochloride salt (177.2 mg, 0.924 mmol), followed by 1-hydroxy-7-azabenzotriazole (103.4 mg, 0.760 mmol), was then added, followed by a solution of tert-butyl (3S,6R)-6-(bis(trimethylsilyl)amino)-3-((tert-butyldimethylsilyl)oxy)-6-((3aS,4S,6S,7aR)-3a,5,5-trimethylhexahydro-4,6-methanobenzo[d][1,3,2]dioxaborol-2-yl) hexanoate (0.598 mmol, prepared as described above) in 5 mL dimethylformamide. Finally, N-methylmorpholine (0.20 mL, 1.8 mmol) was added and the mixture was allowed to stir for 3 h at room temperature. The reaction mixture was transferred to a separatory funnel containing a mixture of sat. NaCl (aq.) and 0.5 M $K_2CO_3$ (aq.). After extracting twice with 40 mL dichloromethane, the combined organic phase was dried over $MgSO_4$ (s), filtered and then solvent was removed under reduced pressure. The crude product was loaded onto a plug of Bondesil-C18 SPE material and eluted by running through portions of methanol/water mixture, going stepwise from 70% up to pure methanol. Fractions containing pure product were collected, and solvent removed under reduced pressure to afford 191.4 mg product (39.4%). $^1$H NMR (400 MHz, chloroform-d) δ 8.93 (m, 1H), 8.53 (m, 2H), 8.10 (m, 1H), 7.67-7.62 (m, 3H), 7.52 (d, J=7.8 Hz, 2H), 7.15 (m, 2H), 4.31 (m, 1H), 4.12 (m, 1H), 3.93 (s, 2H), 3.88 (s, 4H), 3.20 (m, 1H), 2.46-2-31 (m, 3H), 2.17 (m, 1H), 2.02 (m, 1H), 1.92-1.57 (m, should be 6H, but integrates to 9H, probably due to overlap from diastereomeric shifts), 1.43 (s, 3H), 1.41 (s, 9H), 1.34 (d, J=10.8 Hz, 1H), 1.28 (s, 3H), 0.85 (s, 9H), 0.84 (s, 3H), 0.054 (s, 3H), 0.048 (s, 3H). The product appears to be a 5:2 mixture of diastereomers, most easily determined from the multiplet pattern at $δ_H$ 8.93 ppm. Of the same reason most peaks appear split. $^{13}$C NMR (100 MHz, chloroform-d) δ 172.0, 167.4, 163.6, 159.2, 149.3, 148.0, 136.6, 135.9, 126.1, 123.2, 122.7, 122.3, 85.2, 81.0, 77.6, 68.2, 60.4, 60.0, 51.9, 43.6, 40.0, 39.5 (only visible from HSQC spectrum), 36.2, 34.7, 29.0, 28.3, 27.4, 26.7, 26.4, 26.0, 24.3, 18.1, −4.4, −4.5. Shifts only given for major diastereomer. MS (APCI, pos. mode) m/z 812.5 [M+H]$^+$, HR-MS (APCI, pos. mode) m/z 811.4984 calculated for $C_{45}H_{67}N_5O_6Si^{10}B$, found m/z 811.4981.

Example 163a—2-((3R,6S)-3-(6-((Bis(pyridin-2-ylmethyl)amino)methyl)nicotinamido)-2-hydroxy-1,2-oxaborinan-6-yl)acetic acid

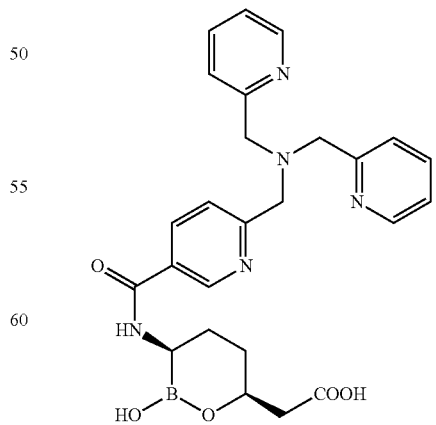

From the triply protected compound described above (109 mg, 0.132 mmol), global deprotection was achieved by dissolving the starting material in 4 mL dioxane, and adding 2 mL 4 M HCl in dioxane and heating to 70° C. for 30 min. After cooling down, a pale yellow hygroscopic precipitate deposited on the glass surface, which was isolated by way of suction filtration. The precipitate was washed on the filter with diethyl ether and redissolved in water. Final purification was achieved by way of preparative HPLC, with multiple injections, on a preparative scale hybrid silica C18 reversed phase column eluted with 28:72 water/methanol mixture containing 0.5% trifluoroacetic acid. Fractions were collected as timeslices and analysed with analytical HPLC using a similar column and eluent. The fractions containing product in satisfactory purity was loaded directly onto a plug of strong cation exchange material, and excess acid washed out using 1:1 methanol/water. The product was eluted using the same 1:1 mixture, with addition of $NH_3$ (aq.). Removal of volatiles under reduced pressure gave 14.8 mg of the title compound as a colourless solid, with approximately 95% purity according to HPLC (27.7%). $^1$H NMR (300 MHz, methanol-$d_4$) δ 8.90 (m, 1H), 8.48 (m, 2H), 8.18 (dd, J=8.2 Hz, 2.3 Hz, 1H), 7.82 (app dt, J=1.8 Hz, 7.7 Hz, 2H), 7.70-7.63 (m, 3H), 7.31 (m, 2H), 4.21 (m, 1H), 3.98 (s, 2H), 3.97 (s, 4H), 3.07 (dd, J=10.4 Hz, 5.7 Hz, 1H), 2.68 (dd, J=17.4 Hz, 7.2 Hz, 1H), 2.26 (dd, J=17.2 Hz, 1.5 Hz, 1H), 2.11 (m, 1H), 1.87 (m, 1H), 1.53 (m, 1H), 1.36 (m, 1H). The spectrum shows no signs of diastereomers and no excessive broadening due to equilibria. $^{13}$C NMR (100 MHz, methanol-$d_4$) δ 179.0, 162.7 (only visible from HMBC spectrum), 159.8, 149.6, 149.5, 148.7, 138.8, 138.7, 137.0, 125.0, 124.2, 123.9, 68.3, 61.3, 61.0, 43.3 (only visible from HSQC spectrum), 37.4 (br), 33.6 (br), 27.3. MS (ESI, neg. mode) m/z 488.2 [M−H]$^-$.

Example 163b—Hydrochloride Salt of the Compounds of Example 163a

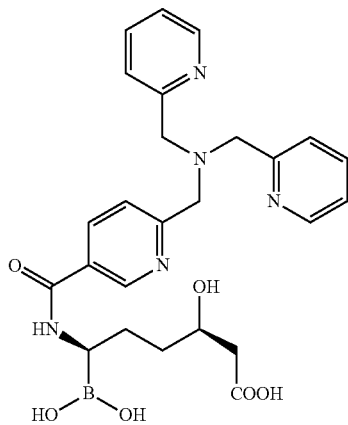 [SMILES: O=C(O)C[C@H](O)CC[C@H](NC(=O)c1ccc(CN(Cc2ccccn2)Cc2ccccn2)nc1)B(O)O]

In an alternative preparation, the compound in example 162 (41.2 mg, 0.0507 mmol) was dissolved in 2 mL dioxane, 1 mL 4 M HCl in dioxane added, and the mixture heated on reflux for 30 min. After transfer to a separatory funnel using 20 mL water, and washing the aqueous phase two times with 20 mL diethyl ether, the water phase was evaporated to yield 30.0 mg product (quantitative, with unknown amount of HCl present). Purity by way of HPLC was less than 70%, and NMR showed some evidence of partial deprotection. MS (ESI, neg. mode) m/z 488.2 [M−H]$^-$, HR-MS (ESI, neg. mode) m/z 487.2147 calculated for $C_{25}H_{27}N_5O_5{}^{10}B$, found m/z 487.2150.

Example 164—tert-Butyl 3-((R)-2-(6-((bis(pyridin-2-ylmethyl)amino)methyl) nicotinamido)-2-((3aS, 4S,6S,7aR)-3a,5,5-trimethylhexahydro-4,6-methanobenzo[d][1,3,2]dioxaborol-2-yl)ethyl)-2-((tert-butoxycarbonyl)oxy)benzoate

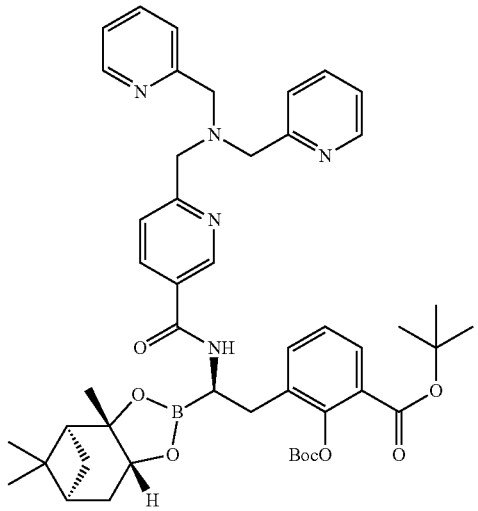

To a flask containing 6-((bis(pyridin-2-ylmethyl)amino) methyl)nicotinic acid (0.471 mmol), prepared in situ by hydrolysis, neutralization and subsequent solvent removal from the corresponding methyl ester, dimethylformamide (5 mL) was added, and the resulting solution cooled down on an ice bath under nitrogen. 1-Ethyl-3-(3-dimethylaminopropyl)carbodiimide hydrochloride salt (115.2 mg, 0.601 mmol), followed by 1-hydroxy-7-azabenzotriazole (65.5 mg, 0.481 mmol), was then added, followed by a solution of tert-butyl 3-((R)-2-(bis(trimethylsilyl)amino)-2-((3aS,4S, 6S,7aR)-3a,5,5-trimethylhexahydro-4,6-methanobenzo[d] [1,3,2]dioxaborol-2-yl)ethyl)-2-((tert-butoxycarbonyl)oxy) benzoate (0.387 mmol, prepared in an adapted procedure from Hecker et al. J. Med. Chem., 2015, 58, 3682-3692 and Reddy et al WO2016003929A1, in 5 mL dimethylformamide. Finally, N-methylmorpholine (0.13 mL, 1.2 mmol) was added and the mixture was allowed to stir for 4 h at room temperature. The reaction mixture was transferred to a separatory funnel containing a mixture of sat. NaCl (aq.) and 0.5 M $K_2CO_3$ (aq.). After extracting twice with 40 mL dichloromethane, the combined organic phase was dried over $MgSO_4$ (s), filtered and then solvent was removed under reduced pressure. The crude product was loaded onto a plug of Bondesil-C18 SPE material and eluted by running through portions of methanol/water mixture, going stepwise from 60% up to pure methanol. Fractions containing pure product were collected, and solvent removed under reduced pressure to afford 168.4 mg product (52.3%). $^1$H NMR (400 MHz, chloroform-d) δ 8.89 (br d, 1H), 8.53 (m, 2H), 8.03 (dd, J=8.2 Hz, 2.3 Hz, 1H), 7.79 (dd, J=7.8 Hz, 1.7 Hz, 1H), 7.67-7.62 (m, 3H), 7.54-7.48 (m, 3H), 7.24 (m, 1H), 7.14 (m, 2H), 4.34 (m, 1H), 3.92 (s, 2H), 3.86 (s, 4H), 3.12 (m, 1H), 3.00 (m, 2H), 2.38 (m, 1H), 2.21 (m, 1H), 2.05 (t, J=5.5 Hz, 1H), 1.93-1.87 (m, 2H), 1.57-1.54 (m, 10H), 1.46 (s, 3H), 1.34 (br s, 7-8H, possibly some in situ hydrolysis), 1.30 (s, 3H), 0.89 (s, 3H). $^{13}$C NMR (100 MHz, chloroform-d) δ 168.8, 164.6, 163.9, 159.1, 149.4, 148.8, 148.7, 136.6, 136.1, 135.2, 130.2, 126.2, 125.5, 123.2, 123.1, 122.6, 122.3, 84.3, 84.2, 81.8, 77.4, 60.4, 60.0, 52.4, 44.2 (only visible in HSQC spectrum), 40.2, 38.4, 36.7, 31.3 (br), 29.2, 28.3, 27.7, 27.5, 26.9, 24.4. Additional unreported minor peaks visible in $^{13}$C spectrum, probably from a diastereomer. Two carbonyl signals could not be identified. MS (APCI, pos. mode) m/z 832.4 [M+H]$^+$, HR-MS (APCI, pos. mode) m/z 831.4488 calculated for $C_{47}H_{59}N_5O_8{}^{10}B$, found m/z 831.4483.

Example 165—(R)-3-(6-((Bis(pyridin-2-ylmethyl)amino)methyl)nicotinamido)-2-hydroxy-3,4-dihydro-2H-benzo[e][1,2]oxaborinine-8-carboxylic acid

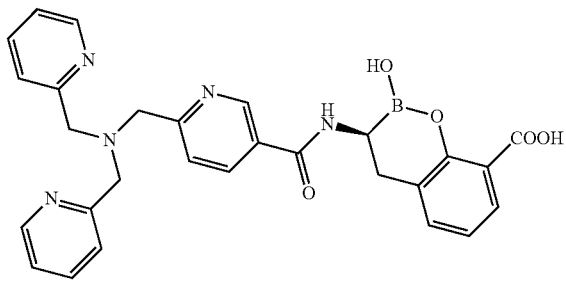 [SMILES: O=C(N[C@@H]1Cc2cccc(C(=O)O)c2OB1O)c1ccc(CN(Cc2ccccn2)Cc2ccccn2)nc1]

Global deprotection of the precursor described above was achieved by dissolving the precursor (90.8 mg, 0.109 mmol) in 8 mL dry dioxane, followed by addition of 2 mL 4 M HCl in dioxane. After heating to 70° C. for 1 h, and subsequent cooling to room temperature, an inhomogenous, hygroscopic precipitate was isolated by way of suction filtration, washed with diethyl ether, and redissolved in water prior to loading onto a plug of strong cation exchange material. The plug was washed with 1:1 methanol/water and the product eluted with the same solvents, with the addition of some aqueous ammonia. Removal of solvent under reduced pressure gave the product as a film which could be scraped off the glass wall to provide a yellow powder (35.4 mg, 62.1%). No meaningful NMR data could be recorded. HPLC purity was estimated to 70-80%, using phosphate buffing to pH 11.5, as described above. MS (ESI, neg. mode) m/z 522.2 [M−H]$^-$, HR-MS (ESI, neg. mode) m/z 521.1991 calculated for $C_{28}H_{25}N_5O_5{}^{10}B$, found m/z 521.1989.

Example 166—tert-butyl 3-(3a,5,5-trimethylhexahydro-4,6-methanobenzo[d][1,3,2]dioxaborol-2-yl)benzoate

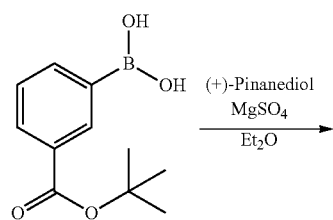

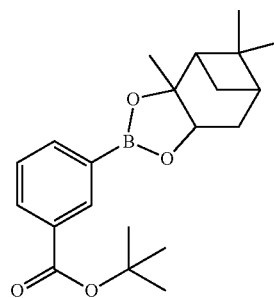

(3-(tert-Butoxycarbonyl)phenyl)boronic acid (978 mg, 4.40 mmol) was suspended in 40 mL Et$_2$O and mixed with (+)-pinanediol (750 mg, 4.40 mmol) and anhydrous MgSO$_4$ (1 gram, 8.30 mmol). The mixture was stirred at room temperature under argon for 3 hours before the inorganic material was filtered off and the filtrate concentrated under reduced pressure. This gave a sticky clear oil (1568 mg, 4.40 mmol, >99%) which solidified overnight at room temperature. $^1$H NMR (600 MHz, Chloroform-d) δ 8.41 (t, J=1.5 Hz, 1H), 8.07 (dt, J=7.8, 1.6 Hz, 1H), 7.95 (dt, J=7.4, 1.4 Hz, 1H), 7.42 (t, J=7.6 Hz, 1H), 4.47 (dd, J=8.8, 1.9 Hz, 1H), 2.42 (ddt, J=14.8, 8.8, 2.4 Hz, 1H), 2.30-2.20 (m, 1H), 2.16 (t, J=5.5 Hz, 1H), 2.05-1.89 (m, 2H), 1.60 (s, 10H), 1.49 (s, 3H), 1.31 (s, 3H), 1.19 (s, 1H), 0.89 (s, 3H). $^{13}$C NMR (151 MHz, CDCl$_3$) δ 166.04, 138.84, 135.78, 132.22, 131.60, 127.79, 86.62, 81.12, 78.57, 77.37, 77.16, 76.95, 66.00, 51.53, 39.67, 38.35, 35.64, 28.84, 28.37, 27.25, 26.65, 24.20, 15.43. MS (ESI positive mode): m/z 379.2 (M+Na$^+$)

Example 167—6-((bis(pyridin-2-ylmethyl)amino)methyl)nicotinic acid

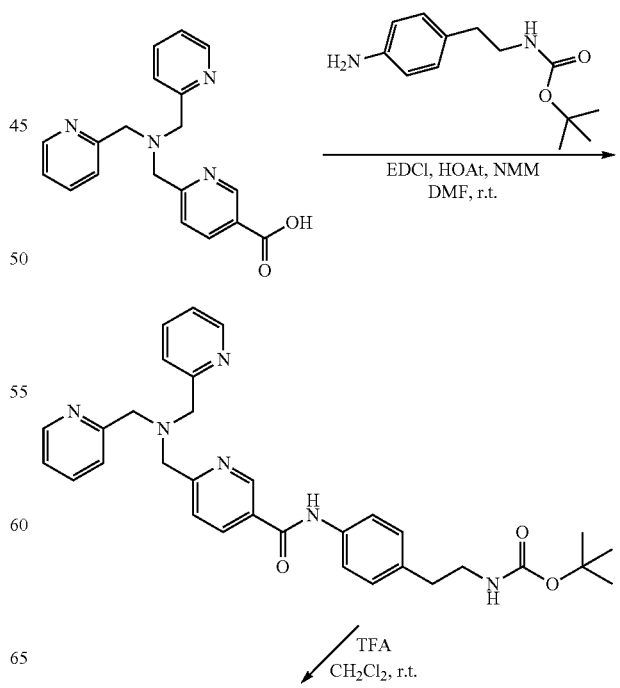

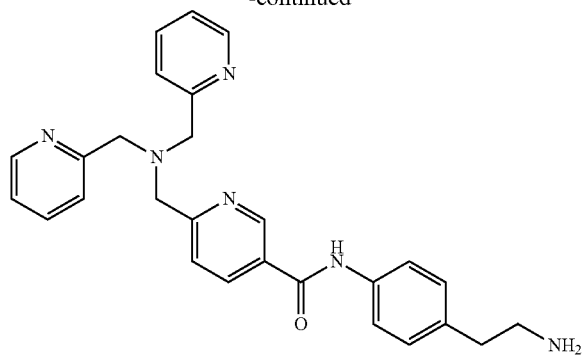

Example 167a—tert-Butyl 4-(6-((bis(pyridin-2-ylmethyl)amino)methyl)nicotinamido) phenethylcarbamate

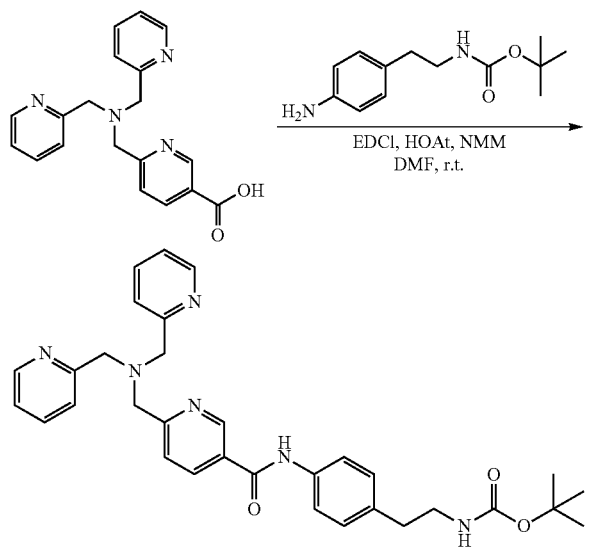

6-((bis(pyridin-2-ylmethyl)amino)methyl)nicotinic acid from Example 13 (1.66 g, 4.97 mmol, 1.0 eq.) was dissolved in 20 mL dry DMF at room temperature and filtered into a 50 mL round bottomed flask prior to reaction to remove the insoluble inorganics. To this solution was added tert-butyl 4-aminophenethylcarbamate (1.76 g, 7.45 mmol, 1.5 eq.), followed by EDCl (1.428 g, 7.45 mmol, 1.5 eq.), HOAt (1.014 g, 7.45 mmol, 1.5 eq.) and NMM (0.821 mL, 7.45 mmol, 1.5 eq.). The reaction mixture was stirred at room temperature for 16 h and then concentrated under reduced pressure. The residual crude mixture was dissolved in 100 mL CHCl$_3$, transferred into a separation funnel and washed with sat. aq. K$_2$CO$_3$ solution (100 mL) and brine (100 mL). The organic phase was dried oved Na$_2$SO$_4$, filtered and concentrated under reduced pressure. Purification of the product was performed by column chromatography on Alumina using 1% MeOH in CH$_2$Cl$_2$ giving the product with minor impurities, followed by C18-SPE using gradient elution from 10% to 90% methanol in water affording 1.697 g (3.07 mmol, 62%) of the product as a yellow oil. $^1$H NMR (300 MHz, MeOH) δ 8.96 (d, J=1.8 Hz, 1H), 8.46-8.39 (m, 2H), 8.23 (dd, J=8.2, 2.3 Hz, 1H), 7.76 (td, J=7.7, 1.5 Hz, 3H), 7.62 (dd, J=13.5, 8.1 Hz, 4H), 7.24 (ddd, J=7.3, 5.0, 1.1 Hz, 2H), 7.17 (d, J=8.5 Hz, 2H), 3.89 (s, 2H), 3.85 (s, 4H), 3.24 (t, J=7.3 Hz, 2H), 2.72 (t, J=7.3 Hz, 2H), 1.40 (s, 9H). $^{13}$C NMR (101 MHz, MeOD) δ 166.10, 163.40, 159.85, 158.28, 149.56, 148.92, 138.55, 137.76, 137.41, 137.15, 130.88, 130.16, 124.83, 124.14, 123.81, 122.23, 79.86, 61.10, 60.84, 42.95, 36.59, 28.79. APCI-HRMS e/z calc. for C$_{32}$H$_{36}$N$_6$O$_3$: 552.2849, found: 553.2920 [M+H].

Example 167b—N-(4-(2-aminoethyl)phenyl)-6-((bis(pyridin-2-ylmethyl)amino) methyl)nicotinamide

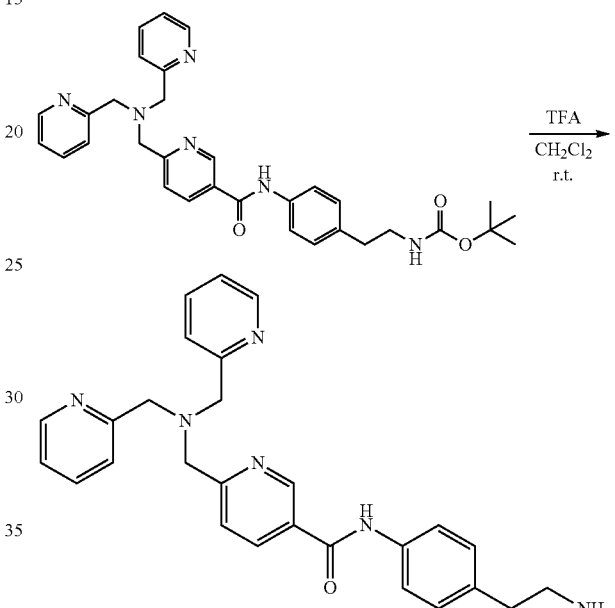

The tert-butyl 4-(6-((bis(pyridin-2-ylmethyl)amino)methyl)nicotinamido)phenethylcarbamate from example 167a (1.697 g, 3.07 mmol, 1.0 eq.) was dissolved in 10 mL CH$_2$Cl$_2$ at room temperature. To this solution was added TFA (5 mL) and the mixture stirred at room temperature until TLC (Alumina, 5% MeOH in CH$_2$Cl$_2$) or NMR indicated full conversion. The mixture was concentrated under reduced pressure, the residue dissolved in a mixture of CHCl$_3$/dest. H$_2$O/sat. aq. K$_2$CO$_3$ (100 mL/10 mL/100 mL) and transferred into a separation funnel. The organic phase was separated, the aq. phase extracted with CHCl$_3$ (2 times 50 mL) and the combined organics washed with brine (100 mL), dried over K$_2$CO$_3$/Na$_2$SO$_4$, filtered and concentrated under reduced pressure to afford N-(4-(2-aminoethyl)phenyl)-6-((bis(pyridin-2-ylmethyl)amino)methyl)nicotinamide in quantitative yield. $^1$H NMR (300 MHz, MeOH) δ 8.97 (d, J=1.7 Hz, 1H), 8.45 (ddd, J=5.0, 1.7, 0.9 Hz, 2H), 8.26 (dd, J=8.2, 2.3 Hz, 1H), 7.80 (td, J=7.6, 1.6 Hz, 3H), 7.68 (d, J=7.8 Hz, 2H), 7.62 (d, J=8.5 Hz, 2H), 7.28 (ddd, J=7.4, 5.0, 1.2 Hz, 2H), 7.23 (d, J=8.5 Hz, 2H), 3.94 (s, J=4.3 Hz, 2H), 3.90 (s, 4H), 2.88 (t, J=6.7 Hz, 2H), 2.76 (t, J=6.9 Hz, 2H). $^{13}$C NMR (101 MHz, MeOD) δ 163.55, 159.96, 149.62, 148.93, 138.69, 137.51, 131.02, 130.19, 124.99, 124.32, 123.92, 122.54, 79.46, 61.24, 60.96, 44.03, 39.22. APCI-HRMS e/z calc. for C$_{27}$H$_{28}$N$_6$O: 452.2325, found: 453.2396 [M+H].

Example 168—6-((bis(pyridin-2-ylmethyl)amino)methyl)-N-(4-(2-(6-((bis(pyridin-2-ylmethyl)amino)methyl)nicotinamido)ethyl)phenyl)nicotinamide

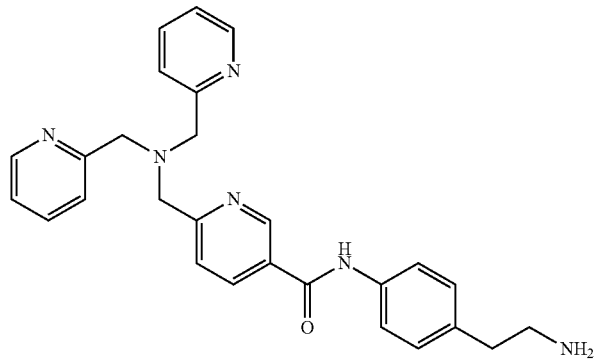

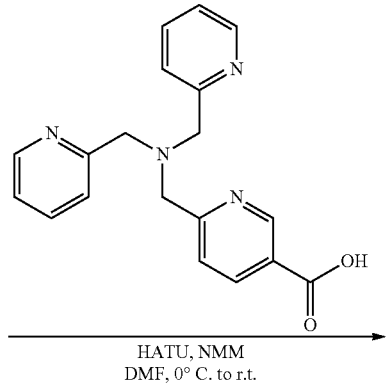

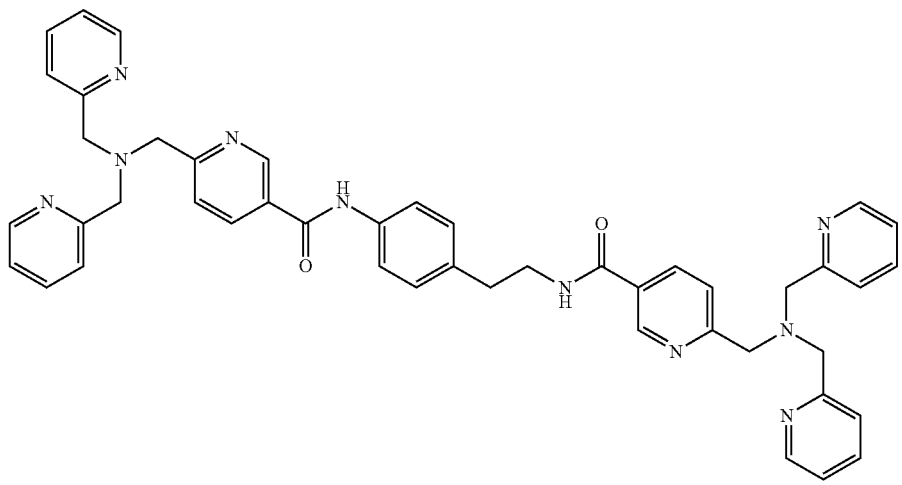

6-((bis(pyridin-2-ylmethyl)amino)methyl)nicotinic acid from example 13 (70.9 mg, 0.212 mmol, 1.05 eq.) and N-(4-(2-aminoethyl)phenyl)-6-((bis(pyridin-2-ylmethyl)amino)methyl)nicotinamide from example 17 (91.3 mg, 0.202 mmol, 1.0 eq.) were dissolved in 3 mL dry DMF cooled to 0° C. in an ice bath. HATU (80.6 mg, 0.212 mmol, 1.05 eq.) and NMM (49 μL, 0.444 mmol, 2.1 eq.) were added and the mixture stirred at 0° C. for 1 h, then at room temperature for 16 h. The mixture was concentrated under reduced pressure and the product purified by dry column vacuum chromatography on C18 material, using a stepwise elution from 10% to 90% methanol in water affording 84 mg (0.11 mmol, 55%) of product. $^1$H NMR (300 MHz, MeOH) δ 8.96 (d, J=1.7 Hz, 1H), 8.80 (d, J=1.6 Hz, 1H), 8.43 (tdd, J=2.5, 1.6, 0.8 Hz, 4H), 8.25 (dd, J=8.2, 2.3 Hz, 1H), 8.09 (dd, J=8.2, 2.3 Hz, 1H), 7.78 (dtd, J=7.9, 6.3, 1.8 Hz, 5H), 7.73-7.58 (m, 7H), 7.27 (ddd, J=8.7, 6.1, 3.0 Hz, 6H), 3.93 (s, 2H), 3.89 (s, 2H), 3.88 (s, 4H), 3.86 (s, 4H), 3.61 (t, J=7.2 Hz, 2H), 2.91 (t, J=7.2 Hz, 2H). $^{13}$C NMR (101 MHz, CDCl$_3$) δ 167.80, 166.28, 163.50, 163.27, 159.91, 149.60, 149.56, 148.97, 148.58, 138.67, 138.65, 137.96, 137.49, 137.12, 137.07, 130.99, 130.43, 130.28, 124.96, 124.28, 123.91, 123.88, 122.38, 61.27, 61.20, 60.95, 42.50, 35.88. APCI-HRMS e/z calc. for C$_{46}$H$_{44}$N$_{10}$O$_2$: 768.3649, found: 769.3719 [M+H].

Example 169—6-((bis(pyridin-2-ylmethyl)amino)methyl)-N-(2-(tritylthio)ethyl) nicotinamide—Examples 169 and 170 are an alternative method to prepare the compound of Example 158

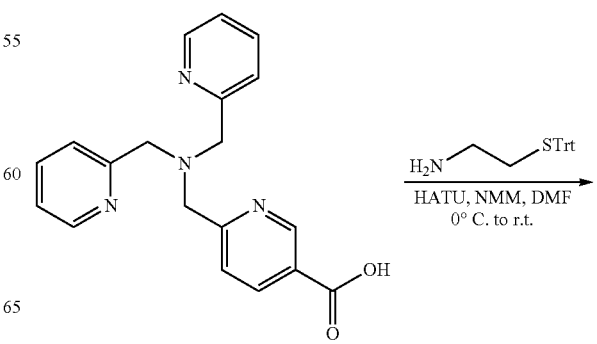

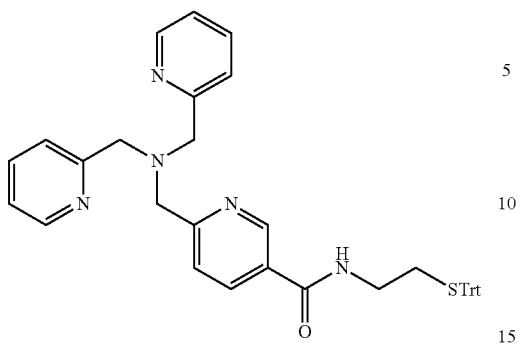

6-((bis(pyridin-2-ylmethyl)amino)methyl)nicotinic acid (0.763 g, 2.343 mmol, 1.0 eq.), prepared in example 13, and 2-(tritylthio)ethanamine (0.823 g, 2.577 mmol, 1.1 eq.) were dissolved in 15 mL dry DMF cooled to 0° C. in an ice bath. HATU (0.98 g, 2.577 mmol, 1.1 eq.) and NMM (0.284 mL, 2.577 mmol, 2.0 eq) were added. The mixture was stirred at 0° C. for 30 min, then at room temperature for 16 h and concentrated under reduced pressure. Purification of the product was achieved by way of dry column vacuum chromatography on C18 material, using a stepwise elution from 10% to 90% methanol in water affording 1.053 g (1.65 mmol, 71%) of product.

$^1$H NMR (400 MHz, MeOD) δ 8.82 (d, J=2.0 Hz, 1H), 8.41 (d, J=4.9 Hz, 2H), 8.09 (dd, J=8.2, 2.1 Hz, 1H), 7.75 (td, J=7.7, 1.3 Hz, 2H), 7.70 (d, J=8.2 Hz, 1H), 7.63 (d, J=7.8 Hz, 2H), 7.36 (d, J=7.5 Hz, 6H), 7.22 (dd, J=9.9, 4.8 Hz, 8H), 7.16 (t, J=7.2 Hz, 3H), 3.89 (s, J=7.4 Hz, 2H), 3.86 (s, 4H), 3.28 (d, J=6.8 Hz, 2H), 2.45 (t, J=6.9 Hz, 2H).

$^{13}$C NMR (101 MHz, MeOD) δ 148.18, 147.30, 137.28, 135.85, 129.31, 127.54, 126.44, 123.57, 122.93, 122.51, 59.88, 59.58, 38.56, 31.31.

Example 170—6-((bis(pyridin-2-ylmethyl)amino) methyl)-N-(2-mercaptoethyl) nicotinamide (same as Example 158)

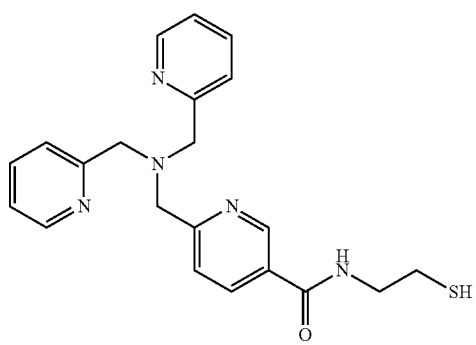

6-((bis(pyridin-2-ylmethyl)amino)methyl)-N-(2-(tritylthio)ethyl)nicotinamide (1.053 g, 1.65 mmol, 1.0 eq.) was dissolved in 25 mL CH$_2$Cl$_2$ at room temperature. To this solution was added TFA (25 mL, 330 mmol, 200 eq.) and HSiEt$_3$ (0.527 mL, 3.3 mmol, 2.0 eq.). The mixture was stirred at room temperature for 30 min, then concentrated under reduced pressure to remove as much TFA as possible. The residue was dissolved in 100 mL CH$_2$Cl$_2$ and transferred into a separation funnel. The organic phase was extracted with 100 mL H2O, the aqueous phase washed with CH$_2$Cl$_2$ (5 times 50 mL), and the pH adjusted to 10 with sat. aq. K$_2$CO$_3$ solution. The aqueous phase was then extracted with CH$_2$Cl$_2$ (3 times 100 mL), the combined organics dried over Na$_2$SO$_4$ and K$_2$CO$_3$, filtered and concentrated under reduced pressure to afford 0.549 g (1.397 mmol, 85%) of the thiol which was used immediately for the next step without further purification or stored in a tightly sealed vial in the freezer. $^1$H NMR (300 MHz, MeOH) δ 8.87 (d, J=1.8 Hz, 1H), 8.44 (d, J=4.2 Hz, 2H), 8.16 (dd, J=8.2, 2.3 Hz, 1H), 7.78 (ddd, J=12.1, 9.0, 5.0 Hz, 3H), 7.66 (d, J=7.8 Hz, 2H), 7.36-7.19 (m, 2H), 3.92 (s, 2H), 3.88 (s, 4H), 3.54 (t, J=7.0 Hz, 2H), 2.72 (t, J=6.9 Hz, 2H). APCI-HRMS e/z calc. for C$_{21}$H$_{23}$N$_5$O$_5$S: 393.1623, found 394.1695 [M+H]Example X (OAHA-VII-75).

Example 171—Tert-Butyl 2-(3-((S)-2-Chloro-2-((3aS,4S,6S,7aR)-3a,5,5-Trimethylhexahydro-4,6-Methanobenzo[d][1,3,2]Dioxaborol-2-yl)Ethyl)benzoate

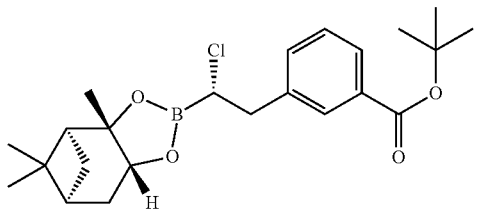 [SMILES: CC(C)(C)OC(=O)c1cccc(C[C@@H](Cl)B2O[C@@H]3C[C@@H]4C[C@@H](C4(C)C)[C@]3(C)O2)c1]

Matteson-homologation of tert-butyl (3-((((3aS,4S,6S,7aR)-3a,5,5-trimethylhexahydro-4,6-methanobenzo[d][1,3,2]dioxaborol-2-yl)methyl)benzoate (3.03 g, 6.24 mmol) was performed as described in Example 154 and in Reddy et al WO2016003929 to yield the title compound.

Example 172—tert-butyl 3-(2-((2-(6-((bis(pyridin-2-ylmethyl)amino)methyl) nicotinamido)ethyl)thio)-2-(3a,5,5-trimethylhexahydro-4,6-methanobenzo[d][1,3,2]dioxaborol-2-yl)ethyl)benzoate The thiol (254 mg, 0.64 mmol) from Example 174 was dissolved in 8 mL THF and placed under argon and cooled to 0° C. DIPEA (250 μL) was then added followed by the chloride from Example 175 (52 mg, 0.12 mmol) with the aid of 2 mL THF. The mixture was stirred for 30 minutes at 0° C. and then at room temperature overnight. The mixture was then concentrated under reduced pressure and the crude material was purified on neutral $Al_2O_3$ using 0-5% MeOH in DCM giving 32 mg of a pale yellow oil. MS (APCI positive mode) m/z 776.401 (M+H). $C_{44}H_{54}BN_5O_5S$ calculated to 775.39.

Example 173—3-(2-((2-(6-((bis(pyridin-2-ylmethyl)amino)methyl)nicotinamido) ethyl)thio)-2-borono-ethyl)benzoic acid

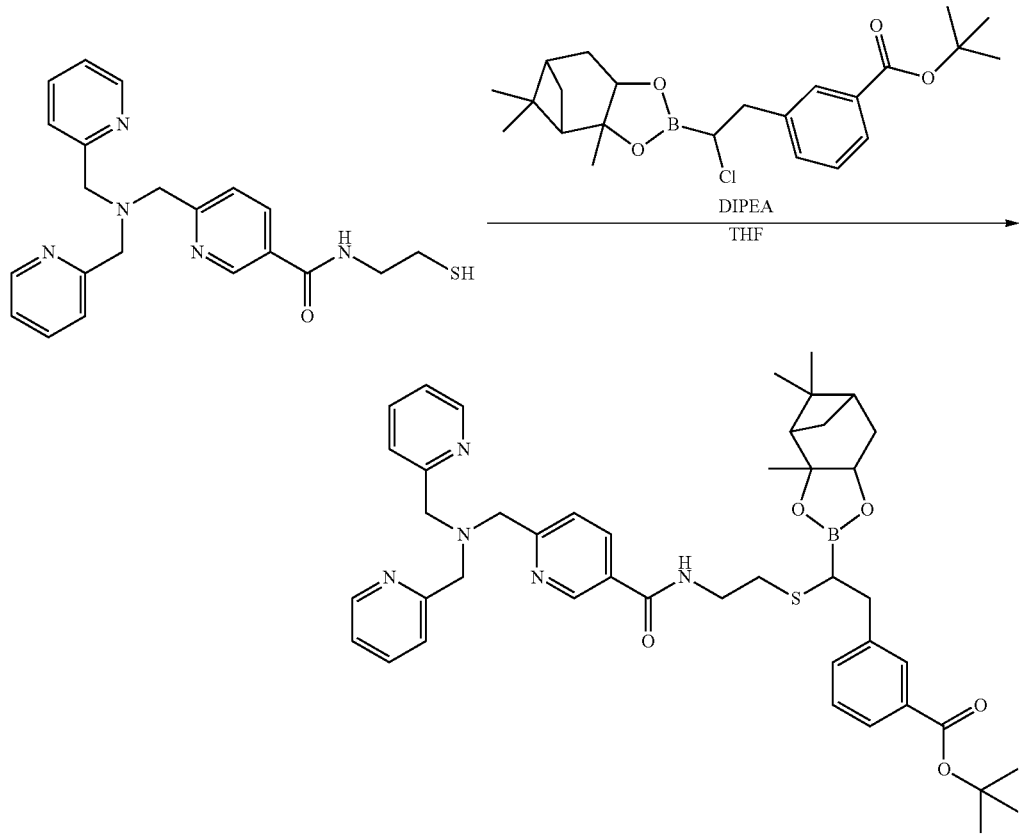

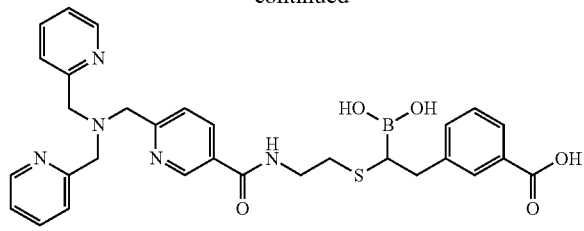

Global deprotection and cyclisation was achieved as described in Example 157 by treatment of a solution of the doubly protected precursor from Example 172 (64.1 mg, 0.0703 mmol) in 2 mL dioxane with 1 mL 4 M HCl in dioxane.

Example 174—3-(2-((2-(6-((bis(pyridin-2-ylmethyl) amino)methyl)nicotinamido) ethyl)thio)-2-borono-ethyl)benzoic acid sodium salt

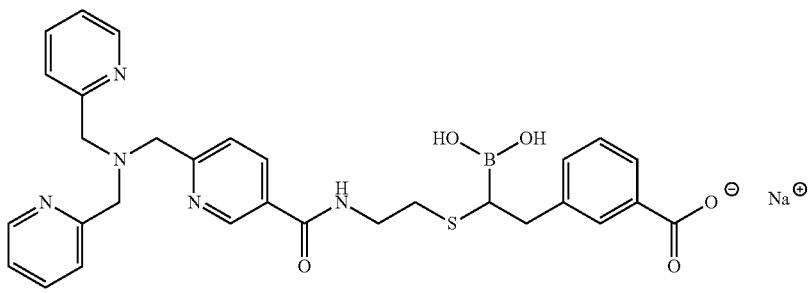 [SMILES: O=C([O-])c1cccc(CC(SCCNC(=O)c2ccc(CN(Cc3ccccn3)Cc3ccccn3)nc2)B(O)O)c1 ; [Na+]]

A solution of the the sodium salt of Example 173 is prepared by adding 1 molar equivalent NaOH to a solution of Example 173 in 50:50 dioxane/water.

Example 175—N-allyl-6-((bis(pyridin-2-ylmethyl) amino)methyl)nicotinamide

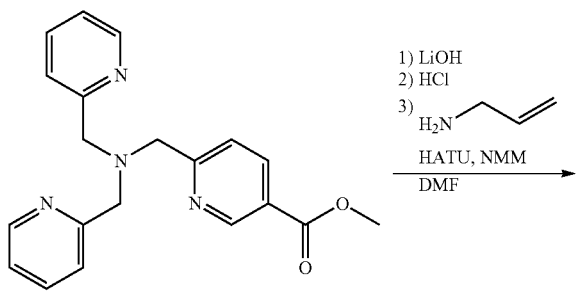

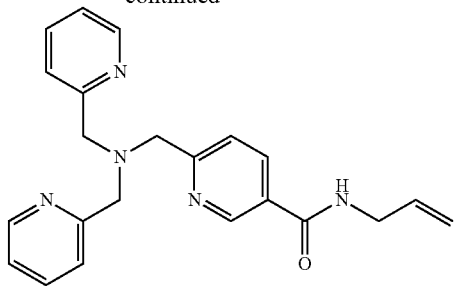

The ester (1043 mg, 2.99 mmol) was dissolved in THF (5 mL) and LiOH hydrate (376 mg, 8.97 mmol) was added with the aid of 5 mL water. The mixture was stirred for 3 hours at room temperature before 10 mL 1M HCl was added and the mixture was concentrated under reduced pressure. The crude acid was taken up into 20 mL DMF and HATU (1140 mg, 2.99 mmol), the amine (751 μL, 9.99 mmol) and NMM (751 μL, 4.00 mmol) was added. The mixture was stirred at room temperature overnight before it was concentrated under reduced pressure. The crude material was suspended in 250 mL 1M K2CO3 and extracted with 5×25 mL EtOAc. The combinder organic fractions were pooled, dried over K2CO3, filtered and concentrated under reduced pressure to give a pale brown oil. The material was purified on neutral Al$_2$O$_3$ using 0-5% MeOH in DCM as eluent. A total of 726 mg (65%) of clean product was obtained. $^1$H NMR (400 MHz, DMSO-d$_6$) δ 8.93 (dd, J=2.3, 0.8 Hz, 1H), 8.77 (t, J=5.7 Hz, 1H), 8.49 (ddd, J=4.9, 1.8, 0.9 Hz, 2H), 8.17 (dd, J=8.1, 2.3 Hz, 1H), 7.77 (td, J=7.6, 1.9 Hz, 2H), 7.69 (dd, J=8.2, 0.8 Hz, 1H), 7.58 (dt, J=7.8, 1.1 Hz, 2H), 7.25 (ddd, J=7.4, 4.8, 1.2 Hz, 2H), 5.89 (ddt, J=17.2, 10.4, 5.3 Hz, 1H), 5.27-5.01 (m, 2H), 3.91 (tt, J=5.5, 1.7 Hz, 2H), 3.85 (s, 2H), 3.80 (s, 4H). $^{13}$C NMR (101 MHz, DMSO) δ 164.52, 161.79, 158.75, 148.82, 147.70, 136.52, 135.41, 135.09, 128.29, 122.59, 122.14, 121.95, 115.27, 59.37, 59.15, 41.40. MS (APCI positive mode) m/z 374.20 [M+H]$^-$, HRMS (APCI positive mode) m/z 373.1904 calculated for C$_{22}$H$_{23}$N$_5$O, found m/z 374.1975.

Example 176—Methyl 5-(hydroxymethyl)thiophene-2-carboxylate

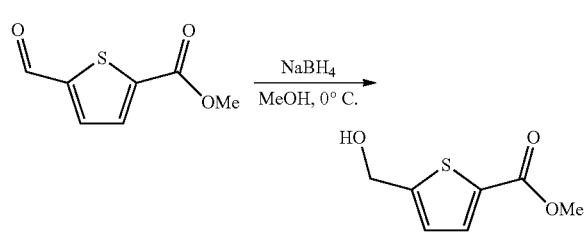

Methyl 5-formylthiophene-2-carboxylate (1.0 g, 5.87 mmol, 1.0 eq.) was dissolved in 50 mL MeOH cooled to 0° C. in an ice bath. To this solution was added NaBH4 (0.445 g, 11.75 mmol, 2.0 eq.) slowly in portions and the reaction was monitored by TLC (SiO2, 9:1 n-hexanes:EtOAc). Upon full conversion of the aldehyde, the reaction was quenched by slow addition of ice cooled water (10 mL). The mixture was then transferred into a separation funnel, diluted with 50 mL H2O end extracted with diethyl ether (3 times 100 mL). The combined organics were washed with brine (50 mL), dried over Na2SO4, filtered and concentrated under reduced pressure. The product was obtained pure (0.935 g, 5.4 mmol, 92%) and used for the next step without further purification.

$^1$H NMR (300 MHz, CDCl$_3$) δ 7.67 (d, J=3.8 Hz, 1H), 6.98 (dt, J=3.8, 0.8 Hz, 1H), 4.85 (d, J=0.7 Hz, 2H), 3.87 (s, 3H), 1.95 (s (br), 1H).

Example 177—Methyl 5-(chloromethyl)thiophene-2-carboxylate

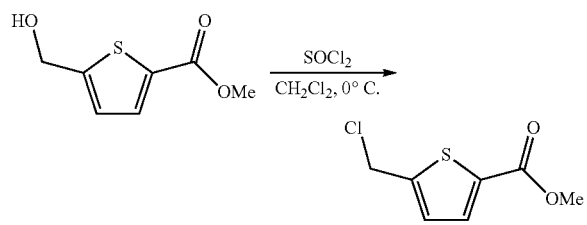

The methyl 5-(hydroxymethyl)thiophene-2-carboxylate prepared in the previous reaction (0.935 g, 5.4 mmol, 1.0 eq.) was dissolved in 50 mL CH2Cl2 cooled to 0° C. in an ice bath. To this was added a solution of SOCl2 (0.787 mL, 10.8 mmol, 2.0 eq.) in 10 mL CH2Cl2 dropwise via a dropping funnel. The mixture was stirred at 0° C. for 1 h, then at room temperature for 16 h. TLC control indicated full conversion of the alcohol (SiO2, 5:1 n-hexanes:EtOAc) and the mixture was concentrated under reduced pressure. The residue was dissolved in CH2Cl2 (100 mL), transferred into a separation funnel and washed with sat. aq. K2CO3 solution (50 mL), dried over Na2SO4, filtered and concentrated under reduced pressure. Column chromatography on silica using gradient elution (n-hexanes to 9:1 n-hexanes:EtOAc) afforded 0.754 g (3.9 mmol, 73%) of methyl 5-(chloromethyl)thiophene-2-carboxylate as a pale yellow oil. $^1$H NMR (300 MHz, CDCl$_3$) δ 7.65 (d, J=3.8 Hz, 1H), 7.07 (dt, J=3.8, 0.7 Hz, 1H), 4.76 (d, J=0.6 Hz, 2H), 3.88 (s, J=1.6 Hz, 3H).

Example 178—Methyl 5-((bis(thiophen-2-ylmethyl)amino)methyl)thiophene-2-carboxylate

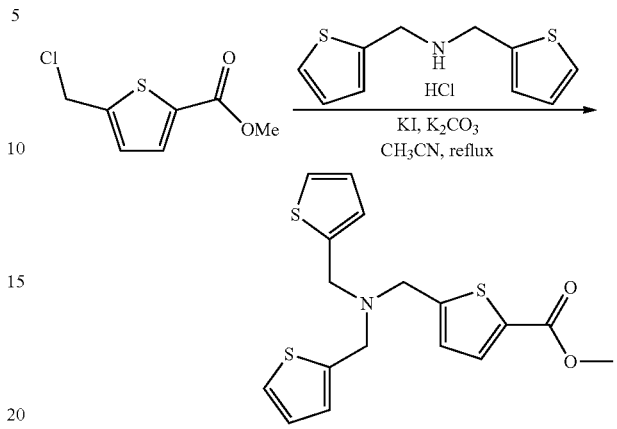

The methyl 5-(chloromethyl)thiophene-2-carboxylate obtained in the previous reaction (0.405 g, 2.12 mmol, 1.0 eq.) was dissolved in 25 mL dry CH3CN at room temperature. To this solution was added bis(thiophen-2-ylmethyl)amine hydrochloride (0.575 g, 2.34 mmol, 1.1 eq.), KI (0.352 g, 2.12 mmol, 1.0 eq.) and K2CO3 (0.877 g, 6.3 mmol, 3.0 eq.). The mixture was heated to reflux and stirred for 16 h, then filtered into a new flask and concentrated under reduced pressure. The oily residue was treated with 50 mL EtOAc, transferred into a separation funnel and washed with H2O (30 mL), sat. aq. K2CO3 (30 mL) and brine (30 mL). The organic phase was dried over Na2SO4, filtered and concentrated under reduced pressure. Column chromatography on silica using gradient elution (n-hexanes to 9:1 n-hexanes:EtOAc) afforded 0.488 g (1.34 mmol, 63%) of methyl 5-((bis(thiophen-2-ylmethyl)amino)methyl)thiophene-2-carboxylate. $^1$H NMR (300 MHz, CDCl$_3$) δ 7.26 (d, J=2.0 Hz, 1H), 7.25 (d, J=1.9 Hz, 1H), 7.00-6.93 (m, 5H), 3.89 (s, 4H), 3.88 (s, 3H), 3.85 (s, 2H). $^{13}$C NMR (101 MHz, CDCl$_3$) δ 162.92, 151.22, 141.95, 133.48, 132.57, 126.63, 126.26, 126.12, 125.30, 52.16, 51.85, 51.81. APCI-HRMS e/z calc. for C$_{17}$H$_{17}$NO$_2$S$_3$: 363.0421, found 364.0494 [M+H]

Example 179—Methyl 6-((bis(thiophen-2-ylmethyl)amino)methyl)nicotinate

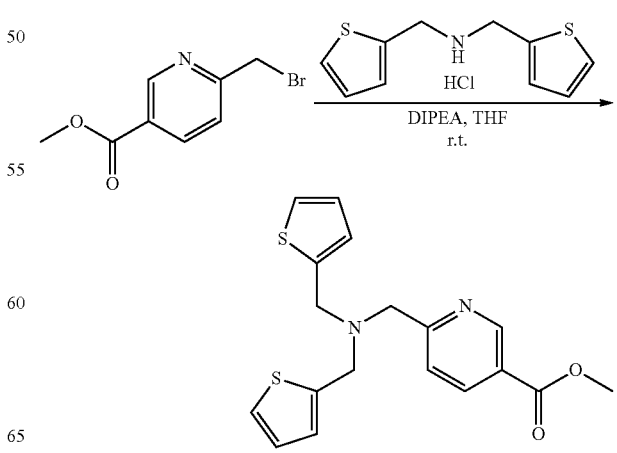

Methyl 6-(bromomethyl)nicotinate (1.044 g, 4.53 mmol, 1.0 eq.) was suspended in 60 mL THF at room temperature. To this mixture was added bis(thiophen-2-ylmethyl)amine hydrochloride (1.222 g, 5.0 mmol, 1.1 eq.) and DIPEA (2.13 mL, 12.23 mmol, 2.7 eq.) and stirred at room temperature for 16 h. The mixture was filtered into a new flask and concentrated under reduced pressure, resulting in a brownish semi-solid. The residue was treated with diethyl ether (100 mL), transferred into a separation funnel and washed with H2O (50 mL) and brine (50 mL). The organic phase was dried over Na2SO4, filtered and concentrated under reduced pressure. Column chromatography on silica using gradient elution (n-hexanes to 5:1 n-hexanes:EtOAc) afforded 0.184 g (0.51 mmol, 11%) of methyl 6-((bis(thiophen-2-ylmethyl)amino)methyl)nicotinate. $^1$H NMR (400 MHz, CDCl$_3$) δ 9.10 (d, J=1.6 Hz, 1H), 8.30 (dd, J=8.2, 2.2 Hz, 1H), 7.83 (d, J=8.1 Hz, 1H), 7.24 (dd, J=4.9, 1.3 Hz, 2H), 7.01-6.91 (m, 4H), 3.94 (s, 3H), 3.90 (s, 6H). $^{13}$C NMR (101 MHz, CDCl$_3$) δ 166.02, 150.29, 137.83, 126.73, 126.20, 125.25, 52.54, 52.45, 31.07. APCI-HRMS e/z calc. for C$_{18}$H$_{18}$N$_2$O$_2$S$_2$: 358.0810, found 359.0882 [M+H].

Example 180—Methyl 5-((bis(pyridin-2-ylmethyl)amino)methyl)thiophene-2-carboxylate

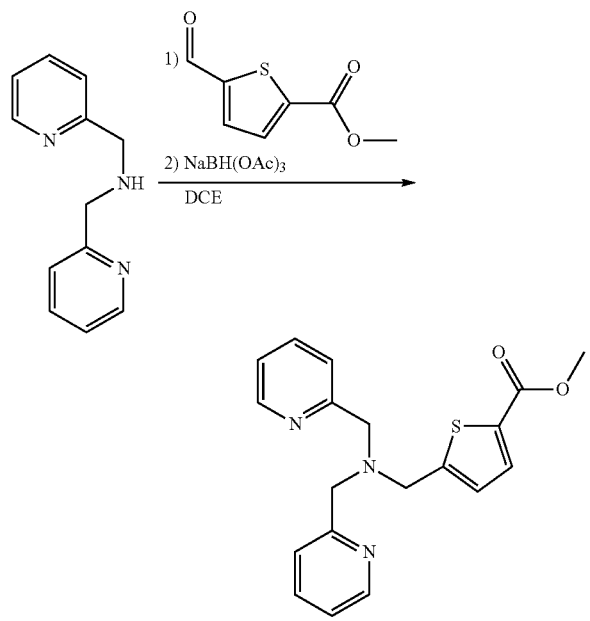

The aldehyde (851 mg, 5.0 mmol) was added in one portion to a stirring solution of the amine (996 mg, 5.0 mmol) in 20 mL dichloroethane. The mixture was stirred for 3 hours at room temperature before NaBH(OAc)3 (5.3 grams, 25 mmol) was added. The mixture was then stirred overnight before it was concentrated under reduced pressure to a sticky pale orange solid. This was diluted with 100 mL 0.5M K2CO3 and extracted with 3×25 mL DCM. The combined organic fractions were pooled, dried over K2CO3, filtered and concentrated under reduced pressure. The crude mixture was purified on neutral Al$_2$O$_3$ using 10-100% EtOAc in DCM which gave 885 mg (50%) of a brown solid. $^1$H NMR (400 MHz, DMSO-d$_6$) δ 8.50 (ddd, J=4.8, 1.8, 0.9 Hz, 2H), 7.81 (td, J=7.7, 1.8 Hz, 2H), 7.67 (d, J=3.7 Hz, 1H), 7.57 (dt, J=7.8, 1.1 Hz, 2H), 7.27 (ddd, J=7.5, 4.9, 1.2 Hz, 2H), 7.14-7.04 (m, 1H), 3.93-3.86 (m, 2H), 3.80 (s, 3H), 3.78 (s, 4H). $^{13}$C NMR (101 MHz, DMSO) δ 161.87, 158.51, 151.56, 148.87, 136.70, 133.66, 131.34, 126.85, 122.40, 122.29, 58.85, 52.21, 52.07.

Example 181—5-((bis(pyridin-2-ylmethyl)amino)methyl)thiophene-2-carboxylic acid

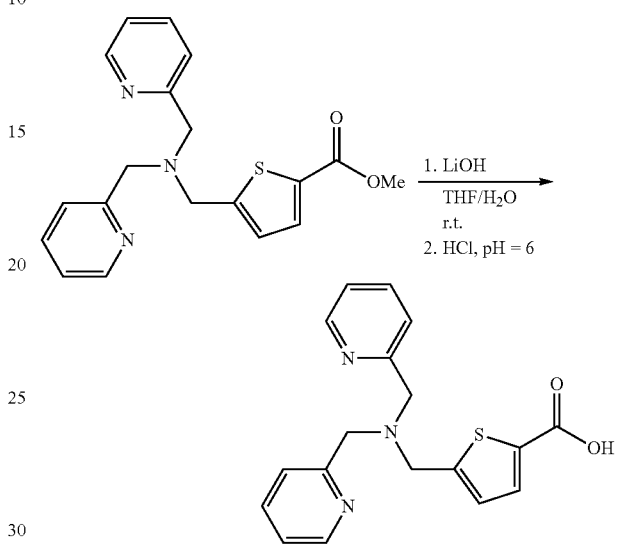

The methyl 5-((bis(pyridin-2-ylmethyl)amino)methyl)thiophene-2-carboxylate (0.325 g, 0.919 mmol, 1.0 eq.), prepared in the previous example, was dissolved in a mixture of 10 mL THF and 10 mL H2O at room temperature. To this solution was added LiOH.H2O (0.193 g, 4.6 mmol, 5 eq.) and the reaction progress monitored by TLC on alumina using 5% MeOH in CH2Cl2. Upon full conversion, the crude reaction mixture was concentrated under reduced pressure and the residue dissolved in 5 mL dest. H2O. The pH of the basic solution was adjusted to 4 with 2M HCl and the mixture concentrated under reduced pressure. The obtained 5-((bis(pyridin-2-ylmethyl)amino)methyl)thiophene-2-carboxylic acid was used for the next reaction without further purification after confirmation of purity by 1H NMR.

$^1$H NMR (300 MHz, D$_2$O) δ 8.37 (d, J=4.7 Hz, 2H), 7.76 (t, J=7.7 Hz, 2H), 7.52 (d, J=7.9 Hz, 2H), 7.38 (d, J=3.7 Hz, 1H), 7.34-7.23 (m, 2H), 6.93 (d, J=3.5 Hz, 1H), 3.88 (s, 2H), 3.80 (s, 4H).

Example 182—5-((bis(pyridin-2-ylmethyl)amino)methyl)-N-methyl-N-((2S,3R,4R,5R)-2,3,4,5,6-pentahydroxyhexyl)thiophene-2-carboxamide

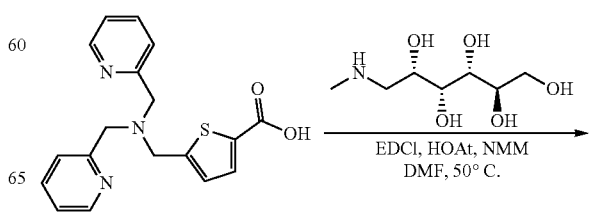

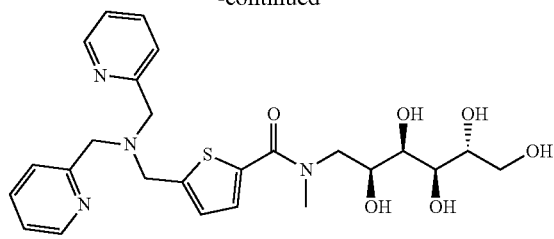

The 5-((bis(pyridin-2-ylmethyl)amino)methyl)thiophene-2-carboxylic acid obtained in the previous reaction (0.312 g, 0.919 mmol, 1.0 eq.) was dissolved in 5 mL dry DMF at room temperature. N-Methyl-D-Glucamine (0.269 g, 1.378 mmol, 1.5 eq.), EDCl (0.264 g, 1.378 mmol, 1.5 eq.), HOAt (0.187 g, 1.378 mmol, 1.5 eq.) and NMM (0.152 mL, 1.378 mmol, 1.5 eq.) were then added. The mixture was heated to 50° C. for 16 h with stirring and then concentrated under reduced pressure. Purification of the product was achieved by way of dry column vacuum chromatography on C18 bondesil material, using a stepwise elution from 10% to 90% methanol in water affording 0.357 g (0.691 mmol, 75%) of product.

$^1$H NMR (400 MHz, MeOD) δ 8.44 (d, J=4.5 Hz, 2H), 7.83 (t, J=7.6 Hz, 2H), 7.72 (d, J=7.9 Hz, 2H), 7.39 (d, J=7.2 Hz, 1H), 7.32-7.26 (m, 2H), 6.98 (s, 1H), 4.16-4.06 (m, 1H), 3.90 (s, 2H), 3.84 (s, 4H), 3.81-3.55 (m, 6H), 3.34 (d, J=8.2 Hz, 1H), 2.15 (s, 3H).
$^{13}$C NMR (101 MHz, MeOD) δ 149.21, 138.53, 131.04, 126.94, 124.36, 123.67, 72.73, 64.47, 60.16, 53.80, 30.39.
APCI-HRMS e/z calc. for $C_{25}H_{32}N_4O_6S$: 516.2043, found 517.2115 [M+H].

Example 183—methyl 6-((dibenzylamino)methyl)nicotinate

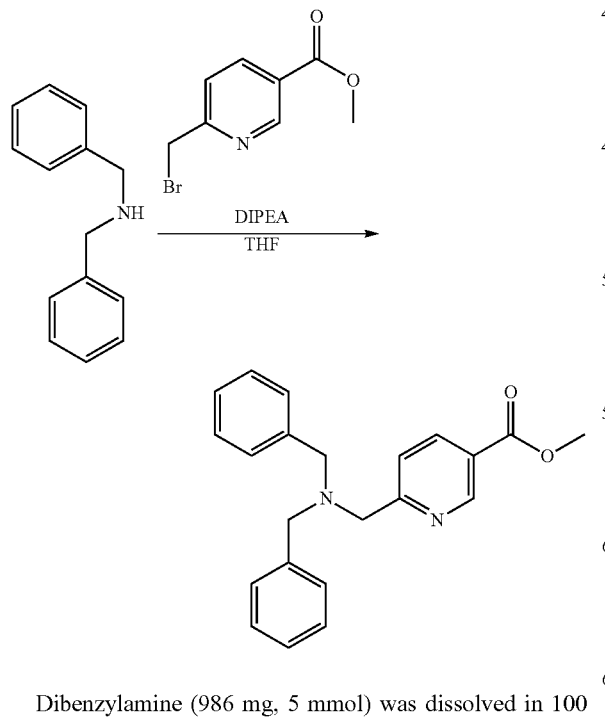

Dibenzylamine (986 mg, 5 mmol) was dissolved in 100 mL THF and mixed with methyl bromomethyl nicotinate (1150 mg, 5 mmol) and DIPEA (1,275 mL, 7.5 mmol). The mixture was stirred at room temperature for 24 hours before it was filtered through a plug of celite. The filtrate was concentrated under reduced pressure, re-dissolved in 50 mL Et2O and filtered through a plug of celite. The fitrate was concentrated under reduced pressure to give 1.66 grams (96%) of material. $^1$H NMR (400 MHz, DMSO-d$_6$) δ 8.98 (d, J=2.2 Hz, 1H), 8.27 (dd, J=8.1, 2.2 Hz, 1H), 7.72 (d, J=8.1 Hz, 1H), 7.39 (d, J=7.1 Hz, 4H), 7.33 (t, J=7.5 Hz, 4H), 7.24 (t, J=7.2 Hz, 2H), 3.86 (s, 3H), 3.71 (s, 2H), 3.57 (s, 4H). $^{13}$C NMR (101 MHz, DMSO) δ 165.19, 164.31, 149.38, 138.61, 137.33, 128.57, 128.29, 127.04, 123.99, 122.25, 58.66, 57.35, 52.29.

Example 184—N-benzyl-1-(pyridin-2-yl)methanamine

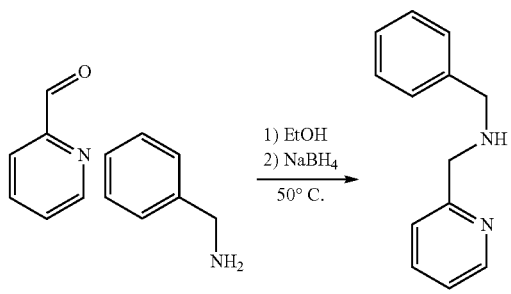

Benzylamine (1000 mg, 9.33 mmol) was dissolved in 50 mL absolute ethanol at room temperature and mixed with 2-pyridinecarboxaldehyde (1000 mg, 9.34 mmol). The solution turned read and it was heated to 50° C. and stirred for 24 hours before NaBH4 (2500 mg, 66.09 mmol) was added in portions. The mixture was then stirred for 4 days at 50° C. before it was concentrated under reduced pressure to give a yellow solid. The crude solid was dissolved in 1M K2CO3 (100 mL) and extracted with DCM (3×50 mL). The combined organic fractions were pooled, dried over K2CO3, filtered and concentrated under reduced pressure to give 1.826 grams (99%) of a pale yellow oil. $^1$H NMR (400 MHz, DMSO-d$_6$) δ 8.70-8.21 (m, 1H), 7.75 (td, J=7.7, 1.8 Hz, 1H), 7.46 (d, J=7.8 Hz, 1H), 7.39-7.28 (m, 5H), 7.27-7.19 (m, 2H), 3.78 (s, 2H), 3.72 (s, 2H), 2.70 (s, 1H). $^{13}$C NMR (101 MHz, DMSO) δ 160.29, 148.70, 140.69, 136.40, 128.10, 127.92, 126.54, 121.81, 121.74, 53.81, 52.41.

Example 185—6-((dibenzylamino)methyl)-N-methyl-N-((2S,3R,4R,5R)-2,3,4,5,6-pentahydroxy-hexyl)nicotinamide

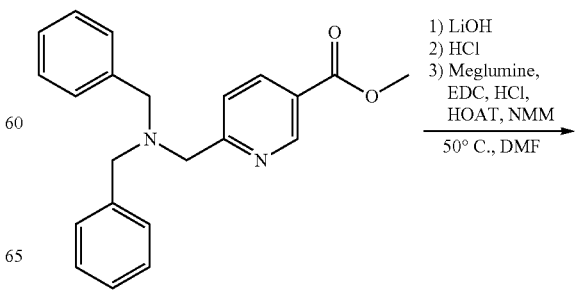

215
-continued

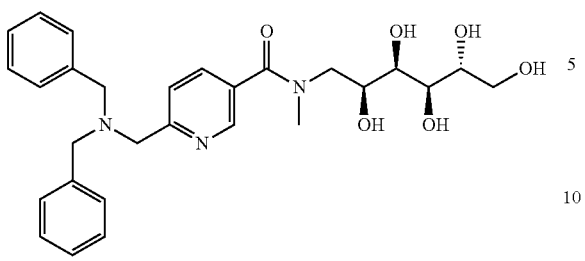

216
-continued

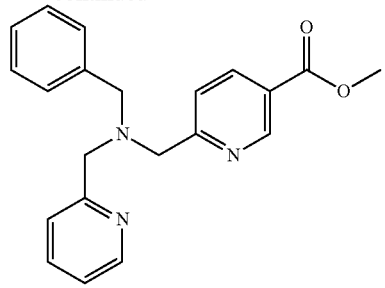

N-benzyl-1-(pyridin-2-yl)methanamine (991 mg, 5 mmol) was dissolved in 30 mL THF and mixed with methyl bromomethyl nicotinate (1150 mg, 5 mmol) and DIPEA (1.36 mL, 8.0 mmol). The mixture was stirred at room temperature for 24 hours before it was filtered through a plug of celite. The filtrate was concentrated under reduced pressure, re-dissolved in 50 mL Et2O and filtered through a plug of celite. The fitrate was concentrated under reduced pressure to give 1.66 grams (96%) of material.

Example 187—6-((benzyl(pyridin-2-ylmethyl)amino)methyl)-N-methyl-N-((2S,3R,4R,5R)-2,3,4,5,6-pentahydroxyhexyl)nicotinamide

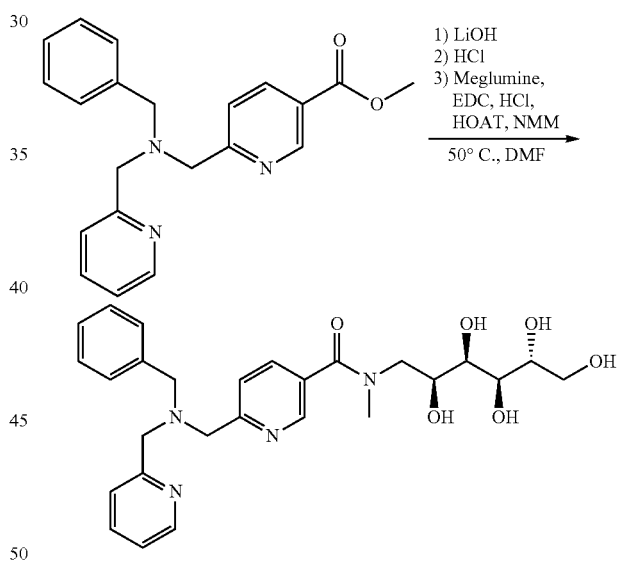

The ester (1.73 grams, 5.0 mmol) was dissolved in 10 mL THF and LiOH monohydrate (1049 mg, 25.0 mmol) was added with the aid of 2 mL water. The mixture was stirred for 2 hours at room temperature before 20 mL 1M HCl (20.0 mmol) was added to neutralize the reaction. The mixture was then concentrated under reduced pressure to give a white powder which was dissolved in 15 mL DMF. EDC hydrochloride (959 mg, 5.0 mmol), meglumine (976 mg, 5.0 mmol) and HOAT (681 mg, 5.0 mmol) was added before NMM (1.10 mL, 10.0 mmol) was added. The mixture was heated to 50° C. and left for 18 hours before it was cooled to room temperature and concentrated under reduced pressure. Purification of the product was achieved by way of dry column vacuum chromatography on C18 bondesil material, using a stepwise elution from 10% to 80% methanol in water affording 0.457 g (0.9 mmol, 18%) of product.

$^1$H NMR (400 MHz, MeOD) δ 8.54 (d, J=21.2 Hz, 1H), 7.91 (dd, J=36.5, 7.6 Hz, 1H), 7.73 (d, J=8.1 Hz, 1H), 7.40 (d, J=7.4 Hz, 4H), 7.35-7.25 (m, 4H), 7.22 (t, J=7.0 Hz, 2H), 4.24-3.98 (m, 1H), 3.87-3.45 (m, 12H), 3.14, 3.07 (2×s, 3H). $^{13}$C NMR (101 MHz, MeOD) δ 172.09, 171.47, 162.93, 162.35, 148.23, 147.65, 140.21, 137.80, 137.05, 132.52, 132.24, 130.01, 129.37, 128.23, 124.04, 123.75, 73.96, 73.49, 73.01, 72.91, 72.42, 71.62, 71.51, 71.01, 64.75, 60.21, 59.96, 59.64, 59.37, 55.24, 52.44, 40.02, 33.75. APCI-HRMS e/z calc. for $C_{28}H_{35}N_3O_6$: 509.2526, found 510.2599 [M+H].

Example 186—methyl 6-((benzyl(pyridin-2-ylmethyl)amino)methyl)nicotinate

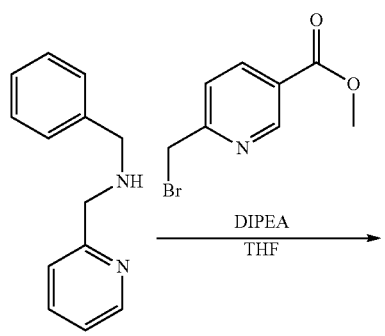

The ester (973 mg, 2.8 mmol) was dissolved in 10 mL THF and LiOH monohydrate (588 mg, 14.0 mmol) was added with the aid of 2 mL water. The mixture was stirred for 2 hours at room temperature before 11.2 mL 1M HCl (11.2 mmol) was added to neutralize the reaction. The mixture was then concentrated under reduced pressure to give a white powder which was dissolved in 10 mL DMF. EDC hydrochloride (537 mg, 2.8 mmol), meglumine (547 mg, 2.8 mmol) and HOAT (381 mg, 2.8 mmol) was added before NMM (616 µL, 5.6 mmol) was added. The mixture was heated to 50° C. and left for 18 hours before it was cooled to room temperature and concentrated under reduced pressure. Purification of the product was achieved by way of dry column vacuum chromatography on C18 bondesil material, using a stepwise elution from 10% to 70% methanol in water affording 0.72 g (1.4 mmol, 50%) of product. $^1$H NMR (400 MHz, MeOD) δ 8.56 (d, J=17.6 Hz, 1H), 8.43 (dd, J=4.9, 0.7 Hz, 1H), 7.91 (ddd, J=33.7, 8.0, 1.8 Hz, 1H), 7.80 (t, J=7.6 Hz, 1H), 7.72 (dd, J=7.7, 5.8 Hz, 1H), 7.68 (d, J=7.9 Hz, 1H), 7.40 (d, J=7.4 Hz, 2H), 7.35-7.15 (m, 4H), 4.21-3.97 (m, 1H), 3.88-3.46 (m, 12H), 3.14, 3.07 (2×s, 3H). $^{13}$C NMR (101 MHz, MeOD) δ 172.03, 171.41, 162.28, 161.70, 160.43, 149.42, 148.37, 147.83, 139.69, 138.72, 137.78, 137.06, 132.58, 132.31, 130.10, 129.42, 128.36, 124.79, 124.15, 123.84, 73.93, 73.45, 73.00, 72.90, 72.40, 71.63, 71.51, 71.02, 64.70, 60.92, 60.70, 60.62, 60.40, 60.02, 59.83, 57.57, 55.22, 52.43, 44.78, 40.01, 33.77. APCI-HRMS e/z calc. for $C_{27}H_{34}N_4O_6$: 510.2478, found 511.2551 [M+H]

Example 188—(2R,3R,4R,5S)-6-(methylamino)hexane-1,2,3,4,5-pentayl pentaacetate hydrochloride

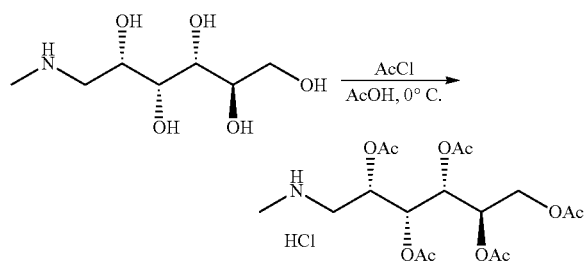

*Angew. Chem. Int. Ed.* 2007, 46, 3284-3287.

N-Methyl-D-Glucamine (2.6 g, 13.3 mmol, 1.0 eq.) was dissolved in 15 mL conc. acetic acid and cooled to 0° C. in an ice bath. To this solution was added acetyl chloride (21.8 mL, 306 mmol, 23 eq.) dropwise over a period of approximately 1 h. The mixture was left stirring for 16 h while the ice bath expired. The colorless solution was then concentrated under reduced pressure to dryness. The obtained oily residue was dissolved in a mixture of methanol (8 mL) and ethanol (5 mL) and diluted with EtOAc (50 mL). Diethyl ether was added with stirring until the mixture became cloudy and was then placed in the freezer for 12 h. The white precipitate formed was filtered off with suction, though appeared to be hygroscopic and turned into an oil. The oily compound was then dissolved in MeOH, collected and concentrated under reduced pressure to afford a colorless semi-solid that was used for the next reaction without further purification.

Example 189—(2R,3R,4R,5S)-6-(6-((bis(pyridin-2-ylmethyl)amino)methyl)-N-methylnicotinamido)hexane-1,2,3,4,5-pentayl pentaacetate

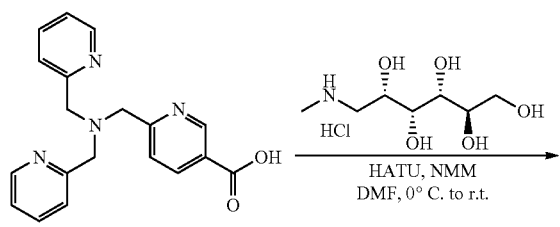

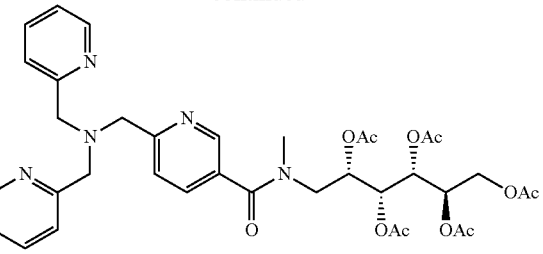

6-((bis(pyridin-2-ylmethyl)amino)methyl)nicotinic acid (0.275 g, 0.823 mmol, 1.0 eq.) was dissolved in 5 mL dry DMF and cooled to 0° C. in an ice bath. To this solution was added (2R,3R,4R,5S)-6-(methylamino)hexane-1,2,3,4,5-pentayl pentaacetate hydrochloride (0.655 g, 1.48 mmol, 1.8 eq.), prepared in the previous reaction, HATU (0.328 g, 0.864 mmol, 1.05 eq.) and NMM (0.272 mL, 2.47 mmol, 3.0 eq.) dropwise. The mixture was stirred at 0° C. for 30 min, then at room temperature for 16 h and concentrated under reduced pressure. Purification of the product was achieved by way of dry column vacuum chromatography on C18 material, using a stepwise elution from 10% to 90% methanol in water, followed by column chromatography on basic alumina using 1% MeOH in CH2Cl2 affording 177.6 mg (0.246 mmol, 30%) of product. APCI-HRMS e/z calc. for $C_{36}H_{43}N_5O_{11}$: 721.2959, found 722.3027 [M+H]

Example 190—6-((bis(pyridin-2-ylmethyl)amino)methyl)-N-ethyl-N-((2S,3R,4R,5R)-2,3,4,5,6-pentahydroxyhexyl)nicotinamide

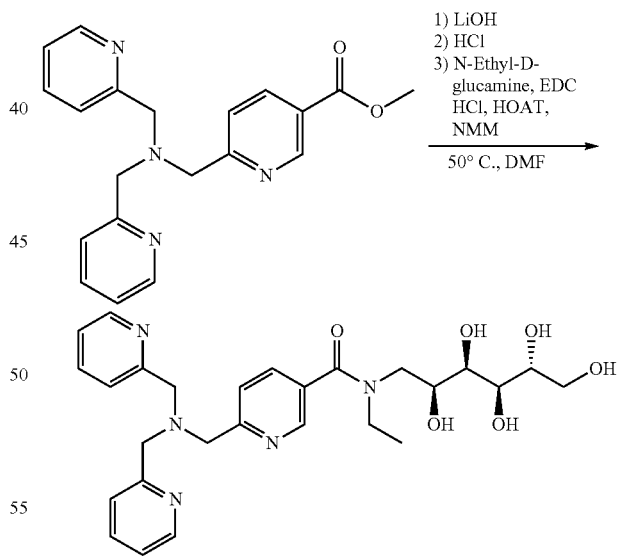

The ester (255 mg, 0.73 mmol) was dissolved in 5 mL THF and LiOH monohydrate (154 mg, 3.67 mmol) was added with the aid of 2 mL water. The mixture was stirred for 2 hours at room temperature before 2.94 mL 1M HCl (2.94 mmol) was added to neutralize the reaction. The mixture was then concentrated under reduced pressure to give a white powder which was dissolved in 5 mL DMF. EDC hydrochloride (140 mg, 0.73 mmol), n-ethyl-d-glucamine (153 mg, 0.73 mmol) and HOAT (99 mg, 0.73 mmol) were added before NMM (161 µL, 1.47 mmol) was added. The mixture was heated to 50° C. and left for 18 hours before it was cooled to room temperature and concentrated under reduced pressure. Purification of the product was achieved by way of dry column vacuum chromatography on C18 bondesil material, using a stepwise elution from 20% to 50% methanol in water affording 0.135 g (0.22 mmol, 30%) of product.

$^1$H NMR (400 MHz, MeOD) δ 8.55 (d, J=23.8 Hz, 1H), 8.44 (d, J=4.5 Hz, 2H), 7.85 (dt, J=15.6, 7.4 Hz, 3H), 7.70 (dd, J=19.7, 8.4 Hz, 3H), 7.33-7.23 (m, 2H), 4.22-3.94 (m, 1H), 3.94-3.85 (m, 6H), 3.84-3.33 (m, 9H), 1.27, 1.12 (2×t, J=6.7 Hz, 1H). $^{13}$C NMR (101 MHz, MeOD) δ 171.72, 171.57, 161.58, 160.98, 159.93, 149.55, 148.36, 147.32, 138.71, 137.60, 136.47, 133.00, 132.74, 124.98, 124.41, 124.06, 123.92, 74.09, 73.37, 73.00, 72.62, 71.75, 71.44, 64.73, 61.35, 61.12, 60.85, 52.65, 46.66, 41.62, 14.08, 12.66. APCI-HRMS e/z calc. for $C_{27}H_{35}N_5O_6$: 525.2587, found 526.2660 [M+H]

Example 191—Methyl 4-((bis(pyridin-2-ylmethyl)amino)methyl)benzoate

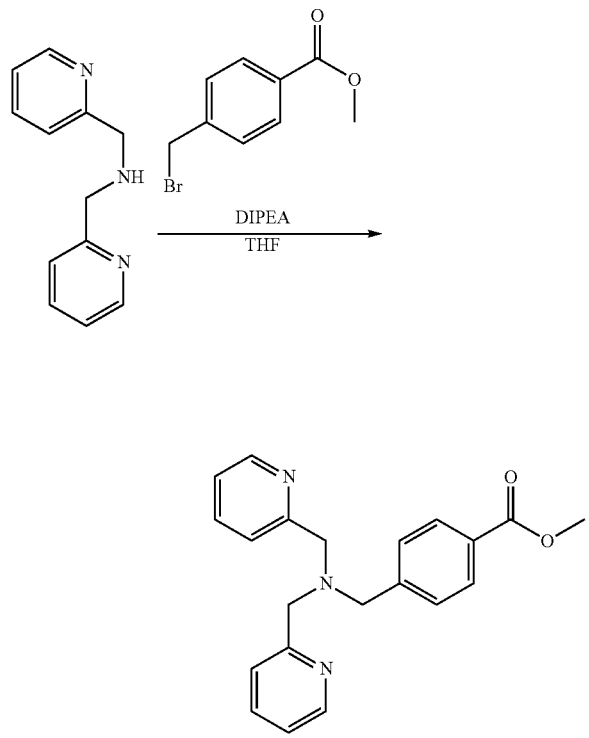

Dipicolylamine (1.84 mL, 10 mmol) was dissolved in 150 mL THF and mixed with methyl 2-bromomethyl benzoate (2.29 mg, 10 mmol) and DIPEA (2.7 mL, 16.0 mmol). The mixture was stirred at room temperature for 24 hours before it was filtered through a plug of celite. The filtrate was concentrated under reduced pressure, re-dissolved in 50 mL Et$_2$O and filtered through a plug of celite. The fitrate was concentrated under reduced pressure to give 3.683 grams (>99%) of material with trace solvent impurities.

Example 192—4-((bis(pyridin-2-ylmethyl)amino) methyl)-N-methyl-N-((2S,3R,4R,5R)-2,3,4,5,6-pentahydroxyhexyl)benzamide

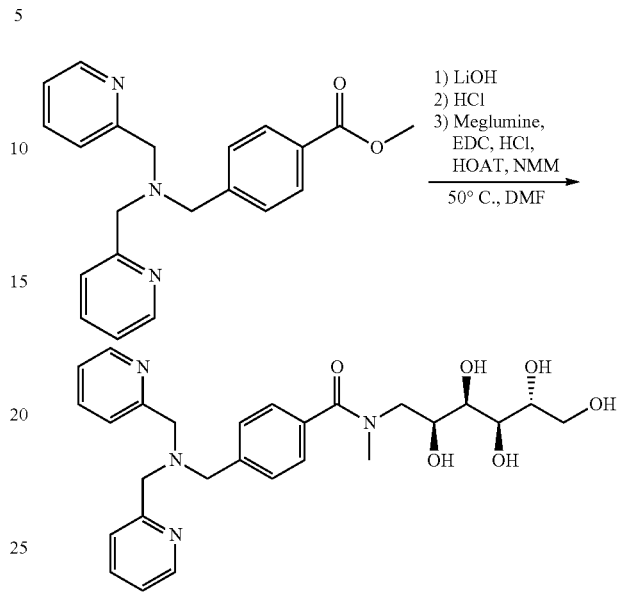

The methyl 4-((bis(pyridin-2-ylmethyl)amino)methyl) benzoate (0.560 g, 1.61 mmol, 1.0 eq.), prepared in the previous example, was dissolved in a mixture of 10 mL THF and 10 mL H2O at room temperature. To this solution was added LiOH.H$_2$O (0.203 g, 4.84 mmol, 3 eq.) and the reaction progress monitored by TLC on alumina using 5% MeOH in CH2Cl2. After 16 h, the crude reaction mixture was concentrated under reduced pressure and the residue dissolved in 5 mL dest. H2O. The pH of the basic solution was adjusted to 4 with 2M HCl and the mixture concentrated under reduced pressure. The obtained 4-((bis(pyridin-2-ylmethyl)amino)methyl)benzoic acid was used for the next reaction without further purification. The 4-((bis(pyridin-2-ylmethyl)amino)methyl)benzoic acid obtained in the previous reaction (0.537 g, 1.61 mmol, 1.0 eq.) was dissolved in 20 mL dry DMF at room temperature. N-Methyl-D-Glucamine (0.471 g, 2.41 mmol, 1.5 eq.), EDCl (0.462 g, 2.41 mmol, 1.5 eq.), HOAt (0.328 g, 2.41 mmol, 1.5 eq.) and NMM (0.266 mL, 2.41 mmol, 1.5 eq.) were then added. The mixture was heated to 50° C. for 16 h with stirring and then concentrated under reduced pressure. Purification of the product was achieved by way of dry column vacuum chromatography on C18 bondesil material, using a stepwise elution from 10% to 90% methanol in water affording 0.108 g (0.212 mmol, 13%) of product. $^1$H NMR (400 MHz, MeOD) δ 8.43 (d, J=4.5 Hz, 2H), 7.81 (t, J=7.3 Hz, 2H), 7.68 (d, J=7.8 Hz, 2H), 7.46 (ddd, J=29.4, 16.9, 8.5 Hz, 4H), 7.33-7.19 (m, 2H), 4.21-3.91 (m, 1H), 3.86-3.42 (m, 13H), 3.13, 3.05 (2×s, 3H). $^{13}$C NMR (101 MHz, MeOD) δ 174.87, 174.42, 174.29, 167.61, 160.36, 151.72, 149.45, 143.89, 142.08, 141.70, 141.53, 140.45, 138.73, 136.78, 136.42, 131.67, 130.11, 129.94, 128.94, 128.59, 128.40, 128.07, 127.37, 124.78, 124.64, 123.85, 121.06, 74.06, 73.72, 73.61, 73.33, 73.02, 72.92, 72.59, 71.98, 71.62, 71.43, 70.99, 64.76, 62.10, 60.88, 60.72, 60.20, 59.49, 59.36, 55.83, 55.38, 54.38, 52.33, 40.07, 34.01. APCI-HRMS e/z calc. for $C_{27}H_{35}N_4O_6$: 510.2478, found 511.2551 [M+H]

M. N. Discovery of a Cyclic Boronic Acid β-Lactamase Inhibitor (RPX7009) with Utility vs Class A Serine Carbapenemases Hecker et al. *J. Med. Chem.*, 2015, 58, 3682-3692.

Example 193—tert-butyl 3-((3a,5,5-trimethylhexahydro-4,6-methanobenzo[d][1,3,2]dioxaborol-2-yl)methyl)benzoate

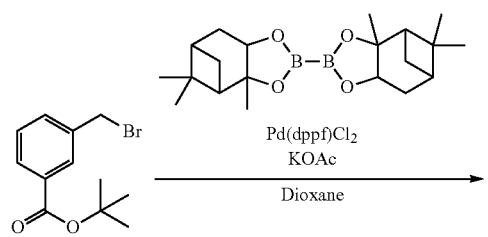

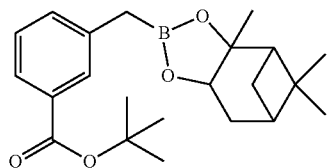

tert-butyl 3-(bromomethyl)benzoate (1000 mg, 3.69 mmol) was mixed with KOAc (542 mg, 5.53 mmol) and Pd(dppf)Cl2 DCM complex (139 mg, 0.17 mmol) and suspended in 20 mL dioxane. The mixture was purged with argon three times, heated to 90° C. and stirred overnight. The mixture was then cooled to room temperature, concentrated under reduced pressure, dissolved in a 1:1 mixture of heptane:DCM (15 mL) and filtered. The solids were washed with DCM (3×15 mL) and the combined organic filtrate was concentrated under reduced pressure. The crude material was purified by column chromatography on SiO2 using 2-5% EtOAc in heptane giving 899 mg (66%) of a clear oil. $^1$H NMR (300 MHz, Chloroform-d) δ 7.81 (td, J=1.8, 0.6 Hz, 1H), 7.76 (dt, J=7.5, 1.6 Hz, 1H), 7.36 (ddd, J=7.7, 2.0, 1.4 Hz, 1H), 7.30 (dd, J=7.6, 0.6 Hz, 1H), 4.28 (dd, J=8.7, 2.0 Hz, 1H), 2.38 (s, 2H), 2.31 (ddt, J=14.4, 8.9, 2.4 Hz, 1H), 2.19 (dtd, J=10.9, 6.0, 2.2 Hz, 1H), 2.04 (dd, J=6.0, 5.0 Hz, 1H), 1.93-1.76 (m, 2H), 1.38 (s, 3H), 1.27 (s, 3H), 1.07 (d, J=10.9 Hz, 1H), 0.83 (s, 3H). NMR in according to literature (J. Med. Chem. 2010, 53, 7852)

Examples 194 and 195—Examples of Peptide-Based Analogs for Experimental Comparison with Non-Peptidic Compounds in the Present Invention

Example 194—peptide-based analog—Methyl (2-(4-((bis(pyridin-2-ylmethyl)amino)methyl)1H-1,2,3-triazol-1-yl)acetyl)-D-alanyl-D-alaninate

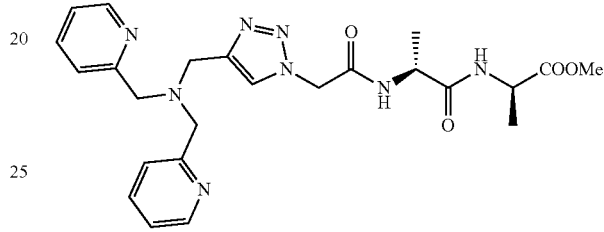

CLogP: -0.6678

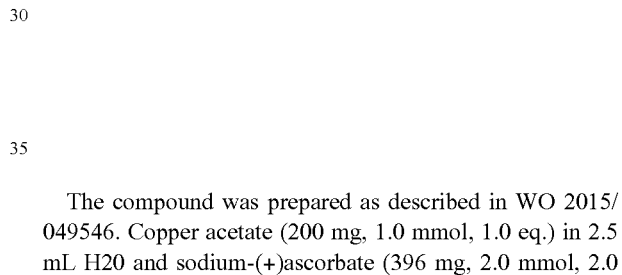

The compound was prepared as described in WO 2015/049546. Copper acetate (200 mg, 1.0 mmol, 1.0 eq.) in 2.5 mL H20 and sodium-(+)ascorbate (396 mg, 2.0 mmol, 2.0 eq.) in 2.5 mL H20 were added simultaneously to a stirring solution of the alkyne (237 mg, 1.0 mmol, 1.0 eq.) in 2.5 mL tBuOH. The acid prepared in Example 32 (257 mg, 1.0 mmol, 1.0 eq) was then added and the solution was stirred at room temperature for 16 hours. EDTA (293 mg, 1.0 mmol, 1.0 eq) was then added to the stirring solution and left for 60 minutes before the mixture was diluted with 50 mL H20 and the pH of the mixture was adjusted to >10 with 1M NaOH. The slurry was then extracted with 2×50 mL dichloromethane. The combined organic phases were dried over K2C03 and concentrated under reduced pressure to give a dark red oil. The crude products were purified using column chromatography by eluting a neutral Al2O3 column with 0-5% methanol in dichloromethane to give 134 mg of the title compound as a pale orange oil (27%). 1H NMR (400 MHz, DMSO-d6) δ 8.59 (d, J=7.5 Hz, 1H), 8.49 (d, J=4.7 Hz, 2H), 8.43 (d, J=7.2 Hz, 1H), 8.04 (s, 1H), 7.77 (t, J=7.7 Hz, 2H), 7.57 (d, J=7.8 Hz, 2H), 7.29-7.21 (m, 2H), 5.13 (s, 2H), 4.42-4.21 (m, 2H), 3.77-3.70 (m, 6H), 3.62 (s, 3H), 1.31-1.21. (m, 6H). 13C NMR (101 MHz, DMSO) δ 172.8, 171.8, 165.0, 159.0, 148.8, 143.1, 136.5, 125.3, 122.5, 122.1, 58.7, 51.8, 51.4, 48.0, 47.9, 47.5, 31.3, 18.3, 16.8. HRMS e/z calculated for C24H30Ns04: 494.2390, found 495.2463 (M+H).

Example 195—peptide-based analog—N-(4-(2-((R)-2-((R)-2-aminopropanamido)propanamido)ethyl)phenyl)-6-((bis(pyridin-2-ylmethyl)amino)methyl)nicotinamide hydrochloride Example 195a—Tert-butyl (R)-1-((R)-1-(4-(6-((bis(pyridin-2-ylmethyl)amino) methyl)nicotinamido)phenethylamino)-1-oxopropan-2-ylamino)-1-oxopropan-2-yl carbamate

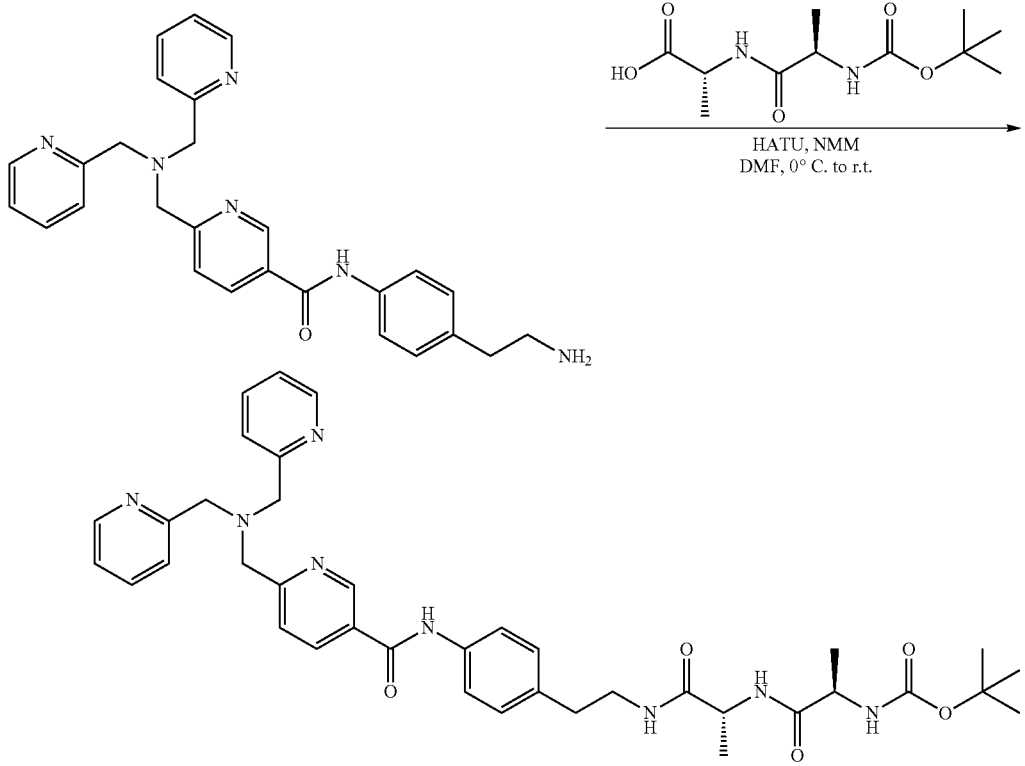

N-(4-(2-aminoethyl)phenyl)-6-((bis(pyridin-2-ylmethyl)amino)methyl)nicotinamide from Example 167b (218 mg, 0.48 mmol, 1.0 eq.) was dissolved in 3 mL dry DMF, cooled to 0° C. in an ice bath. To this solution was added Boc-D-Ala-D-Ala-OH (132 mg, 0.506 mmol, 1.05 eq.), HATU (192 mg, 0.506 mmol, 1.05 eq.) and NMM (116 μL, 1.056 mmol, 2.2 eq.) and the solution stirred at 0° C. for 30 min, then at room temperature for 16 h. The mixture was concentrated under reduced pressure and the product purified by dry column vacuum chromatography on C18 material, using a stepwise elution from 10% to 90% methanol in water affording 217.7 mg (0.313 mmol, 65%) of the product as a pale yellow oil. $^1$H NMR (600 MHz, MeOD) δ 8.96 (d, J=1.7 Hz, 1H), 8.44 (d, J=4.3 Hz, 2H), 8.25 (dd, J=8.2, 2.2 Hz, 1H), 7.78 (ddd, J=10.3, 6.1, 2.2 Hz, 3H), 7.67 (d, J=7.9 Hz, 2H), 7.61 (d, J=8.4 Hz, 2H), 7.27 (ddd, J=7.3, 5.1, 0.8 Hz, 2H), 7.20 (d, J=8.5 Hz, 2H), 4.30 (q, J=7.0 Hz, 1H), 4.03 (q, J=7.0 Hz, 1H), 3.92 (s, 2H), 3.88 (s, 4H), 3.48-3.41 (m, 1H), 3.38-3.32 (m, 1H), 2.78 (t, J=7.0 Hz, 2H), 1.44 (s, 9H), 1.30 (dd, J=13.2, 7.0 Hz, 6H). $^{13}$C NMR (151 MHz, MeOD) δ 175.63, 174.74, 166.17, 163.43, 159.86, 157.98, 149.57, 148.92, 138.68, 137.89, 137.50, 136.92, 130.97, 130.23, 124.92, 124.24, 123.90, 122.28, 80.73, 61.15, 60.88, 51.95, 50.36, 41.96, 35.88, 28.73, 18.21, 18.02. APCI-HRMS e/z calc. for $C_{38}H_{46}N_8O_5$: 694.3591, found: 695.3659 [M+H].

Example 195b—N-(4-(2-((R)-2-((R)-2-aminopropanamido)propanamido)ethyl)phenyl)-6-((bis(pyridin-2-ylmethyl)amino)methyl)nicotinamide hydrochloride

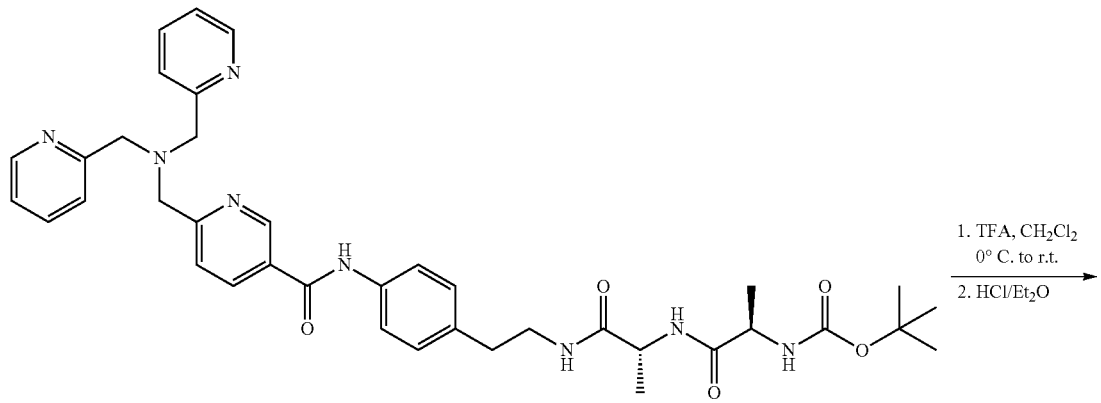

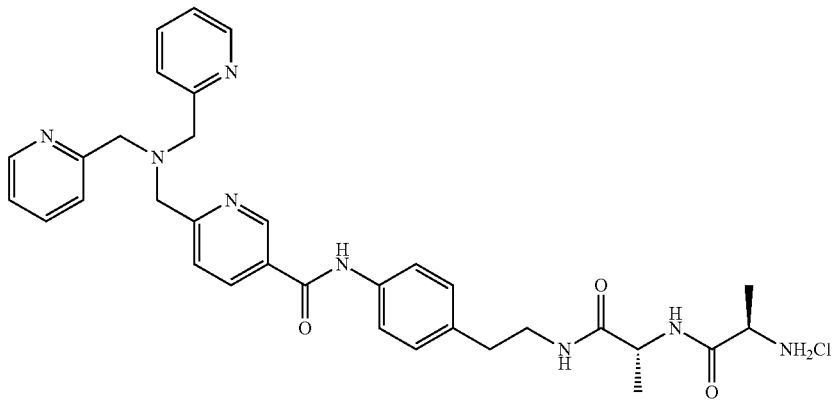

(R)-1-((R)-1-(4-(6-((bis(pyridin-2-ylmethyl)amino)methyl)nicotinamido)phenethylamino)-1-oxopropan-2-ylamino)-1-oxopropan-2-ylcarbamate from example 195a (176 mg, 0.253 mmol, 1.0 eq.) was dissolved in 5 mL $CH_2Cl_2$, cooled to 0° C. in an ice bath. To this solution was added TFA (0.97 mL, 12.65 mmol, 50 eq.) and the mixture was stirred at room temperature until full conversion monitored by $^1$H-NMR. The mixture was concentrated under reduced pressure, the residue dissolved in a mixture of EtOAc/dest. $H_2O$/sat. aq. $K_2CO_3$ (30 mL/10 mL/30 mL) and transferred into a separation funnel. The organic phase was separated, the aq. phase extracted with EtOAc (2 times 30 mL) and the combined organics dried over $K_2CO_3$, filtered and concentrated under reduced pressure affording a white foamy solid. This was dissolved in 2 mL $CH_2Cl_2$ and 2 M HCl in diethyl ether was added in excess resulting in a white precipitate. The mixture was stored in the fridge for 4 h, filtered with suction and the solid washed with diethyl ether, turning into a yellowish oil. This oil was dissolved in warm $H_2O$, collected into a flask and concentrated under reduced pressure to afford 59.4 mg (0.094 mmol, 37%) of product as a yellowish oil. $^1$H NMR (400 MHz, $D_2O$) δ 9.14 (s, 1H), 8.78 (d, J=5.8 Hz, 2H), 8.66 (dd, J=8.2, 1.9 Hz, 1H), 8.55 (t, J=7.9 Hz, 2H), 8.10 (t, J=13.5 Hz, 2H), 8.00 (dd, J=11.3, 6.3 Hz, 3H), 7.52 (d, J=7.7 Hz, 2H), 7.33 (d, J=7.2 Hz, 2H), 4.47 (s, 4H), 4.38 (s, J=7.6 Hz, 2H), 4.24 (q, J=7.0 Hz, 1H), 4.09 (q, J=7.0 Hz, 1H), 3.66-3.54 (m, 1H), 3.48-3.33 (m, 1H), 2.96-2.76 (m, 2H), 1.51 (d, J=7.0 Hz, 3H), 1.29 (d, J=7.1 Hz, 3H). $^{13}$C NMR (101 MHz, $D_2O$) δ 174.42, 170.44, 164.00, 156.34, 151.62, 147.44, 144.52, 142.00, 141.71, 137.18, 134.69, 131.72, 129.77, 129.72, 127.46, 126.65, 126.30, 122.54, 57.78, 56.36, 49.96, 48.91, 40.27, 34.08, 16.75, 16.52. APCI-HRMS e/z calc. for $C_{33}H_{38}N_8O_3$ (free amine): 594.3067, found: 595.3135 [M+H].

Example 196—HPLC Purity of Example 26

Isocratic HPLC analysis of the product from Example 26 with 91% MeOH/9% 0.5 M HCOOH as eluent detected at 254 nm showed >99.5% purity of the compound as shown in FIG. 1.

Example 197—General Protocol for Microbroth Dilution Method for Evaluating Antibacterial Activity of Compounds or Synergistic Effect of Compound-Antibiotic Combination Preparation of Bacteria
Day 1:
  Plate bacterial strain(s) on appropriate media:
  Gram-negative bacteria with ESBLs or carbapenemases: green agar plates with 100 mg/L ampicillin
  Gram-negative bacteria without β-lactamases: green agar plates
  Gram-positive bacteria (Staphylococci and Enterococci): blood agar plates
  Incubate o.n. at 37° C.
Day 2:
Prepare the Bacterial Inoculum:
  Prepare a 0.5 McFarland suspension of bacteria in 0.85% NaCl. (Should be used within 15 min of preparation).
  Dilute the 0.5 McFarland suspension 1:100 into MH broth.
  Check the inoculum by diluting the prepared bacterial suspension 1:100 (10 µl bacterial suspension+990 µl 0.85% NaCl). Plate 10 µl of the dilution on MH agar plates (×2). Incubate o.n. at 37° C., count the colonies and calculate the final CFU/ml inoculum in the plate by multiplying the average number of colonies with 10000 and divide by 2. The final inoculum should be between 3-7×10$^5$ CFU/ml.
  Add 50 µl of the prepared bacterial suspension to each well in the microtiter plate except negative growth control.
Preparation of Compounds/Antibiotics
  Calculate the desired concentration-range and volume of the compounds/antibiotics in the assay. For antibiotics this will depend on the MIC to meropenem of the bacterial strains to be tested. Dilute the stock solution in MH broth. Make subsequent 2-fold dilutions in MH broth of the desired concentrations if a concentration range is to be tested (remember the extra dilution factor in the assay plate). Always include extra volume for pipetting. Take into consideration stock solutions that are made in buffers that have an effect on bacterial growth (e.g. DMSO).
Assay:
  Determining the MIC of compounds/antibiotics alone:
  Add 25 µl of each concentration of compound/antibiotic to row 2-11 (highest concentration in row 2)
  Add 25 µl MH broth to row 2-11
  Add 50 µl MH broth to row 12 (positive control)
  Add 100 µl MH broth to row 1
  Add 50 µl bacterial suspension to row 2-12.
  Determining the MIC of antibiotics+compounds:
  Add 25 µl of each concentration of antibiotic to row 2-11 (highest concentration in row 2)
  Add 25 µl of compound to row 2-11
  Add 50 µl MH broth to row 12 (positive control)
  Add 100 µl MH broth to row 1
  Add 50 µl bacterial suspension to row 2-12.
  Incubate the plate for 20 hrs at 37° C. and determine the MIC in the presence and absence of inhibitor.

This experimental design was used for the results in Tables 2-6 below. In Table 2, inhibitor concentration dependency on the MIC of meropenem was studied.

TABLE 2

Study of inhibitor concentration dependency on the MIC of meropenem

| Ref. no<br>Species<br>MBL | | K66-45<br>K. pneumoniae<br>NDM-1 | | | | | K34-7<br>P. aeruginosa<br>VIM-2 | | | |
|---|---|---|---|---|---|---|---|---|---|---|
| Conc. (µM) Inhibitor | 125 | 62.5 | 50 | 31.25 | 15.63 | 125 | 62.5 | 50 | 31.25 | 15.63 |
| no inhibitor | | | 32-64 | | | | | 32-64 | | |
| Example 9 | ≤0.5 | 0.125 | | 0.125 | 2 | ≤0.5 | 1 | | 16 | 32 |
| Example 12 | | | 0.25 | 0.125 | 4 | | | 1 | 1 | 4 |
| Example 14 | | | 0.125 | 0.125 | 16 | | | 2 | 2 | 32 |
| Example 23 | 0.125 | 0.125 | | 0.125 | 0.125 | 1 | 1 | | 1 | 32 |
| Example 24 | | | 0.125 | 0.125 | 16 | | | 1 | 2 | 32 |
| Example 25 | 0.125 | 0.125 | | 0.125 | 8 | 2 | 1 | | 1 | 32 |
| Example 26 | | | 0.125 | 0.125 | 8 | | | 1 | 1 | |
| Example 27 | 0.125 | 0.125 | | 8 | 64 | 1 | 1 | | 1 | 32 |
| Example 84 | 0.5 | 2 | | 8 | 16 | 2 | 8 | | 16 | 32 |
| Example 85 | 0.5 | 2 | | 8 | 16 | 2 | 8 | | 32 | 32 |
| Example 87 | 0.125 | | | 0.125 | 16 | 2 | | | 0.5 | 32 |
| Example 91 | | 0.125 | | 0.125 | 8 | | | 1 | 2 | 16 |

The results of a study of the minimum inhibitory concentration (MIC) of meropenem against a broad spectrum of clinical isolates of MBL-positive and MBL-negative gram negative bacteria on the MIC of meropenem is given in Table 3. In the presence of inhibitor, the MIC values for meropenem are dramatically lowered, while the effect on bacteria lacking MBL is absent. As shown in Table 4, all examples show the same dramatic effect on the MIC values of meropenem in two strains of clinically isolated multiresistant strains of P. Aeruginosa harbouring VIM-2 and K. pneumoniae harbouring NDM-1, except for Examples 101, 157, 180, 182, 185 and 187.

TABLE 3

Study of inhibitor effect on a broad spectrum of MBL-positive and MBL-negative gram negative bacteria on the MIC of meropenem

| | | Presence of MBL: | MBL-positive Gram-negatives | | | | | | MBL-negative Gram-negatives | |
|---|---|---|---|---|---|---|---|---|---|---|
| | | Ref. no: | K34-7 | 50692172 | K66-45 | A3-81 | K71-77 | 50639799 | 50808021 | 50732159 |
| | | Species: | P. aeruginosa | P. aeruginosa | K. pneumoniae | K. pneumoniae | E. coli | E. coli | P. aeruginosa | K. pneumoniae |
| | | MBL: | VIM-2 | NDM-1 | NDM-1 | VIM-1 | NDM-1 | VIM-1 | No MBL | No MBL |
| | | Meropenem activity without inhibitor: | 32-64 | 32-128 | 32-64 | 64-256 | 1-8 | 8-32 | 128-256 | 32-64 |
| Example | Inhibitor concentration | | Meropenem activity (mg/L) in presence of inhibitor | | | | | | | |
| TPEN | 63 mg/L | | 1 | ≤0.5 | ≤0.5 | ≤0.5 | ≤0.064 | ≤0.064 | 64 | ≤0.064 |
| Captopril | 63 mg/L | | 32 | 32-64 | 64 | 64-128 | 2-4 | 16 | | |
| Example 9 | 63 mg/L | | ≤0.5 | | ≤0.5 | | | | | |
| Example 22a | 63 mg/L | | 1 | | 0.25 | | | | | |
| Example 27 | 63 mg/L | | 1 | | 0.125 | | | | | |
| Example 23 | 25 mg/L | | 1 | 1 | 0.125 | 0.125 | ≤0.03 | ≤0.03 | >64 | 32 |
| Example 25 | 25 mg/L | | 2 | 2 | 0.125 | 0.125 | ≤0.03 | ≤0.03 | >64 | 64 |
| Example 84 | 25 mg/L | | 8 | | 4 | | | | | |
| Example 85 | 25 mg/L | | 8 | | 4 | | | | | |
| Example 91 | 25 mg/L | | 1 | | 0.125 | | | | | |
| Example 83 | 25 mg/L | | 16 | | 8 | | | | | |
| Example 24 | 25 mg/L | | 1 | | 0.125 | | | | | |
| Example 12 | 25 mg/L | | 1 | | 0.25 | | | | | |
| Example 14 | 25 mg/L | | 2 | | 0.125 | | | | | |
| Example 26 | 25 mg/L | | 1 | 4 | 0.125 | 0.125 | ≤0.03 | 0.06 | >64 | 32 |
| Example 95 | 25 mg/L | | 16 | | 4 | | | | | |
| Example 194 | 25 mg/L | | 1 | 32 | 0.125 | 64 | 0.5 | 2 | >64 | 32 |
| Example 104 | 25 mg/L | | 8 | | 4 | | | | | |
| Example 98 | 25 mg/L | | 8-32 | | 4 | | | | | |
| Example 99 | 25 mg/L | | 1 | | 0.25 | 1 | 0.06 | 0.125 | >64 | 32 |
| Example 100 | 25 mg/L | | 1 | | 0.125 | 0.5 | 0.06 | 0.06 | >64 | 32 |

TABLE 4

Study of inhibitor effect on two MBL-positive multiresistant clinical isolates of gram negative bacteria on the MIC of meropenem. In all cases, the concentration of the inhibitor was 25 mg/L

| | Ref. no | |
|---|---|---|
| | K34-7 | K66-45 |
| | Species | |
| | P. aeruginosa | K. pneumoniae |
| | MBL | |
| | VIM-2 | NDM-1 |
| | MIC values (mg/L) of meropenem without inhibitor | |
| | 32-64 | 32-64 |
| Example | MIC values (mg/L) of meropenem in presence of inhibitor | |
| Example 101 | 16 | 8 |
| Example 24 | 1-4 | 0.25 |
| Example 24 | 2 | 0.125 |
| Example 195 | 1 | 0.125 |
| Example 195 | 1 | 0.125 |
| Example 195 | 2 | 0.125 |
| Example 26 | 1 | 0.125 |
| Example 26 | 1 | 0.25 |
| Example 25 | 1 | 0.125 |
| Example 25 | 1 | 0.125 |
| Example 105 | 2 | 0.125 |
| Example 147 | 1 | 0.25-0.125 |
| Example 69 | 1 | 0.25-0.125 |
| Example 147 | 2 | 0.125 |
| Example 157 | 16 | 8 |
| Example 160 | 2 | 0.125 |
| Example 163b | 1 | 0.125 |
| Example 163b | 1 | 0.125 |
| Example 180 | 32 | 8 |
| Example 147 | 1 | 0.25 |

TABLE 4-continued

Study of inhibitor effect on two MBL-positive multiresistant clinical isolates of gram negative bacteria on the MIC of meropenem. In all cases, the concentration of the inhibitor was 25 mg/L

| | Ref. no | |
|---|---|---|
| | K34-7 | K66-45 |
| | Species | |
| | *P. aeruginosa* | *K. pneumoniae* |
| | MBL | |
| | VIM-2 | NDM-1 |
| | MIC values (mg/L) of meropenem without inhibitor | |
| | 32-64 | 32-64 |
| Example | MIC values (mg/L) of meropenem in presence of inhibitor | |
| TPA | 1 | 0.125 |
| Example 182 | 32 | 16 |
| Example 169 | 1 | 0.125 |
| Example 185 | 32 | 64 |
| Example 187 | 32 | 32 |

Summary of Example 197

In Examples 101 and 157, the chelating moiety comprises the structural elements DPA-triazol-β-phenyl-Linker (2B), a structural element showing less activity as an adjuvant at 25 mg/L compared to structural elements based on TPA and tripyridyl-ethylene-diamine in many of the other examples comprising the structural elements in the scheme 23(A). However, compounds comprising the chelator moiety shown in scheme 23(B) achieve full adjuvant effect in concentrations >50 mg/L. Introduction of a thiophene group in the chelator as in Examples 180 and 182 (scheme 23(C)), or removal of one or two nitrogen atoms in the pyridine rings in the chelator as in Examples 185 and 187 (C) completely abolishes the adjuvant effect at an inhibitor concentration of 25 mg/L. In conclusion, scheme 23 shows structural chelator elements leading to superior adjuvant effects. These chelators may give abolishment of antibacterial resistance with carbapenems at concentrations between 8 and 15 mg/L.

Scheme 23-Examples of chelating moieties leading to lower adjuvant effects (*denotes the point of attachment of the chelator to the remainder of the structure)

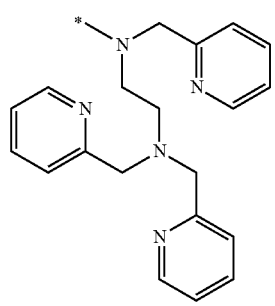

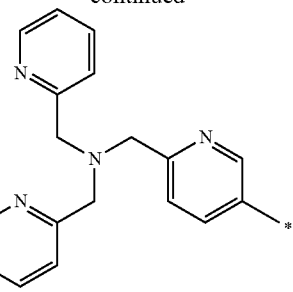

(A) Structural chelator elements in the best performing Examples leading to superior adjuvant effects (Tables 2-4).

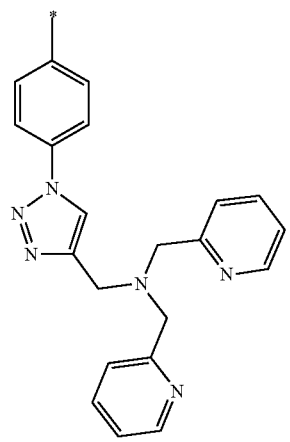

(B) Chelator structure in Examples 101, 157 and 194 (Tables 2-4) Lower adjuvant effects, still efficient at higher (> 50 mg/L) concentrations.

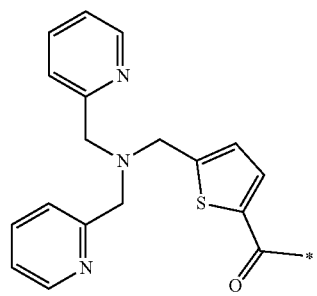

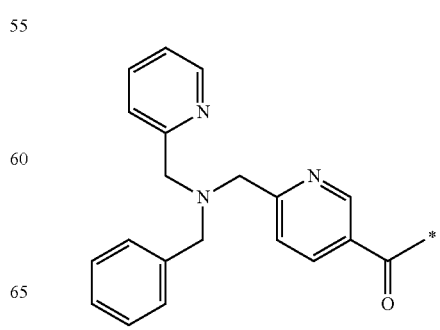

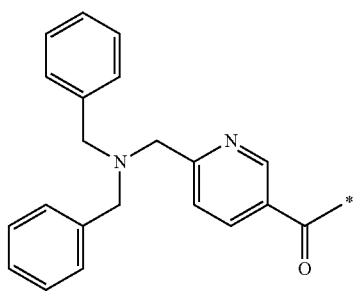

(C) Chelator structural elements in examples leading to loss of MIC efficacy. In examples 108 and 182, one or more 2-pyridyl groups were exhanged with thiophene groups. In Examples 186 and 187, one or more 2-pyridyl groups were exchanged with benzyl groups (Tables 2-4).

Example 198—Effect of Examples 26 and 195 on Different Strains of Gram-Negative Bacteria Harboring an MBL The protocol given in Example 197 was used to compare a non-peptidic compound represented by Example 26 with a peptidic compound represented by Example 195, having the same chelator in both examples (TPA), in a large number of different strains producing MBLs. The results show that the peptidic and the non-peptidic compounds show a similar dramatic adjuvant effect together with meropenem, restoring the effect of the antibacterial drug.

TABLE 5

Effect of Examples 26 and 195 on different strains of Gram-negative bacteria harboring an MBL

| Species | MIC meropenem alone [mg/L] | MIC meropenem + 25 mg/L Example 26 [mg/L] | MIC meropenem + 25 mg/L Example 195 [mg/L] | MBL |
|---|---|---|---|---|
| C. freundii | 4 | 0.06 | 0.125 | NDM-1 |
| P. stuartii | 8 | 0.06 | 0.125 | NDM-1 |
| P. mirabilis | 32 | 0.125 | 0.125 | NDM-1 |
| M. morganii | 8 | 1 | 1 | OXA48 + NDM-1 |
| K. pneumoniae | 64 | ≤0.03 | ≤0.03 | NDM-7 |
| E. coli | 64 | 0.25 | 0.25 | NDM-5 |
| K. pneumoniae | 64 | 0.125 | 0.125 | NDM-1 |
| E. coli | 0.5 | ≤0.03 | ≤0.03 | VIM-1 |
| K. pneumoniae | 4 | 0.06 | 0.125 | VIM |
| K. pneumoniae | 64 | ≤0.03 | ≤0.03 | NDM-1 |
| K. pneumoniae | 64 | ≤0.03 | ≤0.03 | NDM-1 |
| E. coli | 64 | 0.06 | 0.06 | NDM-5 |
| K. pneumoniae | 64 | 0.06 | 0.06 | NDM |
| E. coli | 32 | 0.125 | 0.25 | NDM |
| E. coli | 32 | 0.125 | 0.125 | NDM |
| P. stuartii | 64 | 0.25 | 0.25 | NDM |
| E. coli | 64 | 0.125 | 0.25 | NDM |
| K. pneumoniae | 64 | 0.06 | 0.06 | NDM |
| K. pneumoniae | 64 | 0.06 | 0.06 | NDM |
| E. coli | 32 | 0.125 | 0.125 | NDM |
| C. freundii | 16 | 0.06 | 0.06 | NDM |
| E. coli | 4 | ≤0.03 | ≤0.03 | NDM |
| E. coli | 32 | 0.25 | 0.25 | NDM |
| K. pneumoniae | 8 | 0.06 | 0.06 | NDM |
| E. coli | 8 | 0.06 | 0.06 | NDM |
| E. cloacae | 8 | ≤0.03 | ≤0.03 | VIM |
| E. coli | 32 | 0.06 | 0.125 | NDM |
| K. pneumoniae | 32 | 0.125 | 0.125 | NDM-1 |
| K. pneumoniae | 32 | 0.06 | 0.06 | NDM-1 |
| E. coli | 4 | ≤0.03 | ≤0.03 | NDM-5 |
| E. coli | 8 | ≤0.03 | ≤0.03 | NDM-5 |
| E. coli | 16 | ≤0.03 | ≤0.03 | NDM-5 |
| K. pneumoniae | 32 | 0.06 | 0.06 | NDM-1 |
| E. coli | 4 | ≤0.03 | ≤0.03 | NDM-5 |
| K. pneumoniae | 64 | ≤0.03 | ≤0.03 | NDM-1 |
| E. coli | 64 | 0.06 | 0.125 | NDM-5 |

Example 199—the Effect of Example 26 on Resistant Strains of Clinical Isolates of K. pneumoniae K66-45 and P. aeruginosa K34-7 with Different Carbapenems Table 6 shows the results when the protocol as given in Example 197 was used to test the synergistic effect of Example 26 on a population of growing clinical isolates of K. pneumoniae K66-45 and P. aeruginosa K34-7 harbouring VIM-2 and NDM-1, resistant to carbapenems in general. The two carbapenems chosen was meropemen and doripenem, Three different batches of Example 26 in a concentration of 25 mg/L was used in the study. The results are given in Table 5. A MIC value of 32-64 represents resistance to the carbapenem. The results show that all three batches of Example 26 counteracts resistance in the bacterial strains and potentiates carbapenems with a factor 32-256 times. The results also shows that Example 26 can be resynthesized reproductively.

TABLE 6

The effect of Example 26 on resistant strains of clinical isolates of K. pneumoniae K66-45 and P. aeruginosa K34-7 harbouring VIM-2 and NDM-1

|  |  | MIC of carbapenem in table in mg/L | |
| --- | --- | --- | --- |
|  | Ref. no | | |
|  |  | MIC value in K34-7 | MIC Value in K66-45 |
|  |  | Species | |
| Compound: |  | P. aeruginosa | K. pneumoniae MBL |
| Batches Example 26. |  | VIM-2 | NDM-1 |
| Batch 1 + MEM | MEM | 1 | 0.125 |
| Batch 2 + MEM | MEM | 1 | 0.125 |
| Batch 3 + MEM | MEM | 1 | 0.25 |
| Meropenem alone | MEM | 32-64 | 32-64 |
| Batch 1 + DOR | DOR | 1 | 0.25 |
| Batch 2 + DOR | DOR | 1 | 0.125 |
| Batch 3 + DOR | DOR | 1 | 0.125 |
| Doripenem alone | DOR | 64 | >64 |

Example 200—Checkerboard Study of Example 26 and Meropenem

The following protocol was used to study the synergy of Example 26 with meropenem against meropenem-resistant K. pneumonia and E. coli. A checkerboard MIC assay was using the broth dilution method according to CLSI guidelines. A sample of Example 26 was dissolved in sterile saline (0.9%) to 16 mg/ml and further diluted in Mueller Hinton BBL II-broth (MH-broth) to 1.6 mg/ml. A stock solution of 80 mg/ml concentration of meropenem (Mylan, 51B0424/08-2017) was prepared by dissolving 1 g meropenem in 12.50 ml sterile saline (0.9%). Dilutions to 4 mg/ml was performed by adding +4.75 ml sterile saline to 0.25 ml of the stock solution, and dilutions to 512 jag/ml was performed by adding 10.9 ml MH-broth to the 4 mg/ml solution. Inoculums of bacterial strains as described in Table 4 were prepared by suspending fresh overnight colonies from 5% horse blood agar were to a turbidity of 0.5 McFarland and further diluted to $1\times10^6$ CFU/ml in MH-broth. Aliquots of 50 µl of MH-broth were added to each well of polystyren microtiter plates. Thereafter, the 512 µg/ml meropenem solution was added to column 1 and titrated 2-fold throughout column 11. Solutions of 50 µl pre-titrated Example 26 were added to all wells and finally 100 µl diluted bacterial suspension was added to the wells. The plates were incubated at 35° C., 16-20 hours.

Results:

The results of the checker boards are shown in table 7 as MICs for the single compound and in combination between the two. In addition to the different MBLs, the isolates were producers of a large number of non-MBL J-lactamases. Table 7 shows a strong synergistic effect of EXAMPLE 26 in combination with meropenem for all of the MDR isolates tested. For some of the strains, the amplification of the effect of meropenem was more than a 1000 times.

TABLE 7

Checkerboard results in the study of Example 26 with meropenem with a variety of resistant Gram-negative strains harboring MBL

| Isolate category | β-lactamase/ carbapenemase | Other β-lactamases | isolate id | MIC alone (mg/L) | | MIC in combination (mg/L) | |
| --- | --- | --- | --- | --- | --- | --- | --- |
|  |  |  |  | Example 26 | Meropenem | Example 26 | Meropenem |
| NDM E. coli | NDM-1 | CTX-M-15; CMY-6; OXA-1 | 50676002 | >400 | 32 | 12.5 | ≤0.0625 |
|  | NDM-1 | CTX-M-15; CMY-16(v); OXA10; OXA-1; TEM1 | 50739822 | >400 | 32 | 12.5 | ≤0.0625 |
|  | NDM-1 | CMY-6; DHA-1-like; OXA-1; TEM-1C | AMA817 | >400 | 32 | 12.5 | ≤0.0625 |
|  | NDM-5 | CTX-M14 | AMA1563 | >400 | 64 | 25 | ≤0.0625 |
| VIM E. coli | VIM-4 | CTX-M-15; CTX-M-9; OXA-1 | AMA323 | >400 | 8 | 12.5 | ≤0.0625 |
|  | VIM-1 | nd | 50921466 | >400 | 2 | 12.5 | ≤0.0625 |
| NDM-1 K. pneumonia | NDM-1 | SHV-11; CTX-M-15; OXA-1; OXA-9; TEM-1 | K66-45 | >400 | 64 | 12.5 | ≤0.0625 |
|  | NDM-1 | SHV-11; CTX-M-15; OXA-1; CMY-6 | 50627996 | >400 | 64 | 12.5 | 0.125 |
|  | NDM-1 | SHV-1; CTX-M-15; OXA-1; OXA-9; TEM-1 | 50752501 | >400 | 64 | 25 | ≤0.0625 |
|  | NDM-1 | SHV11(v); OXA-1; TEM-1 | 50690310 | >400 | 16 | 12.5 | ≤0.0625 |

TABLE 7-continued

Checkerboard results in the study of Example 26 with meropenem with a variety of resistant Gram-negative strains harboring MBL

| Isolate category | β-lactamase/ carbapenemase | Other β-lactamases | isolate id | MIC alone (mg/L) Example 26 | MIC alone (mg/L) Meropenem | MIC in combination (mg/L) Example 26 | MIC in combination (mg/L) Meropenem |
|---|---|---|---|---|---|---|---|
| | NDM-1 | SHV-11; CTX-M-15; OXA-9; TEM-1 | 50825040 | >400 | 64 | 12.5 | ≤0.0625 |
| | NDM-1 | CMY-6; SHV-11 | 50877064 | >400 | 64 | 12.5 | ≤0.0625 |
| VIM K. pneumonia | VIM-1 | SHV-12 | K45-67 | >400 | 32 | 12.5 | ≤0.0625 |
| | VIM-1 | SHV-12; TEM-1 | K46-62 | >400 | 32 | 12.5 | ≤0.0625 |
| | VIM | ND | 50923744 | >400 | 2 | 12.5 | ≤0.0625 |

Example 201—General Protocol And Results For In Vitro Toxicity Of Compounds In Human HepG2 Cells Materials and Methods:

Cells

The human hepatoblastoma cell line HepG2 (HB-8065, ATCC, Manassas, Va., USA) was cultured in DMEM-Glutamax™ (5.5 mM glucose) supplemented with 10% foetal bovine serum, streptomycin (100 µg/ml) and penicillin (100 units/ml) at 37° C. in 5% $CO_2$. For viability assays, cells were seeded in white 96-well Nunclon plates at a density of 20,000 cells/well and left overnight to adhere before experiments were conducted.

Cell Viability Assay

Zn chelators dissolved in DMSO were added to white 96-well plates containing 20000 HepG2 cells/well at concentrations ranging from 1 to $1 \times 10^{-6}$ mM (max DMSO concentration never exceeded 1%) and incubated for 24 hours at 37° C. After 24 hours, AlamarBlue® cell viability reagent (Thermo Fisher, Carlsbad, USA) was added (10% final concentration) and incubated for 4 hours at 37° C. This dye is a red-ox indicator yielding a fluorescent signal proportional to viable cells in each well that was measured in a fluorescence plate reader at ex550 nm/em603 nm (Clariostar, BMGlabtech, Germany) (O'Brien et al., 2000). Data from 8 replicates were fitted by non-linear regression to estimate IC50 values using GraphPad Prism (GraphPad Software Inc, USA).

REFERENCES

O'Brien, J., Wilson, I., Orton, T., Pognan, F., 2000. Investigation of the Alamar Blue (resazurin) fluorescent dye for the assessment of mammalian cell cytotoxicity. Eur J Biochem 267, 5421-5426.

Figure 2:
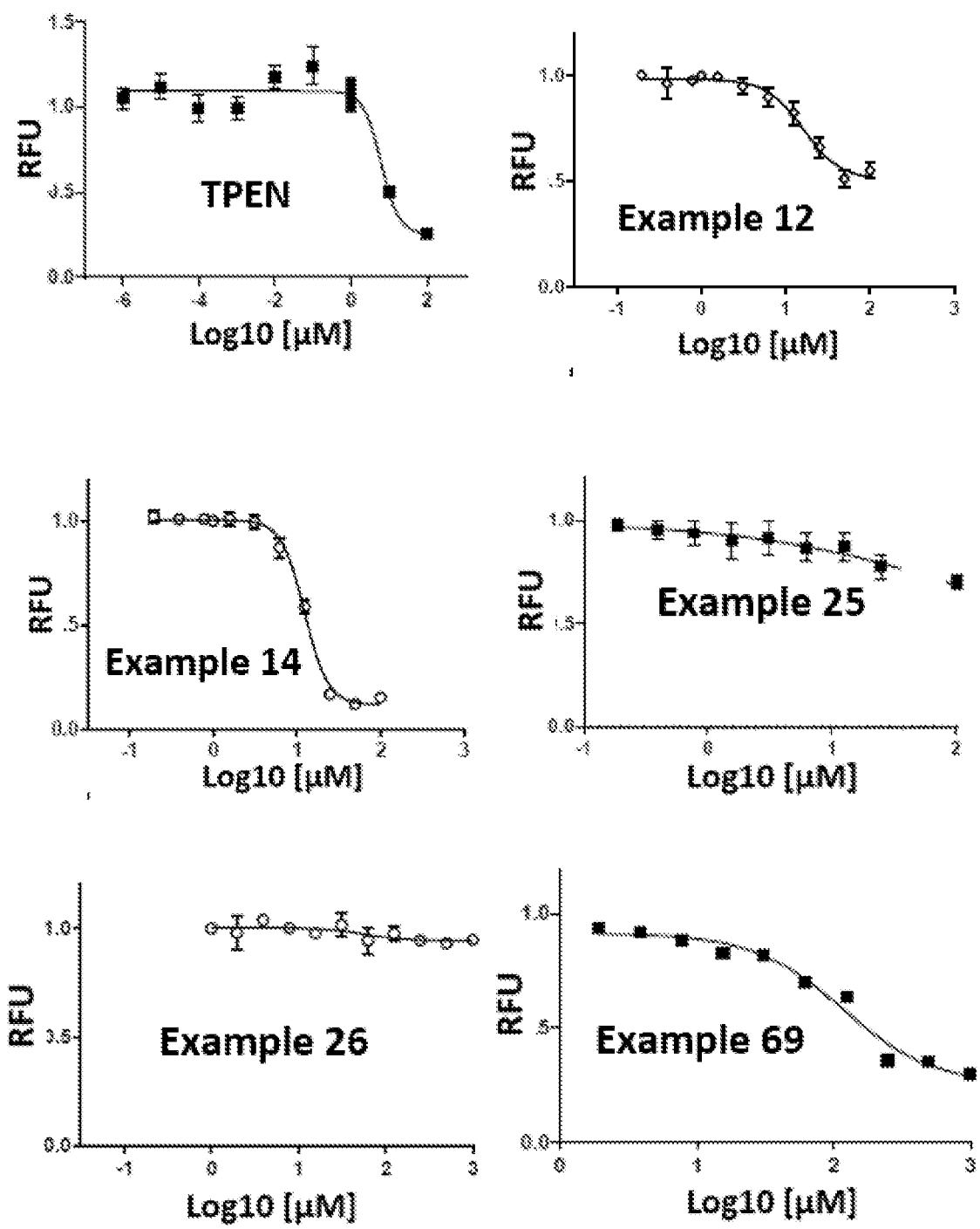
FIG. 2 shows the in vitro toxicity of compounds according to the invention in human hepG2 cells.
Figure 2:
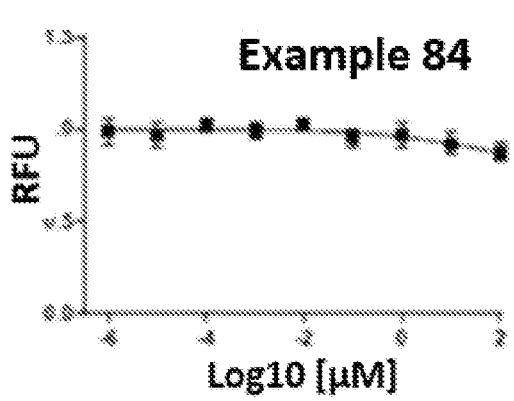
Figure 2:
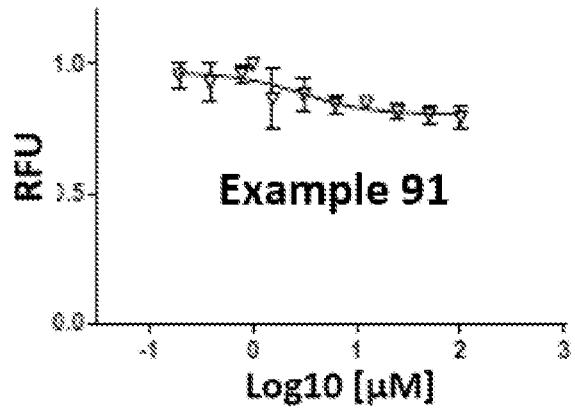
Figure 2:
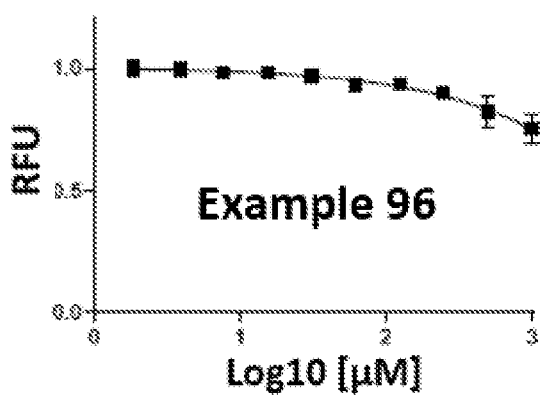
Figure 2:
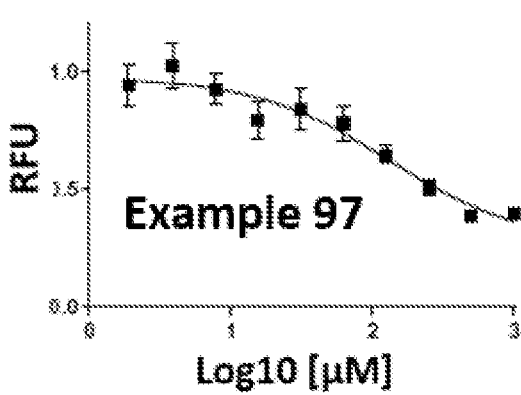
Figure 2:
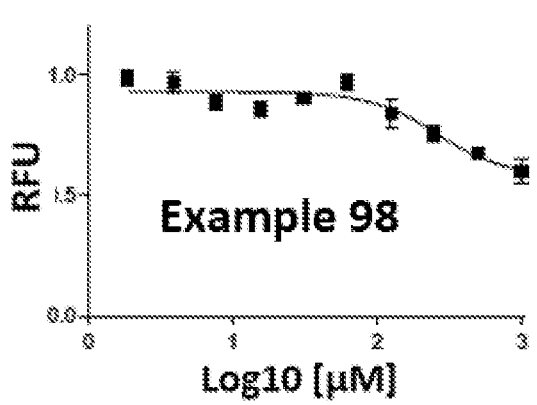
Figure 2:
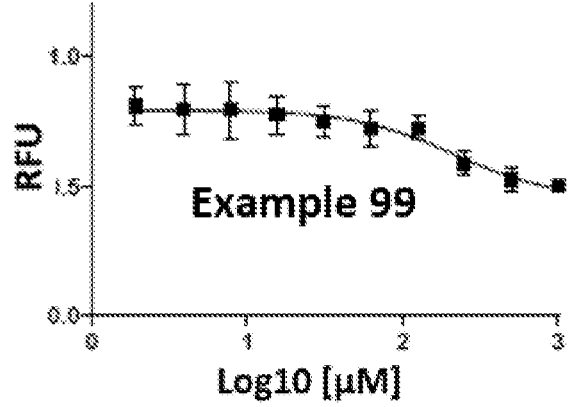
Figure 2:
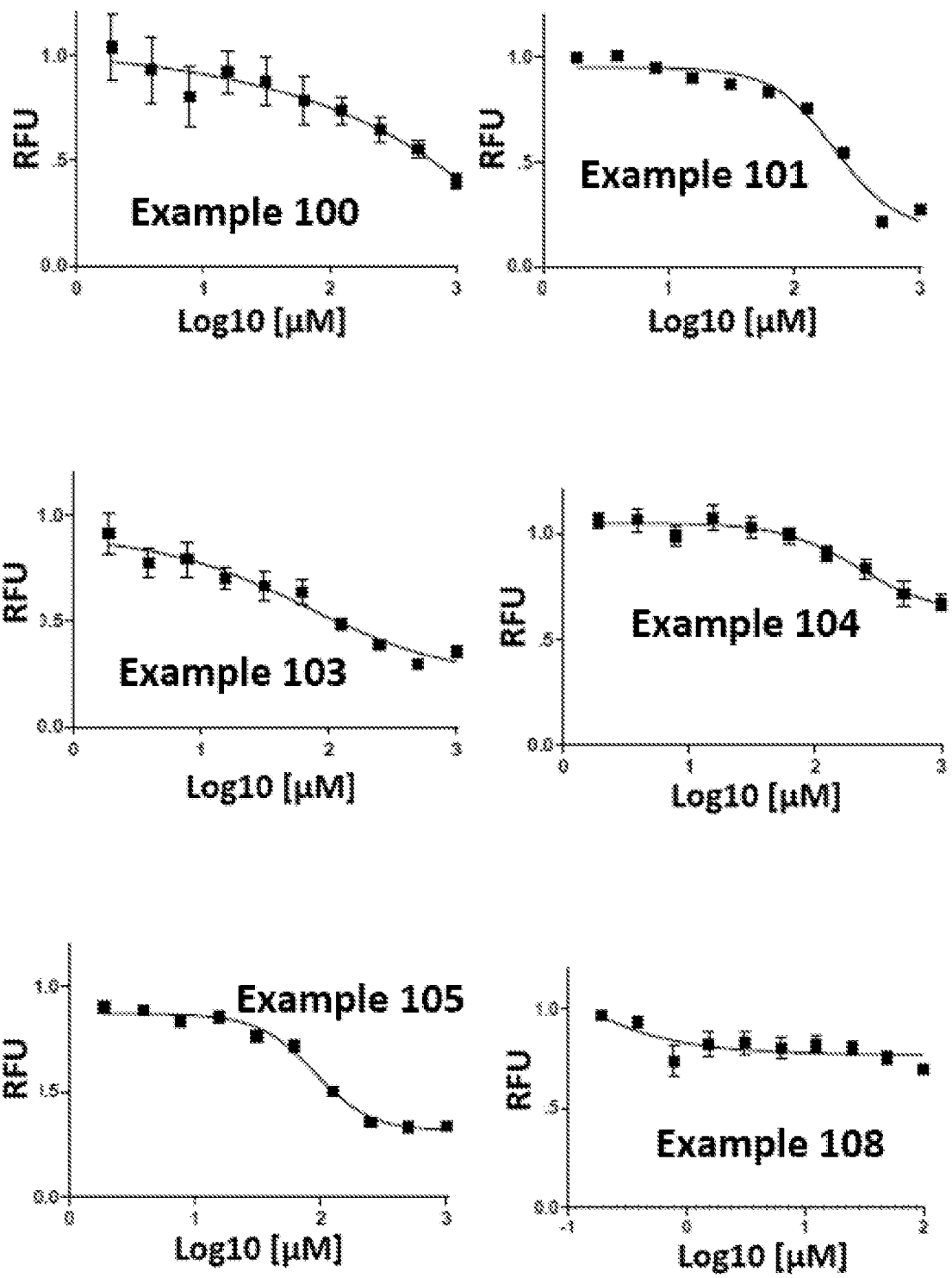
Figure 3:
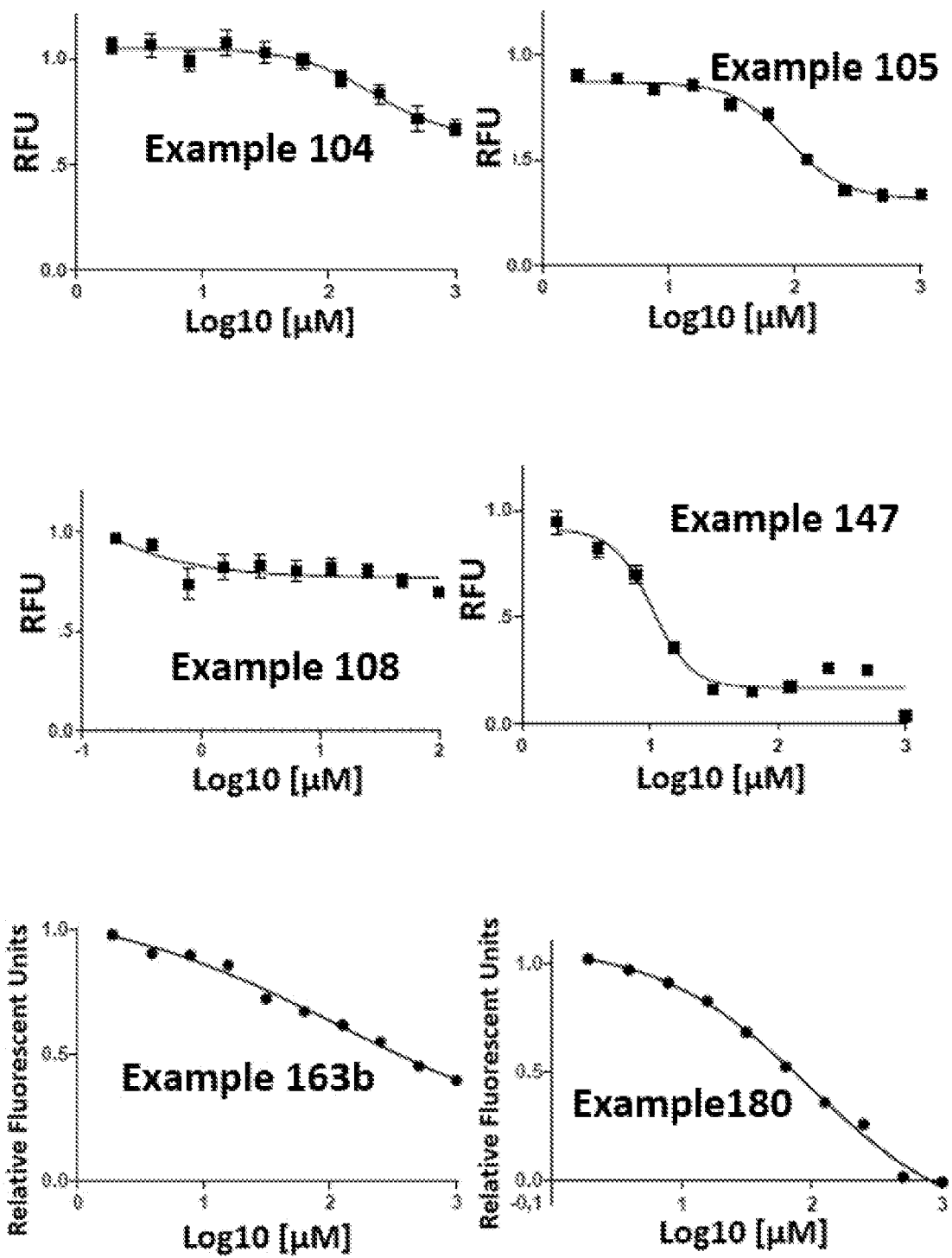
FIG. 3 shows the in vitro toxicity of compounds according to the invention in human hepG2 cells.
Figure 3:
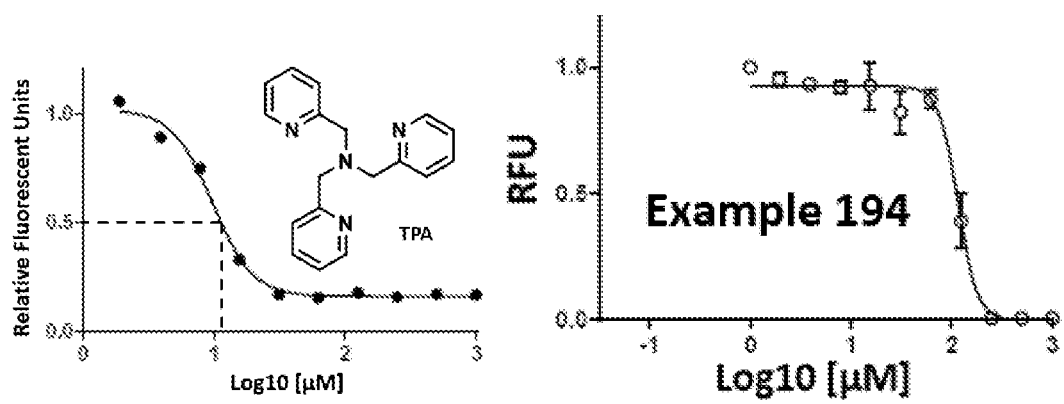
Figure 3:
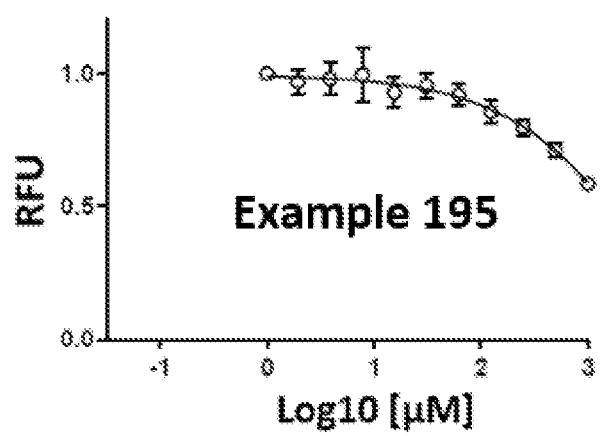

Results:

The numerical calculations of the IC50 values for the in vitro in hepG2 cells for compounds of the invention are given in Table 8. The curves in FIGS. 2 and 3 show the log 10 concentration of Example No. as a function of relative fluorescence units (RFU) in suspensions of hepG2 cells. None of the compounds gave a RFU <$10^3$ in the cell-free medium alone.

TABLE 8

| Compound | IC50 | R square |
|---|---|---|
| TPEN | 7.1 | 0.9372 |
| Example 12 | 16.5 | 0.9363 |

TABLE 8-continued

| Compound | IC50 | R square |
|---|---|---|
| Example 14 | 12.4 | 0.9911 |
| Example 25 | 113.3 | 0.7048 |
| Example 26 | >1000 | 0.2191, calculation and visual inspection |
| Example 84 | >1000 | 0.3462, calculation and visual inspection |
| Example 91 | 165.2 | 0.9321 |
| Example 96 | >1000 | 0.8415, calculation and visual inspection |
| Example 97 | 130.6 | 0.885 |
| Example 98 | 259.1 | 0.8232 |
| Example 99 | 217.3 | 0.7271 |
| Example 100 | >100 | 0.7154 |
| Example 101 | ~220 | Visual inspection |
| Example 103 | 67.61 | 0.89 |
| Example 104 | 224.5 | 0.884 |
| Example 105 | ~210 | Visual inspection |
| Example 107 | >500 | 0.4354, calculation and visual inspection |
| Example 108 | >1000 | 0.5954, calculation and visual inspection |
| Example 109 | 127.7 | 0.839 |
| Example 147 | ~10 | Visual inspection |
| Example 163b | ~600 | Visual inspection |
| Example 180 | ~80 | Visual inspection |
| Example 186 | ~215 | Visual inspection |
| Example 195 | >1000 | 0.8331, calculation and visual inspection |

Example 202—General Protocol and Results for In Vitro Human Red Blood Cell Toxicity Human blood samples were incubated at 37° C. with six concentrations of the compounds given in Table 1 in the range 1-500 µM concentrations. The blood samples were centrifuged to remove whole cells, and the supernatants were analyzed spectrophotometrically. None of the compounds induced hemolysis below 500 µM concentration.

Example 203—General Protocol and Results for In Vitro Identification of Bacterial Ambler Class 1. Isolate a carbapenem-resistant bacterial strain of interest and spread it on an agar plate.
2. Prepare the following disks:
   a. Disk A with meropenem alone.
   b. Disk B with meropenem+Example 26.
   c. Disk C with imipenem alone.
   d. Disk D with imipenem+Example 115.
   e. Disk E with temocillin.
3. Add the five disks at five different places in the agar plate or in four different plates.
4. Incubate overnight at 37° C.
5. Read all zone diameters of the lobes.
6. The response as read by zone diameters may be used to discriminate between producers of MBL, KPC and OXA as described by Teethaisong et al in *Journal of Applied Microbiology* (2016), 121, 408-414, according to Table 9.

TABLE 9

| Disk | Result | | |
|---|---|---|---|
| A | − | − | − |
| B | − | + | − |
| C | − | − | − |
| D | − | + | + |
| E | − | | |
| Suggested conclusion | Pathogen without MBL, KPC but indicates OXA-48 | MBL-based pathogen | KPC-based pathogen |

Symbols: +: increased zone. −: minimally changed zone.

Example 204—Time-Kill Studies

Materials:
Mueller-Hinton broth (MHB) was warmed from fridge temperature cold. Materials used in the study was LB agar, preferably square plates, sterile PBS, 96-well plates, 30 mL Media bottles, inoculating loops, tips for multichannel, sterile micro-centrifuge tubes (1.5 mL), 40 mg/mL freshly prepared meropenem (MEM) solution in DMSO appearing as clear/pale yellow solutions. A sample of Example 26 was dissolved in DMSO.

Method:
The 96-well plates were prepared using a multi-channel pipette, adding 270 mL PBS to columns 2-9, or the required number of dilutions needed in the experiment. Each Inoculum was prepared by picking a single colony from the fresh plate that was dispersed into 1 mL MHB, the loop was agitated to ensure all the colony comes off the loop. The tube was Vortex mixed, and a 100 µL aliquot was taken from the tube into 9.9 mL of MHB into the media bottle. This results in 10 mL with ~$10^5$ CFU/mL. The procedure was repeated for as many samples needed in the study. Aliquots of 5 mL inoculum were transferred to as many media bottles as needed, e.g. 4 mg/L MEM, 4 mg/L MEM+50 µM test substance, 4 mg/L MEM+100 µM test substance. Then 2×60 mL aliquots were taken from each culture and added to Column 1 on the 96 well plate, e.g. culture 1:50 µl into A1, 50 mL into B1 etc. for time point 0 h. Then 4 mg/mL MEM was added into each bottle, followed by the required amount of test substance. The bottles were mixed gently to avoid formation of bubbles, and incubated in a secondary container at 37° C. at 180 rpm. Finally, serial dilutions were performed using multi-channel pipette taking 30 µL for column 1, adding to column 2, mixing well, repeating from column 2 to 3 with clean pipette tips.

Figure 4:
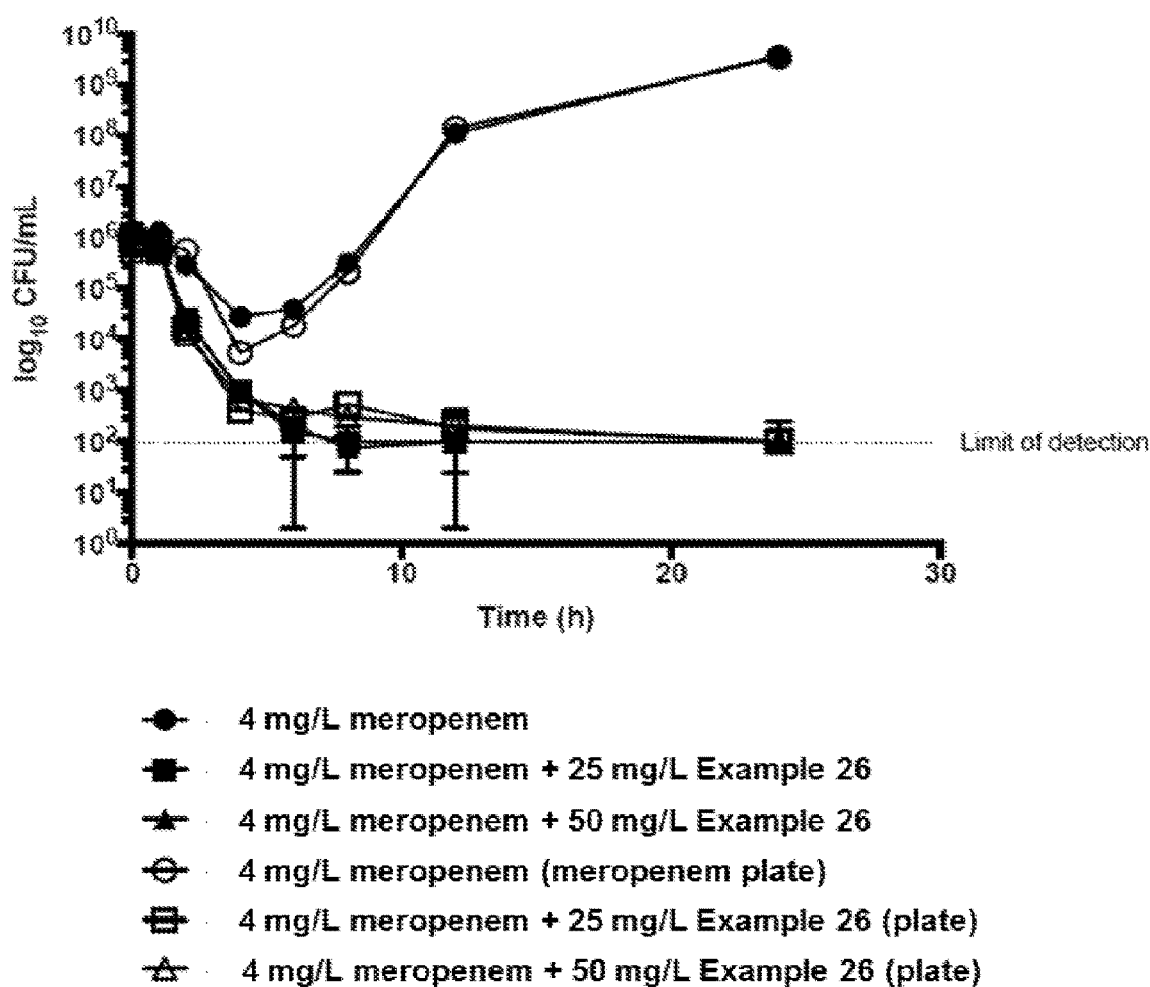
FIG. 4 shows the results of a time-kill study of the compound of Example 26 with meropenem.

Result:
FIG. 4 shows the results from the time-kill studies of a resistant clinical isolate of *Klebsiella pneumonaie* harboring NIDM-1 with Example 26 and 4 mg/L meropenem. The data shows that with 4 mg/L meropenem alone the CFU starts to increase after about 5 hours and continues to grow beyond the starting CFU count. With the same concentration of meropenem added Example 26, the CFU drops to below the limit of detection (LOD) after 5-10 hours irrespective of the concentration of Example 26, and stays below LOD in the period of the study (30 hrs.).

Example 205—Resistance Frequency as a Function of Chelator Strength Using the Compounds of Examples 25, 26, 194 and 195 According to Scheme 23B Example 205A Resistance frequency of *K. pneumoniae* K66-45 to meropenem co-treatment with examples 25, 26, 194 and 195 as determined by single-step selection on agar. The following protocol was used: Mueller-Hinton agar (MHA) plates containing either 15, 25 or 50 mg/L of Example 26 were supplemented with 1, 2, 4 or 8 mg/L meropenem. 4 mg/L meropenem corresponds to the mean steady-state antibiotic level in sera when normal doses of meropenem is administered to healthy volunteers. The CFU of K66-45 was ~$10^9$ (Mueller-Hinton broth, no selection). After plating and grown overnight at 37° C., only single colonies, ignoring any touching the edges of the plate, were counted. Analogously with the same setup, 25 mg/L of Example 196 were run the same way with 1, 2, 4 and 8 mg/L meropenem.

Results and Conclusions
The results are summarized in Table 10. With Example 194, almost-confluent growth with >1000 colonies, too numerous to count/separate, was observed on nearly all plates. With Example 26 comprising a stronger chelator, no colonies were observed at the anticipated clinical concentration 4 mg/L or higher of meropenem. With Example 25 with an even stronger chelator, no colonies were observed at the sub-clinical MEM concentration 2 mg/L.

TABLE 10

Resistance frequency of K. pneumoniae K66-45 to meropenem co-treatment with compounds of Examples 25, 26, 194 and 195, determined by single-step selection on agar Inhibitor concentration in all cases: 25 mg/L
Inhibitor example

| | Example 194 | | | | Example 26 | | | | Example 195 | | | | Example 25 | | | |
|---|---|---|---|---|---|---|---|---|---|---|---|---|---|---|---|---|
| MEM conc. (mg/L) | 1 | 2 | 4 | 8 | 1 | 2 | 4 | 8 | 1 | 2 | 4 | 8 | 1 | 2 | 4 | 8 |
| Sensitivity | S | S | I | I | S | S | I | I | S | S | I | I | S | S | I | I |
| RF* - no of colonies | tntc | tntc | tntc | tntc | 74 | 35 | nc | nc | 163 | nc | nc | nc | 64 | nc | nc | nc |

MEM = meropenem;
n.c. = no colonies,
S = sensitive,
I = intermediate e.g. 2 < I ≥ 8;
tntc = too numerous to count, plates containing either confluent growth or >1000 colonies;
nd = not determined.
MIC of MEM in the absence of Example 26 >32 mg/L.
MIC of MEM in the presence of 31.25 µM, 50 µM and 100 µM Examples 25, 26 and 195 = 0.125 mg/L;
*RF = resistance frequency Example 205B—Determination of Resistance
Frequency of *Klebsiella pneumoniae* K66-45 to
Example 26-Meropenem Co-Treatment To investigate the resistance frequency of Example 26 at varying concentrations, the same protocol as in Example 205A was used to investigate the frequency of resistant mutants in a population of growing *K. pneumoniae* K66-45. Mueller-Hinton agar plates containing either 31.25 or 50 μM Example 26 were supplemented with 1, 2, 4 or 8 mg/L MEM. $10^9$ CFU K66-45 (Mueller-Hinton broth, no selection) was plated and grown overnight, 37° C. Only single colonies, ignoring any touching the edges of the plate, were counted. A concentration of 4 mg/L meropenem corresponds to a clinical steady-state concentration level in sera when normal doses of meropenem used in healthy volunteers, as described by Leroy A, Fillastre J P, Borsa-Lebas F, Etienne I, Humbert G. in Antimicrobial Agents and Chemotherapy 36 (1992), 2794-2798.

Results and Conclusions:
The results are summarized in Table 11. There was a concentration dependency on frequency of number of mutants with increasing concentration of Example 26. At the effective concentration of 25 mg/L of Example 26, no colonies were observed at the anticipated clinical concentration 4 mg/L or higher of meropenem. The 50 mg/L concentration of Example 26 is still a fully acceptable concentration in view of the toxicity data in Examples 202, 203 and 212. At this concentration, no colonies were observed at half the clinical concentration of meropenem on 2 mg/L.

TABLE 11

Resistance frequency of *K. pneumoniae* K66-45 to
the compound of Example 26 - meropenem co-treatment,
determined by single-step selection on agar

| | Resistance/mutant frequency (number of colonies) | | | |
|---|---|---|---|---|
| Inhibitor (mg/L) | 1 mg/L MEM (S) | 2 mg/L MEM (S) | 4 mg/L MEM (I) | 8 mg/L MEM (I) |
| 15 | 137 | 115 | 4 | n.c. |
| 25 | 74 | 35 | n.c. | n.c. |
| 50 | 22 | n.c. | n.c. | n.c. |

MEM = meropenem, n.c. = no colonies, S = sensitive, I = intermediate e.g. 2 < I ≥ 8. MIC of MEM absence of Example 26 > 32 mg/L. MIC of MEM in presence of 31.25 μM, 50 μM and 100 μM Example 26 = 0.125 mg/L Example 206—Protein Binding of Example 26

To determine the protein binding properties of Example 26, the Transil$^{XL}$ protein binding kit (Sovicell) was used. Enzymes in the kit are immobilized at a solid phase. Aliquots of 500 μM of Example 26 were incubated for 12 min under shaking (1200 rpm) at different concentration of human serum albumin and $\alpha_1$-acid glycoprotein (AGP) in a ratio of 24:1 (up to 140 μM). Buffer without inhibitor was included as a control. After incubation, the suspensions were centrifuged and diluted 1:10 in 50 mM HEPES buffer pH 7.5 supplemented with 1 μM zinc$^{2+}$ and VIM-2 (final concentration 1 nM). Enzyme and standard was allowed to incubate for 10 and 30 min at 25° C. and measured the residual enzyme activity was measured by adding Nitrocefin as a reporter substrate (final concentration of 50 μM). The absorbance was recorded at 482 nm and 25° C. and the residual enzyme activity was calculated.

Figure 5:
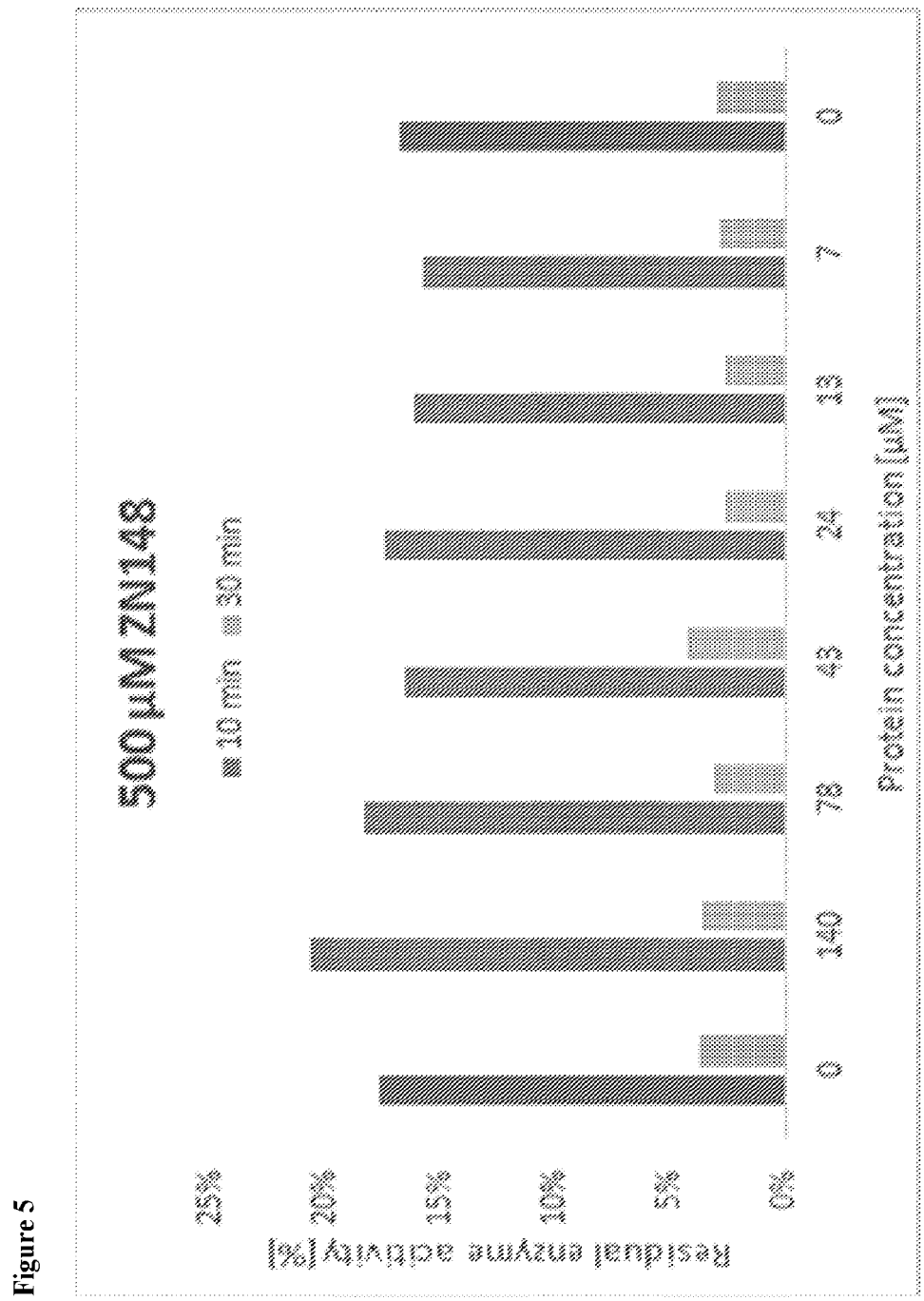
FIG. 5 shows the protein binding of the compound of Example 26 at two different concentrations.

Results:
FIG. 5 shows the results for the study of protein binding of Example 26. The bars denoted as 0 in protein concentration are the results for inhibition of VIM-2 without presence of proteins.

Conclusion:
The results show that protein binding is not affecting the inhibitory activity of Example 26 on VIM-2 in any of the protein concentrations.

Example 207—Zinc Restorability of the NDM
VIM-2 after In Vitro Incubation with Example 26

PD-10 Desalting Columns comprising Sephadex G-25 size exclusion resin (GE Healthcare Life Sciences) were used to study irreversibility of the interaction between Example 26 and the metallo-β-lactamase VIM-2. The stationary phase retains low-molecular compounds and excludes molecules with higher molecular weight than 10 kD. The eluent used was Chelex-treated HEPES 50 mM buffer, pH 7.5. In experiment 207A, a solution of 50 nM VIM-2 was passed through a column. The enzyme activity towards a standard was the same before and after passage through the column. In experiment 207B, a solution of 50 mg/L of Example 26 was loaded to a PD-10 column and it was shown analytically (spectrophotometrically, HPLC) that Example 26 was completely retained on the column. Thus the eluate only contains either the pure enzyme, or the enzyme that has been mixed with inhibitor pre PD10 column treatment. In experiment 207C, a solution of 50 nM VIM-2 and 140 mg/L Example 26 was incubated on ice for 1 hour. In all experiments, 16 aliquots of 250 μL were taken from the PD-10 column runs out and enzyme activity was analysed. Enzyme activity was measured by adding Nitrocefin as a reporter substrate (final concentration of 50 μM).

Figure 6:
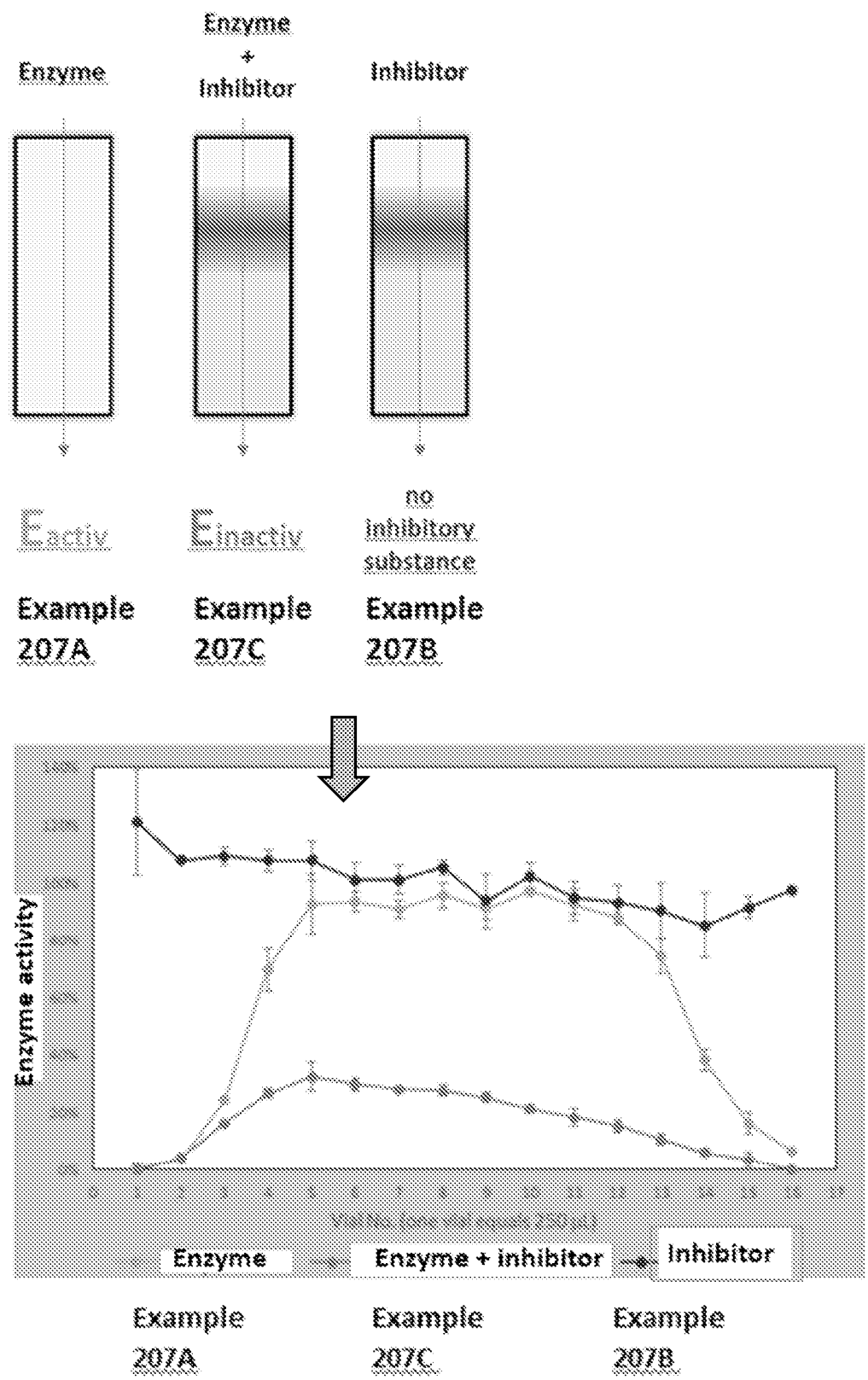
FIG. 6 shows the results of an irreversibility study of the compound of Example 26 with purified VIM-2. The left hand side of the figure shows the experimental set-up; the right hand side shows the enzyme activity with the compounds of Examples 207a-c.

Results:
The results are given in FIGS. 6 and 7. It was shown (FIG. 6) that none of the eluate fractions from Example 207B had inhibitory effect on the enzyme. The eluate fractions 5-12 from 207A had full enzyme activity as expected. Of the eluate fractions from Example 207C, fraction 5 showed only 33% residual enzyme activity.

Conclusion:
the experiment shows that Example 26 irreversibly inhibits VIM-2.

Figure 7:
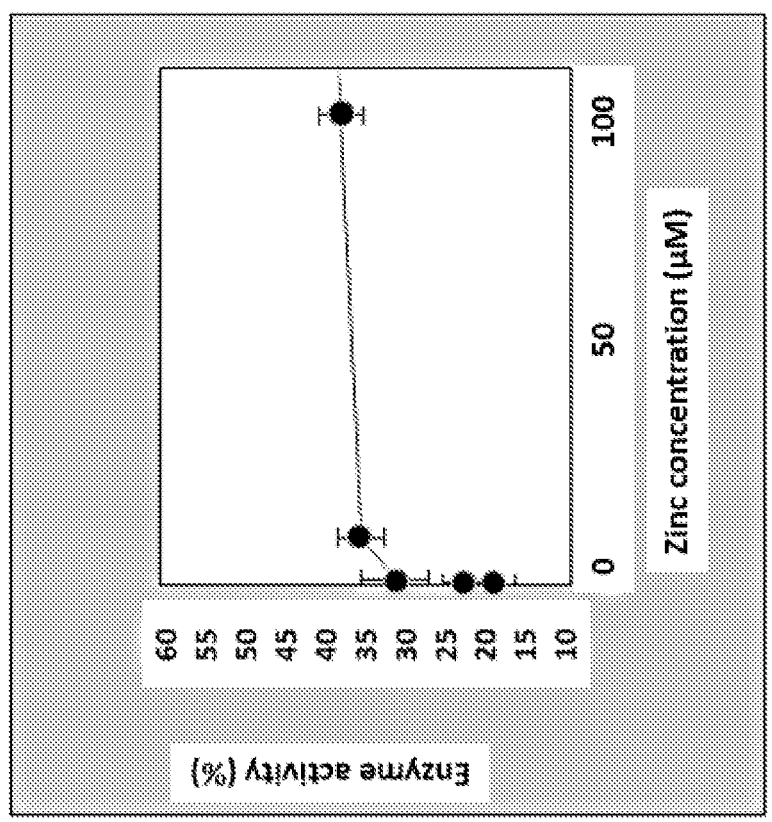
FIG. 7 shows the results of an enzyme restoration study of the compound of Example 207c with $Zn^{2+}$.
Figure 7:
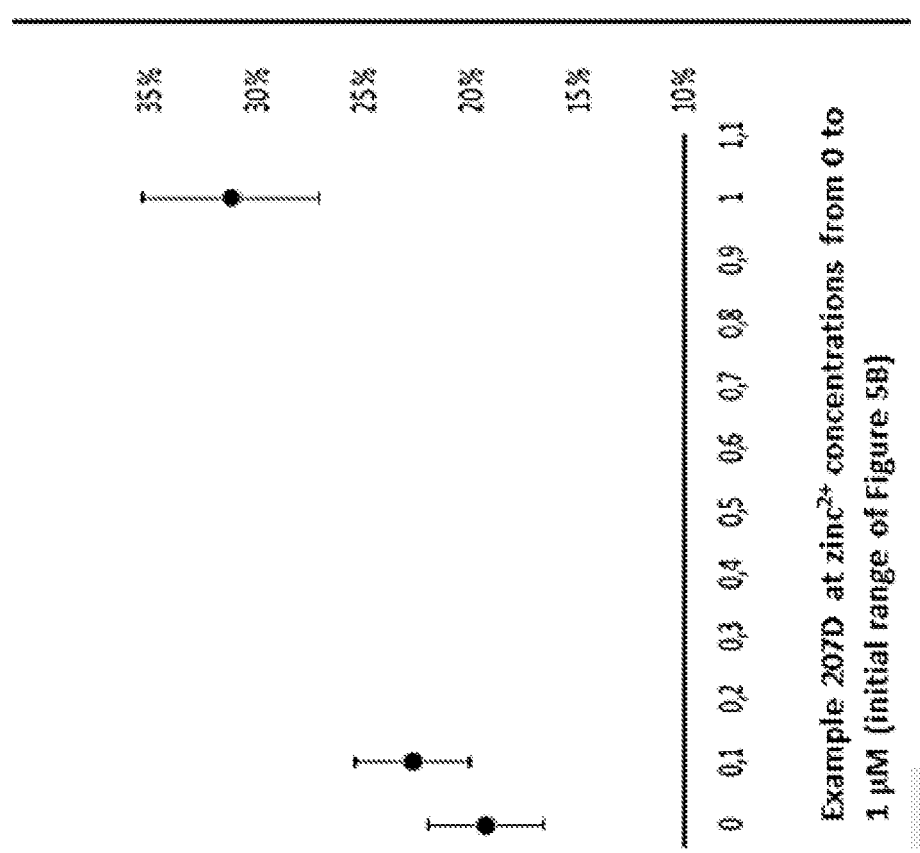

In Example 207D, aliquots containing 15 nM impaired enzyme from Example 207C were spiked with ZnSO4 in concentrations ranging from 0-100 μM. The results are shown in FIG. 7. Enzyme activity could be restored only to 40%. To investigate if more extreme time-dependent and concentration-dependent conditions could restore enzyme activity, aliquots having final concentrations of 30 nM column-treated enzyme and 1000 μM Zn$^{2+}$ on ice and at room temperature over prolonged time. No increase in enzyme activity was observed at any point of time in the experiment.

Conclusion:
The experiment shows that the irreversible inhibition of VIM-2 by Example 26 was not solely a consequence of a reversible removal of Zn$^{2+}$ from the enzyme.

Example 208—Zinc Restorability of the NDM
VIM-2 after In Vitro Incubation with Example 26
Compared to Incubation with the Standards TPEN
and EDTA The protocol from Example 207 was followed to investigate the effect of increasing concentrations of the literature compound TPEN on purified VIM2 enzyme, and compared to the PAC chelator EDTA at a 100 µM concentration (FIG. 8A). In a parallel experiment, it was investigate how corresponding increasing concentrations of Example 26 affected the VIM-2 enzyme compared to the PAC chelator EDTA at a 100 µM concentration (FIG. 8B).

Conclusion:

The experiments show that VIM-2 was irreversibly inhibited by the zinc-selective 2-pyridyl chelators TPEN and Example 26, and that the inhibition was not solely a consequence of a reversible removal of $Zn^{2+}$ from the enzyme. The experiments also show that the typical PAC chelator EDTA did not inhibit VIM-2 irreversibly.

Example 209—In Vitro Interaction of Example 26 with Zinc-Containing Human Enzymes—Comparison to the APC-Chelator EDTA Protocol:

In order to investigate if representative examples in the present invention are able to interact with human metal containing enzyme, Example 26 was incubated for 30 min at different concentrations ranging from 62.5-500 µM at 25° C. with 0.4 ng/µL enzyme. Enzyme activity was measured by adding Nitrocefin as a reporter substrate (final concentration of 50 M). The initial reaction velocity was measured at 405 nm. EDTA was included as a representative example of the APC chelator class described above.

Figure 9:
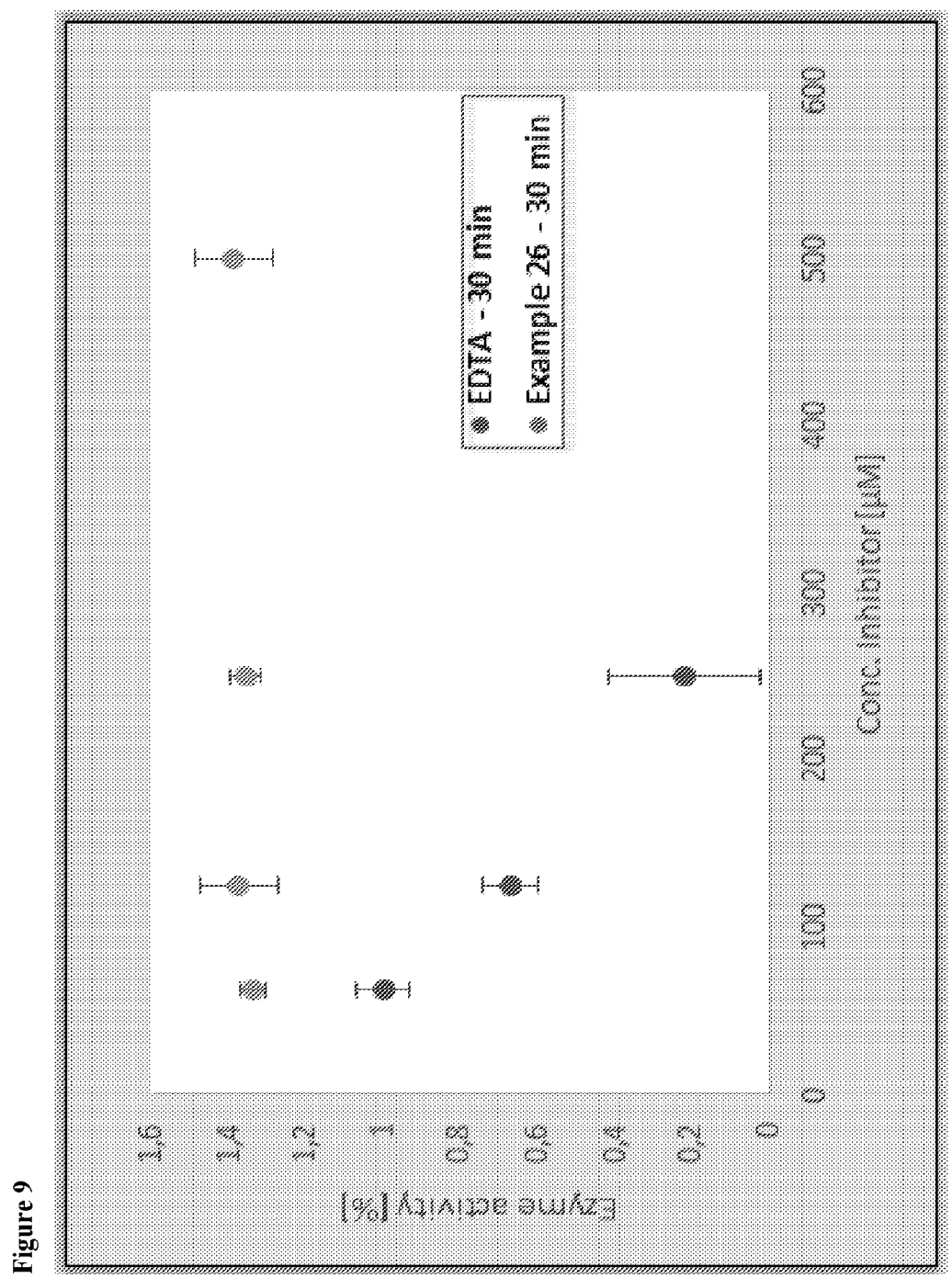
FIG. 9 shows the in vitro interaction of the compound of Example 26 with zinc-containing human enzymes—comparison to the APC-chelator EDTA.

Results and Conclusion:

FIG. 9 summarizes the results of the investigation. The data suggest that the compound of Example 26 does not interact with rH glyoxylase II, whereas the APC chelator EDTA does.

Example 210—Solution Stability of a Peptide-Based Inhibitor (Example 195) Compared to a Non-Peptide Inhibitor in the Present Invention (Example 26)

Protocol:

Example 195 and Example 26 was stored for up to 8 months at 2-8° C. and the stability was measured indirectly by performing MIC studies according to the protocol in Example 187 at a final concentration of 25 mg/L of the inhibitors. *P. aeruginosa* harboring VIM-2 and *K. pneumonia* bearing NDM-1 was used as two indicator strains.

Figure 10:
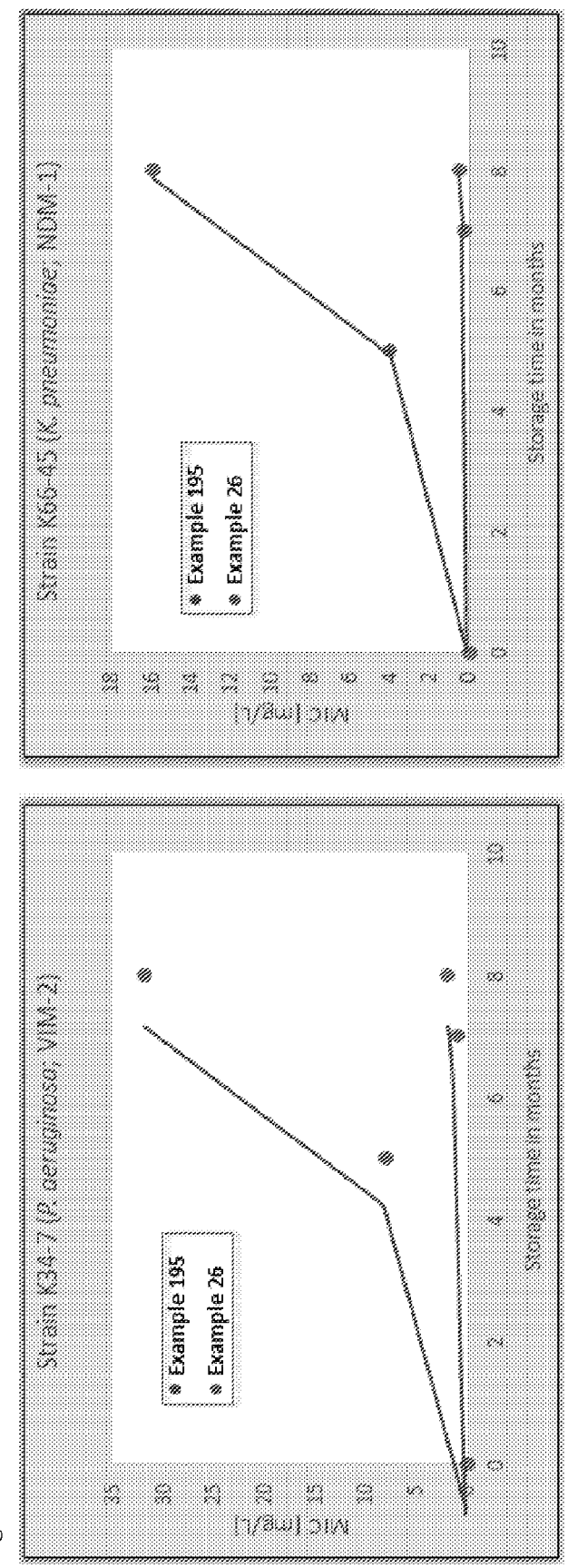
FIG. 10 shows the MIC values of a peptide-based inhibitor (Example 195) compared to a non-peptide inhibitor after storage in solution.

Results and Conclusions:

The results are summarized in FIG. 10. With Example 195, a loss of activity was observed after 5 months storage, and after 8 months the activity was absent. On the other hand, Example 26 showed no loss of activity even after 8 months storage time. These data indicate that a representative non-peptidic Example (Example 26) from the present invention has a significantly better stability in solution compared to a peptidic inhibitor comprising the same chelator. The peptidic chelator may still be handled as a drug product, e.g. in a lyophilized form.

Example 211—In Vivo Toxicity of Example 26 and Example 195 in Healthy Mice

Protocol:

Female Balb/c mice (4 weeks old, approximately 20 g, Charles River, L'Arbresle, France) acclimatized 4 days in the animal facility before initiation of experiments. Stock solutions with a concentration of 25.6 mg/ml were prepared of the two test compounds, Example 26 and Example 195. Groups of 6 mice were either untreated or treated with 200 µL of Example 26 or Example 197 intraperitoneally once a week with increasing doses each time. Individual weights were followed four days a week. Relative weight was calculated as the ratio between the weight of the day and the weight of the first day. The protocol for experiments in mice was approved by the University of Lyon Animal Ethics Committee. Toxicity experiments were performed by Antineo (www.antineo.fr). After 43 days, the mice in the two test groups had received an accumulated dose of 252 mg/kg.

TABLE 12

The changes in bodyweight during the experiment
Relative weight of mice (% ± SEM)

| Treatment (mg/kg) | Day | Untreated mice | Example 26 | Example 195 |
|---|---|---|---|---|
| 4 | 1 | 100 ± 0 | 100 ± 0 | 100 ± 0 |
| 8 | 8 | 102 ± 4 | 101 ± 0 | 98 ± 5 |
| 16 | 16 | 109 ± 3 | 105 ± 0 | 103 ± 3 |
| 32 | 22 | 107 ± 3 | 105 ± 0 | 103 ± 3 |
| 64 | 29 | 112 ± 4 | 106 ± 0 | 106 ± 6 |
| 120 | 36 | 114 ± 9 | 109 ± 0 | 110 ± 8 |
| No injection, reporting | 43 | 114 ± 9 | 107 ± 0 | 110 ± 8 |

Results:

The changes in bodyweight of the mice during the experiment are given in Table 12. After 43 days, no mice had died, and no clinical signs of toxicity were observed. The accumulated dose received in the two test groups was 252 mg/kg. A tendency of reduced growth of body weight compared to the control group was observed during the test period. At the highest dose of 128 mg/kg the reduction of growth of body weight was within the standard error of mean (SEM) compared to the untreated group.

Example 212—In Vivo Infection Study of Example 26 in Mice

Purpose of the Study:

The purpose of this study was to investigate the synergy between a typical example of the present invention and a state of art carbapenem in a clinically relevant multiresistant Gram-negative bacterial strain harboring a metallo-β-lactamase in the treatment of live mice infected with the bacterial strain. The chosen compound was Example 26 and the chosen carbapenem was the clinically relevant β-lactam antibiotic meropenem (MEM). The chosen bacterial strain was a clinical isolate of *Klebsiella pneumoniae* strain 50752501 harbouring NDM-1. The dose of meropenem selected in the present study was 33 mg/kg. This dose was shown to have a minor effect on reducing the bacterial loads but still being a clinically relevant dose for treating susceptible *K. pneumoniae* strain.

Material and Methods:

Materials 36 outbred, NMRI female mice, 26-30 gram (Harlan)
Apodan® (Cyclophosphamid 1 g) Lot 6F0931 (exp. 06/2019)
Meropenem, Mylan 1 g 51B0424 (exp. 06/2019)
NZ148, batch CS3071 received 030317
5% Horse Blood Agar plates (SSI: Exp 2017-06-07)
0.9% sterile saline (SSI:)
Sterile MilliQ water (SSI.)
Nurofen® Junior (20 mg/ml, Novartis)
Zoletil mix
EDTA coated Eppendorf tubes
Vidal glass tubes Laboratory Animal Facilities and Housing of Mice The temperature and humidity were registered daily in the animal facilities. The temperature was 22° C.+/−2° C. and can be regulated by heating and cooling. The humidity was 55+/−10%. The air changes per hour were approximately 8-12 times (70-73 times per hours inside cages), and light/dark period was in 12-hours interval of 6 a.m.-6 p.m./6 p.m-6 a.m. The mice had free access to domestic quality drinking water and food (Teklad Global diet 2916C-Envigo) and occasionally peanuts and sunflower seeds (Køge Korn A/S). The mice were housed in Type 3 IVC cages with bedding from Tapvei. Further, the animals were offered Enviro-Dri nesting material and cardboard houses (Bioserv).

Preparation of Cyclophosphamide

A total of 1 g cyclophosphamide (one ampoule Apondan, 1 g) was dissolved in 50 ml water ~20 mg/ml on each day of use. This stock solution was further diluted to 11 mg/ml (16.5 ml of 20 mg/ml+13.5 ml saline) for use on day −4 or to 5.5 mg/ml (8.25 ml of 20 mg/ml+21.75 ml saline) for use on day −1.

Treatment of Mice with Cyclophosphamide

The mice were rendered neutropenic by injecting 0.5 ml cyclophosphamide solution intraperitoneally 4 days (approximately 200 mg/kg) and 1 day (approximately 100 mg/kg) prior to inoculation.

Inoculation of Mice

Fresh overnight colonies from a 5% Horse Blood Agar plate were suspended and diluted in sterile saline to approximately and $10^7$ CFU/ml. Mice were inoculated intraperitoneally with 0.5 ml of the suspension. Approximately/2 hr prior to inoculation, mice were treated orally with 45 µl neurophen (20 mg ibuprofen/ml corresponding to approximately 30 mg/kg) as a pain relief.

Treatment of Mice with Meropenem and Example 26

One vial Meropenem, 1 gram, was dissolved in saline to 50 mg/ml and further diluted to 5 mg/ml in saline.

Two vials of Example 26 with 25.7 and 23.7 mg respectively was dissolved in PBS pH 7.4 to 15 mg/ml and pooled. pH was verified to 7.5. The 15 mg/ml stock solution was further diluted to 5 mg/ml and 1.5 mg/ml in PBS pH 7.4.

Mice were treated subcutaneously in the neck region with 0.2 ml solutions of Example 26 corresponding to 10, 33 and 100 mg/kg. 30 minutes later mice were treated with 33 mg/kg meropenem or vehicle (see Table 13).

Clinical Scoring of Mice

The mice were observed during the study and scored based on their behaviour and clinical signs.

Score:

0 Healthy

1 Minor clinical signs of infection (slower movements, light piloerection in the skin)

2 Moderate signs of infection (lack of curiosity or changed activity, piloerection in the skin, changed body position 3 Severe signs of infection (reduced movements, piloerection in the skin, slightly pinched eyes, tucked up belly, changed body position).

4 Severe signs of infection (stiff movements, piloerection in the skin, pinched eyes, cold, pain). Sacrificed.

5 The mouse does not move, is cold, lying on the side. Sacrificed.

Sampling

Figure 11:
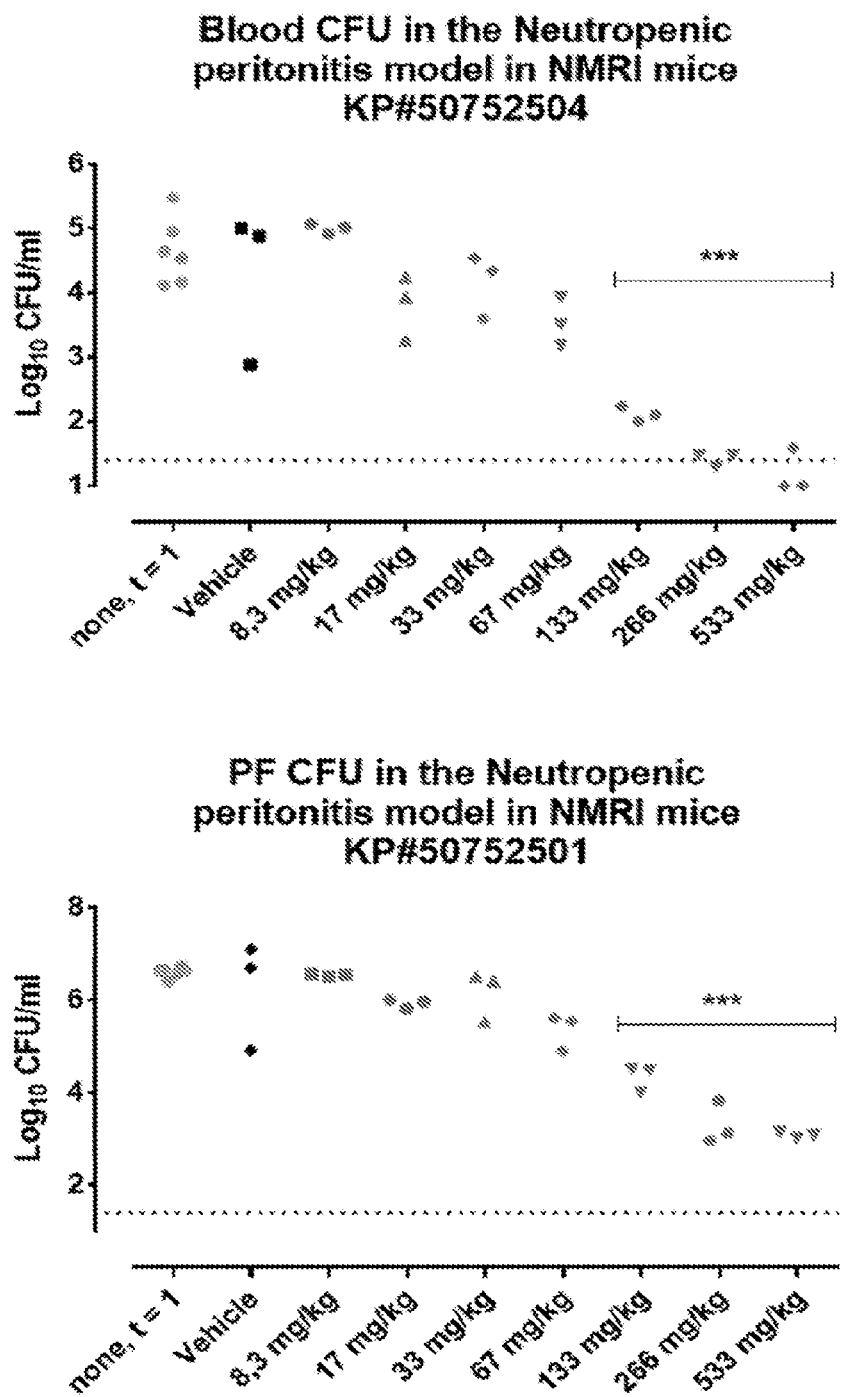
FIG. 11 shows blood and peritoneal fluid CFU of KP #50752504 as a function of MEM concentration.
Figure 12:
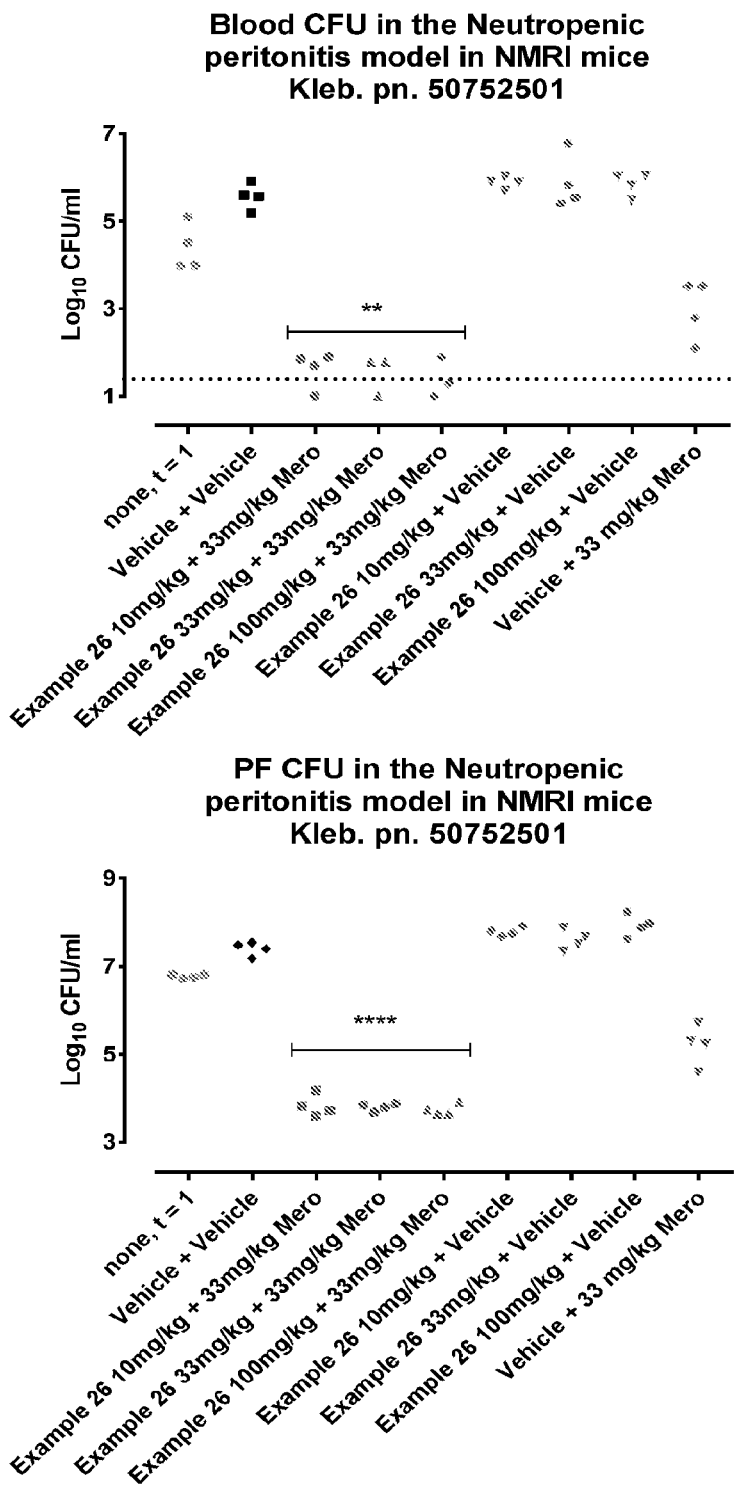
FIG. 12 shows colony counts in blood and peritoneal fluid in neutropenic mice at 1 and 5 hours after inoculation. Detection limit 1.0 $\log_{10}$ CFU/ml.  $p<0.01$, * $p<0.001$ vs vehicle Group.

Colony counts were determined from blood and peritoneal fluid at 1 and 5 hrs post inoculation. The mice were anaesthetized with Zoletil mix and blood was collected from axillary cutdown in 1.5 ml EDTA coated Eppendorf tubes. The mice were sacrificed immediately after blood sampling and a total of 2 ml sterile saline was injected i.p. and the abdomen gently massaged before it was opened and fluid sampled with a pipette. Each sample was then 10 fold serial diluted in saline and 20-µl spots, ranging from undiluted to a $10^6$ dilution, were applied on agar plates in duplicates. In addition, 100 µl undiluted blood from the 4 highest meropenem dosing groups was spread on a separate plate to obtain lowest possible detection limit. All agar plates were incubated 18-22 hrs at 35° C. in ambient air. The overall treatment and sampling schedule is given in Table 13. Colony counts are given in Table 14, and visualized in FIGS. 11 and 12.

TABLE 13

| Treatment and sampling schedule | | | |
| --- | --- | --- | --- |
| Treatment with Example 26 T = 1 | Treatment with meropenem T = 1.5 | Sampling T = 1 | Sampling T = 5 |
| None | None | 1-2-3-4 | |
| 10 mg/kg | 33 mg/kg | | 5-6-7-8 |
| 33 mg/kg | | | 9-10-11-12 |
| 100 mg/kg | | | 13-14-15-16 |
| 10 mg/kg | Vehicle | | 17-18-19-20 |
| 33 mg/kg | | | 21-22-23-24 |
| 100 mg/kg | | | 25-26-27-28 |
| Vehicle | 33 mg/kg | | 29-30-31-32 |
| Vehicle | Vehicle | | 33-34-35-36 |

Results:

The actual CFU counts of each inoculum was as intended 7.44 $\log_{10}$ CFU/ml.

Mice were treated with EXAMPLE 26 and meropenem alone or in combination. Colony counts in blood and peritoneal fluid were performed at 1 hour after inoculation corresponding to start of treatment and at 4 hrs after treatment. The CFU counts and the clinical score for each individual mouse are shown in Table 14 and the CFU numbers are also presented in FIGS. 11 and 12.

Treatment with 10-100 mg/kg Example 26 alone did not result in reduction of the CFU levels compared to vehicle treatment in blood and peritoneal fluid. Treatment with meropenem alone resulted in 2.5 and 2.2 $\log_{10}$ lower CFU levels compared to vehicle treatment in the blood and peritoneal fluid respectively. Combination treatment with Example 26 and meropenem resulted in 3.95-4.38 and 3.57-3.66 $\log_{10}$ lower CFU levels compared to vehicle treatment in the blood and peritoneal fluid respectively. The CFU levels after combination treatment was significantly lower than the CFU levels after treatment with meropenem alone ($p<0.01$ in blood and $p<0.0001$ in peritoneal fluid).

TABLE 14

Colony counts in blood and peritoneal fluid (PF) from neutropenic mice inoculated intraperitoneally with *K. pneumoniae* 50752501

| Mouse id | Score at sampling | Blood log CFU/ml | mean | Pf log CFU/ml | mean |
|---|---|---|---|---|---|
| 1 | 1 | 3.98 | 4.39 | 6.81 | 6.77 |
| 2 | 1 | 5.10 |  | 6.72 |  |
| 3 | 1 | 3.99 |  | 6.80 |  |
| 4 | 1 | 4.51 |  | 6.74 |  |
| 5 | 2 | 1.90 | 1.61 | 4.18 | 3.83 |
| 6 | 2 | 1.00 |  | 3.83 |  |
| 7 | 2 | 1.85 |  | 3.60 |  |
| 8 | 2 | 1.70 |  | 3.72 |  |
| 9 | 1 | 1.78 | 1.26 | 3.88 | 3.80 |
| 10 | 1 | 1.78 |  | 3.80 |  |
| 11 | 1 | 1.00 |  | 3.68 |  |
| 12 | 1 | 0.50 |  | 3.85 |  |
| 13 | 1 | 1.30 | 1.18 | 3.65 | 3.74 |
| 14 | 1 | 0.50 |  | 3.74 |  |
| 15 | 1 | 1.90 |  | 3.92 |  |
| 16 | 1 | 1.00 |  | 3.65 |  |
| 17 | 2 | 6.02 | 5.88 | 7.92 | 7.79 |
| 18 | 2 | 5.70 |  | 7.68 |  |
| 19 | 2 | 5.90 |  | 7.76 |  |
| 20 | 2 | 5.89 |  | 7.81 |  |
| 21 | 1 | 5.83 | 5.89 | 7.68 | 7.60 |
| 22 | 1 | 5.54 |  | 7.51 |  |
| 23 | 1 | 6.78 |  | 7.88 |  |
| 24 | 1 | 5.40 |  | 7.35 |  |
| 25 | 1 | 5.83 | 5.84 | 8.24 | 7.93 |
| 26 | 1 | 6.05 |  | 7.89 |  |
| 27 | 1 | 5.48 |  | 7.63 |  |
| 28 | 1 | 6.02 |  | 7.98 |  |
| 29 | 2 | 3.51 | 2.98 | 5.72 | 5.22 |
| 30 | 2 | 2.80 |  | 4.60 |  |
| 31 | 2 | 3.51 |  | 5.30 |  |
| 32 | 2 | 2.10 |  | 5.24 |  |
| 33 | 2 | 5.60 | 5.56 | 7.40 | 7.40 |
| 34 | 2 | 5.90 |  | 7.48 |  |
| 35 | 2 | 5.18 |  | 7.18 |  |
| 36 | 2 | 5.57 |  | 7.54 |  |

The invention claimed is:

1. A compound selected from any of the following, their stereoisomers, and their pharmaceutically acceptable salts:

2. The compound according to claim 1 selected from any of the following and their pharmaceutically acceptable salts:

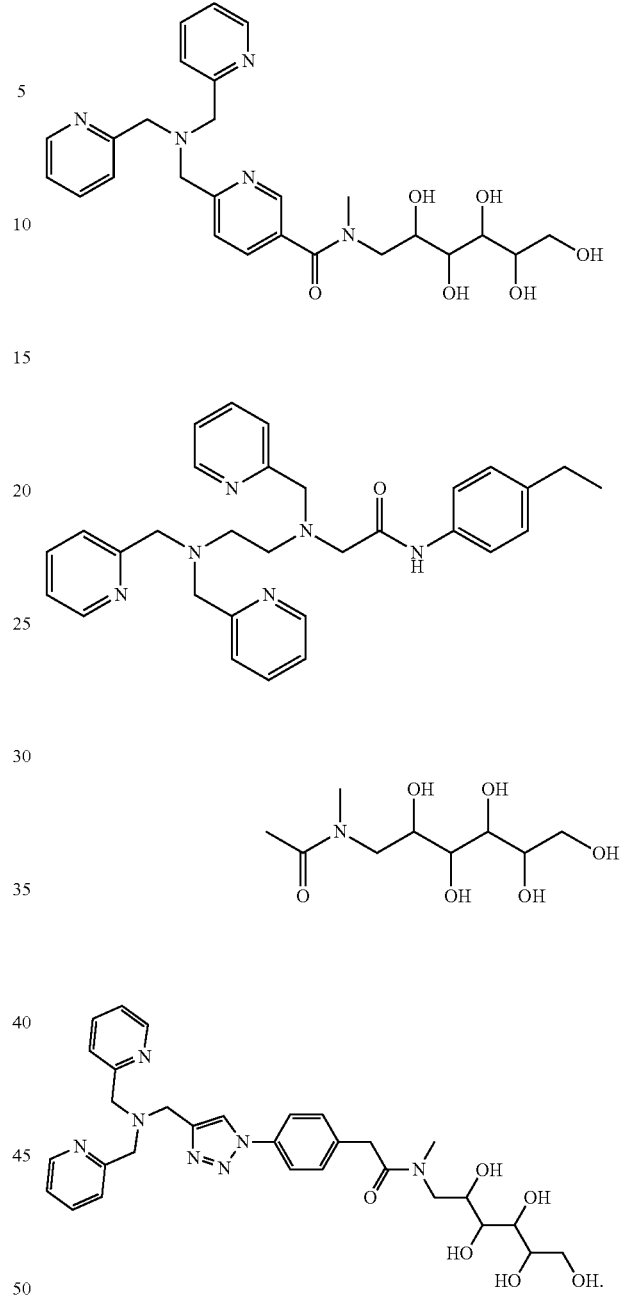

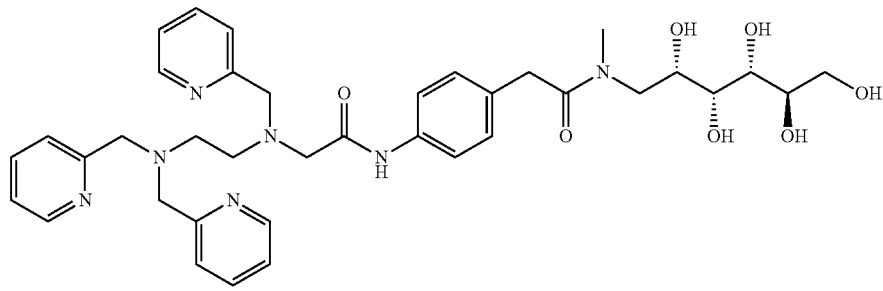

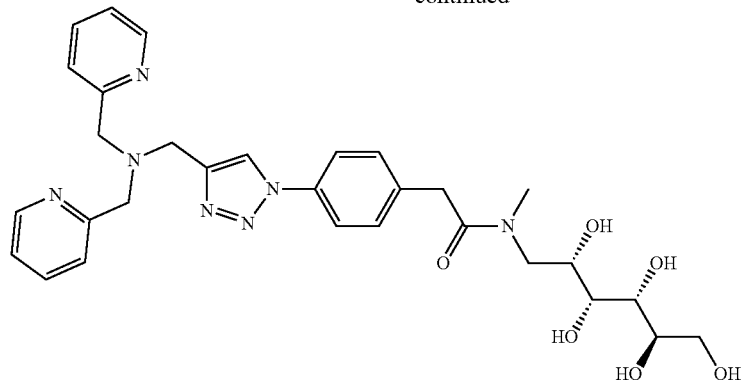

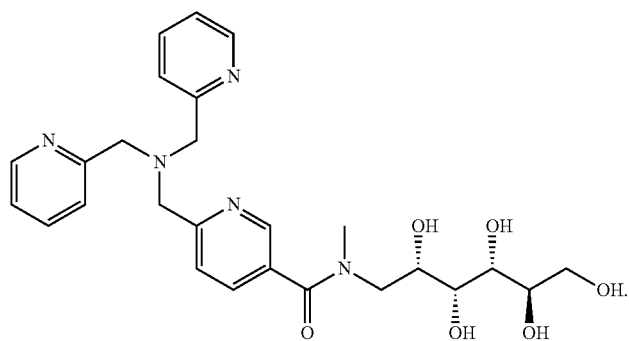

3. A pharmaceutical composition comprising a compound according to claim 1 and one or more pharmaceutically acceptable carriers or excipients, and optionally including one or more antioxidants.

4. A pharmaceutical formulation comprising a compound according to claim 1 together with a β-lactam antibiotic, and optionally one or more pharmaceutically acceptable carriers or excipients.

5. The pharmaceutical formulation according to claim 4, wherein the β-lactam antibiotic is selected from the following: penams, cephems, monobactams, penems, carbapenems, and clavams.

6. The pharmaceutical formulation according to claim 5, wherein the β-lactam antibiotic is a carbapenem.

7. A kit comprising:
a first container containing a compound according to claim 1 or a pharmaceutical composition thereof; and
(ii) a second container containing a β-lactam antibiotic.

8. The kit according to claim 7, wherein the β-lactam antibiotic is selected from the following: penams, cephems, monobactams, penems, carbapenems, and clavams.

9. The kit according to claim 8, wherein the β-lactam antibiotic is a carbapenem.

10. A method of treating a bacterial infection in a human or non-human mammal, the method comprising the step of administering to the mammal an effective amount of a compound selected from any of the following structures below, their stereoisomers, and their pharmaceutically acceptable salts, or a pharmaceutical composition thereof in combination with a β-lactam antibiotic:

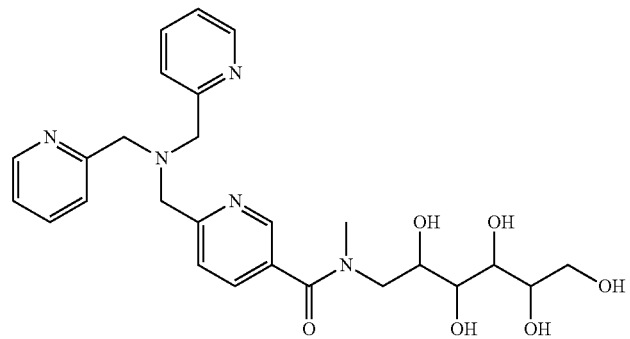

-continued

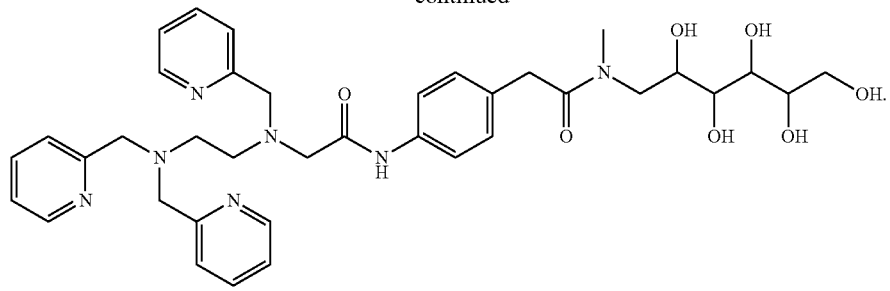

11. The method according to claim 10, wherein the infection is associated with Gram positive or Gram negative bacteria which are resistant to one or more antibiotics.

12. The method according to claim 10, wherein the infection is associated with Gram negative bacteria which are resistant to one or more antibiotics.

13. The method according to claim 10, wherein the infection is associated with Gram negative bacteria which are resistant to a β-lactam antibiotic.

14. The method according to claim 12, wherein the bacteria comprise metallo-β-lactamases.

15. The method according to claim 10, wherein the infection is associated with gram negative multi-resistant bacteria harboring extended spectrum metallo-β-lactamases (ESBL).

16. The method according to claim 10, wherein the compound is administered together with a carbapenem antibiotic agent and the infection is associated with gram negative carbapenem-resistant bacteria harboring metallo-β-lactamases, or with gram negative carbapenem-resistant bacteria harboring *Klebsiella pneumoniae* carbapenemases, KPC and/or metallo-β-lactamases.

17. The method according to claim 10, wherein the compound and β-lactam antibiotic are provided in the same formulation.

18. The method according to claim 10, wherein the compound and β-lactam antibiotic are provided in different formulations.

19. The method according to claim 10, wherein the β-lactam antibiotic is selected from the following: penams, cephems, monobactams, penems, carbapenems, and clavams.

20. The method according to claim 19, wherein the β-lactam antibiotic is a carbapenem.

* * * * *